United States Patent
Brand et al.

(10) Patent No.: US 7,786,177 B2
(45) Date of Patent: Aug. 31, 2010

(54) PHENYLALANINE ENAMIDE DERIVATIVES

(75) Inventors: Stephen Brand, Reading (GB); Stuart Bailey, Dorking (GB); Julien A. Brown, Reading (GB); James A. Johnson, Slough (GB); John R. Porter, Chinnor (GB); John C. Head, Maidenhead (GB)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 12/415,546

(22) Filed: Mar. 31, 2009

(65) Prior Publication Data

US 2009/0186914 A1 Jul. 23, 2009

Related U.S. Application Data

(60) Division of application No. 11/533,117, filed on Sep. 19, 2006, now Pat. No. 7,531,549, which is a continuation of application No. 10/947,032, filed on Sep. 22, 2004, now Pat. No. 7,122,556, which is a continuation of application No. 10/081,072, filed on Feb. 22, 2002, now Pat. No. 6,878,718.

(30) Foreign Application Priority Data

| Feb. 22, 2001 | (GB) | ................................. | 0104418.9 |
| Jun. 8, 2001 | (GB) | ................................. | 0114000.3 |
| Nov. 16, 2001 | (GB) | ................................. | 0127562.7 |

(51) Int. Cl.
C07D 215/14 (2006.01)
A61K 31/47 (2006.01)
A61K 31/438 (2006.01)
A61P 11/06 (2006.01)
A61P 29/00 (2006.01)

(52) U.S. Cl. ...................... 514/741; 564/440; 564/441; 564/442

(58) Field of Classification Search ................ 564/440, 564/441, 442; 514/741
See application file for complete search history.

(56) References Cited

U.S. PATENT DOCUMENTS

| 3,938,367 | A | 2/1976 | Fletcher et al. |
| 6,518,283 | B1 | 2/2003 | Langham et al. |
| 6,610,700 | B2 | 8/2003 | Norman et al. |
| 6,780,874 | B2 | 8/2004 | Norman et al. |
| 6,835,738 | B1 | 12/2004 | Brown et al. |
| 6,872,719 | B1 | 3/2005 | Brown et al. |
| 6,878,718 | B2 | 4/2005 | Brand et al. |
| 6,953,798 | B1 | 10/2005 | Porter et al. |
| 7,122,556 | B2 | 10/2006 | Brand et al. |
| 2007/0027174 | A1 | 2/2007 | Brand et al. |

FOREIGN PATENT DOCUMENTS

| WO | 00/23419 A1 | 4/2000 |
| WO | 00/32575 A1 | 6/2000 |
| WO | 00/73260 A1 | 12/2000 |
| WO | 01/79173 A2 | 10/2001 |

OTHER PUBLICATIONS

Abraham, W. M. et al., "α4-Integrins Mediate Antigen-Induced Late Bronchial Responses and Prolonged Airway Hyperresponsiveness in Sleep", J. Clin. Invest., 1994, 93, 776-787.

Alhaique, F. et al., "Cyclisation of dinitriles by sodium alkoxides a new synthesis of naphthyridines", Tetrahedron Letters, 1975, 3, 173-174.

Alhaique, F. et al., "91/Studies on 2,6-Naphthyridines: Hydrogenated Derivatives and a New Ring-Closure Reaction", Gazzetta Chimica Italiana, 1975, 105, 1001-1009.

(Continued)

Primary Examiner—Kahsay T Habte
(74) Attorney, Agent, or Firm—McDonnell Boehnen Hulbert & Berghoff LLP

(57) ABSTRACT

Phenylalanine enamide derivatives of formula (1) are described:

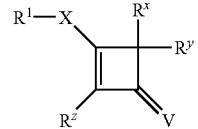

(1)

wherein
R$^1$ is a group Ar$^1$ L$^2$Ar$^2$Alk- in which:
Ar$^1$ is an optionally substituted aromatic or heteroaromatic group;
L$^2$ is a covalent bond or a linker atom or group;
Ar$^2$ is an optionally substituted arylene or heteroarylene group; and Alk is a chain
—CH$_2$—CH(R)—, —CH=C(R)— or

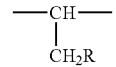

in which R is a carboxylic acid (—CO$_2$H) or a derivative or biostere thereof;
X is an —O— or —S— atom or —N(R$^2$)— group in which:
R$^x$, R$^y$ and R$^z$ which may be the same or different is each a hydrogen atom or an optional substituent;
or R$^z$ is an atom or group as previously defined and R$^x$ and R$^y$ are joined together to form an optionally substituted spiro linked cycloaliphatic or heterocycloaliphatic group;
and the salts, solvates, hydrates and N-oxides thereof.

The compounds are able to inhibit the binding of integrins to their ligands and are of use in the prophylaxis and treatment of immuno or inflammatory disorders or disorders involving the inappropriate growth or migration of cells.

23 Claims, No Drawings

OTHER PUBLICATIONS

Ames, D. E. et al., "Condensation of β-dicarbonyl compounds with halogenopyridinecarb-oxylic acids. A convenient synthesis of some naphthyridine derivatives", J.C.S. Perkin I, 1972, 705-710.

Baldwin, J. J. et al., "A Novel Naphthridinone Synthesis via Enamine Cyclization", J. Org. Chem., 1978, 43(25), 4878-4880.

Berlin, C. et al., "α4β7 Integrin Mediates Lymphocyte Binding to the Mucosal Vascular Addressin MAdCAM-1", Cell, 1993, 74, 185-195.

Binns, R. M. et al., "The Role of E-Selectin in Lymphocyte and Polymorphonuclear Cell Recruitment into Cutaneous Delayed Hypersensitivity Reactions in Sensitized Pigs", J. Immunol., 1996, 157, 4094.

Bodor, N., "Novel approaches in prodrug design", Alfred Benzon Symposium, 1982, 17, 156-177.

Bordner, J. et al., "1,3-Diamino-6,7-dimethoxyisoquinoline Derivatives as Potential α1-Adrenoceptor Antagonist", J. Med. Chem., 1988, 31, 1036-1039.

Briskin, M. J. et al., "Structural Requirements for Mucosal Vascular Addressin Binding to its Lymphocyte Receptor α4β7", J. Immunol., 1996, 156, 719-726.

Brooks, P. C. et al., "Antiintegrin αvβ3 blocks human breast cancer growth and angiogenesis in human skin", J. Clin. Invest., 1995, 96, 1815-1822.

Brun, E. M. et al., "Dienediolates of α,β-Unsaturated Carboxylic Acids in Synthesis:A New Synthetic Method to 2-Pyridones", Synlett, 1999, 7, 1088-1090.

Brun, E. M. et al., "A New Synthetic Method to 2-Pyridones", Synthesis, 2000, 2, 273-280.

Cardarelli, P. M. et al., "Cyclic RGD Peptide Inhibits α4β7 Interaction with Connecting Segment I and Vascular Cell Adhesion Molecule", J. Biol. Chem., 1994, 269(28) 18668-18673.

Deady, L. W. et al., "Ethoxycarbonylation of α-Cyano-o-toluonitrile and Cyclization to Isoquinolines and Pyrimido[4,5-c]isoquinolines", Aust. J. Chem., 1989, 42, 1029-1034.

Erle, D. J. et al., "Expression and function of the MadCAM-1 receptor, integrin α4β7, on human leukocytes", J. Immunol., 1994, 153, 517-528.

Ezcurra, J. E. et al., "Synthesis of o-Quinodimethanes and Benzocyclobutenes from Dimethyl Squarate", Tetrahedron Lett, 1993, 34(39), 6177-80.

Falk, H. et al., "On the Chemistry of Pyrrole Pigments, XCI[1]: Copper Complexes of Pyridinologous Linear Tri- and Tetra-pyrroles as Cyclopropanation Catalysts", Monatshefe Fur Chemie, 1994, 125, 325-333.

Ferguson, T. A. et al., "Two integrin-binding peptides abrogate T cell-mediated immune responses in vivo", Proc. Natl. Acad. Sci. USA, 1991, 88, 8072-8076.

Giacomello et al., "Synthesis of 2,6-naphthyridine", Tetra. Letters, 1965, 16, 1117-1121.

Hammes, H. et al., "Subcutaneous injection of a cyclic peptide antagonist of vitronectin receptor-type integrins inhibits retinal neovascularization", Nature Medicine, 1996, 2, 529-533.

Heileman, M. J. et al., "New Metathesis Methodology Leading to Angularly-Fused Polycyclic Quinones and Related Compounds", J. Am. Chem. Soc., 1998, 120, 3801-3802.

Hergueta, R. A. et al., "Rearrangements of Cyclobutenones. Synthesis of N-Methyl-7,8-dihydrobenzophinanthridine-9,12-diols and Related Compounds", J. Org. Chem., 1999, 64, 5979-83.

Hesterberg, P. E. et al., "Rapid Resolution of Chronic Colitis in the Cotton-top Tamarin with an Antibody to a Gut-Homing Integrin α4β7", Gastroenterol, 1996, 111, 1373-80.

Hiebl, J., "New Synthesis of isoquinoline-3-carboxylates", Tetrahedron Letters 40, 1999, 7935-7938.

Hodivala-Dilke, K. M., "β3-integrin-deficient mice are a model for glanzmann thrombasthenia showing placental defects and reduced survival", J. Clin. Invest., 1999, 103(2), 229-238.

Holzmann, B. et al., "Peyer's patch-specific lymphocyte homing receptors consist of a VLA-4-like α chain associated with either of two integrin β chains, one of which is novel", EMBO J., 1989, 8(6), 1735-1741.

Humphries, M. J. et al., "Mechanisms of VCAM-1 and fibronectin binding to integrin α4β1: implications for integrin function and rational drug design", Ciba Foundation Symposium, 1995, 189, 177-194.

Issekutz, T. B., "Inhibition of Lymphocyte Endothelial Adhesion and In Vivo Lymphocyte Migration to Cutaneous Inflammation by TA-3, a New Monoclonal Antibody to Rat LFA-1", J. Immunol., 1992, 149(10), 3394-3402.

Kaiser, E. M. et al., "Facile Synthesis of 1-Amino-3-aiylisoquinolines", Synthesis, Nov. 1974, 11, 805-806.

Kocienski, P. et al., "A Synthesis of (−)-Tetrahydrosipstatin", Tetrahedron Lett., Jan. 17, 1989, 30, 1833-1836.

Kraus, J. L. et al., "Sur La Reactivite Du Squarate De Dimethyle Vis-a-vis De Thiols", Tetrahedron Lett., 1987, 28, 1765-8.

Li, Z. et al., "Effect of an anti-Mol MAb on ozone-induced airway inflammation and airway hyperresponsiveness in dogs", Am. J. Physiol., 1992, 263(6 Pt. 1), L723-726.

Marlin, S. D. et al., "LFA-1 Immunodeficiency Disease", J. Exp. Med., 1986, 164, 855-867.

Mitjans, F. et al., "An anti-αv-integrin antibody that blocks integrin function inhibits the development of a human melanoma in nude mice", J. Cell Science, 1995, 108, 2825-2838.

Molina, P. et al., "Iminophosphorane-mediated annelation of a pyridine ring into a preformed pyridine one: synthesis of naphthyridine, pyrido [1,2-c] pyrimidine and pyrido [1,2-c] quinazoline derivatives", Tetrahedron, 1992, 48(22), 4601-4616.

Molina, P. et al., "Preparation and Thermal Ring-closure of β-Aryl Vinyl Carbodimides: Synthesis of Isoquinoline Derivatives", J. Chem. Soc. Perkins Trans., 1990, 1727-1731.

Nagarajan, A. et al., "ORganopalladium mediated synthesis of isocarbostyrils", Indian Journal of Chemistry, Jan. 1989, 28B, 67-68.

Newham, P. et al., "Integrin adhesion receptors: structure, function and implications for biomedicine", Molecular Medicine Today, 1996, 304-313.

Nooi and Arens, "Chemistry of Acetylenic Ethers XXXVII. Some new acetylenic ethers", Recl. Trav. Chim. Pays-Bas, 1959, 78, 284-287.

Numata, A. et al., "General synthetic method for naphthyridines and their N-oxides containing isoquinolinic nitrogen", Synthesis, 1999, 2, 306-311.

Ohno, M. et al., "Synthesis of γ-Acylmethylenetetronates from Squaric Acid", Tetrahedron Lett., 1993, 34, 4807-10.

Osborn, L., "Leukocyte Adhesion to Endothelium in Inflammation", Cell, 1990, 62, 3-6.

Paterson, I. et al., "O-Silylatd Enolates in Organic Synthesis: α-Alkylation of Carbonyl Compounds by 1,3-Dithienium Fluoroborate", Tet. Lett., 1981, 22(29), 2829-2832.

Petasis, N. A. et al., "Titanium-Mediated Olefinations of Cyclobutenedione Derivatives", Tetrahedron Lett., 1995, 36, 6001-4.

Petasis, N. A. et al., "Synthesis of Substituted Benzonorbonadienes from Cyclobutenediones", Synlett, 1996, 155-6.

Podolsky, D. K. et al., "Attenuation of Colitis in the Cotton-top Tamarin by Anti-α4 integrin Moloclonal Antibody", J. Clin. Invest., 1993, 92, 372-380.

Sakamoto, T. et al., "Condensed heteroaromatic ring systems. III. Synthesis of naphthyridine derivatives by cyclization of ethynylpyridinecarboxamides", Chem. Pharm. Bull., 1985, 33(2), 626-633.

Sakamoto, F. et al., "Studies on Prodrugs. II. Preparation and Characterization of (5-Substituted 2-Oxo-1,3-dioxolen-4-yl)methyl Esters of Ampicillin", Chem. Pharm. Bull., 1985, 32, 2241-2248.

Sheffield, D. J. et al., "Synthesis of Some 4-Pyridylpyruvic Acids as Potential Lactate Dehydrogenase Inhibitors", J. C.S. Perkin I, 1972, 2506-2509.

Shroff, H. N. et al., "Small peptide inhibitors of α4β7 mediated MadCAM-1 adhesion to lymphocytes", Bioorg. Med. Chem. Letts., 1996, 6(21), 2495-2500.

Singh, G. et al., "Prodrug approach in new drug design and development", J. Sci. Ind. Res., 1996, 55, 497-510.

Sonnenberg, A., "Integrins and their ligands", Cur. Topics Microbiol. Immunol., 1993, 184, 7-35.

Springer, T. A., "Traffic Signals for Lymphocyte Recirculation and Leukocyte Emigration: The Multistep Paradigm", Cell, 1994, 76, 301-314.

Springer, T. A., "Adhesion receptors of the immune system", Nature, 1990, 346, 425-434.

Srivatsa, S. S. et al., "Selective α4β3 integrin blockade potently limits neointimal hyperplasia and lumen stenosis following deep coronary arterial stent injury: evidence for the functional importance of integrin α4β3 and osteopontin expression during neointima formation", Cariovascular Research, 1997, 36, 408-428.

Still, I. W. J. et al., "Convenient Method for the Conversion of Thiols and Disulfides to the Corresponding Chlorides", J. Org. Chem., 1982, 47, 560.

Tan, R. et al., "Synthesis of 2,6-naphthyridine and some of its derivatives", Tetrahedron Letters, 1965, 31, 2737-2744.

Tovar, J. D. et al., "Pyrylium Salts via Electrophilic Cyclization" Applications for Novel 3-Arylisoquinoline Synthesis, J. Org. Chem., 1999, 64, 6499-6504.

Turnbull, P. et al., "Regioselective Synthesis of Highly Substituted Naphthols", J. Org. Chem., 1995, 60, 644-9.

Vanderslice, P. et al., "A Cyclic Hexapeptide is a Potent Antagonist of α4 Integrins", J. Immunol., 1997, 158, 1710-1718.

Wasserman, H. H. et al., "Cyclobutenone Derivatives from Ethoxyacetylene", J. Org. Chem., 1973, 38, 1451-1455.

Wenkert, E. et al., "General Methods of Synthesis of Indole Alkaloids. VI. Synthesis of dl-Corynantheidine and a Camptothecin Model 1,2", J. Amer. Chem. Soc., 1967, 89(25), 6741-6745.

Xu, S. L. et al., "Synthesis of p-Chlorophenols (and -naphthols) from the Thermal Rearrangement of 4-Chlorocyclobutenones", J. Org. Chem., 1992, 57, 326-8.

Yamamoto, Y. et al., "2[1-(Trimethylsilyl)alkylidene]-4-cyclopentene-1,3-dione from Lewis Acid-Catalyzed Reaction of Cyclobutenedione Monoacetal with Alkynylsilane: Novel Cationic 1,2-Silyl Migrative Ring Opening and Subsequent 5-Exo-Trig Ring Closure", J. Org. Chem., 1997, 62, 1292-8.

Yang, X. "A predominant role of integrin α4 in the spontaneous development of autoimmune diabetes in nonobese diabetic mice", Proc. Natl. Acad. Sci. USA, 1994, 91, 12604-12608.

Yednock, T. A., "Prevention of experimental autoimmune encephalomyelitis by antibodies against α4β1 integrin" Nature, 1992, 356, 63-66.

Yerxa, B. R. et al., "Synthesis of Indolizine-5-8-diones and [3.2.2]Cyclazines", Tetrahedron Lett., 1992, 33, 7811-14.

Yerxa, B. R. et al., "Synthesis of (±)-Septicine" Tetrahedron, 1994, 50, 6173-80.

Zhang, D. et al., "A Versatile Synthesis of 3-Subtituted Indolines and Indoles", J. Org. Chem., 1996, 61, 2594-5.

Bundgaard, H., Design of Prodrugs, 1985, Elsevier, Amsterdam.

Katritzky et al., Comprehensive Organic Functional Group Transformations, vols. 1-7, 1995 (Pergamon).

Katritzky et al., Comprehensive Heterocyclic Chemistry, vols. 1-8, 1984 (Pergamon).

Katritzky et al., Comprehensive Heterocyclic Chemistry, vols. 1-11, 1994 (Pergamon).

Trost and Flemming, Comprehensive Organic Synthesis, vols. 1-9, 1991 (Pergamon).

Paquette, Encyclopedia of Reagents for Organic Synthesis, vols. 1-8, 1995 (John Wiley and Sons).

Fieser and Fieser's Reagents for Organic Synthesis, vols. 1-19, 1999 (John Wiley and Sons).

Green, T. W., "Protective Groups in Organic Synthesis", 1999 (John Wiley and Sons).

Larock's Comprehensive Organic Transformations, 1989 (VCH Publishers Inc.).

March's Advanced Organic Chemistry, 1992 (John Wiley and Sons).

Rodd's Chemistry of Carbon Compounds, vols. 1-15 and Supplementals, 1989 (Elsevier Science Publishers).

Boehncke et al., "Leukocyte extravasation as a target for anti-inflammatory therapy—which molecule to choose?", Experimental Dematology, 2005, 14, 70-80.

Aust, J. Chem., 1972, 433.

MacDougall, J. M. et al., J. of Org. Chem., 1999, 64, 5979-5983.

Wu, M. J. et al., "A direct anionic cyclization of 2-alkynylbenzonitrile of 3-substituted-1(2H)-isoquinolones and 3-benzylideneisoindol-2-ones initiated by methoxide addition", Tetrahedron, 55, 1999, 13139-13200.

PHENYLALANINE ENAMIDE DERIVATIVES

REFERENCE TO RELATED APPLICATIONS

The present application is a divisional of U.S. application Ser. No. 11/533,117 filed Sep. 19, 2006, which is a continuation of U.S. application Ser. No. 10/947,032 filed Sep. 22, 2004, now U.S. Pat. No. 7,122,556 issued Oct. 17, 2006, which is a continuation of U.S. application Ser. No. 10/081,072 filed Feb. 22, 2002, now U.S. Pat. No. 6,878,718 issued Apr. 12, 2005, and claims priority of Patent Application Ser. No. GBR 1 0104418.9, filed Feb. 22, 2001, Patent Application Ser. No. GBR1 0114000.3, filed Jun. 8, 2001 and Patent Application Ser. No. GBR1 01 27562.7, filed Nov. 16, 2001, which are incorporated by reference herein in their entirety.

FIELD OF INVENTION

This invention relates to a series of phenylalanine enamide derivatives, to compositions containing them, to processes for their preparation, and to their use in medicine.

Each of the patents, publications, and other documents mentioned or referred to in this specification be herein incorporated by reference in their entirety.

Over the last few years it has become increasingly clear that the physical interaction of inflammatory leukocytes with each other and other cells of the body plays an important role in regulating immune and inflammatory responses [Springer, T. A., Nature, 346, 425, (1990); Springer, T. A., Cell, 76, 301, (1994)]. Specific cell surface molecules collectively referred to as cell adhesion molecules mediate many of these interactions.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 16 different integrin alpha chains and 8 different integrin beta chains have been identified [Newman, P. et al., Molecular Medicine Today, 304, (1996)]. The members of the family are typically named according to their heterodimer composition although trivial nomenclature is widespread in the field. Thus the integrin $\alpha4\beta1$ consists of the integrin alpha 4 chain associated with the integrin beta 1 chain, but is also widely referred to as Very Late Antigen 4 or VLA-4. Not all of the potential pairings of integrin alpha and beta chains have yet been observed in nature and the integrin family has been subdivided into a number of subgroups based on the pairings that have been recognised to date [Sonnenberg, A., Current Topics in Microbiology and Immunology, 184, 7, (1993)].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed on leukocytes [Marlin, S. D. et al, J. Exp. Med. 164, 855, (1986)]. Patients suffering from this disease have a reduced ability to recruit leukocytes to inflammatory sites and suffer recurrent infections, which in extreme cases may be fatal. In the case of patients suffering from the disease termed Glanzman's thrombasthenia (a defect in a member of the beta 3 integrin family) there is a defect in blood clotting (Hodivala-Dilke, K. M., J. Clin. Invest. 103, 229, (1999)].

The potential to modify integrin function in such a way as to beneficially modulate cell adhesion has been extensively investigated in animal models using specific antibodies and peptides that block various functions of these molecules [e.g. Issekutz, T. B., J. Immunol. 149, 3394, (1992); Li, Z. et al, Am. J. Physiol. 263, L723, (1992); Mitjans, F. et al, J. Cell Sci. 108, 2825, (1995); Brooks, P. C. et al, J. Clin. Invest. 96, 1815, (1995); Binns, R. M. et al, J. Immunol. 157, 4094, (1996); Hammes, H.-P. et al, Nature Medicine 2, 529, (1996); Srivata, S. et al., Cardiovascular Res. 36, 408 (1997)]. In particular an anti $\alpha_4\beta_7$-antibody has demonstrated both clinical and histologic improvement of inflammatory activity and disease in a non-human primate model of inflammatory bowel disease [Hesterberg, P. E. et al., Gastroenterol, 111, 1373-80 (1996)]. A number of monoclonal antibodies which block integrin function are currently being investigated for their therapeutic potential in human disease, and one, ReoPro, a chimeric antibody against the platelet integrin $\alpha$IIb$\beta$3 is in use as a potent anti-thrombotic agent for use in patients with cardiovascular complications following coronary angioplasty.

Integrins recognize both cell surface and extracellular matrix ligands, and ligand specificity is determined by the particular alpha-beta subunit combination of the molecule [Newman, P., ibid]. One particular integrin subgroup of interest involves the $\alpha4$ chain which can pair with two different beta chains $\beta1$ and $\beta7$ [Sonnenberg, A., ibid]. The $\alpha4\beta1$ pairing occurs on many circulating leukocytes (for example lymphocytes, monocytes, eosinophils and basophils) although it is absent or only present at low levels on circulating neutrophils. $\alpha4\beta1$ binds to an adhesion molecule (Vascular Cell Adhesion Molecule-1 also known as VCAM-1) frequently up-regulated on endothelial cells at sites of inflammation [Osborne, L., Cell, 62, 3, (1990)]. The molecule has also been shown to bind to at least three sites in the matrix molecule fibronectin [Humphries, M. J. et al, Ciba Foundation Symposium, 189, 177, (1995)]. Based on data obtained with monoclonal antibodies in animal models it is believed that the interaction between $\alpha4\beta1$ and ligands on other cells and the extracellular matrix plays an important role in leukocyte migration and activation [Yednock, T. A. et al, Nature, 356, 63, (1992); Podolsky, D. K. et al, J. Clin. Invest. 92, 372, (1993); Abraham, W. M. et alt J. Clin. Invest. 93, 776, (1994)].

The integrin generated by the pairing of $\alpha4$ and $\beta7$ has been termed LPAM-1 [Holzmann, B. and Weissman, I. L., EMBO J. 8, 1735, (1989)]. The $\alpha4\beta7$ pairing is expressed on certain sub-populations of T and B lymphocytes and on eosinophils [Erie, D. J. et al, J. Immunol. 153, 517 (1994)]. Like $\alpha4\beta1$, $\alpha4\beta7$ binds to VCAM-1 and fibronectin. In addition, $\alpha4\beta7$ binds to an adhesion molecule believed to be involved in the homing of leukocytes to mucosal tissue such as gastrointestinal mucosa termed MAdCAM-1 [Berlin, C. et al, Cell, 74, 185, (1993)]. MAdCAM-1 is preferentially expressed in the gastrointestinal track. The interaction between $\alpha4\beta7$ and MAdCAM-1 may also be important at sites of inflammation outside of mucosal tissue [Yang, X.-D. et al, PNAS, 91, 12604, (1994)].

Regions of the peptide sequence recognized by $\alpha4\beta1$ and $\alpha4\beta7$ when they bind to their ligands have been identified. $\alpha4\beta1$ seems to recognise LDV, IDA or REDV peptide sequences in fibronectin and a QIDSP sequence in VCAM-1 [Humphries, M. J. et al, ibid] whilst $\alpha4\beta7$ recognises a LDT sequence in MAdCAM-1 [Birskin, M. J. et al, J. Immunol. 156, 719, (1996)]. There have been several reports of inhibitors of these interactions being designed from modifications of these short peptide sequences [Cardarelli, P. M. et al, J. Biol. Chem., 269, 18668, (1994); Shorff, H. N. et al, Biorganic Med. Chem. Lett., 6, 2495, (1996); Vanderslice, P. et al, J. Immunol., 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A., et al, PNAS, 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is important to be able to identify selective inhibitors of the alpha 4 subgroup.

We have now found a group of compounds which are potent and selective inhibitors of α4 integrins. Members of the group are able to inhibit α4 integrins such as α4β1 and/or α4β7 at concentrations at which they generally have no or minimal inhibitory action on a integrins of other subgroups. These compounds possess the additional advantage of good pharmacokinetic properties, especially low plasma clearance.

Thus according to one aspect of the invention we provide a compound of formula (1):

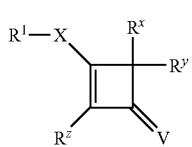

(1)

wherein
$R^1$ is a group $Ar^1 L^2 Ar^2 Alk-$ in which:
$Ar^1$ is an optionally substituted aromatic or heteroaromatic group;
$L^2$ is a covalent bond or a linker atom or group;
$Ar^2$ is an optionally substituted arylene or heteroarylene group;
and Alk is a chain
—$CH_2$—$CH(R)$—, —$CH$=$C(R)$— or

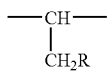

in which R is a carboxylic acid (—$CO_2H$) or a derivative or biostere thereof;
X is an —O— or —S— atom or —$N(R^2)$— group in which:
$R^2$ is a hydrogen atom or a $C_{1-6}$alkyl group;
V is an oxygen (O) or sulphur (S) atom;
$R^x$, $R^y$ and $R^z$ which may be the same or different is each an atom or group -$L^1(Alk^1)_n(R^3)_v$ in which $L^1$ is a covalent bond or a linker atom or group, $Alk^1$ is an optionally substituted aliphatic or heteroaliphatic chain, $R^3$ is a hydrogen or halogen atom or group selected from —$OR^{3a}$ [where $R^{3a}$ is a hydrogen atom or an optionally substituted straight or branched $C_{1-6}$alkyl group or $C_{3-8}$cycloalkyl group], —$SR^{3a}$, —CN or an optionally substituted cycloaliphatic, heterocycloaliphatic, polycycloaliphatic, heteropolycycloaliphatic, aromatic or heteroaromatic group, n is zero or the integer 1 and v is the integer 1, 2 or 3 provided that when n is zero and $L^1$ is a covalent bond v is the integer 1;
or $R^z$ is an atom or group as previously defined and $R^x$ and $R^y$ are joined together to form an optionally substituted spiro linked cycloaliphatic or heterocycloaliphatic group;

and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto ($CH_2C$=O)-enol (CH=CHOH) tautomers. Formula (1) and the formulae hereinafter are intended to represent all individual tautomers and mixtures thereof, unless stated otherwise.

Optionally substituted aromatic groups represented by $Ar^1$ when present in the group $R^1$ include for example optionally substituted monocyclic or bicyclic fused ring $C_{6-12}$aromatic groups, such as phenyl, 1- or 2-naphthyl, 1- or 2-tetrahydronaphthyl, indanyl or indenyl groups.

Optionally substituted heteroaromatic groups represented by the group $Ar^1$ when present in the group $R^1$ include for example optionally substituted $C_{1-9}$heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—$C_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, e.g. 2,6-naphthyridinyl or 2,7-naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Each aromatic or heteroaromatic group represented by the group $Ar^1$ may be optionally substituted on any available carbon or, when present, nitrogen atom. One, two, three or more of the same or different substituents may be present and each substituent may be selected for example from an atom or group -$L^3(Alk^2)_tL^4(R^4)_u$ in which $L^3$ and $L^4$, which may be the same or different, is each a covalent bond or a linker atom or group, t is zero or the integer 1, u is an integer 1, 2 or 3, $Alk^2$ is an optionally substituted aliphatic or heteroaliphatic chain and $R^4$ is a hydrogen or halogen atom or a group selected from optionally substituted $C_{1-6}$alkyl or $C_{3-8}$cycloalkyl, —$OR^5$ [where $R^5$ is a hydrogen atom, an optionally substituted $C_{1-6}$alkyl or $C_{3-8}$cycloalkyl group], —$SR^5$, —$NR^5R^6$ [where $R^6$ is as just defined for $R^5$ and may be the same or different], —$NO_2$, —CN, —$CO_2R^5$, —$SO_3H$, —$SOR^5$, —$SO_2R^5$, —$SO_3R^5$, —$OCO_2R^5$, —$CONR^5R^6$, —$OCONR^5R^6$, —$CSNR^5R^6$, —$COR^5$, —$OCOR^5$, —$N(R^5)COR^6$, —$N(R^5)CSR^6$, —$SO_2N(R^5)(R^6)$, —$N(R^5)SO_2R^6$, $N(R^5)CON(R^6$ ($R^7$) [where $R^7$ is a hydrogen atom, an optionally substituted $C_{1-6}$alkyl or $C_{3-8}$cycloalkyl group], —N($R^5$)CSN($R^6$)($R^7$) or —N($R^5$)SO$_2$N($R^6$)($R^7$), provided that when t is zero and each of $L^3$ and $L^4$ is a covalent bond then u is the integer 1 and $R^4$ is other than a hydrogen atom.

When $L^3$ and/or $L^4$ is present in these substituents as a linker atom or group it may be any divalent linking atom or group. Particular examples include —O— or —S— atoms or —C(O)—, —C(O)O—, —OC(O)—, —C(S)—, —S(O)—, —S(O)$_2$—, —N($R^8$)— [where $R^8$ is a hydrogen atom or an optionally substituted straight or branched $C_{1-6}$alkyl group], —CON($R^8$)—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)O—, —ON($R^8$)—, —N($R^8$)N($R^8$)—, —N($R^8$)CON($R^8$)—, —N($R^8$)CSN($R^8$)—, or —N($R^8$)SO$_2$N($R^8$)— groups. Where the linker group contains two $R^8$ substituents, these may be the same or different.

When $R^{3a}$, $R^4$, $R^5$, $R^6$, $R^7$ and/or $R^8$ is present as a $C_{1-6}$alkyl group it may be a straight or branched $C_{1-6}$alkyl group, e.g. a $C_{1-3}$alkyl group such as a methyl, ethyl or i-propyl group. $C_{3-8}$cycloalkyl groups represented by $R^{3a}$, $R^4$, $R^5$, $R^6$ and/or $R^7$ include $C_{3-6}$cycloalkyl groups e.g. cyclopropyl, cyclobutyl, cyclopentyl and cyclohexyl groups. Optional substituents which may be present on such alkyl or cycloalkyl groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When the groups $R^5$ and $R^6$ or $R^6$ and $R^7$ are both $C_{1-6}$alkyl groups these groups may be joined, together with the N atom to which they are attached, to form a heterocyclic ring. Such heterocyclic rings may be optionally interrupted by a further heteroatom selected from —O—, —S— or —N($R^5$)—. Particular examples of such heterocyclic rings include piperidinyl, morpholinyl, thiomorpholinyl, pyrrolidinyl, imidazolidinyl and piperazinyl rings.

When $Alk^2$ is present as an optionally substituted aliphatic or heteroaliphatic chain it may be any optionally substituted aliphatic or heteroaliphatic chain as described hereinafter for $Alk^1$.

Halogen atoms represented by $R^4$ in the optional $Ar^1$ substituents include fluorine, chlorine, bromine, or iodine atoms.

Examples of the substituents represented by -$L^3$($Alk^1$)$_t$$L^4$($R^4$)$_u$ when present in $Ar^1$ groups in compounds of the invention include atoms or groups -$L^3$$Alk^2$$L^4$$R^4$, -$L^3$$Alk^2$$R^4$, -$L^3$$R^4$, —$R^4$ and -$Alk^2$$R^4$ wherein $L^3$, $Alk^2$, $L^4$ and $R^4$ are as defined above. Particular examples of such substituents include -$L^3$CH$_2$$L^4$$R^4$, -$L^3$CH(CH$_3$)$L^4$$R^4$, -$L^3$(CH$_2$)$_2$$L^4$$R^4$, -$L^3$CH$_2$$R^4$, -$L^3$CH(CH$_3$)$R^4$, -$L^3$(CH$_2$)$_2$$R^4$, —CH$_2$$R^4$, —CH(CH$_3$)$R^4$, —(CH$_2$)$_2$$R^4$ and —$R^4$ groups.

Thus $Ar^1$ in compounds of the invention may be optionally substituted for example by one, two, three or more halogen atoms, e.g. fluorine, chlorine, bromine or iodine atoms, and/or $C_{1-6}$alkyl, e.g. methyl, ethyl, n-propyl, i-propyl, n-butyl or t-butyl, $C_{3-8}$cycloalkyl, e.g. cyclopropyl, cyclobutyl, cyclopentyl or cyclohexyl, $C_{1-6}$hydroxyalkyl, e.g. hydroxymethyl, hydroxyethyl or —C(OH)(CF$_3$)$_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. —CF$_3$, —CHF$_2$, —CH$_2$F, halo$C_{1-6}$alkoxy, e.g. —OCF$_3$, —OCHF$_2$, —OCH$_2$F, $C_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy or dimethylaminopropoxy, nitro, cyano, amidino, hydroxyl (—OH), formyl [HC(O)—], carboxyl (—CO$_2$H), —CO$_2$$R^5$ e.g. —CO$_2$CH$_3$ or —CO$_2$C(CH$_3$)$_3$, $C_{1-6}$alkanoyl e.g. acetyl, thiol (—SH), thio$C_{1-6}$alkyl, e.g. thiomethyl or thioethyl, sulphonyl (—SO$_3$H), —SO$_3$$R^5$, $C_{1-6}$alkylsulphinyl, e.g. methylsulphinyl, $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$alkylamino$C_{1-6}$alkylaminocarbonyl, e.g. ethylaminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocarbonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino groups.

$L^2$ when present as part of the group $R^1$ in compounds of the invention may be a linker atom or group $L^{2a}$ or a linker -($Alk^3$)$_r$$L^{2a}$-, where $Alk^3$ is an optionally substituted aliphatic or heteroaliphatic chain which may be any such chain as described hereinafter for $Alk^1$, and $L^{2a}$ may be any linker atom or group as described hereinbefore for $L^3$.

Optionally substituted arylene groups represented by $Ar^2$ when present as part of the group $R^1$ include those aromatic groups as previously described for $Ar^1$.

Optionally substituted heteroarylene groups represented by $Ar^2$ when present as part of the group $R^1$ include those heteroaromatic groups as previously described for $Ar^1$.

Each divalent arylene or heteroarylene group represented by $Ar^2$ may be attached to the remainder of the molecule through any available ring carbon or nitrogen atoms.

The arylene and heteroarylene groups represented by $Ar^2$ may be optionally substituted by one, two or more substituents selected from the atoms or groups -$L^3$($Alk^2$)$_t$$L^4$($R^4$)$_u$ described herein. Where two of these atoms or groups are present they may be the same or different.

When the group $R^2$ is present in compounds of the invention as a $C_{1-6}$alkyl group it may be for example a straight or branched $C_{1-6}$alkyl group e.g. a $C_{1-3}$alkyl group such as a methyl or ethyl group.

When the group R is present in $R^1$ in compounds of the invention as a derivative of a carboxylic acid it may be for example an acyclic or cyclic carboxylic acid ester or an amide. Particular acyclic esters and amides include —$CO_2Alk^7$ and —$CONR^5R^6$ groups as defined herein. When R is a biostere of a carboxylic acid it may be for example a tetrazole or other acid such as phosphonic acid, phosphinic acid, sulphonic acid, sulphinic acid or boronic acid or an acylsulphonamide group.

Esters (—$CO_2Alk^7$) and amide (—$CONR^5R^6$) derivatives of the carboxylic acid group (—$CO_2H$) in compounds of formula (1) may advantageously be used as prodrugs of the active compound. Such prodrugs are compounds which undergo biotransformation to the corresponding carboxylic acid prior to exhibiting their pharmacological effects and the invention particularly extends to prodrugs of the acids of formula (1). Such prodrugs are well known in the art, see for example International Patent Application No. WO00/23419, Bodor, N. (Alfred Benzon Symposium, 1982, 17, 156-177), Singh, G. et al (J. Sci. Ind. Res., 1996, 55, 497-510) and Bundgaard, H., (Design of Prodrugs, 1985, Elsevier, Amsterdam).

Esterified carboxyl groups represented by the group —$CO_2Alk^7$ include groups wherein $Alk^7$ is a straight or branched optionally substituted $C_{1-8}$alkyl group such as a methyl, ethyl, n-propyl, i-propyl, n-butyl, i-butyl, s-butyl, t-butyl, pentyl or neopentyl group; an optionally substituted $C_{2-8}$alkenyl group such as a propenyl e.g. 2-propenyl or butenyl e.g. 2-butenyl or 3-butenyl group, an optionally substituted $C_{2-8}$alkynyl group such as a ethynyl, propynyl e.g. 2-propynyl or butynyl e.g. 2-butynyl or 3-butynyl group, an optionally substituted $C_{3-8}$cycloalkyl group such as a cyclopropyl, cyclobutyl, cyclopentyl, cyclohexyl or cycloheptyl group; an optionally substituted $C_{3-8}$heterocycloalkyl group such as a tetrahydrofuanyl e.g. tetrahydrofuran-3-yl, pyrrolidinyl e.g. 1-methylpyrrolidinyl such as 1-methylpyrrolidin-3-yl, piperidinyl e.g. 1-methylpiperidinyl such as 1-methylpiperidin-4-yl, tetrahydropyranyl e.g. tetrahydropyran-4-yl or 2-oxo-[1,3]dioxol-4-yl e.g. 5-methyl-2-oxo-[1,3]dioxol-4-yl group; an optionally substituted $C_{3-8}$cycloalkyl$C_{1-6}$alkyl group such as a cyclopentylmethyl, cyclohexylmethyl or cyclohexylethyl group; an optionally substituted $C_{3-8}$heterocycloalkyl$C_{1-8}$alkyl group such as a morpholinyl-N-ethyl, thiomorpholinyl-N-methyl, pyrrolidinyl-N-ethyl, pyrrolidinyl-N-propyl, piperidinyl-N-ethyl, pyrazolidinyl-N-methyl or piperazinyl-N-ethyl group; an optionally substituted $C_{1-6}$alkyloxy$C_{1-6}$alkyl group such as a methyloxyethyl or propyloxyethyl group; an optionally substituted hydroxy$C_{1-6}$alkyl group such as a hydroxyethyl e.g. 2-hydroxyethyl or hydroxypropyl e.g. 2-hydroxypropyl, 3-hydroxypropyl or 2,3-dihydroxypropyl group; an optionally substituted $C_{1-6}$alkylthio$C_{1-6}$alkyl group such as an ethylthioethyl group; an optionally substituted $C_{1-6}$alkylsulfinyl$C_{1-6}$alkyl group such as an methylsulfinylethyl group; an optionally substituted $C_{1-6}$alkylsulfonyl$C_{1-6}$alkyl group such as an methylsulfonylmethyl group; an optionally substituted $C_{3-8}$cycloalkyloxy$C_{1-6}$alkyl group such as a cyclohexyloxymethyl group; an optionally substituted $C_{3-8}$cycloalkylthio$C_{1-6}$alkyl group such as a cyclopentylthiomethyl group; an optionally substituted $C_{3-8}$cycloalkylsulfinyl$C_{1-6}$alkyl group such as a cyclo pentyl-sulfinylmethyl group; an optionally substituted $C_{3-8}$cycloalkylsulfonyl$C_{1-16}$alkyl group such as a cyclopentylsulfonylmethyl group; an optionally substituted $C_{1-6}$alkyloxycarbonyl$C_{1-6}$alkyl group such as isobutoxy-carbonylpropyl group; an optionally substituted $C_{1-6}$alkyloxycarbonyl $C_{1-6}$alkenyl group such as isobutoxycarbonylpentenyl group; an optionally substituted $C_{1-6}$alkyloxycarbonyloxy$C_{1-6}$alkyl group such as an ethyloxycarbonyloxymethyl or isopropoxycarbonyloxyethyl e.g 1-(isopropoxycarbonyloxy)ethyl or 2-(isopropoxycarbonyloxy)ethyl group; an optionally substituted $C_{1-6}$alkyloxycarbonyloxy$C_{1-6}$alkenyl group such as a isopropoxycarbonyloxybutenyl group, an optionally substituted $C_{3-8}$cycloalkyloxycarbonyloxy$C_{1-6}$alkyl group such as a cyclohexyloxycarbonyloxyethyl, e.g. a 2-(cyclohexyloxycarbonyloxy)ethyl group, an optionally substituted N-di-$C_{1-8}$alkylamino$C_{1-8}$alkyl group such as a N-dimethylaminoethyl or N-diethylaminoethyl group; an optionally substituted N—$C_{6-12}$aryl-N—$C_{1-6}$alkylamino$C_{1-6}$alkyl group such as a N-phenyl-N-methylaminomethyl group; an optionally substituted N-di-$C_{1-8}$alkyl-carbamoyl$C_{1-8}$alkyl group such as a N-diethylcarbamoylmethyl group; an optionally substituted $C_{6-12}$aryl$C_{1-6}$alkyl group such as an optionally substituted benzyl, phenylethyl, phenylpropyl, 1-naphthylmethyl or 2-naphthylmethyl group; an optionally substituted hetero$C_{6-10}$aryl$C_{1-6}$alkyl group, such as a pyridinylmethyl e.g. pyridin-4-ylmethyl or imidazolylethyl e.g. 2-imidazol-1-ylethyl group; a $C_{6-12}$aryl group such as an optionally substituted phenyl, 1-naphthyl or 2-naphthyl group; a $C_{6-12}$aryloxy$C_{6-8}$alkyl group such as an optionally substituted phenyloxymethyl, phenyloxyethyl, 1-naphthyloxymethyl, or 2-naphthyloxymethyl group; a $C_{6-12}$arylthio$C_{1-8}$alkyl group such as an optionally substituted phenylthioethyl group; a $C_{6-12}$arylsulfinyl$C_{1-8}$alkyl group such as an optionally substituted phenyl-sulfinylmethyl group; a $C_{6-12}$arylsulfonyl$C_{1-8}$alkyl group such as an optionally substituted phenylsulfonylmethyl group; an optionally substituted $C_{1-8}$alkanoyloxy$C_{1-8}$alkyl group, such as a acetoxymethyl, ethoxycarbonyloxyethyl, pivaloyloxymethyl, propionyloxyethyl or propionyloxypropyl group; an optionally substituted $C_{4-8}$imido$C_{1-8}$alkyl group such as a succinimidomethyl or phthalamidoethyl group; a $C_{6-12}$aroyloxy$C_{1-8}$alkyl group such as an optionally substituted benzoyloxyethyl or benzoyloxypropyl group or a triglyceride such as a 2-substituted triglyceride e.g. a 1,3-di-$C_{1-8}$alkylglycerol-2-yl group such as a 1,3-diheptylglycerol-2-yl group. Optional substituents present on the $Alk^7$ group include $R^{13a}$ substituents described below.

It will be appreciated that in the forgoing list of $Alk^7$ groups the point of attachment to the remainder of the compound of formula (1) is via the last described part of the $Alk^7$ group. Thus, for example a methoxyethyl group would be attached by the ethyl group, whilst a morpholinyl-N-ethyl group would be attached via the N-ethyl group.

It will be further appreciated that in the forgoing list of $Alk^7$ groups, where not specifically mentioned, alkyl groups may be replaced by alkenyl or alkynyl groups where such groups are as previously defined for $Alk^1$. Additionally these alkyl, alkenyl or alkynyl groups may optionally be interrupted by one, two or three linker atoms or groups where such linker atoms and groups are as previously defined for $L^3$.

Further prodrugs of compounds of formula (1) include cyclic esters where X is a —$N(R^2)$— group in which $R^2$ becomes a $C_{1-6}$alkyl joining chain, especially a —$CH_2$— or —CH$_2$CH$_2$— chain, which is also connected to the acid group R to form a cyclic ester of formula (1a):

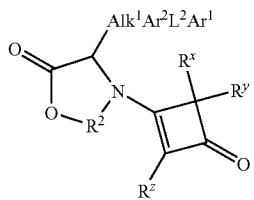

(1a)

When present in the group R$^x$, R$^y$ and/or R$^z$ in compounds of formula (1) the linker atom or group represented by L$^1$ may be any linker atom or group as described above for the linker atom or group L$^3$. In addition L$^1$ may also be a —Se— atom.

When Alk$^1$ is present in the group R$^x$, R$^y$ and/or R$^z$ in compounds of formula (1) as an optionally substituted aliphatic chain it may be an optionally substituted C$_{1-10}$aliphatic chain. Particular examples include optionally substituted straight or branched chain C$_{1-6}$alkylene, C$_{2-6}$alkenylene or C$_{2-6}$alkynylene chains.

Particular examples of aliphatic chains represented by Alk$^1$ include optionally substituted —CH$_2$—, —(CH$_2$)$_2$—, —CH(CH$_3$)CH$_2$—, —(CH$_2$)$_2$CH$_2$—, —(CH$_2$)$_3$CH$_2$—, —CH(CH$_3$)(CH$_2$)$_2$—, —CH$_2$CH(CH$_3$)CH$_2$—, —C(CH$_3$)$_2$CH$_2$—, —CH$_2$C(CH$_3$)$_2$CH$_2$—, —(CH$_2$)$_2$C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$— or —(CH$_2$)$_2$CC— chains.

Heteroaliphatic chains represented by Alk$^1$ when present in the group R$^x$, R$^y$ and/or R$^z$ in compounds of formula (1) include the aliphatic chains just described for Alk$^1$ but with each additionally containing one, two, three or four heteroatoms or heteroatom-containing groups. Particular hetero-atoms or groups include atoms or groups L$^5$ where L$^5$ is as defined above for L$^3$ when L$^3$ is a linker atom or group. Each L$^5$ atom or group may interrupt the aliphatic chain, or may be positioned at its terminal carbon atom to connect the chain to an adjoining atom or group. Particular examples include optionally substituted —CH$_2$L$^5$-, —CH$_2$CH$_2$L$^5$-, -L$^5$CH$_2$—, -L$^5$CH$_2$CH$_2$—, -L$^5$CH(CH$_3$)CH$_2$—, -L$^5$CH$_2$CH(CH$_3$)CH$_2$—, L$^5$CH$_2$CH$_2$CH(CH$_3$)—, -L$^5$C(CH$_3$)$_2$CH$_2$—, —CH$_2$L$^5$CH$_2$CH$_2$—, —(CH$_2$)$_2$L$^5$CH$_2$—, —(CH$_2$)$_3$L$^5$CH$_2$—, -L$^5$(CH$_2$)$_3$—, -L$^5$(CH$_2$)$_4$—, —CH$_2$L$^5$CH$_2$CHL$^5$CH$_2$— and —(CH$_2$)$_2$L$^5$CH$_2$CH$_2$— chains.

The optional substituents which may be present on aliphatic or heteroaliphatic chains represented by Alk$^1$ include one, two, three or more substituents where each substituent may be the same or different and is selected from halogen atoms, e.g. fluorine, chlorine, bromine or iodine atoms, or —OH, —CO$_2$H, —CO$_2$R$^9$, where R$^9$ is an optionally substituted straight or branched C$_{1-6}$alkyl group as defined above for R$^4$, —CONHR$^9$, —CON(R$^9$)$_2$, —COR$^9$, e.g. —COCH$_3$, C$_{1-6}$alkoxy, e.g. methoxy or ethoxy, thiol, —S(O)R$^9$, —S(O)$_2$R$^9$, C$_{1-6}$alkylthio e.g. methylthio or ethylthio, amino or substituted amino groups. Substituted amino groups include —NHR$^9$ and —N(R$^9$)$_2$ groups. Where two R$^9$ groups are present in any of the above substituents these may be the same or different.

Optionally substituted cycloaliphatic groups represented by the group R$^3$ when present in the group R$^x$, R$^y$ and/or R$^z$ in compounds of the invention include optionally substituted C$_{3-10}$cycloaliphatic groups. Particular examples include optionally substituted C$_{3-10}$cycloalkyl, e.g. C$_{3-8}$cycloalkyl or C$_{3-10}$cycloalkenyl, e.g C$_{3-8}$cycloalkenyl groups.

Optionally substituted heterocycloaliphatic groups represented by the group R$^3$ when present in the group R$^x$, R$^y$ and/or R$^z$ include optionally substituted C$_{3-10}$heterocycloaliphatic groups. Particular examples include optionally substituted C$_{3-10}$heterocycloalkyl, e.g. C$_{3-7}$heterocycloalkyl, or C$_{3-10}$heterocycloalkenyl, e.g. C$_{3-7}$heterocycloalkenyl groups, each of said groups containing one, two, three or four heteroatoms or heteroatom-containing groups L$^5$ as defined above.

Optionally substituted polycycloaliphatic groups represented by the group R$^3$ when present in the group R$^x$, R$^y$ and/or R$^z$ include optionally substituted C$_{7-10}$ bi- or tricycloalkyl or C$_{7-10}$bi- or tricycloalkenyl groups. Optionally substituted heteropolycycloaliphatic groups represented by the group R$^3$ include the optionally substituted polycycloaliphatic groups just described, but with each group additionally containing one, two, three or four L$^5$ atoms or groups.

Particular examples of cycloaliphatic, polycycloaliphatic, heterocycloaliphatic and heteropolycycloaliphatic groups represented by the group R$^3$ include optionally substituted cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl, 2-cyclobuten-1-yl, 2-cyclopenten-1-yl, 3-cyclopenten-1-yl, adamantyl, norbornyl, norbornenyl, tetrahydrofuranyl, tetrahydrothiophenyl, tetrahydrothiophene-1-oxide, tetrahydrothiophene-1,1-dioxide, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, tetrahydropyranyl, tetrahydrothiopyranyl, tetrahydrothiopyran-1-oxide, tetrahydrothiopyran-1,1-dioxide, piperidinyl, piperidinone, dioxanyl e.g. 1,3-dioxanyl or 1,4-dioxanyl, morpholinyl, morpholinone, dithianyl, e.g. 1,3-dithianyl or 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2, 5 or 1,2,6-oxathiazinyl, or 1,3,5,-oxadiazinyl groups.

The optional substituents which may be present on the cycloaliphatic, polycycloaliphatic, heterocycloaliphatic or heteropolycycloaliphatic groups represented by the group R$^3$ include one, two, three or more substituents each selected from halogen atoms, e.g. fluorine, chlorine, bromine or iodine atoms, or C$_{1-6}$alkyl, e.g. methyl, ethyl, propyl or i-propyl, haloC$_{1-6}$alkyl, e.g. halomethyl or haloethyl such as difluoromethyl or trifluoromethyl, optionally substituted by hydroxyl, e.g. —C(OH)(CF$_3$)$_2$, C$_{1-6}$alkoxy, e.g. methoxy, ethoxy or propoxy, haloC$_{1-6}$alkoxy, e.g. halomethoxy or haloethoxy such as difluoromethoxy or trifluoromethoxy, thiol, C$_{1-6}$alkylthio e.g. methylthio, ethylthio or propylthio, or -(Alk$^4$)$_g$R$^{10}$ groups in which Alk$^4$ is a straight or branched C$_{1-3}$alkylene chain, g is zero or an integer 1 and R$^{10}$ is a —OH, —SH, —N(R$^{11}$)$_2$, (in which R$^{11}$ is an atom or group as defined herein for R$^7$)—CN, —CO$_2$R$^{11}$, —NO$_2$, —CON(R$^{11}$)$_2$, —CSN(R$^{11}$)$_2$, —COR$^{11}$, —CSN(R$^{11}$)$_2$, —N(R$^{11}$)COR$^{11}$, —N(R$^{11}$)CSR$^{11}$, —SO$_2$N(R$^{11}$)$_2$, —N(R$^{11}$)SO$_2$R$^{11}$, —N(R$^{11}$)CON(R$^{11}$)$_2$, —N(R$^{11}$)CSN(R$^{11}$), N(R$^{11}$)SO$_2$N(R$^{11}$)$_2$ or optionally substituted phenyl group, Where two R$^{11}$ atoms or groups are present in these substituents these may be the same or different or joined to form a heterocyclic ring as previously described when R$^5$ and R$^6$ are joined together.

Optionally substituted phenyl groups include phenyl substituted by one, two or three of the $R^{13}$ groups described below.

Additionally, when the group $R^3$ is a heterocycloaliphatic group containing one or more nitrogen atoms each nitrogen atom may be optionally substituted by a group $-(L^6)_p(Alk^5)_q R^{12}$ in which $L^6$ is $-C(O)-$, $-C(O)O-$, $-C(S)-$, $-S(O)_2-$, $-CON(R^8)-$, $-CSN(R^8)-$ or $SO_2N(R^8)-$; p is zero or an integer 1; $Alk^5$ is an optionally substituted aliphatic or heteroaliphatic chain; q is zero or an integer 1; and $R^{12}$ is a hydrogen atom or an optionally substituted cycloaliphatic, heterocycloaliphatic, polycycloaliphatic, polyheterocycloaliphatic, aromatic or heteroaromatic group.

$C_{1-3}$alkylene chains represented by $Alk^4$ include $-CH_2-$, $-CH_2CH_2-$, $-CH_2CH_2CH_2-$, $-CH(CH_3)CH_2-$ and $-CH_2CH(CH_3)-$ chains.

Optionally substituted aliphatic or heteroaliphatic chains represented by $Alk^5$ include those optionally substituted chains described above for $Alk^1$. Optional substituents which may be present on these groups include those described above in relation to $Alk^1$.

Cycloaliphatic, heterocycloaliphatic, polycycloaliphatic or polyheterocycloaliphatic groups represented by $R^{12}$ include those groups just described for the group $R^3$. Optional substituents which may be present on those groups include those described above in relation to $R^3$ cycloaliphatic groups.

Aromatic or heteroaromatic groups represented by $R^{12}$ include those groups described herein for the group $Ar^1$. Optional substituents which may be present on these groups include those $R^{13}$ optional substituents described hereinafter.

When the group $R^3$ is an optionally substituted aromatic or heteroaromatic group it may be for example an aromatic or heteroaromatic group as described herein for the group $Ar^1$.

Optional substituents which may be present on the aromatic or heteroaromatic groups represented by the group $R^3$ include one, two, three or more substituents, each selected from an atom or group $R^{13}$ in which $R^{13}$ is $-R^{13a}$ or $-Alk^6(R^{13a})_m$, where $R^{13a}$ is a halogen atom, or an amino ($-NH_2$), substituted amino, nitro, cyano, amidino, hydroxyl ($-OH$), substituted hydroxyl, formyl, carboxyl ($-CO_2H$), esterified carboxyl, thiol ($-SH$), substituted thiol, $-COR^{14}$ [where $R^{14}$ is an $-Alk^6(R^{13a})_m$, aryl or heteroaryl group], $-CSR^{14}$, $-SO_3H$, $-SOR^{14}$, $-SO_2R^{14}$, $-SO_3R^{14}$, $-SO_2NH_2$, $-SO_2NHR^{14}$, $SO_2N(R^{14})_2$, $-CONH_2$, $-CSNH_2$, $-CONHR^{14}$, $-CSNHR^{14}$, $-CON[R^{14}]_2$, $-CSN(R^{14})_2$, $-N(R^{11})SO_2R^{14}$, $-N(SO_2R^{14})_2$, $-NH(R^{11})SO_2NH_2$, $-N(R^{11})SO_2NHR^{14}$, $-N(R^{11})SO_2N(R^{14})_2$, $-N(R^{11})COR^{14}$, $-N(R^{11})CONH_2$, $-N(R^{11})CONHR^{14}$, $-N(R^{11})CON(R^{14})_2$, $-N(R^{11})CSNH_2$, $-N(R^{11})CSNHR^{14}$, $-N(R^{11})CSN(R^{14})_2$, $-N(R^{11})CSR^{14}$, $-N(R^{11})C(O)OR^{14}$, $-SO_2NHet^1$ [where $-NHet^1$ is an optionally substituted $C_{5-7}$cyclicamino group optionally containing one or more other $-O-$ or $-S-$ atoms or $-N(R^{11})-$, $-C(O)-$, $-C(S)-$, $S(O)$ or $-S(O)_2$ groups], $-CONHet^1$, $-CSNHet^1$, $-N(R^{11})SO_2NHet^1$, $-N(R^{11})CONHet^1$, $-N(R^{11})CSNHet^1$, $-SO_2N(R^{11})Het^2$ [where $Het^2$ is an optionally substituted monocyclic $C_{5-7}$carbocyclic group optionally containing one or more $-O-$ or $-S-$ atoms or $-N(R^{11})-$, $-C(O)-$ or $-C(S)-$ groups], $-Het^2$, $-CON(R^{11})Het^2$, $-CSN(R^{11})Het^2$, $-N(R^{11})CON(R^{11})Het^2$, $-N(R^{11})CSN(R^{11})Het^2$, aryl or heteroaryl group; $Alk^6$ is a straight or branched $C_{1-6}$alkylene, $C_{2-6}$alkenylene or $C_{2-6}$alkynylene chain, optionally interrupted by one, two or three $-O-$ or $-S-$atoms or $-S(O)_n$ [where n is an integer 1 or 2] or $-N(R^{15})-$ groups [where $R^{15}$ is a hydrogen atom or $C_{1-6}$alkyl, e.g. methyl or ethyl group]; and m is zero or an integer 1, 2 or 3. It will be appreciated that when two $R^{11}$ or $R^{14}$ groups are present in one of the above substituents, the $R^{11}$ or $R^{14}$ groups may be the same or different.

When in the group $-Alk^6(R^{13a})_m$ m is an integer 1, 2 or 3, it is to be understood that the substituent or substituents $R^{13a}$ may be present on any suitable carbon atom in $-Alk^6$. Where more than one $R^{13a}$ substituent is present these may be the same or different and may be present on the same or different atom in $-Alk^6$. Clearly, when m is zero and no substituent $R^{13a}$ is present the alkylene, alkenylene or alkynylene chain represented by $Alk^6$ becomes an alkyl, alkenyl or alkynyl group.

When $R^{13a}$ is a substituted amino group it may be for example a group $-NHR^{14}$ [where $R^{14}$ is as defined above] or a group $-N(R^{14})_2$ wherein each $R^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group $-OR^{14}$ or a $-SR^{14}$ or $-SC(=NH)NH_2$ group respectively.

Esterified carboxyl groups represented by the group $R^{13a}$ include groups of formula $-CO_2Alk^8$ wherein $Alk^8$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxy-propyl group. Optional substituents present on the $Alk^8$ group include $R^{13a}$ substituents described above.

When $Alk^6$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three $-O-$ or $-S-$, atoms or $-S(O)-$, $-S(O)_2-$ or $-N(R^8)-$ groups.

Aryl or heteroaryl groups represented by the groups $R^{13a}$ or $R^{14}$ include mono- or bicyclic optionally substituted $C_{6-12}$aromatic or $C_{1-9}$hetero-aromatic groups as described above for the group $Ar^1$. The aromatic and heteroaromatic groups may be attached to the remainder of the compound of formula (1) by any carbon or hetero e.g. nitrogen atom as appropriate.

When $-NHet^1$ or $-Het^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally $Het^2$ may represent for example, an optionally substituted cyclopentyl or cyclohexyl group. Optional substituents which may be present on $-NHet^1$ or $-Het^2$ include those optional substituents described above in relation to aliphatic chains represented by $Alk^1$.

Particularly useful atoms or groups represented by $R^{13}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, $C_{1-6}$hydroxyalkyl, e.g.

hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{4-7}$cycloalkyl, e.g. cyclobutyl, cyclopentyl, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino, ethylamino or propylamino, $C_{6-12}$aryl$C_{1-6}$alkylamino, e.g. benzylamino, 4-fluorobenzylamino or 4-hydroxyphenylethylamino, amino (—NH$_2$), amino$C_{1-6}$alkyl, e.g. aminomethyl or aminoethyl, $C_{1-6}$dialkylamino, e.g. dimethylamino or diethylamino, amino$C_{1-6}$alkylamino, e.g. aminoethylamino or aminopropylamino, optionally substituted Het$^1$N$C_{1-6}$alkylamino, e.g. 3-morpholinopropylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, hydroxy$C_{1-6}$alkylamino, e.g. 2-hydroxyethylamino, 3-hydroxypropylamino or 3-hydroxybutylamino, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^8$ [where Alk$^8$ is as defined above], $C_{1-6}$alkanoyl e.g. acetyl, propyryl or butyryl, optionally substituted benzoyl, thiol (—SH), thio$C_{1-6}$alkyl, e.g. thiomethyl or thioethyl, —SC(=NH)NH$_2$, sulphonyl (—SO$_3$H), —SO$_3$Alk$^8$, $C_{1-6}$alkylsulphinyl, e.g. methylsulphinyl, ethylsulphinyl or propylsulphinyl, $C_{1-6}$alkylsulphonyl, e.g. methylsulphonyl, ethylsulphonyl or propylsulphonyl, aminosulphonyl (—SO$_2$NH$_2$), $C_{1-6}$alkylaminosulphonyl, e.g. methylaminosulphonyl, ethylaminosulphonyl or propylaminosulphonyl $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl, ethylaminocarbonyl or propylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$alkylamino$C_{1-6}$alkylaminocarbonyl, e.g. methylaminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)NH$_2$, $C_{1-6}$alkylsulphonylamino, e.g. methylsulphonylamino or ethylsulphonylamino, halo$C_{1-6}$alkylsulphonylamino, e.g. trifluoromethylsulphonylamino, $C_{1-6}$dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonyl amino or diethylamino-sulphonylamino, optionally substituted morpholinesulphonylamino or morpholinesulphonyl$C_{1-6}$ alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$ alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, thiobenzyl, pyridylmethylthio or thiazolylmethylthio groups.

Where desired, two $R^{13}$ substituents may be linked together to form a cyclic group such as a cyclic ether, e.g. a $C_{1-6}$alkylenedioxy group such as methylenedioxy or ethylenedioxy.

It will be appreciated that where two or more $R^{13}$ substituents are present, these need not necessarily be the same atoms and/or groups. In general, the substituent(s) may be present at any available ring position in the aromatic or heteroaromatic group represented by $R^3$.

When the groups $R^x$ and $R^y$ are joined together to form an optionally substituted spiro linked cycloaliphatic or heterocycloaliphatic group joined to the cyclobutenone ring as defined by formula (1) it may be any such cycloaliphatic or heterocycloaliphatic group as previously described for $R^3$. Optional substituents which may be present on such spiro linked cycloaliphatic or heteroaliphatic groups include those optional substituents as described in relation to $R^3$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharma-ceutically acceptable salts.

In the compounds according to the invention the group $R^1$ is preferably an $Ar^1L^2Ar^2Alk$- group. In compounds of this type $Ar^1$ is preferably an optionally substituted phenyl, monocyclic heteroaromatic or bicyclic heteroaromatic group. Particularly useful monocyclic heteroaromatic groups are optionally substituted five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. Particularly useful substituents present on these monocyclic $Ar^1$ groups include halogen atoms or alkyl, haloalkyl, —OR$^5$, —SR$^5$, —NR$^5$R$^6$, —CO$_2$H, —CO$_2$CH$_3$, —NO$_2$, —N(R$^5$)COR$^6$ or —CN groups as described above in relation to the compounds of formula (1). Particularly useful bicyclic heteroaromatic groups represented by $Ar^1$ include optionally substituted tenmembered fused-ring heteroaromatic groups containing one, two or three, especially one or two heteroatoms, especially nitrogen atoms. Particular examples include optionally substituted naphthyridinyl, especially 2,6-naphthyridinyl, 2,7-naphthyridinyl, quinolinyl and isoquinolinyl, especially isoquinolin-1-yl groups. Particular optional substituents include those just described for monocyclic heteroaromatic groups. Additionally, in compounds according to the invention X is preferably an —N($R^2$)— group and V is preferably an oxygen atom.

A particularly useful group of compounds according to the invention has the formula (2a):

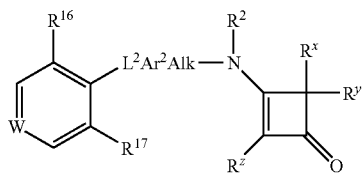

(2a)

wherein —W= is —$CR^{18}$=, —N= or —N(O)=;
$R^{16}$, $R^{17}$ and $R^{18}$, which may be the same or different is each a hydrogen atom or an atom or group -$L^3(Alk^2)_tL^4(R^4)_u$ in which $L^3$, $Alk^2$, t, $L^4$, $R^4$ and u are as defined previously;
$L^2$, $Ar^2$, Alk, $R^2$, $R^x$, $R^y$ and $R^z$ are as defined for formula (1);

and the salts, solvates, hydrates and N-oxides thereof.

In one preferred class of compounds of formula (2a) where W is a —$CR^{18}$= group $R^{18}$ is a hydrogen atom. In another preferred class of compounds $R^{18}$ is a preferred atom or group as hereinafter defined for $R^{16}$, especially a $C_{1-6}$alkoxy, especially a methoxy or ethoxy, group.

In another preferred class of compounds of formula (2a) W is a —N= or —N(O)=group.

$R^{16}$ and $R^{17}$ in compounds of formula (2a) is each preferably as particularly described above for compounds of formula (1), other than a hydrogen atom. Particularly useful $R^{16}$ and $R^{17}$ substituents include halogen atoms, especially fluorine or chlorine atoms, or $C_{1-6}$alkyl, especially methyl, ethyl or isopropyl, halo$C_{1-6}$alkyl especially halomethyl, most especially —$CF_3$, —$CHF_2$ or —$CH_2F$, $C_{1-6}$alkoxy especially methoxy or etoxy or halo$C_{1-6}$alkoxy especially halomethoxy, most especially —$OCF_3$, —$OCHF_2$ or —$OCH_2F$ groups.

A further particularly useful group of compounds according to the invention has the formula (2b):

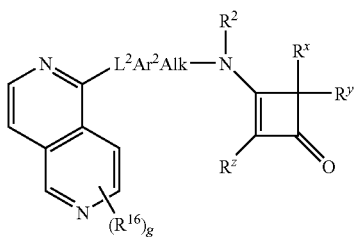

(2b)

wherein g is the integer 1, 2, 3 or 4;
$R^{16}$, is an atom or group -$L^3(Alk^2)_tL^4(R^4)_u$ in which $L^3$, $Alk^2$, t, $L^4$, $R^4$ and u are as defined previously;
$L^2$, $Ar^2$, Alk, $R^2$, $R^x$, $R^y$ and $R^7$ are as defined for formula (1);

and the salts, solvates, hydrates and N-oxides thereof.

Particularly useful $R^{16}$ substituents when present in compounds of formula (2b) include halogen atoms, especially fluorine, chlorine or bromine atoms, or $C_{1-6}$alkyl e.g. methyl, ethyl or isopropyl, halo$C_{1-6}$alkyl, especially halomethyl, most especially —$CF_3$, $C_{1-6}$alkoxyl, especially methoxy, halo$C_{1-6}$alkoxy, especially halomethoxy, most especially —$OCF_3$, —CN, —$CO_2CH_3$, —$NO_2$, amino (—$NH_2$), substituted amino (—$NR^5R^6$) especially —$NHCH_3$ and —$N(CH_3)_2$, —$N(R^5)COCH_3$, especially —$NHCOCH_3$ groups or optionally substituted phenyl, furyl, thienyl, imidazolyl, pyridyl and pyrimidinyl groups.

A further particularly useful group of compounds according to the invention has the formula (2c):

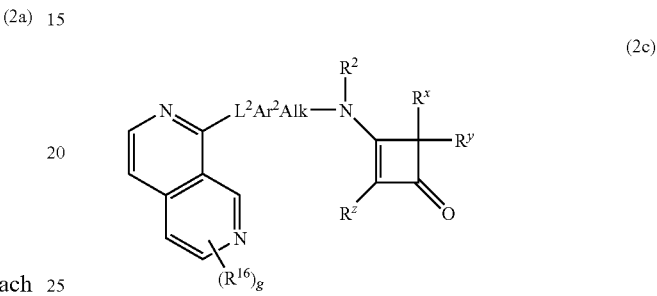

(2c)

wherein $R^{16}$, g, $L^2$, $Ar^2$, Alk, $R^2$, $R^x$, $R^y$ and $R^z$ are as defined for formula (2b);

and the salts, solvates, hydrates and N-oxides thereof.

Each $R^{16}$ atom or group in compounds of formula (2c) may be independently selected from an atom or group -$L^3(Alk^2)_n$ $L^4(R^4)_u$ as previously particularly defined for compounds of formula (2b).

A further particularly useful group of compounds according to the invention has the formula (2d):

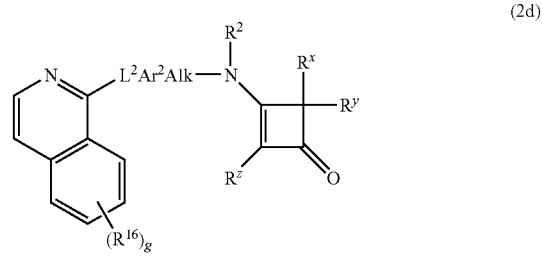

(2d)

wherein $R^{16}$, g, $L^2$, $Ar^2$, Alk, $R^2$, $R^x$, $R^y$ and $R^z$ are as defined for formula (2b):

and the salts, solvates, hydrates and N-oxides thereof.

Each $R^{16}$ atom or group in compounds of formula (2d) may be independently selected from an atom or group -$L^3(Alk^2)_t$ $L^4(R^4)_u$ as previously defined for compounds of formula (2b).

In one preferred class of compounds of formula (2d) at least one $R^{16}$ atom or group is present at the 3-position of the isoquinoline ring. In a preferred group of compounds of this class $R^{16}$ is an optionally substituted phenyl ring. Optional substituents which may be present on the phenyl ring include halogen atoms, especially fluorine or chlorine atoms, or $C_{1-6}$alkyl, especially methyl, ethyl or isopropyl, halo$C_{1-6}$ alkyl especially halomethyl, most especially —$CF_3$, —$CHF_2$ or —$CH_2F$, $C_{1-6}$alkoxy especially methoxy or etoxy or haloC$_{1-6}$alkoxy especially halomethoxy, most especially —OCF$_3$, —OCHF$_2$ or —OCH$_2$F groups.

It will be understood that compounds according to formulae (2a), (2b), (2c) and (2d) include, where applicable, the corresponding hydroxy tautomers.

Alk in compounds of the invention is preferably:

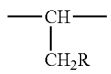

or, especially, —CH$_2$CH(R)—.

In one preferred class of compounds of formulae (1), (2a), (2b), (2c) and (2d) R is a —CO$_2$H group.

In another preferred class of compounds of formulae formulae (1), (2a), (2b), (2c) and (2d) R is an esterified carboxyl group of formula —CO$_2$Alk$^7$ which may advantageously be used as a prodrug of the active compound. In this class of compound Alk$^7$ is preferably a C$_{1-8}$alkyl group, especially a methyl, ethyl, propyl, i-propyl, butyl, t-butyl, pentyl or neopenyl group; an optionally substituted C$_{3-8}$cycloalkyl group, especially a cyclopropyl, cyclobutyl, cyclopentyl, cyclohexyl or cycloheptyl group; an optionally substituted C$_{3-8}$heterocycloalkyl group especially a tetrahydrofuanyl e.g. tetrahydrofuran-3-yl, pyrrolidinyl e.g. 1-methylpyrrolidinyl such as 1-methylpyrrolidin-3-yl, piperidinyl e.g. 1-methylpiperidinyl such as 1-methylpiperidin-4-yl, tetrahydropyranyl e.g. tetrahydropyran-4-yl or 2-oxo-[1,3]dioxol-4-yl e.g. 5-methyl-2-oxo-[1,3]dioxol-4-yl group; an optionally substituted C$_{6-10}$aryl group, especially a phenyl group; an optionally substituted C$_{6-10}$arylC$_{1-6}$alkyl group, especially a benzyl group; an optionally substituted heteroC$_{6-10}$arylC$_{1-6}$alkyl group, especially a pyridinylC$_{1-3}$alkyl group such as pyridinylmethyl e.g. pyridin-4-ylmethyl or pyridinylethyl e.g. pyridine-4-ylethyl or a imidazolylC$_{1-3}$alkyl group such as imidazolylethyl e.g. 2-imidazol-1-ylethyl or imidazolylpropyl e.g. 2-imidazol-1-ylpropyl group; an optionally substituted hydroxyC$_{1-6}$alkyl group, especially a hydroxyethyl e.g. 2-hydroxyethyl or hydroxypropyl e.g. 3-hydroxypropyl or 2,3-dihydroxypropyl group; an optionally substituted C$_{3-8}$heterocycloalkylC$_{1-6}$alkyl group, especially a morpholinyl-N-ethyl group; an optionally substituted N-di-C$_{1-8}$alkylaminoC$_{1-8}$alkyl group, especially a N-dimethylaminoethyl or N-diethylaminoethyl group; or an optionally substituted C$_{1-6}$alkyloxyC$_{1-6}$alkyl group, especially a methyloxyethyl group. Especially preferred esterified carboxyl groups include —CO$_2$CH$_3$, —CO$_2$CH$_2$CH$_3$, —CO$_2$CH$_2$CH$_2$CH$_3$, —CO$_2$CH(CH$_3$)$_2$ and —CO$_2$C(CH$_3$)$_3$ groups. A most especially preferred esterified carboxyl group is —CO$_2$(hydroxyC$_{1-6}$alkyl), especially —CO$_2$CH$_2$CH$_2$OH.

In general in compounds of formula (1) when X is a —N(R$^2$) group and in particular in compounds of formulae (2a), (2b), (2c) and (2d) R$^2$ is preferably a hydrogen atom.

In one preferred class of compounds of formula (2a) L$^2$ is preferably L$^{2a}$ where L$^{2a}$ is a —CON(R$^8$)— group [where R$^8$ is preferably a hydrogen atom or a C$_{1-3}$alkyl group], especially a —CONH— group or a -(Alk$^3$)L$^{2a}$- group, especially a -(Alk$^3$)O— group [where Alk$^3$ is preferably a C$_{1-3}$alkyl group], most especially a —CH$_2$O— group. In this class of compounds —W═ is preferably —N═ or —N(O)═. Most preferably W is —N═.

In another preferred class of compounds of formula (2a) L$^2$ is preferably a covalent bond. In this class of compounds —W═ is preferably —C(R$^{18}$)═, where R$^{18}$ is as hereinbefore generally and particularly defined.

In general in compounds of formulae (2b), (2c) and (2d) L$^2$ is preferably L$^{2a}$ where L$^{2a}$ is an —O— atom or —N(R$^8$)— group [where R$^8$ is preferably a hydrogen atom or a C$_{1-3}$alkyl group]. An especially useful —N(R$^8$)— group is —NH—.

The group Ar$^2$ in compounds of formulae (1), (2a), (2b), (2c) and (2d) is preferably an optionally substituted phenylene or optionally substituted pyridinediyl group or formula:

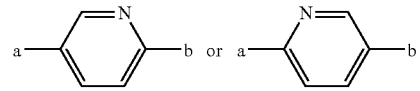

where a and b signify the points of attachment of L$^2$ and Alk respectively. Most preferably Ar$^2$ is an optionally substituted 1,4-phenylene group.

Particularly preferred optional substituents which may be present on Ar$^2$ in compounds of the invention include halogen atoms, especially fluorine, chlorine or bromine atoms, or C$_{1-6}$alkyl e.g. methyl, ethyl or i-propyl, haloC$_{1-6}$alkyl especially halomethyl, most especially —CF$_3$, C$_{1-6}$alkoxy especially methoxy or haloC$_{1-6}$alkoxy, especially halomethoxy, most especially —OCF$_3$, —CN, —CO$_2$CH$_3$, —NO$_2$, amino (—NH$_2$), substituted amino (NR$^5$R$^6$) especially —NHCH$_3$ and —N(CH$_3$)$_2$ and —N(R$^5$)COCH$_3$, especially —NHCOCH$_3$ groups.

In one generally preferred class of compounds of formulae (1), (2a), (2b), (2c) and (2d) R$^x$, R$^y$ and/or R$^z$ is an optionally substituted alkyl group, most preferably an optionally substituted C$_{1-8}$alkyl group such as a methyl, ethyl, n-propyl, i-propyl, n-butyl, n-heptyl, or n-hexyl group. Particularly preferred optional substituents which may be present on such R$^x$, R$^y$ and/or R$^z$ alkyl groups include halogen atoms, especially fluorine or chlorine atoms, C$_{1-6}$alkoxy groups, especially methoxy, haloC$_{1-6}$alkoxy groups, especially —OCF$_3$, —CN, —CO$_2$CH$_3$, —NO$_2$, substituted amino (—NR$^5$R$^6$) especially —NHCH$_3$ and —N(CH$_3$)$_2$ and optionally substituted phenyl groups where the optional substituents are as herein defined for optional substituents on Ar$^2$.

In another preferred class of compounds of formulae (1), (2a), (2b), (2c) and (2d) R$^z$ is a hydrogen atom.

In another preferred class of compounds of formulae (1), (2a), (2b), (2c) and (2d) R$^x$ is a hydrogen atom.

In another preferred class of compounds of formulae (1), (2a), (2b), (2c) and (2d) R$^z$ is a halogen atom, especially a fluorine, chlorine, bromine or iodine atom, most especially a chlorine or bromine atom.

In another preferred class of compounds of formulae (1), (2a), (2b), (2c) and (2d) R$^z$ is a group -L$^1$(Alk$^1$)$_n$R$^3$. In this class of compounds L$^1$ is preferably a covalent bond or an —O—, —S— or —Se— atom or —S(O)— or —N(R$^8$)—, especially —NH— or —N(CH$_3$)— group. Most preferably L$^1$ is a —S— atom or —S(O)— group. In this class of compounds R$^3$ is preferably a hydrogen atom or an optionally substituted C$_{3-10}$cycloaliphatic, especially C$_{3-7}$cycloalkyl group, most especially an optionally substituted cyclopentyl, cyclohexyl or cycloheptyl group; or an optionally substituted C$_{3-10}$heterocycloaliphatic, especially C$_{3-7}$heterocycloalkyl group, most especially an optionally substituted piperidinyl, piperazinyl, pyrrolidinyl, imidazolidinyl, dithianyl or pyrazolidinyl group, or an optionally substituted C$_{6-12}$aromatic group, preferably an optionally substituted phenyl group or an optionally substituted C$_{1-9}$heteroaromatic group, preferably an optionally substituted monocyclic C$_{1-9}$heteroaromatic group, most preferably a 5- or 6-membered monocyclic heteroaromatic group containing one, two, three or four heteroatoms selected from oxygen, sulphur or nitrogen atoms, especially an optionally substituted furyl, thienyl, imidazolyl e.g. 1-methylimidazol-2-yl, triazolyl, tetrazolyl, pyridyl, pyrimidinyl or pyrazinyl group. Optional substituents which may be present on such heterocycloaliphatic groups include those substituents as described hereinafter when $R^x$ and $R^y$ are joined to form an optionally substituted spiro linked heterocycloaliphatic group. Optional substituents which may be present on such aromatic and heteroaromatic groups include those substituents as described hereinbefore in relation to $R^{16}$ substituents in compounds of formula (2a). In one preferred group of compounds of this class n is zero. In another preferred group of compounds of this class $L^1$ is a covalent bond and n is zero. In this group of compounds $R^3$ is preferrably an optionally substituted $C_{3-10}$cycloaliphatic, $C_{3-10}$heterocycloaliphatic, $C_{6-12}$aromatic or monocyclic $C_{1-9}$heteroaromatic group as just described. In a further preferred group of compounds of this class n is the integer 1 and $Alk^1$ is preferably an optionally substituted aliphatic chain, most preferably an optionally substituted $C_{1-6}$alkylene chain, especially a —$CH_2$—, —$CH_2CH_2$— or —$CH_2CH(CH_3)$— chain. In a further preferred group of compounds of this class $L^1$ is a covalent bond, n is the integer 1 and $Alk^1$ is preferably an optionally substituted aliphatic chain, most preferably an optionally substituted $C_{1-6}$alkylene chain, especially a —$CH_2$—, —$CH_2CH_2$—, —$CH_2CH_2CH_2$— or —$CH_2CH(CH_3)$— chain. In a further preferred group of compounds of this class $L^1$ is a preferred atom or group as just described, most especially a —S— atom, n is the integer 1 and $Alk^1$ is preferably an optionally substituted aliphatic chain, most preferably an optionally substituted $C_{1-6}$alkylene chain, especially a —$CH_2$—, —$CH_2CH_2$—, —$CH_2CH_2CH_2$— or —$CH_2CH(CH_3)$— chain. In this class of compounds $R^3$ is preferably a hydrogen atom.

Most especially useful $R^z$ groups which may be present in compounds of the invention include a hydrogen or halogen atom, especially fluorine, chlorine, bomine or iodine atom or a group of formula -$L^1(Alk^1)_nR^3$ as just defined, especially an alkyl group as previously described or a hydroxyl (—OH); $C_{1-6}$alkoxymethoxy, ethoxy or i-propoxy; $C_{3-7}$cycloalkyl, especially cyclopentyl or cyclohexyl; $C_{1-6}$alkylsulfanyl, especially methyl- ethyl- or i-propylsulfanyl; $C_{1-6}$alkylsulfinyl, especially methyl- ethyl- or i-propylsulfinyl; $C_{3-7}$heterocycloalkyl, especially piperidinyl most especially piperidin-3-yl such as 1-methylpiperidin-3-yl or dithianyl especially [1,3]dithian-2-yl; $C_{6-12}$arylselenenyl, especially phenylselenenyl; $C_{6-12}$arylsulfanyl, especially phenylsulfanyl or pentafluorophenylsulfanyl; monocyclic $C_{1-9}$heteroaromaticsulfanyl, especially tetrazol-5-ylsulfanyl most especially 1-methyl-1H-terazol-5-ylsulfanyl or imidazolylsulfanyl especially imidazol-2-ylsulfanyl most especially 1-methyl-1H-imidazol-2-ylsulfanyl; monocyclic $C_{1-9}$heteroaromatic, especially pyridinyl most especially pyridin-3-yl, 1-methylpyridinium or pyrazinyl especially pyrazin-2-yl; or a $C_{6-12}$aryl$C_{1-3}$alkyl, especially benzyl group.

In another preferred class of compounds of formulae (1), (2a), (2b), (2c) and (2d) $R^x$ and $R^z$ is each a hydrogen atom.

In another preferred class of compounds of formulae (1), (2a), (2b), (2c) and (2d) $R^x$ is a hydrogen atom and $R^z$ is a halogen atom, especially a fluorine, chlorine, bromine or iodine atom, most especially a chlorine or bromine atom, or $R^z$ is a group -$L^1(Alk^1)_nR^3$ as just described.

In another preferred class of compounds of formulae (1), (2a), (2b), (2c) and (2d) $R^x$ and $R^y$ is each a hydrogen atom and $R^z$ is a halogen atom, especially a fluorine, chlorine, bromine or iodine atom, most especially a chlorine or bromine atom, or $R^z$ is a group -$L^1(Alk^1)_nR^3$ as just described.

In another preferred class of compounds of formulae (1), (2a), (2b), (2c) and (2d) $R^x$ is a hydrogen atom and $R^y$ is an optionally substituted alkyl group as just described for generally preferred alkyl groups.

In another preferred class of compounds of formulae (1), (2a), (2b), (2c) and (2d) $R^x$ and $R^z$ is each a hydrogen atom and $R^y$ is an optionally substituted alkyl group as just described.

In another preferred class of compounds of formulae (1), (2a), (2b), (2c) and (2d) $R^x$ is a hydrogen atom, $R^z$ is a halogen atom, especially a fluorine, chlorine, bromine or iodine atom, most especially a chlorine or bromine atom or $R^z$ is a group -$L^1(Alk^1)_nR^3$, especially a group as just particularly described, and $R^y$ is an optionally substituted alkyl group as just described for generally preferred alkyl groups.

In another preferred class of compounds of formulae (1), (2a), (2b), (2c) and (2d) $R^x$ is a hydrogen atom and $R^y$ and $R^z$ is each an optionally substituted alkyl group as just described for generally preferred alkyl groups.

In another preferred class of compounds of formulae (1), (2a), (2b), (2c) and (2d) $R^x$ and $R^y$ is each an optionally substituted alkyl group as just described for generally preferred alkyl groups.

In another preferred class of compounds of formulae (1), (2a), (2b), (2c) and (2d) $R^x$ and $R^y$ is each an optionally substituted alkyl group as just described for generally preferred alkyl groups and $R^z$ is a hydrogen atom.

In another preferred class of compounds of formulae (1), (2a), (2b), (2c) and (2d) $R^x$ and $R^y$ is each an optionally substituted alkyl group as just described for generally preferred alkyl groups and $R^z$ is a halogen atom, especially a fluorine, chlorine, bromine or iodine atom, most especially a chlorine or bromine atom, or $R^z$ is a group -$L^1(Alk^1)_nR^3$ as just described.

In another preferred class of compounds of formulae (1), (2a), (2b), (2c) and (2d) $R^x$, $R^y$ and $R^z$ is each an optionally substituted alkyl group as just described for generally preferred alkyl groups.

In another preferred class of compounds of formulae (1), (2a), (2b), (2c) and (2d) $R^x$ and $R^y$ are joined to form an optionally substituted spiro linked cycloaliphatic group particularly a $C_{3-10}$cycloaliphatic group, most particularly a $C_{3-8}$cycloalkyl group, especially an optionally substituted cyclopentyl, cyclohexyl, cycloheptyl or cyclooctyl group, or a $C_{3-8}$cycloalkenyl group, especially an optionally substituted cyclopentenyl, cyclohexenyl, cycloheptenyl or cyclooctenyl group. Particularly preferred optional substituents which may be present on such spiro linked cycloaliphatic groups include halogen atoms, especially fluorine or chlorine atoms, $C_{1-6}$alkyl groups, especially methyl, ethyl, propyl or i-propyl, $C_{1-6}$alkoxy groups, especially methoxy or ethoxy, halo$C_{1-6}$alkoxy groups, especially —$OCF_3$, —CN, —$CO_2CH_3$, —$NO_2$ and substituted amino (—$N(R^{11})_2$), especially —$NHCH_3$ and —$N(CH_3)_2$ groups. In a preferred group of compounds of this class $R^z$ is a hydrogen atom. In another preferred group of compounds of this class $R^z$ is an alkyl group as just described. In a further preferred group of compounds of this class $R^z$ is a halogen atom, especially a fluorine, chlorine, bromine or iodine atom, most especially a chlorine or bromine atom, particularly a bromine atom. In a still further preferred group of compounds of this class $R^z$ is a group -$L^1(Alk^1)_nR^3$ as just described.

In another preferred class of compounds of formulae (1), (2a), (2b), (2c) and (2d) $R^x$ and $R^y$ are joined to form an optionally substituted spiro linked heterocycloaliphatic group, particularly an optionally substituted $C_{3-7}$heterocycloaliphatic group, most particularly an optionally substituted $C_{3-7}$heterocycloalkyl group, especially an optionally substituted $C_{3-7}$heterocycloalkyl group containing one or two —O—, —S—, —S(O)—, —S(O)$_2$—, —NH— or —C(O)— heteroatoms or heteroatom-containing groups. Especially preferred optionally substituted heterocycloaliphatic groups include optionally substituted 5- and 6-membered heterocycloalkyl groups containing one heteroatom or heteroatom-containing group as just described, especially optionally substituted pyrrolidinyl, tetrahydrofuranyl, tetrahydrothiophenyl, tetrahydrothiophene-1-oxide, tetrahydrothiophene-1,1-dioxide, piperidinyl, tetrahydropyranyl, tetrahydrothiopyranyl tetrahydrothiopyran-1-oxide or tetrahydrothiopyran-1,1-dioxide groups. Particularly preferred optional substituents which may be present on such spiro linked heterocycloaliphatic groups include halogen atoms, especially fluorine or chlorine atoms, $C_{1-6}$alkyl groups, especially methyl, ethyl, propyl or i-propyl, $C_{1-6}$alkoxy groups, especially methoxy or ethoxy, halo$C_{1-6}$alkoxy groups, especially —OCF$_3$, —CN, —CO$_2$CH$_3$, —NO$_2$ and substituted amino (—N(R$^{11}$)$_2$), especially —NHCH$_3$ and —N(CH$_3$)$_2$ groups. In addition when the spiro linked heterocycloaliphatic group contains a nitrogen atom this may be substituted by a group -(L$^6$)$_p$(Alk$^5$)$_q$R$^{12}$ where L$^6$ is preferably —C(O)— or —S(O)$_2$—, Alk$^5$ is preferably an optionally substituted $C_{1-6}$alkylene chain, especially a —CH$_2$—, —(CH$_2$)$_2$— or —CH(CH$_3$)CH$_2$— chain or an optionally substituted hetero$C_{1-6}$alkylene chain, especially —CH$_2$L$^5$-, —CH$_2$CH$_2$L$^5$-, -L$^5$CH$_2$— or -L$^5$CH$_2$CH$_2$ chain where L$^5$ is an —O— or —S— atom or —NH or —N(CH$_3$)— group and R$^{12}$ is a hydrogen atom or an optionally substituted phenyl ring where preferred optional substituents include those atoms and groups as defined hereinbefore for R$^{16}$ in relation to formula (2b). In one preferred group of compounds of this class R$^z$ is a hydrogen atom. In another preferred group of compounds of this class R$^z$ is an alkyl group as just described. In a further preferred group of compounds of this class R$^z$ is a halogen atom, especially a fluorine, chlorine, bromine or iodine atom, most especially a chlorine or bromine atom In a still further preferred group of compounds of this class R$^z$ is a group -L$^1$(Alk$^1$)$_n$R$^3$ as just described.

Particularly useful compounds of the invention include:

(2S)-2-[(3-Oxospiro[3.5]non-1-en-1-yl)amino]-3-{4-[(3,5-dichloroisonicotinoyl)amino]phenyl}propanoic acid (2S)-2-[(3-Oxospiro[3.5]non-1-en-1-yl)amino]-3-{4-[(3-methyl[2,7]naphthyridin-1-yl)oxy]phenyl}propanoic acid (2S)-2-[(2-Bromo-3-oxospiro[3,5]non-1-en-1-yl)amino]-3-{4-[(3,5-dichloroisonicotinoyl)amino]phenyl}propanoic acid (2S)-2-[(2-Bromo-4,4-dimethyl-3-oxo-1-cyclobutenyl)amino]-3-{4-[(3,5-dichloroisonicotinoyl)amino]phenyl}propanoic acid (2S)-2-[(2-Bromo-3-oxospiro[3.5]non-1-en-1-yl)amino]-3-{4-[(2,7)naphthyridin-1-yloxy]phenyl}propanoic acid (2S)-2-[(2-Bromo-3-oxo-7-oxaspiro[3.5]non-1-en-1-yl)amino]-3-{4-[(3,5-dichloroisonicotinoyl)amino]phenyl}propanoic acid (2S)-2-{(2-Bromo-3-oxospiro[3.5]non-1-en-1-yl)amino}-3-(2,6-dimethoxy[1,1'-biphenyl]-4-yl)propanoic acid (2S)-2-[(3-Oxospiro[3.6]dec-1-en-1-yl)amino]3-{4-[(3,5-dichloroisonicotinoyl)amino]phenyl}propanoic acid (2S)-2-[(2-Bromo-3-oxospiro[3.6]dec-1-en-1-yl)amino]-3-{4-[(3,5-dichloroisonicotinoyl)amino]phenyl}propanoic acid (2S)-2-{[4,4-Dimethyl-2-(phenylselenenyl)-3-oxo-1-cyclobutenyl]amino}-3-{4-[(3,5-dichloroisonicotinoyl)amino]phenyl}propanoic acid (2S)-2-[(2-Bromo-7-methoxy-3-oxospiro[3.5]non-1-en-1-yl)amino]-3-{4-[(3,5-dichloroisonicotinoyl)amino]phenyl}propanoic acid (2S)-2-{(2-Bromo-3-oxospiro[3.5]non-1-en-1-yl)amino}-3-{4-[(3-methyl[2,7]naphthyridin-1-yl)oxy]phenyl}propanoic acid (2S)-2-{[2-(Phenylsulfanyl)-4,4-dimethyl-3-oxo-1-cyclobutenyl]-amino}-3-{4-[(3,5-dichloroisonicotinoyl)amino]phenyl}propanoic acid (2S)-2-[(2-Chloro-3-oxospiro[3.5]non-1-en-1-yl)amino]-3-{4-[(3,5-dichloroisonicotinoyl)amino]phenyl}propanoic acid (2S)-3-{4-[(3,5-Dichloroisonicotinoyl)amino]phenyl}-2-(3-oxo-2-pyridin-3-yl-spiro[3.5]non-1-en-1-ylamino)-propanoic acid (2S)-2-[(2-Iodo-3-oxospiro[3.6]non-1-en-1-yl)amino]-3-{4-[(3,5-dichloroisonicotinoyl)amino]phenyl}propanoic acid (2S)-2-[(2-Bromo-3-oxospiro[3.5]non-1-en-1-yl)amino]-3-{5-[(3,5-dichloroisonicotinoyl)amino]pyridin-2-yl}propanoic acid (2S)-2-[(2-Chloro-3-oxospiro[3.5]non-1-en-1-yl)amino]-3-{5-[(3,5-dichloroisonicotinoyl)amino]pyridin-2-yl}propanoic acid (2S)-2-[(2-Chloro-3-oxo-7-oxa-spiro[3.5]non-1-en-1-yl)amino]-3-{4-[(3,5-dichloroisonicotinoyl)amino]phenyl}propanoic acid (2S)-2-[(2-Chloro-3-oxo-spiro[3.6]dec-1-en-1-yl)amino]-3-{4-[(3,5-dichloroisonicotinoyl)amino]phenyl}propanoic acid (2S)-2-[4,4-Dimethyl-2-(1-methyl-1H-tetrazol-5-ylsulfanyl)-3-oxo-cyclobut-1-enylamino]-3-{4-[(3,5-dichoroisonicotinoyl)amino]phenyl}propanoic acid (2S)-2-[(2-Bromo-3,7,7-trioxo-7$\lambda^6$-thia-spiro[3.5]non-1-en-1-yl)amino]-3-{4-[(3,5-dichloroisonicotinoyl)amino]phenyl}propanoic acid (2S)-2-[(2-Chloro-3-oxo-spiro[3.4]oct-1-en-1-yl)amino]-3-{4-[(3,5-dichloro-isonicotinoyl)amino]phenyl}propanoic acid (2S)-2-[(2-Bromo-3-oxo-spiro[3.4]oct-1-en-1-yl)amino]-3-{4-[(3,5-dichloroisonicotinoyl)amino]phenyl}propanoic acid (2S)-2-[(2-Methylsulfanyl-3-oxo-spiro[3.5]non-1-en-1-yl)amino]-3-{4-[(3,5-dichloroisonicotinoyl)amino]phenyl}propanoic acid (2S)-2-(2-Fluoro-3-oxo-spiro[3.5]non-1-en-1-ylamino)$_3$-{4-[(3,5-dichloroisonicotinoyl)amino]phenyl}propanoic acid (2S)-2-[(2-Fluoro-3-oxo-7-oxa-spiro[3.5]non-1-en-1-yl)amino]-3-{4-[(3,5-dichloroisonicotinoyl)amino]phenyl}propanoic acid (2S)-2-[(4,4-Dimethyl-2-methylsulfanyl-3-oxo-cyclobut-1-enyl)amino]-3-{4-[(3,5-dichloroisonicotinoyl)amino]phenyl}propanoic acid (2S)-2-[(2-Isopropylsulfanyl-4,4-dimethyl-3-oxo-cyclobut-1-enyl)amino]-3-{4-[(3,5-dichloroisonicotinoyl)amino]phenyl}propanoic acid (2S)-2-[(2-Isopropylsulfanyl-3-oxo-spiro[3.5]non-1-en-1-yl)amino]-3-{4-[(3,5-dichloroisonicotinoyl)amino]phenyl}propanoic acid (2S)-2-[(2-Isopropylsulfanyl-4,4-dimethyl-3-oxo-cyclobut-1-enyl)amino]-3-[4-([2,7]naphthyridin-1-ylamino)phenyl]propanoic acid (2S)-2-[(2-Isopropylsulfanyl-3-oxo-spiro[3.5]non-1-en-1-yl)amino]-3-[4-([2,7]naphthyridin-1-ylamino)phenyl]propanoic acid (2S)-2-[(2-Isopropylsulfanyl-3-oxo-7-oxa-spiro[3.5]non-1-en-1-yl)amino]-3-[4-([2,7]naphthyridin-1-ylamino)phenyl]propanoic acid (2S)-2-[(2-Bromo-3-oxo-spiro[3.4]octa-1,6-dien-1-yl)amino]-3-{4-[(3,5-dichloroisonicotinoyl)amino]phenyl}propanoic acid (2S)-2-[(4,4-Dimethyl-3-oxo-2-pentafluorophenyl sulfanyl-cyclobut-1-enyl)amino]-3-{4-[(3,5-dichloroisonicotinoyl)amino]phenyl}propanoic acid (2S)-2-[(4,4-Dimethyl-3-oxo-2-pyrazin-2-yl-cyclobut-1-enyl)amino]-3-{4-[(3,5-dichloroisonicotinoyl)amino]phenyl}propanoic acid (2S)-2-[(7-Acetyl-2-bromo-3-oxo-7-aza-spiro[3.5]non-1-en-1-yl)amino]-3-{4-[(3,5-dichloroisonicotinoyl)amino]phenyl}propanoic acid (2S)-2-{[2-(Isopropylsulfanyl)-3-oxo-7-oxaspiro[3.5]non-1-en-1-yl)]amino}-3-(2,6-dimethoxy[1,1'-biphenyl]-4-yl)propanoic acid (2S)-2-[(2-Cyclohexyl-3-oxo-spiro[3.5]non-1-en-1-yl)amino]-3-{4-[(3,5-dichloroisonicotinoyl)amino]phenyl}propanoic acid (2S)-3-{4-[(3,5-Dichloroisonicotinoyl)amino]phenyl}-2-(2-methyl-3-oxo-spiro[3.5]non-1-en-1-ylamino)propanoic acid (2S)-3-{4-[(3,5-Dichloroisonicotinoyl)amino]phenyl}-2-(3-oxo-2-propyl-spiro[3.5]non-1-en-1-ylamino)propanoic acid (2S)-3-{4-[(3,5-Dichloroisonicotinoyl)amino]phenyl}-2-(2-methyl-3-oxo-7-oxa-spiro[3.5]non-1-en-1-ylamino)propanoic acid (2S)-3-{4-[(3,5-Dichloroisonicotinoyl)amino]phenyl}-2-(3-oxo-2-propyl-7-oxa-spiro[3.5]non-1-en-1-ylamino)propanoic acid (2S)-3-{4-[(3,5-Dichloroisonicotinoyl)amino]phenyl}-2-(2-[1,3]dithian-2-yl-3-oxo-spiro[3.5]non-1-en-1-ylamino)propanoic acid (2S)-3-{4-[(3,5-Dichloroisonicotinoyl)amino]phenyl}-2-(2-ethyl-3-oxo-spiro[3.5]non-1-en-1-ylamino)propanoic acid (2S)-3-{4-[(3,5-Dichloro-1-oxy-pyridine-4-carbonyl)amino]phenyl}-2-(3-oxo-spiro[3.5]non-1-en-1-ylamino)propanoic acid (2S)-2-(2-Bromo-3-oxo-spiro[3.5]non-1-en-1-ylamino)-3-{4-[(3,5-dichloro-1-oxy-pyridine-4-carbonyl)amino]phenyl}propanoic acid (2S)-2-(2-Chloro-3-oxo-spiro[3.5]non-1-en-1-ylamino)-3-{4-[(3,5-dichloro-1-oxy-pyridine-4-carbonyl)amino]phenyl}propanoic acid (2S)-3-{4-[(3,5-Dichloro-1-oxy-pyridine-4-carbonyl)-amino]-phenyl}-2-(2-methanesulfinyl-4,4-dimethyl-3-oxo-cyclobut-1-enylamino)-propanoic acid (2S)-2-(2-Bromo-3-oxo-spiro[3.5]non-1-en-1-ylamino)-3-[4-(3-methyl-[2,7]naphthyridin-1-ylamino)phenyl]propanoic acid (2S)-2-(2-Bromo-3-oxo-spiro[3.5]non-1-en-1-ylamino)-3-[4-([2,7]naphthyridin-1-ylamino)phenyl]propanoic acid (2S)-2-(2-Bromo-4,4-dimethyl-3-oxo-cyclobut-1-enylamino)-3-[4-(3-methyl-[2,7]naphthyridin-1-yloxy)phenyl]propanoic acid (2S)-2-[(2-Bromo-3-oxo-spiro[3.4]oct-1-en-1-yl)amino]-3-{4-[(3,5-dichloroisonicotinoyl)amino]phenyl}propanoic acid and the salts, solvates, hydrates, N-oxides and carboxylic acid esters thereof.

Particularly useful carboxylic acid esters thereof include the methyl, ethyl, propy, i-propyl and t-butyl esters.

Most especially useful compounds of the invention include:

(2S)-2-[(2-Bromo-3-oxospiro[3.5]non-1-en-1-yl)amino]-3-{4-[(3,5-dichloroisonicotinoyl)amino]phenyl}propanoic acid (2S)-2-[(2-Bromo-3-oxo-7-oxaspiro[3.5]non-1-en-1-yl)amino]-3-{4-[(3,5-dichloroisonicotinoyl)amino]phenyl}propanoic acid (2S)-2-[(2-Bromo-3-oxospiro[3.6]dec-1-en-1-yl)amino]-3-{4-[(3,5-dichloroisonicotinoyl)amino]phenyl}propanoic acid (2S)-2-{(2-Bromo-3-oxospiro[3.5]non-1-en-1-yl)amino}-3-{4-[(3-methyl[2,7]naphthyridin-1-yl)oxy]phenyl}propanoic acid (2S)-2-{[2-(Phenylsulfanyl)-4,4-dimethyl-3-oxo-1-cyclobutenyl]-amino}-3-{4-[(3,5-dichloroisonicotinoyl)amino]phenyl}propanoic acid (2S)-2-[(2-Chloro-3-oxospiro[3.5]non-1-en-1-yl)amino]-3-{4-[(3,5-dichloroisonicotinoyl)amino]phenyl}propanoic acid (2S)-3-{4-[(3,5-Dichloroisonicotinoyl)amino]phenyl}-2-(3-oxo-2-pyridin-3-yl-spiro[3.5]non-1-en-1-ylamino)propanoic acid (2S)-2-[(2-Iodo-3-oxospiro[3.5]non-1-en-1-yl)amino]-3-{4-[(3,5-dichloroisonicotinoyl)amino]phenyl}propanoic acid (2S)-2-[(2-Bromo-3-oxospiro[3.5]non-1-en-1-yl)amino]-3-{5-[(3,5-dichloroisonicotinoyl)amino]pyridin-2-yl}propanoic acid (2S)-2-[(2-Chloro-3-oxospiro[3.5]non-1-en-1-yl)amino]-3-{5-[(3,5-dichloroisonicotinoyl)amino]pyridin-2-yl}propanoic acid (2S)-2-[(2-Chloro-3-oxo-7-oxa-spiro[3.5]non-1-en-1-yl)amino]-3-{4-[(3,5-dichloroisonicotinoyl)amino]phenyl}propanoic acid (2S)-2-[(2-Chloro-3-oxo-spiro[3.6]dec-1-en-1-yl)amino]-3-{4-[(3,5-dichloroisonicotinoyl)amino]phenyl}propanoic acid (2S)-2-[(2-Bromo-3,7,7-trioxo-7$\lambda^6$-thia-spiro[3.5]non-1-en-1-yl)amino]-3-{4-[(3,5-dichloroisonicotinoyl)amino]phenyl}propanoic acid (2S)-2-[(2-Chloro-3-oxo-spiro[3.4]oct-1-en-1-yl)amino]-3-{4-[(3,5-dichloro-isonicotinoyl)amino]phenyl}propanoic acid (2S)-2-[(2-Bromo-3-oxo-spiro[3.4]oct-1-en-1-yl)amino]-3-{4-[(3,5-dichloroisonicotinoyl)amino]phenyl}propanoic acid (2S)-2-[(2-Methylsulfanyl-3-oxo-spiro[3.5]non-1-en-1-yl)amino]-3-{4-[(3,5-dichloroisonicotinoyl)amino]phenyl}propanoic acid (2S)-2-(2-Fluoro-3-oxo-spiro[3.5]non-1-en-1-ylamino)$_3$-{4-[(3,5-dichloroisonicotinoyl)amino]phenyl}propanoic acid (2S)-2-[(2-Fluoro-3-oxo-7-oxa-spiro[3.5]non-1-en-1-yl)amino]-3-{4-[(3,5-dichloroisonicotinoyl)amino]phenyl}propanoic acid (2S)-2-[(4,4-Dimethyl-2-methylsulfanyl-3-oxo-cyclobut-1-enyl)amino]-3-{4-[(3,5-dichloroisonicotinoyl)amino]phenyl}propanoic acid (2S)-2-[(2-Isopropylsulfanyl-4,4-dimethyl-3-oxo-cyclobut-1-enyl)amino]-3-{4-[(3,5-dichloroisonicotinoyl)amino]phenyl}propanoic acid (2S)-2-[(2-Isopropylsulfanyl-3-oxo-spiro[3.5]non-1-yl)amino]-3-{4-[(3,5-dichloroisonicotinoyl)amino]phenyl}propanoic acid (2S)-2-[(2-Isopropylsulfanyl-4,4-dimethyl-3-oxo-cyclobut-1-enyl)amino]-3-{4-([2,7]naphthyridin-1-ylamino)phenyl}propanoic acid (2S)-2-[(2-Isopropylsulfanyl-3-oxo-spiro[3.5]non-1-en-1-yl)amino]-3-{4-([2,7]naphthyridin-1-ylamino)phenyl}propanoic acid (2S)-2-[(2-Isopropylsulfanyl-3-oxo-7-oxa-spiro[3.5]non-1-en-1-yl)amino]-3-[4-([2,7]naphthyridin-1-ylamino)phenyl]propanoic acid (2S)-2-[(2-Bromo-3-oxo-spiro[3.4]octa-1,6-dien-1-yl)amino]-3-{4-[(3,5-dichloroisonicotinoyl)amino]phenyl}propanoic acid (2S)-2-[(7-Acetyl-2-bromo-3-oxo-7-aza-spiro[3.5]non-1-en-1-yl)amino]-3-{4-[(3,5-dichloroisonicotinoyl)amino]phenyl}propanoic acid (2S)-2-[(2-Cyclohexyl-3-oxo-spiro[3.5]non-1-en-1-yl)amino]-3-{4-[(3,5-dichloroisonicotinoyl)amino]phenyl}propanoic acid (2S)-3-{4-[(3,5-Dichloroisonicotinoyl)amino]phenyl}-2-(2-methyl-3-oxo-spiro[3.5]non-1-en-1-ylamino)propanoic acid (2S)-3-{4-[(3,5-Dichloroisonicotinoyl)amino]phenyl}-2-(3-oxo-2-propyl-spiro[3.5]non-1-en-1-ylamino)propanoic acid (2S)-3-{4-[(3,5-Dichloroisonicotinoyl)amino]phenyl}-2-(2-[1,3]dithian-2-yl-3-oxo-spiro[3.5]non-1-en-1-ylamino)propanoic acid (2S)-2-(2-Bromo-3-oxo-spiro[3.5]non-1-en-1-ylamino)-3-{4-[(3,5-dichloro-1-oxy-pyridine-4-carbonyl)amino]phenyl}propanoic acid (2S)-2-(2-Chloro-3-oxo-spiro[3.5]non-1-en-1-ylamino)-3-{4-[(3,5-dichloro-1-oxy-pyridine-4-carbonyl)amino]phenyl}propanoic acid and the salts, solvates, hydrates, N-oxides and carboxylic acid esters thereof.

Particularly useful carboxylic acid esters thereof include the methyl, ethyl, propy, i-propyl and t-butyl esters.

Particularly useful ester prodrugs of compounds of the invention include:

Ethyl (2S)-2-(2-bromo-3-oxo-spiro[3.5]non-1-en-1-ylamino)-3-{4-[(3,5-dichloroisonicotinoyl)amino]phenyl}propanoate Isopropyl (2S)-2-(2-bromo-3-oxo-spiro[3.5]non-1-en-1-ylamino)-3-{4-[(3,5-dichloroisonicotinoyl)amino]phenyl}propanoate t-Butyl (2S)-2-(2-bromo-3-oxo-spiro[3.5]non-1-en-1-ylamino)-3-{4-[(3,5-dichloroisonicotinoyl)amino]phenyl}propanoate 1-Methyl-piperidin-4-yl (2S)-2-(2-bromo-3-oxo-spiro[3.5]non-1-en-1-ylamino)-3-{4-[(3,5-dichloroisonicotinoyl)amino]phenyl}propanoate Phenyl (2S)-2-(2-bromo-3-oxo-spiro[3.5]non-1-en-1-ylamino)-3-{4-[(3,5-dichloroisonicotinoyl)amino]phenyl}propanoate Cyclopentyl (2S)-2-(2-bromo-3-oxo-spiro[3.5]non-1-en-1-ylamino)-3-{4-[(3,5-dichloroisonicotinoyl)amino]phenyl}propanoate 2-Imidazol-1-yl-ethyl (2S)-2-(2-bromo-3-oxo-spiro[3.5]non-1-en-1-ylamino)-3-{4-[(3,5-dichloroisonicotinoyl)amino]phenyl}propanoate Neopentyl (2S)-2-(2-bromo-3-oxo-spiro[3.5]non-1-en-1-ylamino)-3-{4-[(3,5-dichloroisonicotinoyl)amino]phenyl}propanoate Tetrahydro-furan-3-yl (2S)-2-(2-bromo-3-oxo-spiro[3.5]non-1-en-1-ylamino)-3-{4-[(3,5-dichloroisonicotinoyl)amino]phenyl}propanoate Pyridin-4-ylmethyl (2S)-2-(2-bromo-3-oxo-spiro[3.5]non-1-en-1-ylamino)-3-{4-[(3,5-dichloroisonicotinoyl)amino]phenyl}propanoate Tetrahydropyran-4-yl (2S)-2-(2-bromo-3-oxo-spiro[3.5]non-1-en-1-ylamino)-3-{4-[(3,5-dichloroisonicotinoyl)amino]phenyl}propanoate 5-Methyl-2-oxo-[1,3]dioxol-4-ylmethyl (2S)-2-(2-bromo-3-oxo-spiro[3.5]non-1-en-1-ylamino)-3-{4-[(3,5-dichloroisonicotinoyl)amino]-phenyl}propanoate 1-Methyl-pyrrolidin-3-yl (2S)-2-(2-bromo-3-oxo-spiro[3.5]non-1-en-1-ylamino)-3-{4-[(3,5-dichloroisonicotinoyl)amino]phenyl}propanoate 2,3-Dihydroxypropyl (2S)-2-(2-bromo-3-oxo-spiro[3.5]non-1-en-1-ylamino)-3-{4-[(3,5-dichloroisonicotinoyl)amino]phenyl}propanoate Tetrahydrofuran-2-ylmethyl (2S)-2-(2-bromo-3-oxo-spiro[3-5]non-1-en-1-ylamino)-3-{4-[(3,5-dichloroisonicotinoyl)amino]phenyl}propanoate and the salts, solvates, hydrates and N-oxides thereof.

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders including inflammation in which the extravasation of leukocytes plays a role and the invention extends to such a use and to the use of the compounds for the manufacture of a medicament for treating such diseases or disorders, Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^1$, $Ar^2$, Alk, $R^1$, $R^2$, $R^3$, $L^1$, $L^2$, $Alk^1$, $R^x$, $R^y$, $R^z$ and n when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —CO$_2$H group may be obtained by hydrolysis of an ester of formula (1a):

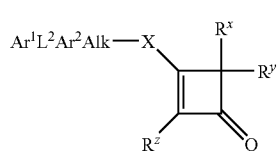

(1a)

where Alk represents a group —CH$_2$CH(CO$_2$Alk$^7$)-, —CH═CH(CO$_2$Alk$^7$)-, or

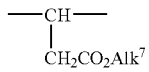

[where Alk$^7$ is an alkyl group for example a C$_{1-6}$alkyl group].

The hydrolysis may be performed using either an acid or a base depending on the nature of Alk$^7$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used.

According to a further aspect of the invention a compound of formula (1) may be prepared by condensation of a compound of formula (3):

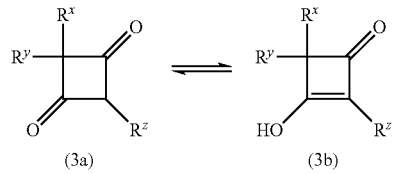

(3a)   (3b)

where compounds of formula (3) exist as two tautomeric isomers, (3a) and (3b) in solution with an amine of formula R$^1$R$^2$NH, an alcohol of formula R$^1$OH or a thiol of formula R$^1$SH.

The reaction may be performed in an inert solvent or mixture of solvents, for example a hydrocarbon such as an aromatic hydrocarbon e.g. benzene or toluene and/or a halogenated hydrocarbon such as 1,2-dichloroethane, or dichloromethane at a temperature from 0° C. to the reflux temperature. Where necessary, for example when a salt of an amine R$^1$R$^2$NH is used, an organic base such as diisopropylethylamine can be added.

Any carboxylic acid group present in the intermediate of formula (3) or the amine R$^1$R$^2$NH, alcohol R$^{10}$H or thiol R$^1$SH may need to be protected during the displacement reaction, for example as an ethyl ester. The desired acid may then be obtained through subsequent hydrolysis, for example as particularly described above and generally described below.

The displacement reaction may also be carried out on an intermediate of formula 4 (see below) under the conditions just described.

Where desired the displacement reaction may also be performed on an intermediate of formulae (3), R$^1$R$^2$NH, R$^1$OH or R$^1$SH which is linked, for example via its R, R$^1$ or R$^3$ group, to a solid support, such as a polystyrene resin. After the reaction the desired compound of formula (1) may be displaced from the support by any convenient method, depending on the original linkage chosen.

Intermediates of formulae (3) R$^1$R$^2$NH, R$^1$OH and R$^1$SH may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2a), (2b), (2c) and (2d) where appropriate functional groups exist in these compounds.

Thus intermediates of formula (3) may be obtained by hydrolysis of intermediates of formula (4):

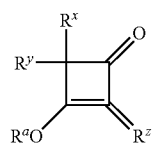

(4)

where $R^a$ represents a $C_{1-6}$alkyl group or a silyl group such as a $^t$butyldimethylsilyl group.

The hydrolysis may be performed using an acid, for example an inorganic acid such as hydrochloric acid in an organic solvent such as an ether e.g. diethylether, or an alcohol e.g. ethanol optionally in the presence of added water at a temperature from about ambient to 80° C.

Intermediates of formula (4) may be obtained by the cycloaddition of an intermediate of formula (5):

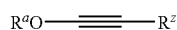

(5)

with a ketene of formula (6):

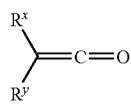

(6)

preformed or generated in situ during the cycloaddition reaction from an acid chloride of formula (7):

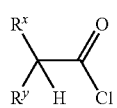

(7)

The reaction may be performed in the presence of an organic base such as an amine e.g. triethylamine or N,N-diisopropylethylamine or a cyclic amine such as pyridine or N-methylmorpholine optionally in an organic solvent such as an ether e.g. diethylether or diisopopylether.

Acid chlorides of formula (7) may be obtained from the corresponding acids by a convenient method of generating acid halides, for example by reaction with thionyl chloride or oxalyl chloride under such standard conditions as are well known in the art.

Compounds of formula (1a) in which $R^z$ is for example a halogen atom may be obtained from compounds of formula (1a) in which $R^z$ is a hydrogen atom by reaction with a halogen source such as bromine or a halosuccinamide e.g. chloro or bromosuccinamide. The reaction may be performed in a solvent such as an ether e.g. a cyclic ether such as tetrahydrofuran at a temperature from about 0° to 30°. When bromine is used as halogen source the reaction may optionally be performed in the presence of added base such as an amine e.g. triethylamine.

Further compounds of formula (1a) in which $R^z$ is a group $-L^1(Alk^1)_n(R^3)_v$ in which $L^1$ is for example a Se, S, O or $N(R^8)$ may be prepared by reaction of an intermediate of formula $HL^1(Alk^1)_n(R^3)_v$ with a compound of formula (1a) in which $R^z$ is a hydrogen atom. The reaction may be performed in an organic solvent such as an ether e.g. a cyclic ether such as tetrahydrofuran at around room temperature optionally in the presence of a base such as an amine e.g. triethylamine.

Intermediate compounds of formula (4) may also be obtained from squaric acid derivations by such well known methods in the art as those of MacDougall, J. M. et al, J. Org. Chem., 64 5979-83 (1999); Hergueta, R. A., J. Org. Chem., 64, 5979-83, (1999); Heileman, M. J. et al., J. Am. Chem. Soc. 120, 3801-2, (1998); Yamamoto, Y. et al., J. Org. Chem., 62, 1292-8 (1997); Zhag, D. et al, J. Org. Chem. 61, 2594-5 (1996); Petasis, N. A. et al, Synleft, 155-6 (1996); Petasis, N. A. et al, Tetrahedron Lett., 36, 6001-4, (1995); Turnbull, P. et al, J. Org. Chem. 60, 644-9 (1995); Yerxa, B. R. et al, Tetrahedron 50, 6173-80 (1994); Ezcurra, J. E. et al, Tetrahedron Lett, 34, 6177-80, (1993); Ohno, M. et al, Tetrahedron Lett., 34, 4807-10, (1993); Yerxa, B. R. et al, Tetrahedron Lett. 33, 7811-14 (1992); Xu, S. L. et al, J. Org. Chem., 57, 326-8 (1992) and Kravs, J. L. et al, Tetrahedron Lett. 28, 1765-8 (1987).

Further compounds of the invention and intermediates thereto may be prepared by alkylation, arylation or heteroarylation. For example, compounds containing a $-L^1H$ or $-L^2H$ group (where $L^1$ and $L^2$ is each a linker atom or group) may be treated with a coupling agent $R^3(Alk^1)_nX^1$ or $Ar^1X^1$ respectively in which $X^1$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, or an organic amine e.g. triethylamine or N,N-diisopropylethylamine or a cyclic amine, such as N-methylmorpholine or pyridine, in a dipolar aprotic solvent such as an amide, e.g. a substituted amide such as dimethylformamide or an ether, e.g. a cyclic ether such as tetrahydrofuran.

Compounds of formula $Ar^1X^1$ may be prepared from alcohols of formula $Ar^1OH$ by reaction with a halogenating agent, for example a phosphorous oxyhalide such as phosphorous oxychloride at an elevated temperature e.g. 110° C.

Intermediate alcohols of formula $Ar^1OH$ in which, for example, $Ar^1$ represents a 2,6-naphthyridine may be prepared by methods well known to a person skilled in the art, e.g. by the method of Sakamoto, T. et al [Chem. Pharm. Bull. 33, 626-633, (1985)].

Alternatively alkylating agents of formula $Ar^1X^1$ in which, for example, $Ar^1$ represents a 2,6-naphthyridine may be prepared by reaction of a 2,6-naphthyridine N-oxide or N,N'-dioxide with a halogenating agent, e.g. a phosphorous oxyhalide such as phosphorous oxychloride to give a 1-halo or 1,5-dihalo-2,6-napthyridine respectively. In the case of 1,5-dihalo-2,6-napthyridines each halogen atom may be substituted separately by a reagent such as $HL^2Ar^2AlkN(R^2)H$ or $HL^3(Alk^2)_tL^4(R^4)_u$ by the particular methods just described above.

2,6-Napthyridine N-oxides and N,N'-dioxides may be generated from the corresponding 2,6-napthyridines by the general methods of synthesis of N-oxides described below or they may be synthesised by the methods of Numata, A. et al (Synthesis, 1999, 306-311).

Further alkylating agents of formula $Ar^1X^1$ in which, for example, $Ar^1$ represents a 2,6-naphthyridine, may be prepared by the methods of Giacomello G. et al [Tetrahedron Letters, 1117-1121 (1965)], Tan, R. and Taurins, A. [Tetrahedron Lett., 2737-2744, (1965)], Ames, D. E. and Dodds, W. D. [J. Chem. Soc. Perkin 1, 705-710 (1972)] and Alhaique, F. et al [Tetrahedron Lett., 173-174 (1975)].

Intermediate alcohols of formula $Ar^1OH$ in which $Ar^1$ represents an optionally substituted 2,7-naphthyridin-1-yl group may be prepared by methods well known to a person skilled in the art, e.g. by the method of Sakamoto, T. et al [Chem. Pharm. Bull. 33, 626-633, (1985)] or Baldwin, J, J. et al [J. Org. Chem., 43, 4878-4880, (1978)]. Thus for example the method of Baldwin may be modified to allow the synthesis of intermediate 3-substituted 2,7-naphthyridin-1-yl groups of formula $Ar^1OH$ as depicted in Scheme 1.

Reaction of an optionally substituted 4-methyl-3-cyano pyridine of formula (8) with a N,N-dimethylformamide di-$C_{1-6}$alkyl acetal, e.g. N,N-dimethylformamide diethyl acetal, in a dipolar solvent such as an amide e.g. a substituted amide such as dimethylformamide at an elevated temperature e.g. 140-150° gives a compound of formula (9) or (10) or a mixture thereof depending on the nature of the group $R^{16}$.

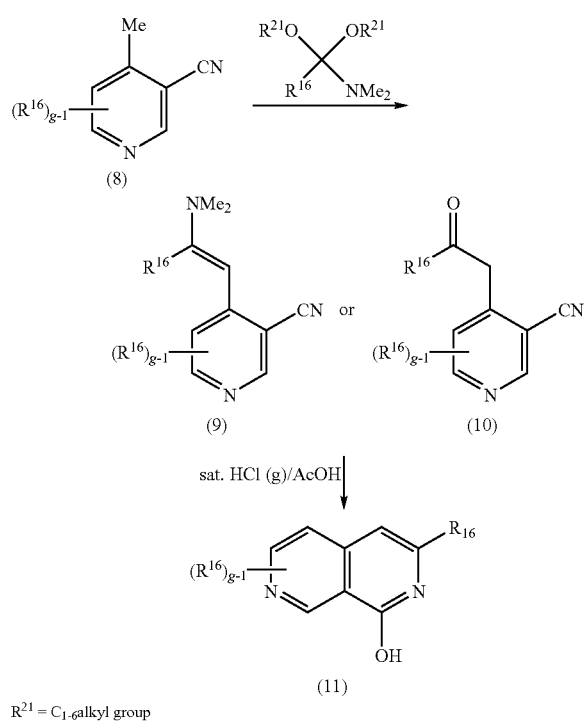

Scheme 1

$R^{21}$ = $C_{1-6}$alkyl group

Compounds of formula (9) or (10) may be cyclised to 3-substituted 2,7-naphthyridin-1-yl alcohol of formula (11) by treatment with an acid e.g. an inorganic acid such as hydrochloric acid or hydrobromic acid or an acidic gas such as hydrogen chloride gas in an organic solvent e.g. an organic acid such as acetic acid optionally in the presence of water at a temperature from about ambient to 50° C.

Alternatively alkylating agents of formula $Ar^1X^1$ in which $Ar^1$ represents an optionally substituted 2,7-naphthyridin-yl group may be prepared by reaction of a 2,7-naphthyridine N-oxide or N,N'-dioxide with a halogenating agent, e.g. a phosphorous oxyhalide such as phosphorous oxychloride to give a 1-halo or 1,6-dihalo- and/or -1,8-dihalo-2,7-napthyridine respectively. In the case of 1,6-dihalo- and/or 1,8-dihalo-2,6-napthyridines each halogen atom may be substituted separately by a reagent such as $HL^2Ar^2AlkN(R^2)H$ or $HL^3(Alk^2)_rL^4(R^4)_u$ by the particular methods just described above.

2,7-Napthyridine N-oxides and N,N'-dioxides may be generated from the corresponding 2,7-napthyridines by the general methods of synthesis of N-oxides described below or they may be synthesised by the methods of Numata, A. et al (Synthesis, 1999, 306-311).

Further alkylating agents of formula $Ar^1X^1$ in which, for example, $Ar^1$ represents a 2,7-naphthyridin-1-yl, may be prepared by the methods of Wenkert E. et al J. Am. Chem. Soc. 89, 6741-5 (1967), and Aust. J. Chem. 433 (1972), and Sheffield D. J. J. Chem. Soc. Perkin. Trans 1, 2506 (1972).

Intermediate alcohols of formula $Ar^1OH$ in which $Ar^1$ represents a 3-substituted isoquinolin-1-yl group may be prepared by methods well known to a person skilled in the art, e.g. by the methods of Wu M.-J. et al Tetrahedron, 55, 13193-200 (1999), Hiebl J. et al Tetrahedron Lett. 40, 7935-8 (1999), Nagarajan A. et al Indian J. Chem., Sect. B, 28B, 67-78 (1989), Brun E. M. et al Synlett, 7, 1088-90 (1999) and Brun, E. M. et a/Synthesis, 273-280 (2000).

Further alkylating agents of formula $Ar^1X^1$ in which, for example, $Ar^1$ represents a isoquinolin-1-yl group, may be prepared by the methods of Falk H. et al Monatsch. Chem. 25, 325-33 (1994), and Deady, L. W. et al Aust. J. Chem 42, 1029-34 (1989).

In a further example intermediates of formula $R^1R^2NH$ may be obtained by reaction of a compound of formula $Ar^1L^2H$ with a compound of formula $X^1Ar^2AlkN(R^2)H$ under the reaction conditions just described Compounds of formula $Ar^1L^2H$ in which, for example $Ar^1$ represents a 2,6-naphthyridine and $L^2$ is a —$N(R^8)$— group, may be prepared from substituted 4-cyano-3-cyanomethylpyridines by the methods of Alhaique, F. et al (ibid and Gazz. Chim. Ital. 1975, 105, 1001-1009) or from 3-fomylpyridines by the methods of Molina, P. at al (Tetrahedron 1992, 48, 4601-4616).

Compounds of formula $Ar^1 L^2H$ in which, for example $Ar^1$ represents a 2,7-naphthyridin-1-yl group and $L^2$ is a —$N(R^8)$— group, may be prepared from substituted 4-formylpyridines by the methods of Molina, P. et al Tetrahedron, 48, 4601-4616, (1992), or by the methods described in U.S. Pat. No. 3,938,367.

Compounds of formula $Ar^1L^2H$ in which, for example $Ar^1$ represents a 3-substituted isoquinolin-1-yl group and $L^2$ is a —$N(R^8)$— group, may be prepared by the methods of Bordner, J. et al J. Med. Chem. 31, 1036-9 (1988), Tovar J. D. et al J. Org. Chem., 64, 6499-6504 (1999), Karser E. M. et al Synthesis, 11, 805-6 (1974), and Molino, P et al J. Chem. Soc. Perkin Trans. 1, 1727-31 (1990).

In another example, compounds containing a -$L^1$H or -$L^2$H or group as defined above may be functionalised by acylation or thioacylation, for example by reaction with one of the alkylating agents just described but in which $X^1$ is replaced by a —$C(O)X^2$, —$C(S)X^2$, —$N(R^8)COX^2$ or —$N(R^8)C(S)X^2$ group in which $X^2$ is a leaving atom or group as described for $X^1$. The reaction may be performed in the presence of a base, such as a hydride, e.g. sodium hydride or an amine, e.g. triethylamine or N-methyl-morpholine, in a solvent such as a halogenated hydrocarbon, e.g. dichloromethane or carbon tetrachloride or an amide, e.g. dimethyl-formamide, at for example ambient temperature. Alternatively, the acylation may be carried out under the same conditions with an acid (for example one of the alkylating agents described above in which $X^1$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction.

In a further example compounds may be obtained by sulphonylation of a compound containing an —OH group by reaction with one of the above alkylating agents but in which $X^1$ is replaced by a —S(O)Hal or —$SO_2$Hal group [in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a -$L^1$H or -$L^2$H group as defined above may be coupled with one of the alkylation agents just described but in which $X^1$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —$CO_2R^5$, —$CO_2R^{11}$ or —$CO_2Alk^7$ in the compounds may be converted to the corresponding acid [—$CO_2H$] by acid- or base-catalysed hydrolysis depending on the nature of the groups $R^5$, $R^{11}$ or $Alk^7$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —$OR^5$ or —$OR^{14}$ groups [where $R^5$ or $R^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around $-78°$ C.

Alcohol [—OH] groups may also be obtained by hydrogenation of a corresponding —$OCH_2R^{14}$ group (where $R^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [$CO_2Alk^7$ or $CO_2R^5$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^5$ or —$OR^{14}$ group by coupling with a reagent $R^5OH$ or $R^{14}OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NHR^3$ or —$NHSO_2NHAr^1$] groups in the compounds may be obtained, in another example, by reaction of a corresponding amine [—$NH_2$] with a sulphamide $R^3NHSO_2NH_2$ or $Ar^1NHSO_2NH_2$ in the presence of an organic base such as pyridine at an elevated temperature, e.g. the reflux temperature.

In another example compounds containing a —$NHCSAr^1$, —$CSNHAr^1$, —$NHCSR^3$ or —$CSNHR^3$ may be prepared by treating a corresponding compound containing a —$NHCOAr^1$, —$CONHAr^1$, —$NHCOR^3$ or —$CONHR^3$ group with a thiation reagent, such as Lawesson's Reagent, in an anhydrous solvent, for example a cyclic ether such as tetrahydrofuran, at an elevated temperature such as the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around $-78°$ C., in a solvent such as tetrahydrofuran and then quenched with an electrophile to introduce a desired substituent, for example, a formyl group may be introduced by using dimethylformamide as the electrophile; a thiomethyl group may be introduced by using dimethyldisulphide as the electrophile.

In another example, sulphur atoms in the compounds, for example when present in a linker group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In another example compounds of formula $Ar^1X^1$ (where $X^1$ is a halogen atom such as a chlorine, bromine or iodine atom) may be converted to such compounds as $Ar^1CO_2R^{20}$ (in which $R^{20}$ is an optionally substituted alkyl, aryl or heteroaryl group), $Ar^1CHO$, $Ar^1CHCHR^{20}$, $Ar^1CCR^{20}$, $Ar^1N(R^{20})H$, $Ar^1N(R^{20})_2$, for use in the synthesis of for example compounds of formula $Ar^1L^2Ar^2AlkN(R^2)H$, using such well know and commonly used palladium mediated reaction conditions as are to be found in the general reference texts *Rodd's Chemistry of Carbon Compounds*, Volumes 1-15 and Supplementals (Elsevier Science Publishers, 1989), *Fieser and Fieser's Reagents for Organic Synthesis*, Volumes 1-19 (John Wiley and Sons, 1999), *Comprehensive Heterocyclic Chemistry*, Ed. Katritzky et al, Volumes 1-8, 1984 and Volumes 1-11, 1994 (Pergamon), *Comprehensive Organic Functional Group Transformations*, Ed. Katritzky et al, Volumes 1-7, 1995 (Pergamon), *Comprehensive Organic Synthesis*, Ed. Trost and Flemming, Volumes 1-9, (Pergamon, 1991), *Encyclopedia of Reagents for Organic Synthesis*, Ed. Paquette, Volumes 1-8 (John Wiley and Sons, 1995), *Larock's Compre-* hensive Organic Transformations (VCH Publishers Inc., 1989) and March's Advanced Organic Chemistry (John Wiley and Sons, 1992).

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above. Alternatively, a particular enantiomer may be obtained by performing an enantiomer specific enzymatic biotransformation e.g. an ester hydrolysis using an esterase and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the invention. All temperatures are in ° C. The following abbreviations are used:

NMM—N-methylmorpholine; EtOAc—ethyl acetate;
MeOH—methanol; BOC—butoxycarbonyl;
DCM—dichloromethane; AcOH—acetic acid;
DIPEA—diisopropylethylamine; EtOH—ethanol;
Pyr—pyridine; Ar—aryl;
DMSO—dimethylsulphoxide; iPr—isopropyl;
$Et_2O$—diethylether; Me—methyl;
THF—tetrahydrofuran, DMF—N,N-dimethylformamide;
FMOC—9-fluorenylmethoxycarbonyl;
DBU—1,8-Diazabicyclo[5, 4-0]undec-7-ene;
DMAP—4-(dimethylamino)pyridine.
HOBT—1-hydroxybenzotriazole All NMR's were obtained either at 300 MHz or 400 MHz.

All Intermediates and Examples were named with the aid of Beilstein Autonom (available from MDL Information Systems GmbH, Therdor-Heuss-Allee 108D 60486, Frankfurt, Germany) or were given names that seemed consistent, with the exception that propanoates were named by the IUPAC name rather than the trivial name (propionate) and isonicotinoyl (trivial name) is used in place of pyridine-4-carbonyl.

INTERMEDIATE 1

(+/−) 3-Ethoxy-4-methyl-4-propyl-2-cyclobuten-1-one

The title compound was prepared using a modification of the method of Wasserman, H. H. et al [J. Org. Chem., 38, 1451-1455, (1973)]; to a solution of 2-methyl pentanoyl chloride (3.91 ml) and ethyl ethynylether (5 g, 40% solution in hexanes, 28.6 mmol) in $Et_2O$ (35 ml) at room temperature was added triethylamine (9.9 ml), with stirring. The reaction was warmed to 50° and stirred for 72 h prior to cooling and filtration. The filtrate was concentrated in vacuo and the residual oil chromatographed ($SiO_2$; hexanes 80: EtOAc 20) to give the title compound as a colourless oil (3.71 g, 17.9 mmol, 77%). δH ($CDCl_3$, 300K), 4.84 (1H, s), 4.24-3.98 (2H, m), 2.04 (3H, s), 1.56-1.43 (4H, m), 1.30-1.26 (3H, m), 0.91 (3H, t, J 7.3 Hz). m/z ($ES^+$, 70V) 178.1 ($MH^+$).

INTERMEDIATE 2

(+/−) 3-Hydroxy-4-methyl-4-propyl-2-cyclobuten-1-one

Intermediate 1 (1 g, 59.5 mmol) and conc. hydrochloric acid (2 ml) were stirred vigorously at room temperature for 48 h. The resulting slurry was filtered and the residue washed with water (3×10 ml) and dried under vacuum to give the title compound as an off-white powder (620 mg, 44.2 mmol, 74%). δH ($CDCl_3$, 300K) 3.79 (2H, s), 1.59-1.53 (2H, m), 1.41-1.27 (2H, m), 1.18 (3H, s), 0.85 (3H, t, J 7.3 Hz). m/z ($ES^+$, 70V) 140.9 ($MH^+$).

INTERMEDIATE 3

3-Ethoxy-4,4-dipropyl-2-cyclobuten-1-one

The title compound was prepared using a modification of the method of Wasserman, H. H. et al, [J. Org. Chem., 38, 1451-1455, (1973)]; triethylamine (29 ml) was added dropwise at room temperature to a well-stirred solution of di-n-propylacetyl chloride (13.9 g, 85.8 mmol) and ethyl ethynylether (15 g, 40% solution in hexanes, 85.7 mmol) in toluene (120 ml. The reaction was warmed to 60° and stirred for 48 h prior to cooling and filtration. The filtrate was concentrated in vacuo and the residual oil chromatographed ($SiO_2$; hexanes 80: EtOAc 20) to give the title compound as a brown oil (11.2 g, 57.1 mmol, 67%). δH($CDCl_3$, 300K) 5.02 (1H, s), 4.32 (2H, q, J 7.1 Hz), 1.69-1.61 (4H, m), 1.45-1.40 (4H, m), 1.02 (6H, t, J 7.3 Hz). m/z ($ES^+$, 70V) 197.1 ($MH^+$).

INTERMEDIATE 4

3-Hydroxy-4,4-dipropyl-2-cyclobuten-1-one

Intermediate 3 (10.2 mmol) and 6M hydrochloric acid (10 ml) were stirred vigorously at 65° for 72 h. The resulting slurry was diluted with DCM (30 ml) and distilled water (30 ml) and extracted with DCM (3×10 ml). The combined extracts were dried ($MgSO_4$), filtered and concentrated in vacuo to give the title compound as a pale yellow oil, which crystallised on standing (1.49 g, 8-87 mmol, 87%).

INTERMEDIATE 5

3-Ethoxy-2-hexyl-4,4-dimethyl-2-cyclobuten-1-one

The title compound was prepared using a modification of the method of Wasserman, H. H. et al, [J. Org. Chem., 38, 1451-1455, (1973)]; triethylamine (22 ml) was added dropwise at room temperature to a well-stirred solution of isobutyryl chloride (7.3 ml, 69 mmol) and 1-ethoxy-1-octyne [prepared according to the method of Kocienski, P. et al Tetrahedron Lett. 1833, 30, (1989)] (6.5 g, 63 mmol) in diethylether (100 ml). The reaction was warmed to 35° and stirred for 96 h prior to cooling and filtration. The filtrate was concentrated in vacuo and the residual oil chromatographed (SiO$_2$; hexanes 80: EtOAc 20) to give the title compound as a brown oil (8.6 g, 38 mmol, 61%). δH (CDCl$_3$, 300K) 4.34 (2H, d, J 7.1 Hz), 2.05 (2H, dd, J 5.6 Hz, 7.3 Hz), 1.44 (3H, t, J 7.1 Hz), 1.27-1.12 (8H, m), 1.23 (6H, s), 0.89 (3H, t, J 2.7 Hz). m/z (ES$^+$, 70 V) 225.0 (MH$^+$).

INTERMEDIATE 6

2-Hexyl-3-hydroxy-4,4-dimethyl-2-cyclobuten-1-one

Intermediate 5 (7.6 g, 34.0 mmol) and 6M hydrochloric acid (10 ml) were stirred vigorously at 100° for 18 h. The resulting slurry was diluted with DCM (30 ml) and distilled water (30 ml) and extracted with DCM (3×10 ml). The combined extracts were dried (MgSO$_4$), filtered and concentrated in vacuo. The residue was triturated with hexanes and filtered to give the title compound as an off-white powder (6.5 g, 33.0 mmol, 98%). δH (CDCl$_3$, 300K) 2.01 (2H, t, J 7.0 Hz), 1.49-1.44 (2H, m), 1.34-1.19 (14H, m), 0.89-0.84 (3H, m). m/z (ES$^+$, 70 V) 197.0 (MH$^+$).

INTERMEDIATE 7

(+/−) 4-Benzyl-3-ethoxy-4-methyl-2-cyclobuten-1-one

The title compound was prepared using a modification of the procedure of Wasserman et al [J. Org. Chem., 38, 1451-1455, (1973)]; triethylamine (20 ml) was added to a stirred solution containing α-methyl tetrahydro-cinnamoyl chloride (5 g, 27.5 mmol) and ethyl ethynylether (6 g, 40% soln. in hexanes, 85.7 mmol) and the resulting slurry heated to 35° for 3 d. The crude reaction mixture was then filtered and the residue concentrated in vacuo. The residual oil was chromatographed (SiO$_2$, EtOAc 20: hexanes 80) to give the title compound as a pale brown oil (4.91 g, 86%) δH (CDCl$_3$, 300K) 7.19-7.05 (5H, m), 4.56 (1H, s), 4.09-4.00 (1H, m), 3.97-3.89 (1H, m), 2.86 (1H, d, J 14.0 Hz), 2.86 (1H, d, J 14.0 Hz), 1.30 (3H, t, J 7.1 Hz), 1.24 (3H, s). m/z (ES$^+$, 70V) 216.9 (MH$^+$).

INTERMEDIATE 8

(+/−) 4-Benzyl-3-hydroxy-4-methyl-2-cyclobuten-1-one

Intermediate 7 (4.5 g, 20.9 mmol) and hydrochloric acid (6M, 10 ml) were stirred at room temperature for 48 h. Filtration of the resulting slurry and washing of the residue with water (3×15 ml) gave the title compound as a pale brown powder (3.92 g, 20.8 mmol, 99%). δH (CDCl$_3$, 300K) 7.03-6.83 (5H, m), 4.24 (1H, s), 2.52 (2H, s), 0.94 (3H, s). m/z (ES$^+$, 70V) 189.1 (MH$^+$).

INTERMEDIATE 9

3-Cyano-4-(2-(N,N-dimethylamino)ethylen-1-yl)pyridine

A solution of 4-methyl-3-cyanopyridine [prepared according to Ref: J. Prakt. Chem. 338, 663 (1996)], (8.0 g, 67.8 mmol) and N,N-dimethylformamide diethyl acetal (11.0 g, 74.8 mmol) in dry DMF (50 ml) was stirred at 140° under N$_2$ for 2 days. An additional portion of N,N,-dimethylformamide diethyl acetal (5 g) was added and stirred at 140° for 4 h. The volatiles were removed in vacuo and the obtained dark oil partitioned between EtOAc (300 ml) and water (50 ml). The phases were separated and the aqueous layer re-extracted with EtOAc (3×100 ml). The combined organic extracts were washed with brine (30 ml), dried (Na$_2$SO$_4$), treated with activated charcoal, filtered and evaporated in vacuo to afford essentially pure title compound as a dull orange solid (10.1 g, 85%). δH (CDCl$_3$) 8.49 (1H, s), 8.25 (1 h, d, J 5.9 Hz), 7.29 (1H, d, J 13.2 Hz), 7.09 (1H, d, J 5.9 Hz), 5.25 (1H, d, J 13.2 Hz) and 2.99 (6H, s); m/z (ES$^+$, 70V) 174 (MH$^+$).

INTERMEDIATE 10

1-Hydroxy-2,7-naphthyridine Hydrochloride Salt

HCl gas was bubbled through a stirred solution of Intermediate 9 (6.2 g, 3.58 mmol) in glacial acetic acid (50 ml) and water (0.64 ml, 3.55 mmol) for 1-2 min. The reaction mixture was stirred in a stoppered flask at 40° for 18 h. The volatiles were removed in vacuo affording a dark residue, which was treated with water (3×20 ml) and re-evaporated in vacuo. The obtained dark semi-solid was treated with 40 ml warm ethanol, ice-cooled, and the undissolved solid collected by filtration affording the title compound as a green coloured solid (5.2 g, 80%) δH (DMSO-d$^6$) 12.5 (1H, br s), 9.38 (1H, s), 8.84 (1H, d, J 7.0 Hz), 8.15 (1H, d, J 7.0 Hz), 7.89 (1H, br dd, J 7.0, 5.0 Hz) and 6.85 (1H, d, J 7.0 Hz); m/z (ES$^+$, 70V), 147 (MH$^+$).

INTERMEDIATE 11

1-Chloro-2,7-naphthyridine

Intermediate 10 (5.2 g, 28.5 mmol) was stirred with phosphorous oxychloride (75 ml) at 110° for 24 h. The volatiles were removed in vacuo affording a dark oil which was poured into an ice-bath cooled mixture of saturated aqueous NaHCO$_3$ (100 ml containing 20 g solid NaHCO$_3$) and EtOAc (100 ml). After thorough mixing the phases were separated and the aqueous layer re-extracted with EtOAc (2×75 ml). The combined organic extracts were washed with brine (15 ml), dried (Na$_2$SO$_4$) and evaporated in vacuo to afford the title compound as a yellow solid (4.0 g, 85%) δH (CDCl$_3$) 9.45 (1H, s), 8.81 (1H, d, J 5.7 Hz), 8.47 (1H, d, J 5.7 Hz), 7.66 (1H, d, J 5.7 Hz) and 7.60 (1H, d, J 5.7 Hz); m/z (ES$^+$, 70V) 165 and 167 (MH$^+$).

INTERMEDIATE 12

Ethyl (2S)-2-amino-3-[4-(2,7-naphthyridin-1-ylamino)phenyl]propanoate

A solution of ethyl-(S)-3-[4-aminophenyl]-2-[t-butoxycarbonylamino]propanoate (638 mg, 2.07 mmol) and Intermediate 11 (310 mg, 1.88 mmol) in ethoxyethanol (2 ml) was stirred at 120° for 15 min and at 100° for 1 h under nitrogen. The volatiles were removed in vacuo and the dark residue partitioned between EtOAc (70 ml) and saturated aqueous NaHCO$_3$ (10 ml). The phases were separated and the aqueous layer re-extracted with EtOAc (2×30 ml). The combined organic extracts were washed with brine (10 ml)T dried (Na$_2$SO$_4$) and evaporated in vacuo to afford a dark foam. Chromatography (SiO$_2$; 5 to 10% MeOH/DCM) afforded a mixture of ethyl-(S)-3-[4-(2,7-naphthyridin-1-ylamino)phenyl]-2-[(t-butoxycarbonyl)amino]propanoate and some of the title compound (730 mg). This mixture was treated with a solution of trifluoroacetic acid (5 ml) and DCM (5 ml) at room temperature for 1 h. The volatiles were removed in vacuo and the residue partitioned between EtOAc (75 ml) and saturated aqueous NaHCO$_3$ (20 ml). The phases were separated and the aqueous layer re-extracted with EtOAc (3×30 ml). The combined organic extracts were washed with brine (10 ml), dried (Na$_2$SO$_4$) and evaporated in vacuo to afford an orange solid. Chromatography (SiO$_2$; 10% MeOH/DCM) afforded the title compound as a straw-coloured solid (420 mg, 60% over two steps). δH (CDCl$_3$) 10.70 (1H, s), 10.31 (1H, s), 9.44 (1H, d, J 5.6 Hz), 8.94 (1H, d, J 5.6 Hz), 8.55 (1H, d, J 7.3 Hz), 8.54 (2H, d, J 8.5 Hz), 8.46 (1H, d, J 5.6 Hz), 7.94 (2H, d, J 8.5 Hz), 4.84 (2H, q, J 7.1 Hz), 4.35 (1H, t, J 6.6 Hz), 4.10 (2H, br s), 3.64 (1H, dd, J 13.5, 6.4 Hz), 3.56 (1H, dd, J 13.5, 7.0 Hz) and 1.95 (3H, t, J 7.1 Hz); m/z (ES$^+$, 70V) 337 (MH$^+$).

INTERMEDIATE 13

Methyl (2S)-2-amino-3-[4-(2,7-naphthyridin-1-yloxy)phenyl]propanoate

A mixture of N-(BOC)—(S)-tyrosine methyl ester (1.71 g, 5.80 mmol) potassium carbonate (0.80 g, 5.80 mmol) and Intermediate 11 (1.0 g, 6.08 mmol) in dry DMF (10 ml) was stirred at room temperature for 18 h, and at 40° for 18 h. The DMF was removed in vacuo and the residue partitioned between EtOAc (80 ml) and 10% aqueous Na$_2$CO$_3$ (20 ml). The phases were separated and the aqueous layer re-extracted with EtOAc (2×20 ml). The combined organic extracts were washed with brine (10 ml), dried (Na$_2$SO$_4$) and evaporated in vacuo to afford a new colourless oil. Chromatography (silica; 2.5% MeOH/DCM) afforded reasonably pure N-t-butoxycarbonyl protected title compound (1.75 g, 71%). This material was dissolved in EtOAc (40 ml) and HCl gas was bubbled through the stirred solution for 1 min. then the mixture was stirred for an additional 0.5 h. The volatiles were removed in vacuo affording a yellow solid which was partitioned between EtOAc (80 ml) and saturated aqueous NaHCO$_3$ (20 ml). The phases were separated and the aqueous layer re-extracted with EtOAc (2×20 ml). The combined organic extracts were washed with brine (10 ml), dried (Na$_2$SO$_4$) and evaporated in vacuo. The obtained oil was chromatographed (SiO$_2$; 5% MeOH/DCM) to afford the title compound as a near colourless oil (0.83 g, 62%) δH (CDCl$_3$) 9.77 (1H, s), 8.75 (1H, d, J 5.8 Hz), 8.10 (1H, d, J 5.8 Hz), 7.58 (1H, d, J 5.8 Hz), 7.29 (2H, d, J 8.4 Hz), 7.25 (1H, d, J 5.9 Hz), 7.21 (2H, d, J 8.4 Hz), 3.80-3.70 (1H, obscured m), 3.72 (3H, s), 3.15 (1H, dd, J 13.6, 5.1 Hz), 2.88 (1H, dd, J 13.6, 8.0 Hz) and 0.78 (2H, br s); m/z (ES$^+$, 70V) 324 (MH$^+$).

INTERMEDIATE 14

4-Acetonyl-3-cyanopyridine

A solution of 4-methyl-3-cyanopyridine (4 g, 33.9 mmol) and N$_1$N-dimethylacetamide dimethylacetal (5.4 g, 40.6 mmol) in dry DMF (20 ml) was stirred at 130° for 7 h. The volatiles were removed in vacuo to afford a dark oil which solidified on standing. This material was chromatographed (SiO$_2$; 50% EtOAc/Hexane—100% EtOAc) affording the title compound as an off-yellow solid (3.73 g, 69%). δH (CDCl$_3$) 8.87 (1H, s), 8.74 (1H, d, J 5.2 Hz), 7.28 (1H, d, J 5.2 Hz), 4.00 (2H, s) and 2.36 (3H, s): m/z (ES$^+$, 70V) 161 (MH$^+$).

INTERMEDIATE 15

1-Hydroxy-3-methyl-2,7-naphthyridine Hydrochloride

HCl gas was bubbled through a stirred solution of Intermediate 14 (3.73 g, 23.3 mmol) in glacial acetic acid (40 ml) for several minutes. The flask was stoppered and reaction stirred for 18 h at ambient temperature. The volatiles were removed in vacuo affording a straw-coloured solid. This was twice treated with water (30 ml portions) and re-evaporated in vacuo to dryness, affording the title compound (contaminated with ~25% unidentified by-product) as a dark straw coloured solid (4.1 g). δH (DMSO-d$^6$) 12.46 (1H, br s), 9.32 (1H, s), 8.71 (1H, d, J 6.5 Hz), 7.98 (1H, d, J 6.5 Hz), 6.67 (1H, s) and 2.38 (3H, s); m/z (ES$^+$, 70V) 161 (MH$^+$). Used without further purification.

INTERMEDIATE 16

1-Chloro-3-methyl-2,7-naphthyridine

Intermediate 15 (4.1 g) was treated with phosphorus oxychloride (50 ml) at 130° for 3 h, affording a dark solution. The volatiles were removed in vacuo and the obtained dark oil extracted with Et$_2$O (100 ml). Saturated aqueous NaHCO$_3$ (ice cold; containing 10 g additional solid NaHCO$_3$) was poured (with CARE!) onto the crude product with swirling and ice-bath cooling. After thorough shaking, addition Et$_2$O (80 ml) was added, the mixture re-shaken, and the phases separated. The aqueous layer was re-extracted with Et$_2$O (2×80 ml) and the combined ethereal extracts washed with brine (20 ml), dried (Na$_2$SO$_4$) and evaporated in vacuo to afford an orange solid (3.6 g). Chromatography (silica; 70% EtOAc/Hexane-100% EtOAc) afforded a more-polar by-product (3-methyl-1H-pyrano[3,4-c]pyridin-1-one, (0.7 g) and the title compound as a white solid (2.82 g, 79% from intermediate 14) δH (CDCl$_3$) 9.66 (1H, s), 8.73 (1H, d, J 5.8 Hz), 7.56 (1H, d, J 5.8 Hz), 7.40 (1H, s) and 2.69 (3H, s); m/z (ES$^+$, 70V) 179 and 181 (MH$^+$).

INTERMEDIATE 17

Ethyl (2S)-2-[(tert-butoxycarbonyl)amino]-3-{4-[(3-methyl[2,7-naphthyridin-1-ylamino] phenyl}propanoate Hydrochloride Acetylchloride (55 mg, 50 ml, 0.70 mmol) was added to absolute ethanol (25 ml) and stirred for one minute. Intermediate 16 (2.50 g, 14.0 mmol) and ethyl-(S)-3-[4-amino phenyl]-2-{tert-butyloxycarbonyl]propanoate (4.31 g, 14.0 mmol) were added and the reaction mixture stirred at 60° for 2.75 h. The volatiles were removed in vacuo to afford a yellow-orange solid. This was treated with EtOAc (~25 ml), warmed, re-cooled and the precipitate collected by filtration, with Et$_2$O washing, affording the title compound as a yellow solid (4.96 g, 73%). δH (CDCl$_3$) 10.44 (1H, br s), 10.33 (1H, br s), 8.60 (1H, d, J 6.5 Hz), 8.00 (1H, d, J 6.5 Hz), 7.85 (2H, d, J 8.5 Hz), 7.28 (1H, d, J 8.0 Hz), 7.23 (2H, d, J 8.5 Hz), 7.16 (1H, s), 4.19-4.01 (1H, m), 4.08 (2H, q, J 7.0 Hz), 2.97 (1H, dd, J 13.8, 5.4 Hz), 2.86 (1H, dd, J 13.8, 10.0 Hz), 2.50 (3H, s), 1.34 (9H, s) and 1.15 (3H, t, J 7.0 Hz); m/z (ES$^+$, 70V) 451 (MH$^+$).

INTERMEDIATE 18

Ethyl-(2S)-2-amino-3-{4-[(3-methyl[2,7]naphthyridin-1-yl)amino]phenyl}propanoate HCl gas was bubbled through a stirred solution of Intermediate 17 (4.95 g, 10.2 mmol) for 1-2 min. After 30 min stirring at ambient temperature the volatiles were removed in vacuo affording a yellow powder. This was treated with saturated aqueous NaHCO$_3$ (30 ml) then extracted with EtOAc (100 ml, and 3×50 ml). The combined organic extracts were washed with brine (10 ml), dried (Na$_2$SO$_4$) and evaporated in vacuo affording the title compound as a yellow solid (3.56, 100%). δH (CDCl$_3$) 9.25 (1H, s), 8.50 (1H, d, J 5.6 Hz), 7.66 (2H, d, J 8.4 Hz), 7.35 (1H, d, J 5.6 Hz), 7.34 (1H, masked s), 7.14 (2H, d, J 8.4 Hz), 6.81 (1H, s), 4.12 (2H, q, 47.2 Hz), 3.65 (1H, dd, J 7.8, 5.2 Hz), 3.02 (1H, dd, J 13.7, 5.2 Hz), 2.80 (1H, dd, J 13.7, 7.8 Hz), 2.48 (3H, s), 1.56 (2H, br s) and 1.21 (3H, t, J 7.2 Hz); m/z (ES$^+$, 70V) 351 (MH$^+$).

INTERMEDIATE 19

Ethyl (2S)-2-[(tert-butoxycarbonyl)amino]-3-{4-[(3-methyl[2,7]naphthyridin-1-yl)oxy]phenyl}propanoate A mixture of N-t-butyloxycarbonyl-(S)-tyrosine ethyl ester (14.5 g, 46.9 mmol), caesium carbonate (14.05 g, 43.1 mmol) and Intermediate 9 (7.0 g, 39.2 mmol) in dry DMF (60 ml) was stirred at room temperature for 48 h. The reaction was diluted with Et$_2$O (150 ml) and filtered off. The filtrate was evaporated under high vacuum and the residue was chromatographed (SiO$_2$; 40%-60% EtOAc/Hexane) which afforded the title compound as a viscous, straw-coloured oil (16.2 g, 77%) δH (CDCl$_3$) 9.56 (1H, s), 8.58 (1H, d, J 5.8 Hz), 7.39 (1H, d, J 5.8 Hz), 7.15-7.10 (4H, m), 7.00 (1H, s), 4.99-4.91 (1H, m), 4.54-4.46 (1H, m), 4.09 (2H, q, J 7.1 Hz), 3.10-2.99 (2H, m), 2.36 (3H, s), 1.34 (9H, s) and 1.15 (3H, t, J 7.1 Hz); m/z (ES$^+$, 70V) 452 (MH$^+$).

INTERMEDIATE 20

Ethyl (2S)-2-amino-3-{4-[(3-methyl[2,7]naphthyridin-1-yl)oxy]phenyl}propanoate HCl gas was bubbled through a stirred solution of Intermediate 19 (16 g) in EtOAc (300 ml) until a persistent fine white precipitate formed (~2 minutes). After stirring for 0.5 h the volatiles were removed in vacuo. The obtained solid was partitioned between EtOAc (250 ml) and saturated aqueous NaHCO$_3$ (80 ml plus 5 g solid NaHCO$_3$). The phases were separated and the aqueous layer re-extracted with EtOAc (5×50 ml). The combined organic extracts were washed with brine (10 ml), dried (Na$_2$SO$_4$) and evaporated in vacuo to afford an oil. Chromatography (SiO$_2$; 100% EtOAC-10% EtOH/EtOAc) afforded the title compound as a viscous oil (11.1 g, 89%). δH (CDCl$_3$) 9.71 (1H, s), 8.70 (1H, d, J 5.Hz), 7.50 (1H, d, J 5.8 Hz), 7.31-7.28 (4H, m), 7.11 (1H, s), 4.23 (2H, q, J 7.1 Hz), 3.79-3.72 (1H, m), 3.14 (1H, dd, J 14.1, 5.4 Hz), 2.94 (1H, dd, J 14.1, 7.8 Hz), 2.47 (3H, s), 1.75-1.50 (2H, br s) and 1.30 (3H, t, J 7.1 Hz); m/z (ES$^+$, 70V) 352 (MH$^+$).

INTERMEDIATE 21

1-Chloro-2,6-naphthyridine

1-Hydroxy-2,6-naphthyridine (550 mg) [prepared according to the method of Sakamoto, T. et al Chem. Pharm. Bull. 33, 626, (1985)] was stirred with phosphorous oxychloride (10 ml) at 110° for 5 h. The volatiles were removed in vacuo and the residue treated carefully with ice. After diluting with water (to ~25 ml), solid NaHCO$_3$ was added to effect neutralisation and the product extracted into EtOAc (2×80 ml). The combined organic extracts were dried (MgSO$_4$), evaporated in vacuo, and the crude product chromatographed (SiO$_2$; EtOAc) affording the title compound as a slightly yellow solid (420 mg, 68%). δH (CDCl$_3$) 9.35 (1H, s), 8.82 (1H, d, J 5.9 Hz), 8.48 (1H, d, J 5.6 Hz), 8.00 (1H, d, J 5.9 Hz), 7.74 (1H, d, J 5.6 Hz); m/z (ES$^+$, 70V) 165 and 167 (MH$^+$).

INTERMEDIATE 22

Ethyl (2S)-2-[(tert-butoxycarbonyl)amino]3-[4-([2,6]naphthyridin-1-ylamino)phenyl]propanoate Ethyl (S)-3-(4-aminophenyl)-2-[N-(t-butyloxycarbonyl)amino]propanoate (600 mg, 1.95 mmol), Intermediate 21 (350 mg, 2.13 mmol) and DIPEA (276 mg, 372 μl, 2.13 mmol) in 2-ethoxyethanol (0.5 ml) were stirred at 130° under N$_2$ for several hours. The reaction was partitioned between EtOAc (70 ml) and saturated aqueous NaHCO$_3$ (30 ml). The phases were separated and the aqueous layer re-extracted with EtOAc (3×30 ml). The combined organic extracts were washed with brine (10 ml), dried (MgSO$_4$) and evaporated in vacuo to afford a dark oil. Chromatography (SiO$_2$; 3% MeOH/DCM) gave the title compound as a dull orange foam (360 mg, 42%). δH (CDCl$_3$) 9.19 (1H, s), 8.67 (1H, d, J 5.9 Hz), 8.24 (1H, d, J 5.8 Hz), 7.66 (1H, d, J 5.9 Hz), 7.65 (2H, d, J 8.5 Hz), 7.21 (1H, d, J 5.8 Hz), 7.16 (2H, d, J 8.5 Hz), 7.15 (1H, obscured s), 5.05-4.97 (1H, m), 4.60-4.51 (1H, m), 4.19 (2H, q, J 7.1 Hz), 3.17-3.04 (2H, m), 1.44 (9H, s), 1.27 (3H, t, J 7.1 Hz); m/z (ES$^+$, 70V) 459 (MNa$^+$), 437 (MH$^+$).

INTERMEDIATE 23

Ethyl (2S)-2-amino-3-[4-([2,6]naphthyridin-1-ylamino)phenyl]propanoate

Intermediate 22 (360 mg) was treated with a solution of trifluoroacetic acid (10 ml) and DCM (10 ml) and stirred at RT for 2 h. The volatiles were removed in vacuo and the residue was partitioned between EtOAc (80 ml) and saturated aqueous NaHCO$_3$ (30 ml). The phases were separated and the aqueous layer re-extracted with EtOAc (3×30 ml). The combined organic extracts were dried (MgSO$_4$) and evaporated in vacuo to afford the title compound as a dark orange viscous oil (280 mg, 100%). 5H (CDCl$_3$) 9.18 (1H, s), 8.66 (1H, d, J 5.9 Hz), 8.22 (1H, d, J 5.8 Hz), 7.67 (1H, d, J 5.9 Hz), 7.64 (2H, d, J 8.5 Hz), 7.22 (2H, d, J 8.5 Hz), 7.19 (1H, d, J 5.8 Hz), 4.20 (2H, q, 47.1 Hz), 3.73 (1H, dd, J 7.9, 5.1 Hz), 3.10 (1H, dd, J 13.6, 5.2 Hz), 2.87 (1H, dd, J 13.6, 7.9 Hz), 1.70 (3H, br s), 1.28 (3H, t, 7.1 Hz); m/z (ES$^+$, 70V) 337 (MH$^+$).

INTERMEDIATE 24

Methyl (2S)-2-(t-butoxycarbonyl)amino]-3-[4-([2,6]naphthyridin-1-yloxy)phenyl]propanoate To N-(t-butyloxycarbonyl)-(S)-tyrosine methyl ester (1.42 g, 4.82 mmol) in dry DMF (10 ml) was added Intermediate 21 (0.79 g, 4.82 mmol) and cesium carbonate (1.65 g, 5.06 mmol) and the reaction stirred at 45° under N2 for 2 days. The DMF was evaporated, EtOAc added and washed (3×) with water, dried (MgSO$_4$), and evaporated in vacuo. The residue was chromatographed (SiO$_2$; 40 to 100% EtOAc/isohexane)

to afford the title compound as white foam (1.61 g, 82%). δH (CDCl$_3$) 9.29 (1H, s), 8.76 (1H, d, J 5.74 Hz), 8.17 (1H, d, J 5.74 Hz), 8.11 (1H, d, J 5.8 Hz), 7.43 (1H, d, J 5.8 Hz), 7.22-7.18 (3H, m), 5.03 (1H, br s), 4.61 (1H, br s), 3.75 (3H, s), 3.15-3.05 (2H, m), 1.44 (9H, s); m/z (ES$^+$, 70V) MH$^+$ 424.

INTERMEDIATE 25

3,5-Dichloropyridine-4-carboxylic Acid

A solution of 3,5-dichloropyridine (5.00 g, 33.8 mmol) in THF (25 ml) was added to a solution of LDA [generated from nBuLi (2.5M solution in hexanes, 14.9 ml, 37.2 mmol) and diisopropylamine (4.10 g, 5.7 ml, 40.6 mmol)] in THF (25 ml) at −78° under nitrogen, to give a yellow/brown slurry. The reaction was stirred for 30 min at −78° then CO$_2$ gas was bubbled through to give a clear brown solution that slowly gave a precipitate, warmed to RT over 2 h, then quenched with water (20 ml) and partitioned between Et$_2$O (100 ml) and 1M NaOH (100 ml). The aqueous layer was separated and acidified to pH 1 with concentrated hydrochloric acid and then extracted with 10% MeOH in DCM (100 ml×3). The combined organic layers were dried (MgSO$_4$) and the solvent removed under vacuum to give a brown solid that was recrystallised from ethanol and dried under vacuum to give the title compound as pinkish crystals (2.63 g, 41%). δH (DMSO-d$^6$) 8.74 (2H, s). δC (DMSO-d$^6$) 163.5, 147.7, 141.0, 126.7.

INTERMEDIATE 26

Ethyl (2S)-2-[(tert-butoxycarbonyl)amino]-3-{4-[(3,5-dichloroisonicotinoyl)amino]phenyl}propanoate A slurry of the compound of Intermediate 25 (51.2 g, 0.267 mol) in DCM (195 ml) and thionyl chloride (195 ml, 2.67 mol) was treated with DMF (5 drops) and heated to reflux for 4 h. The reaction was concentrated in vacuo and azeotroped with toluene (2×50 ml) to give a yellow solid which was used without further purification. A solution of ethyl-(S)-3-(4-aminophenyl)-2-(t-butoxycarbonyl amino)propionate (130.8 g, 0.425 mol) in DCM (800 ml) was cooled to 0° and treated with NMM (56.0 ml, 0.51 mol), stirred for 5 minutes and then a solution of the acid chloride (98.3 g, 0.468 mol) in DCM (200 ml) was added dropwise keeping the reaction temperature below 5°. The reaction was stirred for 1 h, quenched with NaHCO$_3$ solution (500 ml), the organic layer separated, washed with NaHCO$_3$ solution (500 ml), 10% citric acid solution (500 ml) and NaHCO$_3$ solution (500 ml), dried (MgSO$_4$) and concentrated in vacuo to give a yellow solid which was recrystallised (EtOAc/hexane) to give the title compound, (140 g, 69%). δH (DMSO d$^6$), 8.8 (2H, s), 7.55 (2H, d, J 8.5 Hz), 7.23 (2H, d, J 8.5 Hz), 4.0 (3H, m), 3.4 (2H, b s), 2.9 (1H, m), 2.8 (1H, m), 1.3 (9H, s), 1.25 (3H, t); m/z (ES$^+$, 70V) 504 (MNa$^+$).

INTERMEDIATE 27

Ethyl (2S)-2-amino-3-{4-[(3,5-dichloroisonicotinoyl)amino]phenyl}propanoate Hydrochloride A solution of the compound of Intermediate 26 (70 g, 0.146 mol) in EtOAc (500 ml) and 1,4-dioxan (50 ml) was treated with a solution of HCl in EtOAc (500 ml, 3M), and stirred at room temperature for 4 h. The reaction was concentrated in vacuo to give a yellow solid which was triturated with Et$_2$O then recrystallised (EtOAc/hexane) to give the title compound (59.3 g, 92%). δH (DMSO d$^6$), 11.10 (1H, s), 8.70 (2H, s) 7.55 (2H, d, J 8.4 Hz), 7.25 (2H, d, J 8.4 Hz), 4.10 (3H, m), 3.10 (2H, m), 1.10 (3H, m); m/z (ES$^+$, 70V) 382 (MH$^+$).

INTERMEDIATE 28

3-Ethoxy-7-oxaspiro[3.5]non-2-en-1-one

Tetrahydropyranyl-4-carboxylic acid (14.7 g, 0.11 mol) and DMF (0.5 ml) in DCM (150 ml) was treated dropwise with oxalyl chloride (1.1 eq, 10.9 ml, 0.12 mol). After 1 h the reaction mixture was concentrated in vacuo and the residual slurry was diluted with Et$_2$O (200 ml) and the resulting precipitate removed by filtration. The filtrate was treated with ethoxyacetylene (40% w/w solution in hexanes, 1.3 eq, 18 ml) followed dropwise with triethylamine (25 ml, 0.19 mol) and the reaction stirred for lid. Filtration and concentration of the filtrate in vacuo followed by chromatography (SiO$_2$, 5:1 EtOAc:hexanes) gave the title compound as a pale yellow oil (12.1 g, 59%). δH (CDCl$_3$, 300K) 4.85 (1H, s), 4.23 (2H, q, J 7.1 Hz), 3.89-3.75 (4H, m), 1.88-1.79 (4H, m), 1.47 (3H, t, J 7.1 Hz); m/z (ES$^+$, 70V) 182.9 (MH$^+$).

INTERMEDIATE 29

7-oxaspiro[3.5]nonane-1,3-dione

Intermediate 28 (12.1 g, 0.67 mol) and 2M hydrochloric acid (26 ml) were stirred vigorously for 24 h at room temperature. The resulting solution was concentrated to dryness and the residual slurry was washed with Et$_2$O (25 ml) to give the title compound as an off-white powder (8.93 g, 0.062 mol). δH (DMSO d$^6$, 300K) 4.80 (2H, s), 3.78 (4H, t, J 5.5 Hz), 2.62 (4H t J 5.5 Hz); m/z (ES$^+$, 70V) 154.9 (MH$^+$).

INTERMEDIATE 30

3-Ethoxyspiro[3.6]decan-1-one

A solution of cycloheptyl carbonyl chloride (10.0 g, 0.062 mol) and ethoxyacetylene (40% w/w solution in hexanes, 6.0 g, 0.083 mol, 12 ml) in diethylether (50 ml) was treated dropwise with triethylamine (20 ml, 0.14 mol) and the reaction stirred for 5 d at room temperature. Filtration and concentration of the filtrate in vacuo followed by chromatography (SiO$_2$, 5:1 EtOAc:hexanes) gave the title compound as a pale yellow oil (10.5 g, 0.054 mol, 87%). δH (CDCl$_3$, 300K) 4.78 (1H, s), 4.20 (2H, q J 7.1 Hz), 1.94-1.87 (2H, m), 1.83-1.77 (2H, m), 1.71-1.66 (2H, m), 1.63-1.52 (6H, m), 1.45 (3H, t J 7.1 Hz); m/z (ES$^+$, 70V) 194.9 (MH$^+$).

INTERMEDIATE 31

Spiro[3.6]decane-1,3-dione

Intermediate 30 (8.5 g, 0.044 mol) and 2M hydrochloric acid (30 ml) was stirred vigorously for 24 h at room temperature. The resulting slurry was extracted with EtOAc (3×100 ml), the extracts combined and concentrated in vacuo, and the resulting solid was recrystallised from diethyl ether to give the title compound as an off-white powder (7.1 g, 0.043 mol, 95%). SH (DMSO d$^6$, 300K) 4.58 (2H, s), 1.75-1.29 (12H, m); m/z (ES$^+$, 70V) 166.9 (MH$^+$)

INTERMEDIATE 32

7-Acetyl-3-ethoxy-7-azaspiro[3.5]non-2-en-1-one

A solution of 1-acetyl piperidine-4-carbonyl chloride (5.0 g, 26.4 mmol) and ethoxyacetylene (4.0 g, 55.5 mmol) in THF (60 ml) was treated dropwise with triethylamine (7.6 ml, 55.0 mmol). The resulting slurry was stirred at room temperature for 5 d prior to filtration and concentration of the filtrate in vacuo. Chromatography (SiO$_2$, 100% EtOAc to 95:5 EtOAc:MeOH) gave the title compound as a white powder (3.97 g, 17.8 mmol, 67%). δH (CDCl$_3$, 300K) 4.79 (1H, s), 4.17 (2H, q, J 7.1 Hz), 3.87-3.81 (1H, m), 3.56-3.42 (3H, m), 2.02 (3H, s), 1.85-1.67 (4H, m), 1.39 (3H, t, J 7.1 Hz); m/z (ES$^+$, 70V) 223.9 (MH$^+$).

INTERMEDIATE 33

7-Acetyl-7-azaspiro[3.5]nonane-1,3-dione

Intermediate 32 (700 mg, 0.31 mmol) and hydrochloric acid (2M, 5 ml) were stirred at room temperature for 4 h. Concentration of the resulting straw-coloured solution in vacuo gave the title compound as a pale brown water-soluble powder (535 mg, 0.027 mmol, 87%). m/z (ES$^+$, 70V) 195.9 (MH$^+$).

INTERMEDIATE 34

3-Ethoxy-7-methoxyspiro[3.5]non-2-en-1-one

Was prepared from 4-methoxy cyclohexanecarbonyl chloride (10 g, 52.1 mmol) and ethoxyacetylene (7.5 g, 0.10 mol) according to the method of Intermediate 1 to give the title compound as an approx. 1:1 mixture of isomers, as a pale yellow oil (7.2 g, 34.4 mmol, 65%). δH (CDCl$_3$, 300K) 4.81-4.79 (1H, s), 4.22-4.20 (2H q, J 7.1 Hz), 3.34-3.32 (3H, s), 3.31-3.22 (1H, m), 2.04-1.56 (8H, m), 1.44-1.43 (3H t, J 7.1 Hz); m/z (ES$^+$, 70V) 211.0 (MH$^+$).

INTERMEDIATE 35

7-Methoxyspiro[3.5]nonane-1,3-dione

Intermediate 34 (5.0 g, 23.9 mmol) and hydrochloric acid (2M, 20 ml) were stirred at room temperature for 18 h. The resulting slurry was then diluted with water (50 ml) and extracted with EtOAc (3×25 ml), the extracts were dried (MgSO$_4$), filtered, and concentrated in vacuo. Recrystallisation from diethylether gave the title compound as an off-white powder (4.06 g, 22.4 mmol, 94%). δH (CDCl$_3$, 300K) 3.81 (2H, s), 3.25 (4H, m) 1.96-1.90 (2H, m), 1.86-1.79 (2H, m), 1.73-1.66 (2H, m), 1.64-1.56 (2H, m); m/z (ES$^+$, 70V) 182.9 (MH$^+$).

INTERMEDIATE 36

Ethyl (2S)-2-amino-3-hydroxypropanoate Hydrochloride

A mixture of (2S)-2-amino-3-hydroxypropanoate (25 g, 238 mmol) and acetyl chloride (34 ml, 476 mmol) in absolute ethanol (250 ml) was stirred at 50° for 18 hr. The volatiles were removed in vacuo until the volume was reduced to ~100 ml. Upon cooling the resultant precipitate was collected, washed with ether and hexane to give the title compound as a white powder (26.3 g, 65%). δH NMR (DMSO d$^6$) 8.47 (3H, br s), 5.58 (1H, dd), 4.20 (2H, q), 4.08 (1H, t), 3.81 (2H, dd), 1.23 (3H, t).

INTERMEDIATE 37

Ethyl (2S)-2-[(tert-butoxycarbonyl)amino]-3-hydroxypropanoate

Di-tert-butyl dicarbonate (10.26 g, 47 mmol) was added to a stirred mixture of Intermediate 36 (7.98 g, 47 mmol) and NaHCO$_3$ (8.70 g, 2.2 equiv.) in dioxan/water (1:1) (80 ml) and stirred for 4.5 hr. The bulk of the solvent was removed in vacuo and the resultant slurry was treated with EtOAc (150 ml). The inorganics were removed by filtration with EtOAc. The filtrate was washed with 10% aq citric acid (30 ml), water (30 ml), saturated aq. NaHCO$_3$ (20 ml) and brine (20 ml) and dried (Na$_2$SO$_4$) and evaporated in vacuo to afford the title compound as a colourless oil (10.3 g, 94%). δH (CDCl$_3$) 5.45 (1H, br), 4.36 (1H, br), 4.26 (2H, q), 3.94 (2H, br m), 1.47 (9H, s), 1.28 (3H, t); m/z (ES$^+$, 70V) 233 (MH$^+$), 256 (MNa$^+$).

INTERMEDIATE 38

Ethyl (2)-2-[(tert-butoxycarbonyl)amino]-3-[(methylsulfonyl)oxy]propanoate

Methanesulphonyl chloride (730 µL, 9.43 mmol) was added to a stirred, ice-bath cooled solution of Intermediate 37 (2.0 g, 8.5 mmol) and 4-methylmorpholine (1.13 ml, 10.29 mmol) in dry DCM (30 ml) and stirred for 6 hr. The solvent was removed in vacuo and the residue treated with EtOAc (150 ml). The organics were washed with water (40 ml), 10% aq citric acid (20 ml), water (20 ml), sat aq NaHCO$_3$ (20 ml), water (20 ml), brine (10 ml), dried (Na$_2$SO$_4$) and evaporated in vacuo to afford a colourless glass which solidified on standing. This was treated with hexane and the solid was filtered, washed with hexane and dried under N$_2$ atmosphere to give the title compound (2.45 g, 92%). δH (CDCl$_3$), 5.38 (1H, br), 4.63 (3H, br m), 4.27 (2H, q), 3.03 (3H, s), 1.48 (9H, s), 1.33 (3H, t); m/z (ES$^+$, 70V) 333 (MNa$^+$).

INTERMEDIATE 39

Ethyl (2R)-2-[(tert-butoxycarbonyl)amino]-3-iodopropanoate

Intermediate 38 (1.0 g, 3.21 mmol) was stirred in acetone (10 ml) in a foil covered flask with sodium iodide (723 mg, 4.82 mmol) at RT for 18 hr. The acetone was removed in vacuo and the residue partitioned between EtOAc (100 ml) and water (30 ml). The organics washed with brine (10 ml), dried (Na$_2$SO$_4$) and evaporated in vacuo to afford a yellow oil. This was purified by chromatography (SiO$_2$; 30% Et$_2$O/hexane) to afford the title compound as a colourless oil which solidified to a white solid (597 mg, 54%). δH (CDCl$_3$) 5.36 (1H, br), 4.50 (1H, br m), 4.27 (3H, m), 3.59 (2H, m), 1.48 (9H, s), 1.33 (3H, t); m/z (ES$^+$, 70V) 365 (MNa$^+$).

INTERMEDIATE 40

Ethyl (2S)-2-[(tert-butoxycarbonyl)amino]-3-(5-nitropyridin-2-yl)propanoate

Zinc dust (100 mesh) (581 mg, 8.88 mmol) was heated under vacuum and then cooled under N$_2$. 1,2-dibromoethane (32 µL, 0.37 mmol) and dry THF (1 ml) were added with heating to boiling. Heating was stopped and the mixture stirred for 1 min. This heating and stirring was repeated twice more. TMSCl (66 µL, 0.52 mmol) was added and stirred at 50° for ~10 mins. Intermediate 39. (2.54 g, 7.40 mmol) in dry THF (4 ml) was added and stirred at ~35-40° for 40 minutes. 2-bromo-5-nitropyridine (1.50 g, 7.30 mmol) and PdCl$_2$ (PPh$_3$)$_2$ (260 mg, 0.37 mmol) and dry THF (2 ml) were added and the reaction mixture stirred at 35° for 2 hr. The reaction mixture was partitioned between EtOAc (150 ml) and sat. aq. NH$_4$Cl (40 ml). The phases were separated and the aqueous phase re-extracted with EtOAc (50 ml). The combined organic extracts were washed with brine (10 ml), dried (Na$_2$SO$_4$) and evaporated in vacuo to afford a dark straw coloured oil. Purification by chromatography (SiO$_2$; 30-70%

Et₂O/hexane) afforded the title compound as a yellow oil (1.52 g, 61%). δH (CDCl₃), 9.34 (1H, s), 8.39 (1H, d), 7.38 (1H, d), 5.58 (1H, br), 4.75 (1H, br m), 4.20 (2H, m), 3.47 (2H, m), 1.42 (9H, s), 1.23 (3H, t); m/z (ES⁺, 70V) 339 (MH⁺).

INTERMEDIATE 41

Ethyl (2S)-3-(5-aminopyridin-2-yl)-2-[(tert-butoxycarbonyl)amino]propanoate

A stirred solution of Intermediate 40 (1.16 g, 3.42 mmol) in absolute EtOH (20 ml) was hydrogenated at atmospheric pressure with 10% Pd on charcoal (100 mg) for 3.5 hrs. The catalyst was removed by filtration through a celite pad with DCM. The filtrate was evaporated in vacuo. The crude title compound was obtained as a straw-coloured oil (1.03 g, 98%) and used without further purification. δH (CDCl₃), 8.01 (1H, s), 6.92 (2H, s), 5.83 (1H, br), 4.59 (1H, br m), 4.13 (2H, m), 3.63 (2H, br), 3.15 (2H, br), 1.43 (9H, s), 1.21 (3H, t); m/z (ES⁺, 70V) 309 (MH⁺).

INTERMEDIATE 42

Ethyl (2S)-2-[(tert-butoxycarbonyl)amino]-3-{5-[(3,5-dichloroisonicotinoyl)amino]pyridin-2-yl}propanoate 3,5-Dichloroisonicotinoyl chloride (0.51 ml, 3.61 mmol) was added to a stirred, ice-bath cooled solution of Intermediate 41 (1.06 g, 3.43 mmol) and dry pyridine (0.55 ml) in dry DCM (20 ml) and stirred at RT for 1 hr. After evaporation of the solvent the residue was dissolved in EtOAc (80 ml) and washed with saturated sodium bicarbonate (20 ml), water (10 ml), brine (10 ml), then dried (Na₂SO₄) filtered and concentrated in vacuo to a red-brown glass. Chromatography (SiO₂, 75% Et₂O/DCM) afforded a the title compound as tan-coloured solid (1.25 g, 75%). δH NMR (DMSO d⁶) 8.69 (2H, s), 8.58 (1H, s), 7.92 (1H, d), 7.20 (1H, d), 4.26 (1H, m), 3.97 (2H, m), 2.93 (2H, m), 1.21 (9H, s), 1.01 (3H, t); m/z (ES⁺, 70V) 483 (MH⁺).

INTERMEDIATE 43

Ethyl (2S)-2-amino-3-{5-[(3,5-dichloroisonicotinoyl)amino]pyridin-2-yl}propanoate Acetyl chloride (6 ml) was added to absolute EtOH (20 ml) and stirred for 15 min., cooled to RT, then Intermediate 42 (2.74 g, 5.67 mmol) added with and stirring for 3.5 hrs. The solvent removed in vacuo. The resultant yellow residue was treated with sat. sodium bicarbonate (10 ml) and solid sodium bicarbonate till neutralised. Extraction with EtOAc (4×50 ml), drying (Na₂SO₄) and concentrated afforded the title compound as a straw-coloured foam (2.1 g, 97%). δH NMR (DMSO d⁶) 8.67 (2H, s), 8.56 (1H, s), 7.85 (1H, d), 7.16 (1H, d), 3.89 (2H, q), 3.57 (1H, dd), 2.86 (1H, dd), 2.82 (1H, dd), 1.73 (2H, br), 1.00 (3H, t); m/z 7 (ES⁺, 70V) 383 (MH⁺).

INTERMEDIATE 44

3-Ethoxy-7,7-dioxo-7$\lambda^6$-thia-spiro[3.5]non-2-en-1-one

A solution of 1,1-dioxo-hexahydro-1$\lambda^6$-thiopyran-4-carboxylic acid (10.2 g, 57.3 mmol) [prepared according to the procedure of *Org. Prep. Proc. Int*. 1977, 94] and DMF (0.3 ml) in DCM (120 ml) at rt, was treated dropwise with oxalyl chloride and the resulting slurry stirred for 3 d. The crude reaction was then concentrated in vacuo to give an oil which was re-dissolved in THF (100 ml), treated with ethoxyacetylene (10 ml, 50% w/w) and triethylamine (10 ml) and the resulting slurry stirred for 10 d at rt. Filtration and concentration of the filtrate in vacuo gave a crude oil which was purified by chromatography (SiO₂, 30% EtOAc:hexanes) to give the title compound as a yellow oil (8.9 g, 38.6 mmol, 67%). δH (CDCl₃, 300K) 4.88 (1H, s), 4.27 (2H, q, 47.1 Hz), 3.44-3.37 (2H, m), 3.13-3.05 (2H, m), 2.47-2.40 (2H, m), 2.35-2.29 (2H, m), 1.48 (3H, t, J 7.1 Hz); m/z (ES⁺, 70V) 230.9 (MH⁺).

INTERMEDIATE 45

3-Hydroxy-7,7-dioxo-7$\lambda^6$-thia-spiro[3.5]non-2-en-1-one

Intermediate 44 (8.6 g, 37.4 mmol) was stirred with 1M HCl (100 ml) for 3 d and the resulting solution concentrated in vacuo. The residual solid was triturated with EtOAc to give the title compound as an off-white solid (5.1 g, 25.2 mmol, 68%); m/z (ES⁺, 70V) 202.9 (MH⁺).

INTERMEDIATE 46

3-Ethoxy-spiro[3.4]octa-2,6-dien-1-one

A solution of cyclopent-3-ene carboxylic acid (4.0 g, 36.0 mmol) and DMF (0.25 ml) in DCM (30 ml) at 0° was treated dropwise with oxalyl chloride (3.5 ml, 39.0 mmol). After 2 h the reaction mixture was concentrated in vacuo, the residual slurry diluted with Et₂O (100 ml) and the resulting precipitate removed by filtration and the filtrate concentrated in vacuo. The resulting oil was diluted with Et₂O (50 ml), treated with ethoxyacetylene (40% w/w solution in hexanes, 10 ml) followed dropwise with triethylamine (6 ml, 44.0 mmol) and the reaction stirred for 7 d. Filtration and concentration of the filtrate in vacuo followed by chromatography (SiO₂, 5:1 EtOAc:hexanes) gave the title compound as a pale yellow oil (4.3 g, 73%); m/z (ES⁺, 70V) 164.9 (MH⁺).

INTERMEDIATE 47

3-Hydroxy-spiro[3.4]octa-2,6-dien-1-one

Intermediate 46 (2.0 g, 12.0 mmol) and 2M hydrochloric acid (5 ml) were stirred vigorously for 24 h at room temperature. The resulting solution was extracted with EtOAc (25 ml), the extracts dried (MgSO₄), filtered and concentrated in vacuo to give the title compound as an pale brown powder (1.07 g, 7.9 mmol, 65%). δH (DMSO d⁶, 300K) 5.54 (4H, s), 4.57 (2H, s), 2.52 (2H, s); m/z (ES⁺, 70V) 136.9 (MH⁺).

INTERMEDIATE 48

(±)-3-Ethoxy-4-methyl-4-phenyl-cyclobut-2-enone

A solution of (±) 2-phenylpropionic acid (10.0 g, 0.66 mmol) and DMF (0.3 ml) in DCM (150 ml) was treated dropwise with oxalyl chloride (6.4 ml, 0.72 mmol). After 1 h the reaction mixture was concentrated in vacuo, the residual slurry diluted with Et₂O (200 ml) and the resulting precipitate removed by filtration. The filtrate was treated with ethoxyacetylene (40% w/w solution in hexanes, 18 ml) followed dropwise with triethylamine (25 ml, 0.19 mol) and the reaction stirred for 7 d at rt. Filtration and concentration of the filtrate in vacuo followed by chromatography (SiO$_2$, 5:1 EtOAc:hexanes) gave the title compound as a pale yellow oil (6.1 g, 45%). δH (CDCl$_3$, 300K) 7.45-7.24 (5H, m), 5.01 (1H, s), 4.31 (2H, J 7.1 Hz), 1.67 (3H, s), 1.51 (3H, t, J 7.1 Hz); m/z (ES$^+$, 70V) 202.9 (MH$^+$).

INTERMEDIATE 49

(+,−)-3-Hydroxy-4-methyl-4-phenyl-cyclobut-2-enone

Intermediate 48 (4.5 g, 22.2 mmol) was hydrolysed according to the method of Intermediate 29 to give the title compound as an off-white powder (3.29 g, 18.9 mmol, 85%); δH (CDCl$_3$, 300K) 7.53-7.21 (5H, m), 4.04 (1H, d, J 21.7 Hz), 3.93 (1H, d, J 21.7 Hz), 1.62 (3H, s); m/z (ES$^+$, 70V) 174.9 (MH$^+$).

INTERMEDIATE 50

Cyclohexylethynyloxy-triisopropyl-silane

Prepared according to the method of Kowalski, Sankar Lal and Haque, JACS, 1986, 108, 7127-7128.

INTERMEDIATE 51

2-Cyclohexyl-3-triisopropylsilanyloxy-spiro[3.5]non-2-en-1-one

To a stirred solution of the compound of Intermediate 50 (5.6 g, 20 mmol) in t-butylmethyl ether (50 ml) was added cyclohexylcarbonyl chloride (5.3 ml, 40 mmol) and triethylamine (13 ml, 100 mmol). The mixture was stirred under reflux for 24 hours, allowed to cool and filtered to remove triethylammonium chloride. The filtrate was concentrated under reduced pressure and chromatographed on silica gel, mobile phase 3% EtOAc in hexane to afford the title compound as a brown oil (5.8 g, 74%). m/z (ES$^+$, 70V) 235.2 (MH$^+$ of desilylated compound).

INTERMEDIATE 52

2-Cyclohexyl-spiro[3.5]nonane-1,3-dione

Intermediate 51 was stirred with 5 volumes of 2 M hydrochloric acid for 14 days and worked up in a similar manner to Intermediate 4 to afford the title compound as a white crystalline solid in 40% yield. m/z (ES$^+$, 70V) 235.0 (MH$^+$).

INTERMEDIATE 53

1-Butoxyprop-1-yne

Prepared according to the method of Nooi and Arens, Recl. Trav. Chim. Pays-Bas, 1959, 78, 284-287.

INTERMEDIATE 54

1-Butoxybut-1-yne

Prepared in a similar manner to Intermediate 53 from the appropriate starting materials.

INTERMEDIATE 55

1-Butoxypent-1-yne

Prepared in a similar manner to Intermediate 53 from the appropriate starting materials.

INTERMEDIATE 56

3-Butoxy-2,4,4-trimethyl-cyclobut-2-enone

Prepared in a similar manner to Intermediate 1 from Intermediate 53 in 45% yield. δH (CDCl$_3$) 4.35 (2H, t, J 6.5 Hz), 1.79 (2H, m), 1.66 (3H, s), 1.50 (2H, m), 1.22 (6H, s), 0.99 (3H, t, J 7.4 Hz); m/z (ES$^+$, 70V) 183.0 (MH$^+$).

INTERMEDIATE 57

3-Butoxy-2-ethyl-4,4-dimethyl-cyclobut-2-enone

Prepared in a similar manner to Intermediate 1 from Intermediate 54 in 56% yield. δH (CDCl$_3$) 4.31 (2H, t, J 6.5 Hz), 2.07 (2H, q, J 7.6 Hz), 1.80 (2H, m), 1.52 (2H, m), 1.23 (6H, s), 1.10 (3H, t, J 7.6 Hz), 1.00 (3H, t, J 7.3 Hz); m/z (ES$^+$, 70V) 197.0 (MH$^+$).

INTERMEDIATE 58

3-Butoxy-4,4-dimethyl-2-propyl-cyclobut-2-enone

Prepared in a similar manner to Intermediate 1 from Intermediate 55 in 51% yield. δH (CDCl$_3$) 4.30 (2H, t, J 6.5 Hz), 2.04 (2H, q, J 7.4 Hz), 1.75 (2H, m), 1.50 (4H, m), 1.23 (6H, s), 1.00 (3H, t, J 7.4 Hz), 0.92 (3H, t, J 7.4 Hz); m/z (ES$^+$, 70V) 211.0 (MH$^+$).

INTERMEDIATE 59

2,2,4-Trimethyl-cyclobutane-1,3-dione

Prepared in a similar manner to Intermediate 2 from Intermediate 56 in 85% yield. δH (DMSO d$^6$) 1.36 (3H, s), 1.07 (6H, s); m/z (ES$^+$, 70V) 126.9 (MH$^+$).

INTERMEDIATE 60

4-Ethyl-2,2-dimethyl-cyclobutane-1,3-dione

Prepared in a similar manner to Intermediate 2 from Intermediate 57 in 70% yield. δH (DMSO d$^6$) 1.85 (2H, q, J 7.6 Hz), 1.07 (6H, s), 0.95 (3H, t, J 7.6 Hz); m/z (ES$^+$, 70V) 140.9 (MH$^+$).

INTERMEDIATE 61

2,2-Dimethyl-4-propyl-cyclobutane-1,3-dione

Prepared in a similar manner to Intermediate 2 from Intermediate 58 in 64% yield. δH (CDCl$_3$) 1.96 (2H, t, J 7.3 Hz), 1.50 (2H, m), 1.28 (6H, s), 0.90 (3H, t, J 7.3 Hz); m/z (ES$^+$, 70V) 154.9 (MH$^+$).

INTERMEDIATE 62

3-Butoxy-2-methyl-spiro[3.5]non-2-en-1-one

Prepared in a similar manner to Intermediate 1 from Intermediate 53 in 23% yield. δH (CDCl$_3$) 4.34 (2H, t, J 6.5 Hz), 1.77-1.25 (17H, m), 1.00 (3H, t, J 7.4 Hz); m/z (ES$^+$, 70V) 223.0 (MH$^+$).

INTERMEDIATE 63

3-Butoxy-2-propyl-spiro[3.5]non-2-en-1-one

Prepared in a similar manner to Intermediate 1 from Intermediate 55 in 67% yield. δH (CDCl$_3$) 4.31 (2H, t, J 6.4 Hz), 2.07 (2H, t, J 7.2 Hz), 1.80-1.40 (13H, m), 1.00 (3H, t, J 7.1 Hz), 0.93 (3H, t, J 7.3 Hz); m/z (ES$^+$, 70V) 251.1 (MH$^+$).

INTERMEDIATE 64

2-Methyl-spiro[3.5]nonane-1,3-dione

Prepared in a similar manner to Intermediate 2 from Intermediate 62 in 90% yield. δH (DMSO d$^6$) 1.56 (10H, m), 1.37 (3H, s); m/z (ES$^+$, 70V) 166.9 (MH$^+$).

INTERMEDIATE 65

2-Propyl-spiro[3.5]nonane-1,3-dione

Prepared in a similar manner to Intermediate 2 from Intermediate 63 in 64% yield. δH (DMSO d$^6$) 1.82 (2H, t, J 7.2 Hz), 1.58 (8H, m), 1.41 (2H, m), 1.39 (2H, q, J 7.4 Hz), 0.85 (3H, t, J 7.3 Hz); m/z (ES$^+$, 70V) 195.1 (MH$^+$).

INTERMEDIATE 66

3-Butoxy-2-methyl-7-oxa-spiro[3.5]non-2-en-1-one

Prepared in a similar manner to Intermediate 1 from Intermediate 53 in 48% yield. δH (CDCl$_3$) 4.30 (2H, t, J 6.5 Hz), 3.76 (4H, m), 1.70 (6H, m), 1.63 (3H, s), 1.36 (2H, m), 0.92 (3H, t, J 7.4 Hz); m/z (ES$^+$, 70V) 225.0 (MH$^+$).

INTERMEDIATE 67

3-Butoxy-2-propyl-7-oxa-spiro[3.5]non-2-en-1-one

Prepared in a similar manner to Intermediate 1 from Intermediate 55 in 79% yield. δH (CDCl$_3$) 4.33 (2H, t, J 6.4 Hz), 3.81 (4H, m), 2.09 (2H, t, J 7.7 Hz), 1.81 (6H, m), 1.50 (4H, m), 1.00 (3H, t, J 7.4 Hz), 0.94 (3K, t, J 7.3 Hz); m/z (ES$^+$, 70V) 253.0 (MH$^+$).

INTERMEDIATE 68

2-Methyl-7-oxa-spiro[3.5]nonane-1,3-dione

Prepared in a similar manner to Intermediate 2 from Intermediate 66 in 51% yield. δH (DMSO d$^6$) 3.67 (4H, m), 1.68 (4H, m), 1.40 (3H, s). m/z (ES$^+$, 70V) 168.9 (MH$^+$).

INTERMEDIATE 69

2-Propyl-7-oxa-spiro[3.5]nonane-1,3-dione

Prepared in a similar manner to Intermediate 2 from Intermediate 67 in 79% yield. m/z (ES$^+$, 70V) 196.9 (MH$^+$).

INTERMEDIATE 70

(3-Ethoxy-prop-2-ynyl)-benzene

To a solution of ethoxy acetylene (9.95 g of 50% w/w. solution in hexanes, 70 mmol) in THF (100 ml) at −78° was added n-butyl lithium (31 ml of 2.5M solution in hexanes, 78 mmol). The mixture was stirred at this temperature for 2 h. prior to the addition of HMPA (20 ml), stirring was continued for a further 15 min. before the addition of benzyl bromide (9.2 ml). The reaction mixture was allowed to warm to room temperature overnight before partitioning between EtOAc (300 ml) and water (200 ml). The organics were separated, washed with water (5×200 ml), brine (200 ml), dried (Na$_2$SO$_4$), filtered and concentrated in vacuo to give the title compound as a mobile brown oil (11.1 g, 99%). δH (300 MHz, CDCl$_3$) 7.15-7.57 (5H, m), 4.12 (2H, q, J 7.1 Hz), 3.60 (2H, s), 1.41 (3H, t, J 7.1 Hz); m/z (ES$^+$, 70V) MH$^+$ 161.

INTERMEDIATE 71

2-Benzyl-3-ethoxy-4,4-dimethyl-cyclobut-2-enone

To a solution of Intermediate 70 (11 g, 68 mmol) in THF (200 ml) at room temperature was added isobutyryl chloride (11 ml) and triethylamine (19 ml). The mixture was stirred at this temperature for 65 h. filtered, partitioned between EtOAc (400 ml) and water (200 ml), the organics were separated, washed with brine (200 ml), dried (Na$_2$SO$_4$), filtered and concentrated in vacuo. The crude product was purified by column chromatography (SiO$_2$, hexane:diethyl ether, 3:2) to give the title compound as a viscous clear oil (11.8 g, 75%). δH (300 MHz, CDCl$_3$) 7.18-7.32 (5H, m), 4.27 (2H, q, J 7.1 Hz), 3.43 (2H, s), 1.36 (3H, t, J 7.1 Hz), 1.28 (6H, s); m/z (ESI, 70V) MH$^+$231.

INTERMEDIATE 72

4-Benzyl-2,2-dimethyl-cyclobutane-1,3-dione

Intermediate 71 (11.8 g, 51.3 mmol) was stirred in HCl (200 ml, 6M aq.) at room temperature overnight. The solid precipitate was filtered and washed on the sinter with hexane and diethyl ether to give the title compound as a white powder (9.8 g, 95%). δH (300 MHz, DMSO d$^6$). 7.13-7.29 (5H, m), 3.20 (2H, s), 1.11 (6H, s); m/z (ES$^+$, 70V) (MH$^+$) 213.

INTERMEDIATE 73

4-Bromomethyl-5-methyl-2-oxo-1,3-dioxolene

Prepared according to the method of Sakamoto F., Ikeda S. and Tsukamoto G., Chem. Pharm. Bull., 1984, 32, 2241-2248.

INTERMEDIATE 74

Ethyl (2S)-2-tert-Butoxycarbonylamino-3-{4-[(3,5-dichloro-1-oxy-pyridine-4-carbonyl)amino]phenyl}propanoate Intermediate 26 (500 mg, 1.04 mmol) and mCPBA (493 mg, 2.0 mmol) in DCM (10 ml) were stirred together at room temperature for 48 hrs. After this time sodium sulfite (10% solution in water, 20 ml) was added with stirring for 5 mins, prior to separating between DCM (50 ml) and sodium bicarbonate solution (50 ml). The organics were washed with sodium bicarbonate solution (2×50 ml) and water (1×50 ml), dried (MgSO$_4$) and reduced in vacuo. The resulting orange solid was recrystallised from EtOAc/hexane to give title compound as a pale yellow powder (350 mg). δH (DMSO d$^6$) 7.78 (2H, s), 6.78 (2H, d, J 8.3 Hz), 6.46 (2H, d, J 8.4 Hz), 3.55 (1H, m), 3.36 (2H, q, J 7.1 Hz), 2.31 (1H, dd J 13.8, 5.8 Hz), 2.31 (1H, dd, J 13.6, 8.9 Hz), 0.60 (9H, s), 0.43 (3H, t, 3H).

INTERMEDIATE 75

(S)-2-Amino-3-{4-[(3,5-dichloro-1-oxy-pyridine-4-carbonyl)-amino]-phenyl}-propionic Acid Ethyl Ester Intermediate 74 (330 mg, 0.55 mmol) and HCl in EtOAc (2.6M) were stirred together at room temperature overnight. After this time the formed precipitate was filtered off, washed with Et$_2$O, (3×50 ml) and then made basic by separating between EtOAc (50 ml) and sodium bicarbonate solution (50 ml). The organics were dried (MgSO$_4$) and reduced in vacuo to give title compound as white solid (185 mg). δH (CD$_3$OD) 8.40 (2H, s), 7.43 (2H, d, J 8.6 Hz), 7.05 (2H, d, J 8.6 Hz), 3-98 (2H, q, 47.1 Hz), 2.85 (2H, m), 1.04 (3H, t, J 7.1 Hz).

EXAMPLE 1

Ethyl (2S)-2-[(4,4-dimethyl-3-oxo-1-cyclobutenyl) amino]-3-[(4-([2,7]naphthyridin-1-yloxy)phenyl] propanoate A solution of 3-hydroxy-4,4-dimethyl-2-cyclobutenone (57 mg, 0.51 mmol) [prepared according to the method of Wasserman, H. H. et al J. Org. Chem., 38, 1451-1455, (1973)] and the ethyl ester prepared according to the method used to prepare Intermediate 13 (164 mg, 0.51 mmol), in 1,2-dichloroethylene (5 ml), was stirred at room temperature for 72 h. The volatiles were removed in vacuo and the residue chromatographed (SiO$_2$; EtOAc) affording the title compound as a white solid (188 mg, 0.45 mmol, 89%). δH (CDCl$_3$, 300K) 9.92 (1H, s), 8.75 (1H, d, J 5.7 Hz), 8.60 (1H, d, J 8.6 Hz), 8.04 (1H, d, J 5.8 Hz), 7.82 (1H d, J 5.6 Hz), 7.47 (1H, d, J 5.8 Hz), 7.27 (2H, d, J 8.5 Hz), 7.16 (2H, d, J 8.5 Hz), 4.31 (1H, s), 4.30-4.21 (1H, m), 3.68-3.63 (2H, q, J 7.1 Hz), 3.17 (1H, dd, J 13.6, 9.4 Hz), 2.95 (1H, dd, J 5.0, 13.6 Hz), 1.01 (3H, s), 0.93 (3H, s); m/z (ES$^+$, 70V) 418.1 (MH$^+$).

EXAMPLE 2

(2S)-2-[(4,4-Dimethyl-3-oxo-1-cyclobutenyl) amino]-3-[4-([2,7]naphthyridin-1-yloxy)phenyl]propanoic Acid The compound of Example 1 (127 mg, 0.31 mmol) in THF (5 ml) was treated in a single portion with LiOH.H$_2$O (13 mg, 0.32 mmol) in H$_2$O (1 ml) and the reaction stirred at room temperature for 2 h. The reaction was then quenched by the addition of HOAc (glacial, 1 ml) and the volatiles removed in vacuo. Water (10 ml) was then added to the residual foam and stirred vigorously to effect precipitation. The precipitate was then collected by vacuum filtration and the residue washed with water (2×5 ml). Drying under vacuum gave the title compound as a fine white solid (108 mg, 0.27 mmol, 88%). δH (DMSO d$^6$, 300K) 9.67 (1H, s), 8.78 (1H, d, J 5.7 Hz), 8.51 (1H, d, J 8.6 Hz), 8.09 (1H, d, J 5.8 Hz), 7.86 (1H, d, J 5.6 Hz), 7.50 (1H, d, J 5.7 Hz), 7.21 (2H, d, J 8.4 Hz), 4.17 (2H, d, J 8.4 Hz), 4.34 (1H, s), 4.18-4.14 (1H, m), 3.21 (1H, dd, J 4.9, 13.9 Hz), 2.98 (1H, dd, J 13.9, 9.3 Hz), 1.06 (3H, s), 0.99 (3H, s); m/z (ES$^+$, 70V) 404.1 (MH$^+$).

EXAMPLE 3

Ethyl (2S)-2-[(4,4-dimethyl-3-oxo-1-cyclobutenyl) amino]-3-[4-([2,6]naphthyridin-1 ylamino)phenyl] propanoate A solution of 3-hydroxy-4,4-dimethyl-2-cyclobutenone (58 mg, 5.1 mmol) and Intermediate 23 (1.01 g, 2.7 mmol) in DCM (15 ml), was stirred at room temperature for 48 h. The volatiles were removed in vacuo and the residue chromatographed (SiO$_2$; EtOAc) affording the title compound as a white powder (990 mg, 2.3 mmol, 88%). δH (CDCl$_3$, 300K) 9.33 (1H, s), 9.24 (1H, s), 8.69 (1H, d, J 5.9 Hz), 8.63 (1H, d, J 8.5 Hz), 8.42 (1H, dd, J 5.9, 0.8 Hz), 8.15 (1H, d, J 5.7, 1.3 Hz), 7.85-7.80 (3H, m), 7.31-7.22 (4H, m), 4.39 (1H, s), 4.24-4.21 (1H, m), 4.17 (2H, q, 47.1 Hz), 3.15 (1H, dd, J 13.8, 5.6 Hz), 3.00 (1H, dd, J 13.8, 9.0 Hz), 1.19 (3H, t, J 7.1 Hz), 1.11 (3H, s), 1.05 (3H, s); m/z (ES$^+$, 70V) 431.1 (MH$^+$).

EXAMPLE 4

(2S)-2-[(4,4-Dimethyl-3-oxo-1-cyclobutenyl) amino]-3-[4-([2,6]naphthyridin-1-ylamino)phenyl] propanoic Acid The compound of Example 3 (500 mg, 1.16 mmol) was hydrolysed in a similar manner to the method of Example 2 to give the title compound as a fine white solid (421 mg, 1.04 mmol, 90%). δH (DMSO d$^6$, 300K) 9.21 (1H, s), 9.12 (1H, s br), 8.66 (1H, d, J 5.8 Hz), 8.38 (1H, d, J 5.8 Hz), 8.18 (2H, m), 7.81 (2H, d, J 7.9 Hz), 7.27 (2H, d, J 7.9 Hz), 7.26 (1H, obscured s), 4.36 (1H, s), 4.13-4.07 (1H, m), 3.20 (1H, dd, J 14.0, 5.1 Hz) 3.02 (1H, dd, J 41.0, 8.7 Hz), 1.13 (3H, s), 1.09 (3H, s); m/z (ES$^+$, 70V) 403.0 (MH$^+$).

EXAMPLE 5

Ethyl (2S)-2-[(4,4-dimethyl-3-oxo-1-cyclobutenyl) amino]-3-{4-[(3,5-dichloroisonicotinoyl)amino] phenyl}propanoate A solution of 3-hydroxy-4,4-dimethyl-2-cyclobutenone (58 mg, 0.52 mmol) [prepared according to the method of Wasserman, H. H. et al J. Org. Chem., 38, 1451-1455, (1973)] and the free base of Intermediate 27 (200 mg, 5.2 mmol), in DCM (5 ml), was stirred at room temperature for 48 h. The volatiles were removed in vacuo and the residue chromatographed (SiO$_2$; EtOAc) to give the title compound as a white solid (230 mg, 0.45 mmol, 93%). δH (CDCl$_3$, 300K) 8.48 (2H, s), 8.10 (1H, s), 7.51 (2H, d, J 8.2 Hz), 7.04 (2H, d, 8.2 Hz), 5.91 (1H, s), 4.43 (1H, s), 4.22 (2H, q, J 7-1 Hz), 3.17 (1H, dd, J 140, 5.1 Hz), 3.05 (1H, dd, J 14.0, 5.8 Hz), 1.28 (3H, t, J 7.1 Hz), 1.15 (3H, s), 1.14 (3H, s); m/z (ES$^+$, 70V) 476.0 and 478.0 (MH$^+$).

EXAMPLE 6

(2S)-2-[(4,4-dimethyl-3-oxo-1-cyclobutenyl)amino]-3-{4-[(3,5-dichloroisonicotinoyl)amino] phenyl}propanoic Acid The compound of Example 5 (100 mg, 0.21 mmol) was hydrolysed in a similar manner to the method of Example 2 to give the title compound as a fine white solid (76 mg, 0.17 mmol, 81%). δH (DMSO d 6, 350K) 10.5 (1H, s), 8.74 (2H, s), 7.80 (1H, broad s), 7.53 (2H, d, J 8.1 Hz), 7.25 (2H, d, J 8.1 Hz), 7.26 (1H, obscured s), 4.30 (1H, s), 3.88 (1H, m), 3.16 (1H, dd, J 13.5, 4.9 Hz), 3.01 (1H, dd, J 13.5, 3.8 Hz), 1.11 (3H, s), 1.07 (3H, s); m/z (ES$^+$, 70V) 448.0 and 449.9 (MH$^+$).

EXAMPLE 7

Methyl (2S)-2-[(4R,S)-4-methyl-3-oxo-4-propyl-1-cyclobutenyl]amino-3-{4-[(3-methyl[2,7]naphthyridin-1-yl)oxy]phenyl}propanoate A solution of Intermediate 2 (187 mg, 1.33 mmol) and Intermediate 20 (450 mg, 1.2 mmol), in chloroform (10 ml), was stirred at 55° for 48 h. The volatiles were removed in vacuo and the residue chromatographed (SiO$_2$; EtOAc) to give the title compound as a white solid (539 mg, 1.17 mmol, 91%) as an approx. 1:1 mixture of diastereomers. δH (CDCl$_3$, 300K) 9.69 (1H, s), 8.69 (1H, d, J 5.7 Hz), 7.51 (1H, dd, J 9.3, 0.5 Hz), 7.19-7.11 (4H, m), 5.79 (1H, d, J 7.3 Hz), 4.64 (1H, s), 4.36-4.30 (1H, m), 3.84 and 3.82 (3H, s, diastereomeric CH$_3$), 3.31-3.15 (2H, m), 2.45 (3H, s), 1.59-1.54 (1H, m), 1.50-14 (1H, m), 1.34-1.23 (2H, m), 1.28 and 1.27 (3H, s, diastereomeric CH$_3$), 0.91-0.86 (3H, m); m/z (ES$^+$, 70V) 460.1 (MH$^+$).

EXAMPLE 8

(2S)-2-[(4R,S)-4-Methyl-3-oxo-4-propyl-1-cyclobutenyl]amino-3-{4-[(3-methyl[2,7]naphthyridin-1-yl)oxy]phenyl}propanoic Acid The compound of Example 7 (230 mg, 0.5 mmol) was hydrolysed in a similar manner to the method of Example 2 to give the title compound as a fine white solid (198 mg, 0.44 mmol, 79%) as an approx. 1:1 mixture of diastereomers. δH (DMSO d$^6$, 300K) 13.0 (1H, s), 9.60 (1H, d, J 9.7 Hz), 8.72 (1H, d, J 5.6 Hz), 8.49-8.43 (1H, m NH), 7.76 (1H, d, J 4.7 Hz), 741-7.34 (2H, m), 7.27-7.21 (2H, m), 4.47 and 4.43 (1H, s), 4.19-4.13 (1H, m), 3.29-3.23 (3H, s, and 1H as obscured m), 3.02-2.97 (1H, m), 2.36 and 2.35 (3H, s), 1.50-1.10 (4H, m), 1.08 and 0.98 (3H, s), 0.84-0.63 (3H, m); m/z (ES$^+$, 70V) 446.1 and 447.1 (MH$^+$).

EXAMPLE 9

Ethyl (2S)-2-[(4,4-dipropyl-3-oxo-1-cyclobutenyl)amino]-3-[4-([2,7]naphthyridin-1-yloxy)phenyl]propanoate A solution of Intermediate 4 (180 mg, 1.07 mmol) and the ethyl ester of Intermediate 13 (362 mg, 1.07 mmol), in chloroform (7 ml), was stirred at room temperature for 96 h. The volatiles were removed in vacuo and the residue chromatographed (SiO$_2$, EtOAc) to give the title compound as a white solid (406 mg, 0.83 mmol, 78%). δH (CDCl$_3$, 300K) 9.72 (1H, s), 8.71 (1H, d J 5.7 Hz), 8.04 (1H, d, J 5.8 Hz), 7.55 (1H, d, J 5.7 Hz), 7.22-7.16 (4H, m), 5.67 (1H, d, J 7.9 Hz), 4.64 (1H, s), 4.26-4.16 (3H, m), 3.20 (1H, dd, J 14.1, 5.7 Hz), 3.11 (1H, dd, J 14.1, 6.6 Hz), 1.58-1.01 (8H, m), 0.81 (6H, t, J 7.0 Hz); m/z (ES$^+$, 70V) 488.1 and 489.1 (MH$^+$).

EXAMPLE 10

(2S)-2-[(3-Oxo-4,4-dipropyl-1-cyclobutenyl)amino]3-[4-([2,7]naphthyridin-1-yloxy)phenyl]propanoic Acid The compound of Example 9 was hydrolysed in a similar manner to the method of Example 2 to give the title compound as a fine off-white powder (35 mg, 0.07 mmol, 19%). δH (DMSO d$^6$, 350K) 9.68 (1H, s), 8.83 (1H, d, J 5.7 Hz), 8.37 (1, d, J 8.5 Hz), 8.14 (1H, d, J 5.8 Hz), 7.91 (1H, d, J 5.7 Hz), 7.55 (1H, d, J 5.8 Hz), 7.39 (2H, d, J 8.4 Hz), 7.28 (2H, d, J 8.4 Hz), 4.53 (1H, s), 4.14 (1H, dd, J 9.8, 4.3 Hz), 3.25 (1H, dd, J 14.0, 4.6 Hz), 3.0 (1H, dd, J 10.3, 14.0 Hz), 1.50-0.64 (14K, m); m/z (ES$^+$, 70V) 460.1 and 461.1 (MH$^+$).

EXAMPLE 11

Ethyl (2S)-2-[(4R,S)-4-methyl-3-oxo-4-propyl-1-cyclobutenyl]amino-3-[4-([2,7]naphthyridin-1-yloxy)phenyl]propanoate A solution of Intermediate 2 (30 mg, 2.1 mmol) and the ethyl ester of Intermediate 13 (724 mg, 2.14 mmol), in DCM (15 ml), was stirred at room temperature for 24 h. The reaction was then diluted with DCM (30 ml) and distilled water (20 ml) and washed successively with 1M aqueous hydrochloric acid (30 ml) water (30 ml) and saturated, aqueous sodium hydrogen carbonate (30 ml). The organic layer was then dried (MgSO$_4$), filtered and concentrated in vacuo. The residual foam was chromatographed (SiO$_2$, EtOAc) to give the title compound as a white powder (827 mg, 1.8 mmol, 84%) as an approx. 1:1 mixture of diastereomers. δH (CDCl$_3$, 300K) 9.72 (1H, s), 8.71 (1H, d, J 5.7 Hz), 8.04 (1H, d, J 5.8 Hz), 7.55 (1H, d, J 5.7 Hz), 7.22-7.12 (5H, m), 5.80 (1H, d, J 7.6 Hz), 4.57 (1H, s), 4.28-4.20 (3H, m), 3.25-3.07 (2H, m), 1.57-1.21 (7H, m), 1.18 and 1.17 (3H, s) 0.84-0.78 (3H, m); m/z (ES$^+$, 70V) 460.1 (MH$^+$) and 482.0 (MNa$^+$).

EXAMPLE 12

(2S)-2-[(4R,S)-4-Methyl-3-oxo-4-propyl-1-cyclobutenyl]amino-3-[4-([2,7]naphthyridin-1-yloxy)phenyl]propanoic Acid The compound of Example 11 (600 mg, 1.31 mmol) was hydrolysed in a similar manner to the method of Example 2 to give the title compound as a fine white solid (520 mg, 1.21 mmol, 92%) as an approx. 1:1 mixture of diastereomers. δH (DMSO d$^6$, 300K) 9.61 and 9.58 (1H, s), 8.72 (1H, d, J 5.7 Hz), 8.39-8.33 (1H, m NH), 8.04-8.00 (1H, m), 7.80-7.79 (1H, m), 7.45-7.33 (1H, m), 7.32-7.25 (2H, m), 7.18-7.12 (2H, m), 4.37 and 4.32 (1H, s), 4.10-4.04 (1H, m), 3.17-3.12 (1H, m), 2.94-2.82 (1H, m), 1.41-0.86 (4H, m), 0.99 and 0.91 (3H, s) 0.73 and 0.63 (3H, t, J 7.2 Hz); m/z (ES$^+$, 70V) 432.0 (MH$^+$).

EXAMPLE 13

Ethyl (2S)-2-[(4R,S)-4-methyl-3-oxo-4-propyl-1-cyclobutenyl]amino-3-[4-([2,6]naphthyridin-1-ylamino)phenyl]propanoate Prepared from Intermediate 2 (200 mg, 1.43 mmol) and Intermediate 23 (400 mg, 1.19 mmol), in a similar manner to the compound of Example 11 to give the title compound as an approx. 1:1 mixture of diastereomers as a white powder (482 mg, 1.05 mmol, 89%). δH (CDCl$_3$, 300K) 9.13 (1H, s), 8.61 (1H, d, J 5.9 Hz), 8.17 (1H, d, J 5.8 Hz), 7.66-7.60 (3H, m), 7.19-7.04 (5H, m), 5.62 (1H, t, J 4.6 Hz), 4.51 and 4.49 (1H, s), 4.25-4.19 (3H, m), 3.16-3.05 (2H, m), 1.51-1.16 (7H, m), 0.85-0.77 (3H, m); m/z (ES$^+$, 70V) 459.1 (MH$^+$).

EXAMPLE 14

(2S)-2-[(4R,S)-4-Methyl-3-oxo-4-propyl-1-cyclobutenyl]amino-3-[4-([2,6]naphthyridin-1-ylamino)phenyl]propanoic Acid The compound of Example 13 (600 mg, 1.31 mmol) was hydrolysed in a similar manner to the method of Example 2 to give the title compound as a pale yellow powder (521 mg, 1.21 mmol, 95%) (approx. 1:1 mixture of diastereomers). δH (DMSO d$^6$, 300K) 9.10 (1H, s), 8.55-8.53 (1H, m), 8.37 and 8.31 (1H, m NH), 8.27 (1H, d, J 5.9 Hz), 7.72-7.65 (2H, m), 7.15-7.08 (3H, m), 4.30 and 4.25 (1H, s), 3.99-3.94 (1H, m), 3.06-2.99 (1H, m), 2.83-2.76 (1H, m), 1.34-0.96 (4H, m), 0.94 and 0.86 (3H, s), 0.68 and 0.55 (3H, t, J 7.0 Hz); m/z (ES$^+$, 70V) 431.0 (MH$^+$).

EXAMPLE 15

Ethyl (2S)-2-[(4R,S)-4-methyl-3-oxo-4-propyl-1-cyclobutenyl]amino-3-{4-[(3,5-dichloroisonicotinoyl)amino]phenyl}propanoate Prepared from Intermediate 2 (120 mg, 0.86 mmol) and the free base of Intermediate 27 (300 mg, 0.79 mmol), in a similar manner to the compound of Example 11 to give title compound as an approx. 1:1 mixture of diastereomers as a white powder (318 mg, 0.63 mmol, 80%). δH (CDCl$_3$, 300K) 8.56 (2H, s), 8.29 and 8.24 (1H, s), 7.61-7.59 (2H, m), 7.16-7.10 (2H, m), 5.82-5.78 (1H, m), 4.56 (1H, s), 4.32-4.26 (3H, m), 3.29-3.23 (1H, m), 3.16-3.09 (1H, m), 1.59-1.13 (7H, m), 0.89-0.84 (3H, m); m/z (ES$^+$, 70V) 504.0 and 506.0 (MH$^+$).

EXAMPLE 16

(2S)-2-[(4R,S)-4-Methyl-3-oxo-4-propyl-1-cyclobutenyl]amino-3-{4-[(3,5-dichloroisonicotinoyl)amino]phenyl}propanoic Acid The compound of Example 15 (300 mg, 0.59 mmol) was hydrolysed in a similar manner to the method of Example 2 to give the title compound as a fine white solid (261 mg, 0.55 mmol, 92%) (approx. 1:1 mixture of diastereomers). δH (DMSO d$^6$, 300K) 10.90 (1H, s), 8.81 (2H, s), 7.60-7.56 (2H, m), 7.31-7.26 (2H, m), 4.45 and 4.42 (1H, s), 4.15-4.41 (1H, m), 3.23-3.14 (1H, m), 2.99-2.89 (1H, m), 1.49-1.12 (3H, m), 1.07 and 0.99 (3H, s), 0.84-0.54 (4H, m); m/z (ES$^+$, 70V) 476.0 and 478.0 (MH$^+$).

EXAMPLE 17

Ethyl (2S)-2-[(4,4-di methyl-3-oxo-2-hexyl-1-cyclobutenyl)amino]-3-{4-[(3,5-dichloroisonicotinoyl)amino]phenyl}propanoate Prepared from Intermediate 6 (200 mg, 1.0 mmol) and the free base of Intermediate 27 (200 mg, 0.52 mmol), in a similar manner to the compound of Example 11 to give the title compound as a white powder (201 mg, 0.42 mmol, 72%). δH (CDCl$_3$, 300K) 8.99 (1H, s), 8.42 (2H, s), 7.52 (2H, d, J 8.4 Hz), 7.02 (2H, d, J 7.6 Hz), 5.54 (1H, s), 4.34 (1H, s), 4.19 (2H, q, J 7.1 Hz), 3.07 (2H, br s), 1.95-1.81 (2H, br s), 1.27-0.77 (17H, m); m/z (ES$^+$, 70V) 560.0 and 562.0 (MH$^+$).

EXAMPLE 18

(2S)-2-[(4,4-Dimethyl-3-oxo-2-hexyl-1-cyclobutenyl)amino]-3-{4-[(3,5-dichloroisonicotinoyl)amino]phenyl}propanoic Acid The compound of Example 17 (80 mg, 0.14 mmol) was hydrolysed in a similar manner to the method of Example 2 to give the title compound as an off-white powder (62 mg, 0.12 mmol, 82%). δH (DMSO d$^6$, 300K) 10.53 (1H, s), 8.73 (2H, s), 7.60-7.56 (2H, m), 7.57 (2H, d, J 8.4 Hz), 7.30 (2H, d, J 8.4 Hz), 4.14-4.12 (1H, m), 3.17 (1H, dd, J 13.9, 4.8 Hz), 3.03 (1H, dd, J 13.0, 9.1 Hz), 1.87 (2H, t, J 7.3 Hz), 1.41-1.25 (9H, m), 1.15-0.86 (8H, m); m/z (ES$^+$, 70V) 532.0 and 534.0 (MH$^+$).

EXAMPLE 19

Ethyl (2S)-2-[(4,4-dimethyl-3-oxo-2-hexyl-1-cyclobutenyl)amino]-3-[4-([2,7]naphthyridin-1-yloxy)phenyl]propanoate Prepared from Intermediate 6 (200 mg, 1.0 mmol) and the ethyl ester of Intermediate 13 (200 mg, 0.59 mmol), in a similar manner to the compound of Example 11 to give the title compound as a white powder (201 mg, 0.42 mmol, 72%). δH (CDCl$_3$, 300K) 9.72 (1H, s), 8.71 (1H, d, J 5.7 Hz), 8.03 (1H, d, J 5.8 Hz), 7.56-7.51 (1H, m), 7.27-7.17 (4H, m), 5.41 (1H, br m), 4.39 (1H, br m), 4.19 (2H, q, J 7.1 Hz), 3.15-3.12 (2H, m), 1.91-1.75 (2H, m), 1.39-1.09 (18H, m), 0.81-0.74 (2H, m); m/z (ES$^+$, 70V) 516.1 (MH$^+$).

EXAMPLE 20

(2S)-2-[(4,4-Dimethyl-3-oxo-2-hexyl-1-cyclobutenyl)amino]-3-[4-([2,7]naphthyridin-1-yloxy)phenyl]propanoic Acid The compound of Example 19 (200 mg, 0.39 mmol) was hydrolysed in a similar manner to the method of Example 2 to give the title compound as a fine white solid (161 mg, 0.33 mmol, 85%). δH (DMSO d$^6$, 360K) 9.62 (1H, s), 8.74 (1H, d, J 5.6 Hz), 8.04 (1H, d, J 5.6 Hz), 7.82 (1H, d, J 5.6 Hz), 7.47 (1H, d, J 5.5 Hz), 7.30 (2H, d, J 8.3 Hz), 7.17 (2H, d, J 8.3 Hz), 4.02 (1H, br s), 3.21-3.18 (1H, m), 2.97-2.91 (1H, m), 1.74 (2H, m), 1.12-0.62 (17H, m); m/z (ES$^+$, 70V) 488.1 (MH$^+$).

EXAMPLE 21

Ethyl (2S)-2-[(4,4-dimethyl-3-oxo-2-hexyl-1-cyclobutenyl)amino]-3-{4-[(3-methyl[2,7]naphthyridin-1-yl)oxy]phenyl}propanoate Prepared from Intermediate 6 (200 mg, 1.0 mmol) and Intermediate 18 (300 mg, 0.85 mmol), in a similar manner to the compound of Example 11 to give the title compound as a white powder (331 mg, 0.63 mmol, 73%). δH (CDCl$_3$, 300K) 9.70 (1H, s), 8.70 (1H, d, J 5.8 Hz), 7.51 (1H, d, J 5.8 Hz), 7.26-7.19 (4H, m), 5.34 (1H, br s), 4.45 (1H, br s), 4.26 (2H, q, J 7.2 Hz), 3.21 (2H, br s), 2.44 (3H, s), 2.10-1.90 (2H, m), 1.47-1.43 (2H, m), 1.33-1.12 (12H, m), 0.87-0.84 (3H, m); m/z (ES$^+$, 70V) 530.1 (MH$^+$),

EXAMPLE 22

(2S)-2-[(4,4-Dimethyl-3-oxo-2-hexyl-1-cyclobutenyl)amino]-3-{4-[(3-methyl[2,7]naphthyridin-1-yl)oxy]phenyl}propanoic Acid The compound of Example 21 (60 mg, 0.11 mmol) was hydrolysed in a similar manner to the method of Example 2 to give the title compound as a fine white solid (42 mg, 0.08 mmol, 74%). δH (DMSO d$^6$, 360K) 9.59 (1H, s), 8.70 (1H, d, J 5.7 Hz), 7.70-7.68 (1H, m), 7.66 (1H, d, J 9.7 Hz), 7.37 (2H, d J 8.6 Hz), 7.31 (1H, s), 7.23 (2H, d, J 8.6 Hz), 4.18-4.16 (1H, m), 3.24 (1H, dd, J 13.9, 4.4 Hz), 3.04 (1H, dd, J 13.9, 9.9 Hz), 2.38 (3H, s), 1.86 (2H, t, J 7.3 Hz), 1.38-1.19 (8H, m), 1.04 (3H, s), 0.99 (3H, s), 0.83-0.79 (3H, m); m/z (ES$^+$, 70V) 502.1 (MH$^+$).

EXAMPLE 23

Ethyl (2S)-2-[(4R,S)-4-benzyl-4-methyl-3-oxo-1-cyclobutenyl]amino-3-{4-[(3-methyl[2,7]naphthyridin-1-yl)oxy]phenyl}propanoate Prepared from Intermediate 8 (200 mg, 1.0 mmol) and Intermediate 20 (300 mg, 0.85 mmol), in a similar manner to the compound of Example 11 to give the title compound as a white powder (412 mg, 0.79 mmol, 92%) as an approx. 1:1 mixture of diastereomers. δH (CDCl$_3$, 300K) 9.70 (1H, d, J 4.9 Hz), 8.71 and 8.70 (1H, d, J 5.8 Hz), 7.51 (1H, d, J 5.8 Hz), 7.31-7.08 (11H, m), 5.88-5.82 (1H, m), 4.60 and 4.50 (1H, s), 4.33-4.28 (1H, m), 4.26-4.16 (2H, m), 3.25-3.07 (2H, m), 2.98-2.83 (2H, m), 2.45 and 2.40 (3H, m), 1.35-1.21 (6H, m); m/z (ES$^+$, 70V) 522.1 (MH$^+$).

EXAMPLE 24

(2S)-2-[(4R,S)-4-Benzyl-4-methyl-3-oxo-1-cyclobutenyl]amino-3-{4-[(3-methyl[2,7]naphthyridin-1-yl)oxy]phenyl}propanoic Acid The compound of Example 23 (250 mg, 0.48 mmol) was hydrolysed in a similar manner to the method of Example 2 to give the title compound as a fine white solid (221 mg, 0.45 mmol, 94%) as an approx. 1:1 mixture of diastereomers. δH (DMSO d$^6$, 360K) 9.72 (1H, m), 8.81 (1H, m), 8.03 (1H, m), 7.82-7.77 (1H, br m), 7.46-7.20 (9H, m), 4.49 and 4.41 (1H, s), 4.21 (1H, m), 3.39-3.30 (1H, m), 3.21-3.14 (1H, m), 3.01-2.87 (2H, m), 2.51 (3H, s), 1.29 and 1.24 (3H, s); m/z (ES$^+$, 70V) 494.0 (MH$^+$).

EXAMPLE 25

Ethyl (2S)-2-[(4R,S)-4-benzyl-4-methyl-3-oxo-1-cyclobutenyl]amino-3-4-[(3,5-dichloroisonicotinoyl)amino]phenylpropanoate Prepared from Intermediate 8 (185 mg, 0.98 mmol) and the free base of Intermediate 27 (300 mg, 0.79 mmol), in a similar manner to the compound of Example 11 to give the title compound as a white powder (387 mg, 0.70 mmol, 89%) as an approx. 1:1 mixture of diastereomers. δH (CDCl$_3$, 300K) 9.36 and 9.31 (1H, s), 8.36 and 8.35 (2H, s), 7.54 and 7.45 (1H, d, J 8.4 Hz), 7.19-7.02 (8H, m), 6.09-6.03 (1H, m), 4.31 and 4.20 (1H, s), 4.22-4.01 (3H, m) 3.07-2.92 (2H, m), 2.76-2.63 (2H, m), 1.35-1.15 (2H, m), 1.09 and 1.08 (3H, s); m/z (ES$^+$, 70V) 551.9 and 553.9 (MH$^+$).

EXAMPLE 26

(2S)-2-[(4R,S)-4-Benzyl-4-methyl-3-oxo-1-cyclobutenyl]amino-3-{4-[(3,5-dichloroisonicotinoyl)amino]phenyl}propanoic Acid The compound of Example 25 (320 mg, 0.53 mmol) was hydrolysed in a similar manner to the method of Example 12 to give the title compound as a fine white solid (277 mg, 0.53 mmol, 91%) as an approx. 1:1 mixture of diastereomers. δH (DMSO d$^6$, 360K) 13.05 (1H, br s), 8.83 and 8.82 (2H, s), 8.67 and 8.62 (1H, d, J 8.9 Hz), 7.71 and 7.61 (2H, d, J 8.7 Hz), 7.37-6.89 (9H, m), 4.32 and 4.23 (1H, s), 4.09-4.00 (1H, m), 3.20-2.64 (4H, m), 1.24-1.07 (3H, m); m/z (ES$^+$, 70V) 523.9 and 525.9 (MH$^+$).

EXAMPLE 27

Ethyl (2S)-2-[(3-oxospiro[3.5]non-1-en-1-yl)amino]-3-{4-[(3,5-dichloroisonicotinoyl)amino]phenyl}propanoate Prepared from 1-keto-3-hydroxyspiro[3,5]-non-2-ene (400 mg, 2.6 mmol) [prepared according to the method of Wasserman, H. H. et al, J. Org. Chem., 38, 1451-1455 (1973)] and the free amine of Intermediate 27 (400 mg, 1.04 mmol), in a similar manner to the compound of Example 11 to give the title compound as a white powder (512 mg, 0.99 mmol, 95%). δH (CDCl$_3$, 300K) 10.86 (1H, s), 8.78 (2H, s), 8.34 (1H, d, J 8.5 Hz), 7.56 (2H, d, J 8.5 Hz), 7.25 (2H, d, J 8.5 Hz), 4.36 (1H, s), 4.20-4.11 (3H, m), 3.13 (1H, dd, J 13.8, 5.3 Hz), 3.00 (1H, dd, J 9.2, 13.8 Hz), 1.67-1.19 (10H, m), 1.17 (3H, t, J 4.1 Hz); m, z (ES$^+$, 70V) 516.0 and 518.0 (MH$^+$).

EXAMPLE 28

(2S)-2-[(3-Oxospiro[3.5]non-1-en-1-yl)amino]-3-{4-[(3,5-dichloroisonicotinoyl)amino]phenyl}propanoic Acid The compound of Example 27 (700 mg, 1.36 mmol) was hydrolysed in a similar manner to the method of Example 2 to give the title compound as a fine white solid (627 mg, 1.28 mmol, 95%). δH (DMSO d$^6$, 360K) 10.54 (1H, s), 8.73 (2H, s), 7.81 (1H, d, J 8.4 Hz), 7.56 (2H, d, J 8.5 Hz), 7.27 (2H, d, J 8.5 Hz), 4.39 (1H, s), 4.12-4.05 (1H, m), 3.19 (1H, dd, J 13.9, 5.1 Hz), 3.00 (1H, dd, J 13.9, 8.8 Hz), 1.94-1.24 (10H, m); m/z (ES$^+$, 70V) 488.0 and 490.0 (MH$^+$).

EXAMPLE 29

Ethyl (2S)-2-[(3-oxospiro[3.5]non-1-en-1-yl)amino]-3-{4-[(3-methyl[2,7]naphthyridin-1-yl)oxy]phenyl}propanoate Prepared from 1-keto-3-hydroxyspiro[3,5]-non-2-ene (400 mg, 2.6 mmol) and Intermediate 20 (400 mg, 1.14 mmol), in a similar manner to the compound of Example 11 to give the title compound as a white powder (497 mg, 1.02 mmol, 89%). δH (CDCl$_3$, 300K) 9.62 (1H, s), 8.72 (1H, d, J 5.7 Hz), 7.99 (1H, d, J 8.6 Hz), 7.73 (1H, dd, J 5.7, 0.9 Hz), 7.37-7.34 (3H, m), 7.28-7.24 (2H, m), 4.42 (1H, s), 4.26-4.18 (3H, m), 3.25 (1H, dd, J 14.0, 5.6 Hz), 3.12 (1H, dd, J 14.0, 9.1 Hz), 2.42 (3H, s), 1.72-1.55 (10H, m), 1.25 (3H, t, J 7.1 Hz); m/z (ES$^+$, 70V) 486.1 (MH$^+$).

EXAMPLE 30

(2S)-2-[(3-Oxospiro[3.5]non-1-en-1-yl)amino]-3-{4-[(3-methyl[2,7]naphthyridin-1-yl)oxy]phenyl}propanoic Acid The compound of Example 29 (300 mg, 0.62 mmol) was hydrolysed in a similar manner to the method of Example 2 to give the title compound as a fine white solid (237 mg, 0.52 mmol, 84%). δH (DMSO d$^6$, 360K) 9.62 (1H, s), 8.72 (1H, d, J 5.7 Hz), 7.82 (1H, d, J 6.3 Hz), 7.73 (1H, d, J 5.5 Hz), 7.35 (2H, d, J 8.7 Hz), 7.25 (2H, d, J 8.7 Hz), 4.39 (1H, s), 4.12 (1H, dd, J 8.7, 13.2 Hz), 3.34-3.12 (2H, m), 2.42 (3H, s), 1.72-1.53 (10H, m); m/z (ES$^+$, 70V) 458.0 (MH$^+$).

EXAMPLE 31

Ethyl (2S)-2-[(2-bromo-3-oxospiro[3.5]non-1-en-1-yl)amino]-3-{4-[(3,5-dichloroisonicotinoyl)amino]phenyl}propanoate A solution containing the compound of Example 27 (500 mg, 0.97 mmol) and triethylamine (2 eq, 270 μl) in THF (10 ml) at 0° was treated dropwise with a solution of bromine (1.1 eq, 170 mg) in THF (5 ml). After 20 mins the reaction was allowed to warm to room temperature prior to dilution with EtOAc (100 ml). The crude reaction mixture was washed with saturated aqueous NaHCO$_3$ (20 ml) and brine (20 ml), dried (MgSO$_4$) filtered and concentrated in vacuo. The residual foam was chromatographed (SiO$_2$; EtOAc) to give the title compound as a white powder (511 mg, 0.86 mmol, 95%). δH (CDCl$_3$, 300K) 8.48 (2H, s), 8.05 (1H, s br), 7.52 (2H, d J 8.4 Hz), 7.04 (2H, d J 8.5 Hz), 5.81 (1H, d br, J 8.3 Hz), 4.98-4.91 (1H, m), 4.21 (2H, q, J 7.1 Hz), 3.21 (2H, d J 5.3 Hz), 1.70-1.66 (4H, m), 1.53-1.44 (4H, m), 1.28 (3H, t J 7.1 Hz), 1.20-1.16 (2H, m); m/z (ES$^+$, 70V) 597.9 and 595.0 (MH$^+$).

EXAMPLE 32

(2S)-2-[(2-Bromo-3-oxospiro[3.5]non-1-en-1-yl)amino]-3-{4-[(3,5-dichloroisonicotinoyl)amino]phenyl}propanoic Acid The compound of Example 31 (511 mg, 0.86 mmol) was hydrolysed in a similar manner to the method of Example 2 (1.3 eq, 50 mg), to give the title compound as a white powder (421 mg, 0.74 mmol, 87%). δH (DMSO d$^6$, 390K) 10.34 (1H, s). 8.67 (2H, s), 7.53 (2H, s br), 7.26 (2H, d J 8.26 Hz), 4.67 (1H, m), 3.26-3.22 (1H, m), 3.13-3.08 (1H, m), 1.67-1.21 (10H, m); m/z (ES$^+$, 70V) 569.9 and 567.9 (MH$^+$).

EXAMPLE 33

Ethyl (2S)-2-[(2-bromo-4,4-dimethyl-3-oxo-1-cyclobutenyl)amino]-3-{4-[(3,5-dichloroisonicotinoyl)amino]phenyl}propanoate Bromine (1.1 eq, 0.32 ml) was added dropwise to a stirred solution of the compound of Example 5 (2.7 g, 5.67 mmol) in THF (25 ml) at room temperature. After 25 min the reaction was diluted with EtOAc (100 ml) and the crude reaction mixture washed with saturated aqueous NaHCO$_3$ (20 ml) and brine (20 ml), dried (MgSO$_4$) filtered and concentrated in vacuo. The residual foam was chromatographed (SiO$_2$, EtOAc) affording the title compound as a pale yellow powder (2.51 g, 4.53 mmol, 76%). δH (CDCl$_3$, 300K) 8.46 (2H, s), 8.17 (1H, s br), 7.51 (2H, d J 8.4 Hz), 7.04 (2H, d J 8.4 Hz), 6.05 (1H, d br, J 8.4 Hz), 4.98-4.92 (1H, m), 4.22 (2H, q, J 7.1 Hz), 3.21 (2H, d J 5.4 Hz), 1.28 (3H, t J 7.1 Hz), 1.14 (3H, s), 1.13 (3H, s); m/z (ES$^+$, 70V) 555.8 and 557.9 (MH$^+$).

EXAMPLE 34

(2S)-2-[(2-Bromo-4,4-dimethyl-3-oxo-1-cyclobutenyl)amino]-3-{4-[(3,5-dichloroisonicotinoyl)amino]phenyl}propanoic Acid The compound of Example 33 (198 mg, 0.36 mmol) was hydrolysed in a similar manner to the method of Example 2 to give the title compound as a white powder (142 mg, 0.27 mmol, 75%). δH (DMSO d$^6$, 390K) 10.46 (1H, s), 8.74 (2H, s), 7.63 (2H, d J 5.74 Hz), 7.35 (2H, d J 8.26 Hz), 4.80 (1H, s br), 3.32 (1H, dd J 5.14, 14.2 Hz), 3.14 (1H, dd J 8.9 Hz 14.2 Hz), 1.18 (3H, s), 1.15 (3H, s); m/z (ES$^+$, 70V) 527.9 and 529.8 (MH$^+$).

EXAMPLE 35

Ethyl (2S)-2-[(3-oxospiro[3.5]non-1-en-1-yl)amino]-3-{4-[(2,7)naphthyridin-1-yloxy]phenyl}propanoate A solution of the ethyl ester of Intermediate 13 (565 mg, 1.68 mmol) and 1-keto-3-hydroxyspiro[3,5]-non-2-ene (280 mg, 1.84 mmol) in DCM (20 ml) was stirred at room temperature for 24 h. Concentration in vacuo and chromatography (SiO$_2$, EtOAc) to give the title compound as a pale yellow powder (730 mg, 1.5 mmol, 92%). δH (CDCl$_3$, 300K) 9.82 (1H, s), 8.82 (1H, d J 5.7 Hz), 8.14 (1H, d J 5.9 Hz), 7.64 (1H, d J 5.8 Hz), 7.25-7.17 (6H, m), 5.77 (1H, d J 7.6 Hz), 4.60 (1H, s), 4.25 (2H, q J 7.1 Hz), 3.30 (1H, dd J 5.5 Hz 13.9 Hz), 3.18 (1H, dd J 5.5 Hz 13.9 Hz), 1.84-1.53 (10H, m), 1.35 (3H, t J 7.1 Hz); m/z (ES$^+$, 70V) 472.1 (MH$^+$).

EXAMPLE 36

Ethyl (2S)-2-[(2-bromo-3-oxospiro[3.5]non-1-en-1-yl)amino]-3-{4-(2.7)naphthyridin-1-yloxy]phenyl}propanoate A stirred solution of the compound of Example 35 (300 mg. 0.637 mmol) and triethylamine (1.2 eq, 100 µl) at 0° was treated dropwise with a solution of bromine in DCM (2% v/v, 2.1 ml, 1.2 eq). After 12 h the reaction was diluted with DCM (50 ml) and washed successively with saturated aqueous NaHCO$_3$, dried (MgSO$_4$) filtered and concentrated in vacuo. The residual foam was triturated with diisopropylether and the resulting solid collected and dried in vacuo to give the title compound as a pale yellow powder (325 mg, 0.59 mmol, 95%). δH (CDCl$_3$, 300K) 9.83 (1H, s), 8.78 (1H, d J 5.8 Hz), 8.16 (1H, d J 5.8 Hz), 7.69 (1H, d, J 5.7 Hz), 7.32 (1H, d, J 5.8 Hz), 7.27 (4H, s), 5.87 (1H, d, J 8.4 Hz), 5.10-5.03 (1H, m), 4.30 (2H, q, J 7.1 Hz), 3.38-3.32 (2H, m), 1.85-1.69 (4H, m), 1.67-1.50 (6H, m), 1.36 (3H, t, J 7.1 Hz); m/z (ES$^+$, 70V) 552.0 (MH$^+$).

EXAMPLE 37

(2S)-2-[(2-Bromo-3-oxospiro[3,5]non-1-en-1-yl)amino]-3-{4-[(2,7)naphthyridin-1-yloxy]phenyl}propanoic Acid The compound of Example 36 (220 mg, 0.40 mmol) was hydrolysed in a similar manner to the method of Example 2, to give the title compound as a white powder (125 mg, 0.24 mmol, 60%). δH (DMSO-d$^6$, 300K) 9.27 (1H, s), 8.88 (1H, d J 9.4 Hz), 8.83 (1H, d J 5.4 Hz), 8.12 (1H, d J 5.8 Hz), 7.90 (1H, d J 5.7 Hz), 7.55 (1H, d J 5.8 Hz), 7.38 (2H, d J 8.4 Hz), 7.27 (2H, d J 8.4 Hz), 4.83-4.79 (1H, m), 3.08-3.03 (2H, m), 1.80-1.37 (8H, m), 1.19-1.12 (2H, m); m/z (ES$^+$, 70V) 523.9 (MH$^+$).

EXAMPLE 38

Ethyl (2S)-2-[(3-oxo-7-oxaspiro[3.5]non-1-en-1-yl)amino]-3-{4-[(3,5-dichloroisonicotinoyl)amino]phenyl}propanoate Prepared from 7-oxaspirop[3.5]nonane-1,3-dione (1.2 g, 7.8 mmol) and the free amine of Intermediate 27 (2.67 g, 7.0 mmol) in a similar manner to the method of Example 11, to give the title compound (3.31 g, 6.38 mmol, 91%). δH (CDCl$_3$, 300K) 8.61 (1H, s), 8.33 (2H, s), 7.41 (2H, d J 5 Hz), 6.94 (2H, d J 8.5 Hz), 6.30 (1H, s br), 4.35 (1H, s), 4.11 (2H, q J 7.1 Hz) and (1H, m obscured), 5.72 (4H, m), 3.07 (1H, dd J 14.0, 5.0 Hz), 2.94 (1H, dd J 14.0, 6.6 Hz), 1.75-1.66 (2H, m), 155-1.48 (2H, m), 1.17 (3H, t J 7.1 Hz); m/z (ES$^+$, 70V) 517.9 (MH$^+$).

EXAMPLE 39

Ethyl (2S)-2-[(2-bromo-3-oxo-7-oxaspiro[3.5]non-1-en-1-yl)amino]-3-{4-[(3,5-dichloroisonicotinoyl)amino]phenyl}propanoate A solution of the compound of Example 38 (1.64 g, 3.17 mmol) and triethylamine (0.69 g, 970 µl, 6.8 mmol) in THF (15 ml) at 0° was treated dropwise with a solution of bromine (560 mg, 3.1 mmol) in THF (2 ml). After 1 h the resulting precipitate was removed by filtration, washed several times with cold EtOAc and dried to give the title compound as a white powder (1.53 g, 2.56 mmol, 81%). δH (DMSO d⁶, 300K) 10.90 (1H, s), 9.07 (1H, d J 9.0 Hz), 8.81 (2H, s), 7.60 (2H, d J 8.4 Hz), 7.28 (2H, d J 8.4 Hz), 4.85-4.80 (1H, m), 4.21 (2H, q J 7.1 Hz), 3.81-3.76 (2H, m), 3.63-3.58 (2H, m), 3.23 (1H, dd J 13.8, 4.8 Hz), 3.05 (1H, dd J 13.8, 9.4 Hz), 2.07-1.94 (2H, m), 1.52-1.49 (1H, m), 1.34-1.31 (1H, m), 1.24 (3H, t J 7.1 Hz); m/z (ES⁺, 70V) 597.9 and 599.9 (MH⁺).

EXAMPLE 40

(2S)-2-[(2-Bromo-3-oxo-7-oxaspiro[3.5]non-1-en-1-yl)amino]-3-{4-[(3,5-dichloroisonicotinoyl)amino] phenyl}propanoic Acid The compound of Example 39 (575 mg, 0.96 mmol) was hydrolysed in a similar manner to the method of Example 2, to give the title compound as a white powder (283 mg, 0.50 mmol, 52%). δH (DMSO d⁶, 390K) 10.88 (1H, s), 8.98 (1H, d J 9.2 Hz), 8.81 (2H, s), 7.59 (2H, d J 8.5 Hz), 7.27 (2H, d J 8.5 Hz), 4.78-4.72 (1H, m), 3.82-3.75 (2H, m), 3.64-3.54 (2H, m), 3.24 (1H, dd J 13.9, 4.5 Hz), 3.01 (1H, dd J 13.8, 9.5 Hz), 2.08-1.93 (2H, m), 1.52-1.48 (1H, m), 1.30-1.26 (1H, m); m/z (ES⁺, 70V) 569.9 and 571.9 (MH⁺).

EXAMPLE 41

Methyl (2S)-2-{(3-oxospiro[3.5]non-1-en-1-yl) amino}-3-(2,6-dimethoxy[1,1'-bi phenyl]-4-yl)propanoate To a solution of methyl (2S)-2-amino-3-(2,6-dimethoxy[1,1'-biphenyl]-4-yl)propanoate (0.80 g, 2.5 mmol) in DCM (10 ml) at room temperature was added 1-keto-3-hydroxyspiro [3,5]-non-2-ene (0.38 g, 2.5 mmol) and the mixture stirred for 48 h. Volatiles were removed in vacuo and the residue purified by column chromatography (SiO₂, EtOAc) to give the title compound as a white solid (1.05 g, 92%). δH (CDCl₃): 7.32-7.26 (3H, m), 7.12 (2H, d, J 8.2 Hz), 6.92 (2H, d, J 8.3 Hz), 5.90 (1H, br d, J 8.2 Hz), 4.60 (1H, s), 4.33 (1H, br), 3.86 (3H, s), 3.73 (6H, s), 3.30 (1H, dd, J 13.9, 5.3 Hz), 3.13 (1H, dd, J 13.9, 6.3 Hz), 1.82-1.33 (10H, m); m/z (ES⁺, 70V) 450.1 (MH⁺).

EXAMPLE 42

(2S)-2-{(3-Oxospiro[3.5]non-1-en-1-yl)amino}-3-(2,6-dimethoxy-[1,1'-biphenyl]-4-yl)propanoic Acid The compound of Example 41 (0.40 g, 0.9 mmol) was hydrolysed in a similar manner to the method of Example 2, to give the title compound as a white solid (0.19 g, 45%). δH (DMSO d⁶) 8.25 (1H, d, J 8.6 Hz), 7.29-7.19 (3H, m), 7.07 (2H, d, J 7.9 Hz), 6.70 (2H, d, J 8.4 Hz), 4.32 (1H, s), 4.11 (1H, br), 3.61 (6H, s), 3.18 (1H, dd, J 13.7, 4.7 Hz), 2.93 (1H, dd, J 13.7 9.9 Hz), 1.67-1.16 (10H, m); m/z (ES⁺, 70V) 436.1 (MH⁺).

EXAMPLE 43

Methyl (2S)-2-{(2-bromo-3-oxospiro[3.5]non-1-en-1-yl)amino}-3-(2,6-dimethoxy[1,1'-biphenyl]-4-yl) propanoate To a cooled solution (0-5°) of the compound of Example 41 (0.42 g, 0.93 mmol) and triethylamine (0.14 ml, 1.03 mmol) in THF (10 ml) was added a solution of bromine (0.16 g, 1.0 mmol) in DCM (1 ml). The mixture was stirred at this temperature for 1 h prior to partitioning between EtOAc (100 ml) and sodium hydrosulfite (100 ml, 5% aq.). The organics were separated, washed with water (50 ml), brine (50 ml), dried (Na₂SO₄), filtered and concentrated in vacuo to give the crude product as pale yellow foam. Column chromatography (SiO₂, 1:1 EtOAc:hexanes) gave the title compound as a white foam (0.45 g, 92%). δH(CDCl₃) 7.32-7.26 (3H, m), 7.13 (2H, d, J 8.1 Hz), 6.66 (2H, d, J 8.4 Hz), 5.80 (1H, brd, J 8.6 Hz), 5.15-5.08 (1H, m), 3.87 (3H, s), 3.73 (6H, s), 3.35 (1H, d, J 10.0 Hz), 3.31 (1H, d, J 4.9 Hz), 1.80-1.33 (10H, m); m/z (ES⁺, 70V) 529.0 and 530.0 (MH⁺).

EXAMPLE 44

(2S)-27{(2-Bromo-3-oxospiro[3.5]non-1-en-1-yl) amino}-3-(2,6-dimethoxy[1,1'-biphenyl]-4-yl)propanoic Acid The compound of Example 43 (0.36 g, 0.7 mmol) was hydrolysed in a similar manner to the method of Example 2 to give the title compound as a white solid (0.23 g, 58%). δH (DMSO d⁶) 8.83 (1H, d, J 9.4 Hz), 7.28 (1H, d, J 8.4 Hz), 7.24-7.20 (2H, m) 7.10 (2H, d, J 8.1 Hz), 6.70 (2H, d, J 8.4 Hz), 4.83-4.77 (1H, br), 3.61 (6H, s), 3.25 (1H, dd, J 13.8, 9.8 Hz), 2.95 (1H, dd, J 13.8, 10.3 Hz), 1.78-1.35 (10H, m); m/z (ES⁺, 70V) 516.0 and 517.0 (MH⁺).

EXAMPLE 45

Ethyl (2S)-2-[(3-oxospiro[3.6]dec-1-en-1-yl)amino]-3-{4-[(3,5-dichloro-isonicotinoyl)amino] phenyl}propanoate Prepared from Intermediate 31 (400 mg, 2.4 mmol) and the free amine of Intermediate 27 (920 mg, 2.4 mmol) in a similar manner to the method of Example 11, to give the title compound (1.1 g, 20.7 mmol, 86%). δH (CDCl₃, 300K) 8.57 (2H, s), 8.28 (1H, s), 7.61 (2H, d J 8.5 Hz), 7.14 (2H, d J 8.5 Hz), 5.76 (1H, d J 7.5 Hz), 4.33-4.23 (3H, m), 3.25 (1H, dd J 14.0, 5.3 Hz), 3.12 (1H, dd J 13.9, 5.7 Hz), 1.95-1.89 (2H, m), 1.79-1.70 (4H, m), 1.71-1.50 (6H, m), 1.36 (3H, t J 7.1 Hz); m/z (ES⁺, 70V) 530.0 (MH⁺).

EXAMPLE 46

(2S)-2-[(3-Oxospiro[3.6]dec-1-en-1-yl)amino]3-{4-[(3,5-dichloroisonicotinoyl)amino]phenyl}propanoic Acid The compound of Example 45 (257 mg, 0.57 mmol) was hydrolysed in a similar manner to the method of Example 2, to give the title compound as a white powder (257 mg, 0.51 mmol, 89%). δH (DMSO d⁶, 390K) 10.83 (1H, s), 8.84 (2H, s), 7.39 (2H, d J 8.5 Hz), 7.29 (2H, d J 8.5 Hz), 4.30 (1H, s), 4.12-3.98 (1H, m), 3.15 (1H, dd J 13.9, 5.2 Hz), 2.97 (1H, dd J 13.8, 9.5 Hz), 1.85-1.78 (1H, m), 1.77-1.38 (11H, m); m/z (ES⁺, 70V) 502.0 (MH⁺).

EXAMPLE 47

Ethyl (2S)-2-[(2-bromo-3-oxospiro[3.6]dec-1-en-1-yl)amino]-3-{4-[(3,5-dichloroisonicotinoyl)amino] phenyl}propanoate A solution of the compound of Example 45 (988 mg, 1.87 mmol) and triethylamine (520 µl, 3.7 mmol) in THF (20 ml) at 0° was treated dropwise with a solution of bromine (330 mg, 2.1 mmol) in THF (2 ml). After 1 h the crude reaction mixture was diluted with EtOAc (55 ml), saturated aqueous NaHCO₃ (15 ml) and saturated aqueous sodium chloride (15 ml) and the crude product extracted with EtOAc (3×20 ml). The combined extracts were dried (MgSO$_4$), concentrated in vacuo and the crude residue chromatographed (SiO$_2$, 1:1 EtOAc:hexanes) to give the title compound as a white powder (965 mg, 1.58 mmol, 85%). δH (CDCl$_3$, 300K) 8.61 (2H, s), 8.45 (1H, d, J 3.1 Hz), 7.63 (2H, d, J 8.2 Hz), 7.15 (2H, d, J 8.2 Hz), 5.91 (1H, d, J 8.1 Hz), 5.05-5.00 (1H, m), 4.30 (2H, q, J 7.1 Hz), 3.30 (2H, d, J 5.4 Hz), 1.98-1.90 (2H, m), 1.89-1.60 (10H, m), 1.22 (3H, t, J 7.1 Hz); m/z (ES$^+$, 70V) 609.9 and 611.9 (MH$^+$).

EXAMPLE 48

(2S)-2-[(2-Bromo-3-oxospiro[3.6]dec-1-en-1-yl) amino]-3-{4-[(3,5-dichloroisonicotinoyl)amino] phenyl}propanoic Acid The compound of Example 47 (560 mg, 0.92 mmol) was hydrolysed in a similar manner to the method of Example 2, to give the title compound as a white powder (412 mg, 0.71 mmol, 77%). δH (DMSO d$^6$, 380K) 10.40 (1H, s), 8.67 (2H, s), 7.55 (2H, d, J 8.5 Hz), 7.26 (2H, d, J 8.5 Hz), 4.52 (1H, br s), 3.22 (1H dd, J 14.1, 5.3 Hz), 3.11 (1H, dd, J 13.9, 8.0 Hz), 1.82-1.29 (12H, m); m/z (ES$^+$, 70V) 589.1 and 583.9 (MH$^+$).

EXAMPLE 49

Ethyl (2S) 2-{[4,4-dimethyl-2-(phenylselenenyl)-3-oxo-1-cyclobutenyl]amino}3-{4-[(3,5-dichloroisoni-cotinoyl)amino]phenyl}propanoate A stirred solution of the compound of Example 5 (630 mg, 1.41 mmol) in THF (15 ml) at room temperature was treated dropwise with a solution of phenylselenenyl chloride (283 mg, 1.48 mmol). After 10 min the crude reaction mixture was diluted with EtOAc (30 ml) saturated aqueous NaHCO$_3$ solution (50 ml) and brine (50 ml). The mixture was extracted with EtOAc (3×50 ml), the combined extracts dried (MgSO$_4$) and concentrated in vacuo. The residual slurry was chromatographed (SiO$_2$, EtOAc) to give the title compound as a white powder (812 mg, 1.29 mmol, 91%). 5H (CDCl$_3$, 300K) 8.58 (2H, s), 7.75 (1H, s), 7.53 (2H, d, J 8.3 Hz), 7.35-7.11 (5H, m), 7.04 (2H, d, J 8.3 Hz), 6.11 (1H, d, J 8.5 Hz), 5.28-5.25 (1H, m), 4.20 (2H, q, J 7.1 Hz), 3.17 (2H, m), 1.31 (6H, s), 1.28 (3H, t, J 7.1 Hz); m/z (ES$^+$, 70V) 631.9 (MH$^+$).

EXAMPLE 50

(2S)-2-{[4,4-Dimethyl-2-(phenylselenenyl)-3-oxo-1-cyclobutenyl]amino}-3-{4-[(3,5-dichloroisonicoti-noyl)amino]phenyl}propanoic Acid The compound of Example 49 (600 mg, 0.95 mmol) was hydrolysed in a similar manner to the method of Example 2, to give the title compound as a white powder (503 mg, 0.83 mmol, 87%). δH (DMSO d$^6$, 300K) 10.86 (1H, s), 9.11 (1H, d, J 8.9 Hz), 8.81 (2H, s), 7.50 (2H, d, J 8.2 Hz), 7.21 (2H, d, J 8.2 Hz), 4.96-4.92 (1H, br s), 3.13 (1H, dd, J 13.8, 4.5 Hz), 2.94 (1H, dd, J 13.6, 8.7 Hz), 1.22 (3H, s), 1.14 (3H, s); m/z (ES$^+$, 70V) 603.9 (MH$^+$).

EXAMPLE 51

Ethyl (2S)-2-[(3-oxo-7-acetyl-7-azaspiro[3.5]non-1-en-1-yl)amino]-3-{4-[(3,5-dichloroisonicotinoyl) amino]phenyl}propanoate Prepared from Intermediate 33 (150 mg, 0.77 mmol), and the free amine of Intermediate 27 (150 mg, 0.39 mmol) in a similar manner to the method of Example 11, to give the title compound (143 mg, 0.26 mmol, 67%). δH (DMSO d$^6$, 300K) 10.89 (1H, s), 8.89 (2H, s), 8.55-8.48 (1H, m), 7.58 (2H, d, J 7.9 Hz), 7.25 (2H, d, J 7.9 Hz), 4.47 (1H, s), 4.29-4.23 (1H, m), 4.16 (2H, q, J 7.1 Hz), 3.76-3.72 (1H, m), 3.15 (1H, dd, J 13.8, 5.2 Hz), 3.01-2.89 (2H, m), 2.00 (3H, s), 1.90-1.37 (6H, m), 1.21 (3H q J 7.1 Hz); m/z (ES$^+$, 70V) 559.0 (MH$^+$).

EXAMPLE 52

(2S)-2-[(3-Oxo-7-acetyl-7-azaspiro[3.5]non-1-en-1-yl)amino]-3-{4-[(3,5-dichloroisonicotinoyl)amino] phenyl}propanoic Acid The compound of Example 51 (200 mg, 0.35 mmol) was hydrolysed in a similar manner to the method of Example 2, to give the title compound as a white powder (91 mg, 0.16 mmol, 46%). δH (CD$_3$OD, 300K) 8.90 (2H, s), 7.60 (2H, d, J 8.2 Hz), 7.30 (2H, J 8.2 Hz), 4.49 (1H, s), 4.33-4.27 (2H, m), 3.85-3.77 (1H, m), 3.57-3.45 (1H, m), 3.37-3.31 (1H, m), 3.20-3.11 (1H, m), 3.05-2.99 (1H, m), 2.11 (3H, s), 1.97-1.52 (4H, m); m/z (ES$^+$, 70V) 531.0 (MH$^+$).

EXAMPLE 53

Ethyl (2S)-2-[(7-methoxy-3-oxospiro[3.5]non-1-en-1-yl)amino]-3-{4-[(3,5-dichloroisonicotinoyl)amino] phenyl}propanoate Prepared from Intermediate 35 (500 mg, 2.77 mmol) and the free amine of Intermediate 27 (980 mg, 2.6 mmol) in a similar manner to the method of Example 11, to give the title compound as an inseparable 1:1 mixture of isomers (1.23 g, 2.25 mmol, 87%). δH (CDCl$_3$, 300K, 2 isomers) 9.12/8.99 (1H, s), 8.51/8.50 (2H, s), 7.59/7.56 (2H, d, J 8.5 Hz), 7.08 (2H, d, J 8.5 Hz), 6.21/5.98 (1H, d, J 7.9 Hz/7.6 Hz), 4.46/4.43 (1H, s), 4.29/4.10 (3H, m), 3.13-3.08 (1H, m), 3.39 (1H, m), 3.30/3.29 (3H, s), 3.23-3.18 (1H, m), 3.13-3.08 (1H, m), 1.97-1.58 (8H, m), 1.35-1.34 (3H, t, J 7.1 Hz); m/z (ES$^+$, 70V) 546.0 (MH$^+$).

EXAMPLE 54

(2S)-2-[(7-Methoxy-3-oxospiro[3.5]non-1-en-1-yl) amino]-3-{4-[(3,5-dichloroisonicotinoyl)amino] phenyl}propanoic Acid The compound of Example 53 (950 mg, 1.7 mmol) was hydrolysed in a similar manner to the method of Example 2, to give the title compound as a white powder, as an approx. 1:1 mixture of isomers (812 mg, 1.57 mmol, 92%). δH (DMSO d$^6$, 300K) 10.57 (1H, s), 8.73 (2H, s), 7.93 (1H, br s), 7.56 (2H, d, J 8.2 Hz), 7.29-7.21 (2H, m), 4.37 (1H, s), 4.08-4.04 (1H, m), 3.34 (1H, m), 3.25 (3H, s), 3.21-3.02 (2H, m), 1.92-1.34 (8H, m); m/z (ES$^+$, 70V) 518.0 (MH$^+$).

EXAMPLE 55

Ethyl (2S)-2-[(2-bromo-7-methoxy-3-oxospiro[3.5] non-1-en-1-yl)amino]-3-{4-[(3,5-dichloroisonicoti-noyl)amino]phenyl}propanoate Was prepared according to the method of Example 47 from the compound of Example 53 (1.0 g, 1.83 mmol) and bromine (322 mg, 2.0 mmol) to give the title compound as a powder (778 mg, 1.24 mmol, 70%). [Separation of isomers at this stage was achieved chromatographically (SiO$_2$; 1:1 EtOAc: hexanes to 100% EtOAc)]. δH (CDCl$_3$, 300K, fast eluting isomer) 10.65 (1H, s), 10.74 (1H, d, J 9.2 Hz), 8.58 (2H, s), 7.36 (2H, d, J 8.6 Hz), 7.06 (2H, d, J 8.6 Hz) 4.54-4.48 (1H, m), 3.18 (11H, m), 3.03-2.98 (1H, m), 3.00 (3H, s), 2.78 (1H, dd, J 13.9, 10.0 Hz), 1.18-1.65 (2H, m), 1.61-1.44 (4H, m), 1.18-1.15 (1H, m), 0.92 (11H, m); m/z (ES+, 70V) 625.9 (MH+).

EXAMPLE 56

(2S)-2-[(2-Bromo-7-methoxy-3-oxospiro[3,5]non-1-en-1-yl)amino]-3-{4-[(3,5-dichloroisonicotinoyl)amino]phenyl}propanoic Acid The compound of Example 55 (650 mg, 1.04 mmol) was hydrolysed in a similar manner to the method of Example 2, to give the title compound as a white powder (512 mg, 0.86 mmol, 83%). δH (DMSO d6, 300K) 10.86 (1H, s), 9.11 (1H, d, J 8.9 Hz), 8.81 (2H, s), 7.50 (2H, d, J 8.2 Hz), 7.21 (2H, d, J 8.2 Hz), 4.96-4.92 (1H, br s), 3.13 (1H, dd, J 13.8, 4.5 Hz), 2.94 (1H, dd, J 13.6, 8.7 Hz), 1.22 (3H, s), 1.14 (3H, s); m/z (ES+, 70V) 597.9 (MH+).

EXAMPLE 57

Ethyl (2S)-2-[(2-bromo-3-oxospiro[3.5]non-1-en-1-yl)amino]-3-{4-[(3-methyl[2.7]naphthyridin-1-yl)oxy]phenyl}propanoate To the compound of Example 29 (0.54 g, 1.1 mmol) in THF (10 ml) at room temperature was added triethylamine (0.2 ml, 1.4 mmol) and a solution of bromine (224 mg, 1.4 mmol) in DCM (1 ml). The mixture was stirred overnight and then partitioned between EtOAc (50 ml) and water (50 ml). The organics were separated, washed with sodium hydrosulfite (2×50 ml, 5% aq.), water (50 ml), brine (50 ml), dried (Na2SO4), filtered and concentrated in vacuo. The crude product was subjected to column chromatography (SiO2, EtOAc) to give the title compound as a white solid (0.46 g, 73%). δH (CDCl3) 9.75 (1H, s), 8.69 (2H, d, J 5.9 Hz), 7.64 (2H, d, J 6.0 Hz), 7.25 (2H, d, J 8.2 Hz), 7.20 (2H, d, J 8.2 Hz), 5.89 (1H, d, J 8.3 Hz), 5.06 (1H, dt, J 5.4, 8.2 Hz), 4.30 (2H, q, J 7.1 Hz), 3.35 (2H, m), 2.50 (3H, s), 1.84-1.33 (10H, m); m/z (ES+, 70V) 566.1 and 567.1 (MH+).

EXAMPLE 58

(2S)-2-{(2-Bromo-3-oxospiro[3.5]non-1-en-1-yl)amino}-3-{4-[(3-methyl[2.7]naphthyridin-1-yl)oxy]phenyl}propanoic Acid The compound of Example 57 (0.32 g, 0.6 mmol) was hydrolysed in a similar manner to the method of Example 2, to give the title compound as a white solid (0.20 g, 66%). δH (DMSO d6) 9.61 (1H, s), 8.88 (1H, d, J 9.5 Hz), 8.72 (1H, d, J 5.7 Hz), 7.74 (1 HK d, J 5.8 Hz), 7.35 (3H, c), 7.24 (2H, d, J 8.6 Hz), 4.77 (1H, m), 3.18 (1H, dd, J 13.7, 4.70 Hz), 3.01 (1H, dd, J 13.7, 10.4 Hz), 2.49 (3H, s), 1.78-1.12 (10H, m); m/z (ES+, 70V) 537.1 and 538.1 (MH+).

EXAMPLE 59

Ethyl (2S)-2-{[2-(phenylsulfanyl)-4,4-dimethyl-3-oxo-1-cyclobutenyl]amino}-3-{4-[(3,5-dichloroisonicotinoyl)amino]phenyl}propanoate A solution of the compound of Example 5 (340 mg, 0.76 mmol) in THF (25 ml), at room temperature, was treated dropwise with a solution containing phenyl sulphenyl chloride (122 mg, 0.84 mmol) in THF (2 ml). After 10 min the reaction mixture was poured into a mixture of EtOAc (150 ml) and saturated aqueous NaHCO3 solution (50 ml). The organic layer was extracted and washed with brine (25 ml), dried (MgSO4), filtered and concentrated in vacuo. Chroma-tography (SiO2, 100% EtOAc) gave the title compound as a white powder (346 mg, 0.59 mmol, 78%). δH (CDCl3) 8.45 (2H, s), 8.05 (1H, s), 7.43 (1H, d, J 8.4 Hz), 7.15 (2H, d, J 8.4 Hz), 7.11-7.04 (5H, m), 6.25 (1H, d, J 8.5 Hz), 5.10-5.05 (1H, m), 4.09 (2H, q, J 7.1 Hz), 3.11-3.06 (2H, m), 1.18 (3H, s), 1.15 (3H, s), 1.13 (3H, t, 7.1 Hz); m/z (ES+, 70V) 584.0 (MH+).

EXAMPLE 60

(2S)-2-{[2-(Phenylsulfanyl)-4,4-dimethyl-3-oxo-1-cyclobutenyl]-amino}-3-{4-[(3,5-dichloroisonicotinoyl)amino]phenyl}propanoic Acid Hydrolysis of the ethyl ester (340 mg, 0.58 mmol) with lithium hydroxide (60 mg, 1.4 mmol), according to the method of Example 2, gave the title compound (296 mg, 0.53 mmol, 90%) as a white powder. δH (DMSO d6, 390K) 10.30 (1H, br s), 8.68 (2H, s), 7.45 (2H, br s), 7.26-7.22 (2H, m), 7.15-7.08 (7H, m), 4.75-4.66 (1H, m), 3.17 (1H, dd, J 14.0, 5.3 Hz), 3.04 (1H, dd J 14.0, 7.7 Hz), 1.19 (3H, s), 1.16 (3H, s); m/z (ES+, 70V) 556.0, 557.9 (MH+).

EXAMPLE 61

Ethyl (2S)-2-[(2-chloro-3-oxospiro[3.5]non-1-en-1-yl)amino]-3-{4-[(3,5-dichloroisonicotinoyl)amino]phenyl}propanoate A solution of the compound of Example 27 (366 mg, 0.71 mmol) in THF (25 ml), at room temperature, was treated portionwise with N-chloro succinimide (100 mg, 0.75 mmol). After 30 min the reaction mixture was poured into a mixture of EtOAc (150 ml) and saturated aqueous NaHCO3 solution (50 ml). The organic layer was extracted and washed with brine (25 ml), dried (MgSO4), filtered and concentrated in vacuo. Chromatography (SiO2; 70% EtOAc:hexanes) gave the title compound as a white powder (312 mg, 0.56 mmol, 80%). δH (CDCl3) 8.50 (2H, s), 7.73 (1H, s), 7.53 (1H, d, J 8.4 Hz), 7.04 (2H, d, J 8.4 Hz), 5.73 (1H, d, J 8.0 Hz), 4.88-4.81 (1H, m), 4.21 (2H, q, J 7.1 Hz), 3.21-3.16 (2H, m), 1.79-1.65 (4H, m), 1.51-1.36 (6H, m), 1.28 (3H, t, J 7.1 Hz); m/z (ES+, 70V) 550.0 (MH+).

EXAMPLE 62

(2S)-2-[(2-Chloro-3-oxospiro[3.5]non-1-en-1-yl)amino]-3-{4-[(3,5-dichloroisonicotinoyl)amino]phenyl}propanoic Acid Hydrolysis of the compound of Example 61 (300 mg, 0.54 mmol) with lithium hydroxide (60 mg, 1.4 mmol), according to the method of Example 2, gave the title compound. δH (DMSO d6, 390K) 10.44 (1H, br s), 8.69 (2H, s), 8.05-7.85 (1H, s br), 7.54 (2H, d, J 7.8 Hz), 7.25 (2H, d, J 7.8 Hz), 4.60-4.49 (1H, m), 3.21 (1H, dd, J 14.0, 5.3 Hz), 3.04 (1H, dd, J 14.0, 5.1 Hz), 1.80-1.21 (10H, m); m/z (ES+, 70V) 521.9, 525.9 (MH+).

EXAMPLE 63

Ethyl (2S)-2-[(2-iodo-3-oxospiro[3.5]non-1-en-1-yl)amino]-3-{4-[(3,5-dichloroisonicotinoyl)amino]phenyl}propanoate To a stirred solution of the compound of Example 27 (1.0 g, 1.9 mmol) in THF (10 ml) at room temperature was added N-iodosuccinamide (460 mg, 2.0 mmol) in one portion. After 5 minutes the mixture was concentrated in vacuo and the residue triturated with a mixture of ether (10 ml) and water (10 ml), filtered and washed with ether and water. Oven drying gave the title compound (802 mg, 66%) as a yellow solid. δH (DMSO d$^6$) 8.90 (1H, d, J 9.1 Hz), 8.78 (2H, s), 7.58 (2H, d, J 8.5 Hz), 7.25 (2H, d, J 8.5 Hz), 4.91 (1H, m), 4.20 (2H, q, J 7.1 Hz), 3.30-3.00 (2H, m), 1.80-1.24 (10H, m), 1.21 (3H, t, J 7.1 Hz); m/z (ES$^+$, 70V) 642.0 (MH$^+$).

EXAMPLE 64

Ethyl (2S)-3-{4-[(3,5-dichloroisonicotinoyl)amino]phenyl}-2-(3-oxo-2-pyridin-3-yl-spiro[3,5]non-1-en-1-ylamino)propanoate A mixture of the compound of Example 63 (1.0 g, 1.6 mmol), 10% palladium on charcoal (15 mg), triphenylphosphine (100 mg, 0.32 mmol), copper (1) iodide (30 mg, 0.16 mmol), 3-pyridyl tributylstannane (560 μl, 1.7 mmol) in DMF (10 ml) was heated to 100° under a nitrogen atmosphere from 2 hours. The solvent was removed by evaporation in vacuo and the residue purified by column chromatography (SiO$_2$; 666:333:1 EtOAc:hexane; triethylamine) to give the title compound as a yellow oil (378 mg, 41%). δH (DMSO d$^6$) 8.76 (2H, s), 8.60 (1H, m), 8.30 (2H, br. s), 7.94 (1H, d, J 8.0 Hz), 7.54 (2H, m), 7.34 (2H, m), 7.10 (1H, d, J 8.4 Hz), 4.34 (1H, m), 4.24 (2H, q, J 5.3 Hz), 3.25-2.95 (2H, m), 1.86-1.40 (10H, m), 1.26 (3H, t, J 5-3 Hz); m/z (ES$^+$, 70V) 593.0 (MH$^+$).

EXAMPLE 65

(2S)-3-{4-[(3,5-Dichloroisonicotinoyl)amino]phenyl}-2-(3-oxo-2-pyridin-3-yl-spiro[3,5]non-1-en-1-ylamino)propanoic acid The compound of Example 64 was hydrolysed in a similar manner to the method of Example 2 to give the title compound as a white solid (76%). 5H (DMSO d$^6$, 400K) 10.28 (1H, s), 8.66 (2H, s), 8.59 (1H, s), 8.34 (1H, m), 7.80 (1H, m), 7.69 (1H, m), 7.51 (2H, m), 7.24 (4H, m), 4.28 (1H, m, 3.25-3.07 (2H, m), 1.90-1.50 (10H, m); m/z (ES$^+$, 70V) 565.0 (MH$^+$).

EXAMPLE 66

Ethyl (2S)-3-{4-[(3,5-Dichloroisonicotinoyl)amino]phenyl}-2-(2-iodo-4,4-dimethyl-3-oxo-cyclobut-1-enylamino)propanoate Prepared in a similar manner to the compound of Example 63 from the compound of Example 5 to give the title compound as a white solid (72%). δH (DMSO d$^6$) 9.17 (1H, d, J 9.1 Hz), 8.79 (2H, s), 7.58 (2H, d, J 8.5 Hz), 7.29 (2H, d, J 8.5 Hz), 4.94 (1H, m), 4.20 (2H, q, J 7.1 Hz), 3.25-3.00 (2H, m), 1.23 (3H, t, J 7.1 Hz), 1.12 (3H, s), 1.03 (3H, s); m/z (ES$^+$, 70V) 601.8 (MH$^+$).

EXAMPLE 67

Ethyl (2S)-3-{4-[(3,5-Dichloroisonicotinoyl)amino]phenyl}-2-(4,4-dimethyl-3-oxo-2-pyridin-3-yl-cyclobut-1-enylamino)propanoate Prepared in a similar manner to the compound of Example 64 from the compound of Example 66 to give the title compound as a white solid (41%). δH (CDCl$_3$) 8.85 (1H, m), 8.57 (1H, m), 8.34 (3H, m), 7.92 (2H, m), 7.73 (2H, m), 7.28 (1H, m), 4.33 (1H, m), 4.15 (2H, q, J 7.1 Hz), 3.32-3.09 (2H, m), 1.71 (3H, s), 1.33 (3H, s), 1.27 (3H, t, J 7.1 Hz); m/z (ES$^+$, 70V) 553.0 (MH$^+$).

EXAMPLE 68

(2S)-3-{4-[(3,5-Dichloroisonicotinoyl)amino]phenyl}-2-(4,4-dimethyl-3-oxo-2-pyridin-3-yl-cyclobut-1-enylamino)propanoic Acid The compound of Example 67 was hydrolysed in a similar manner to the method of Example 2 to give the title compound as a white solid (43%). δH (DMSO d$^6$, 400K) 10.28 (1H, br. s), 8.66 (3H, m), 8.33 (1H, m), 8.09 (1H, m), 7.75 (1H, m), 7.52 (2H, m), 7.27 (3H, m), 4.25 (1H, m), 3.26 (1H, m), 3.14 (1H, m), 1.22 (3H, s), 1.06 (3H, s); m/z (ES$^+$, 70V) 524.9 (MH$^+$).

EXAMPLE 69

(2S)-2-[(2-Iodo-3-oxospiro[3.5]non-1-en-1-yl)amino]-3-{4-[(3,5-dichloroisonicotinoyl)amino]phenyl}propanoic Acid The compound of Example 63 was hydrolysed in a similar manner to the method of Example 2 to give the title compound as a white solid (98%). 6H (DMSO d$^6$) 10.87 (1H, s), 8.84 (1H, d, J 9.3 Hz), 8.79 (2H, s), 7.58 (2H, d, J 8.5 Hz), 7.27 (2H, d, J 8.5 Hz), 4.87 (1H, m), 3.25 (1H, m), 3.02 (1H, m), 1.70-1.25 (10H, m); m/z (ES$^+$, 70V) 613.8 (MH$^+$).

EXAMPLE 70

(2S)-3-{4-[(3,5-Dichloroisonicotinoyl)amino]phenyl}-2-(2-iodo-4,4-dimethyl-3-oxo-cyclobut-1-enylamino)propanoic Acid The compound of Example 66 was hydrolysed in a similar manner to the method of Example 2 to give the title compound as a white solid (95%). δH (DMSO d$^6$) 10.87 (1H, s), 9.08 (1H, d, J 9.3 Hz), 8.78 (2H, s), 7.58 (2H, d, J 8.5 Hz), 7.26 (2H, d, J 8.5 Hz), 4.88 (1H, m), 3.25 (1H, m), 3.04 (1H, m), 1.12 (3H, s), 1.01 (3H, s); m/z (ES$^+$, 70V) 573.8 (MH$^+$).

EXAMPLE 71

Ethyl (2S)-3-{5-[(3,5-dichloroisonicotinoyl)amino]pyridin-2-yl}-2-[(3-oxaspiro[3.5]non-1-en-1-yl)amino]propanoate To a solution of Intermediate 43 (470 mg, 1.22 mmol) in DCM (10 ml) was added spiro[3.5]nonane-1,3-dione (187 mg, 1.23 mmol) with stirred for 18 hr. After evaporation of the solvent the crude product was purified by chromatography (silica, 3-4% MeOH/DCM) to afford the title compound as a white foam (610 mg, 96%). δH (DMSO d$^6$) 8.81 (2H, s), 8.70 (1H, s), 8.33 (1H, d), 8.02 (1H, d), 7.32 (1H, d), 4.35 (1H, m), 4.13 (2H, m), 3.23 (2H, m), 1.53 (8H, br), 1.37 (2H, br), 1.17 (3H, t); m/z (ES$^+$, 70V) 517 (MH$^+$).

EXAMPLE 72

Ethyl (2S)-2-[(2-bromo-3-oxaspiro[3.5]non-1-en-1-yl)amino]-3-{5-[(3,5-dichloroisonicotinoyl)amino]pyridin-2-yl}propanoate A solution of NBS (169 mg, 0.94 mmol) in dry DCM (5 ml) was added to a stirred solution of the compound of Example 71 (490 mg, 0.94 mmol) in DCM (10 ml) at 0° C. (ice-water bath). After 30 min the solvent was evaporated in vacuo and the residue partitioned between Et$_2$O (80 ml) and saturated sodium bicarbonate (20 ml). The phases were separated and the aqueous layer re-extracted with Et$_2$O (40 ml). The combined organics were washed with water (2×10 ml), brine (10 ml), dried (Na$_2$SO$_4$) and evaporated in vacuo and the residue purified by chromatography (silica, 50-80% Et$_2$O/hexane) to give the title compound as a colourless glass foam (501 mg, 88%). δH (DMSO d$^6$) 11.17 (1H, s), 8.83 (2H, s), 8-73 (1H, s), 8.01 (1H, d), 7.34 (1H, d), 5.06 (1H, dd), 4.20 (2H, q), 3.39-3.20 (2H, brm), 1.73 (1H, m), 1.57 (8H, br), 1.34 (1H, br), 1.22 (3H, t); m/z (ES$^+$, 70V) 596 (MH$^+$).

EXAMPLE 73

Ethyl (2S)-2-[(2-bromo-3-oxaspiro[3.5]non-1-en-1-yl)amino]-3-{5-[(3,5-dichloroisonicotinoyl)amino]pyridin-2-yl}propanoate Hydrochloride The compound of Example 72 (300 mg, 0.50 mmol) was dissolved in EtOAc (20 ml) and HCl gas bubbled through for a short time. The resulting white precipitate was collected by filtration, washed with Et$_2$O and dried to give the title compound as a white powder (155 mg, 48%). δH (DMSO d$^6$) 11.32 (1H, s), 8.84 (2H, s), 8.81 (1H, s), 8.13 (1H, d), 7.43 (1H, d), 5.06 (1H, dd), 4.19 (2H, q), 3.39 (1H, m), 3.28 (1H, m), 1.74 (1H, m), 1.57 (8H, br), 1.35 (1H, br), 1.22 (3H, t); m/z (ES$^+$, 70V) 631 (MH$^+$).

EXAMPLE 74

(2S)-2-[(2-Bromo-3-oxaspiro[3.5]non-1-en-1-yl)amino]-3-{5-[(3,5-dichloroisonicotinoyl)amino]pyridin-2-yl}propanoic acid The compound of Example 72 (370 mg, 0.62 mmol) was hydrolysed in a similar manner to the method of Example 2 to give the title compound as a white solid (200 mg, 56%) as light yellow solid. δH (DMSO d$^6$) 11.16 (1H, s), 8.83 (2H, s), 8.73 (1H, s), 8.05 (1H, d), 7.35 (1H, d), 5.00 (1H, dd), 2.76 (2H, br m), 1.55 (8H, m), 1.27 (1H, br), 1.12 (1H, br); m/z (ES$^+$, 70V) 568 (MH$^+$).

EXAMPLE 75

Ethyl (2S)-2-[(2-chloro-3-oxaspiro[3.5]non-1-en-1-yl)amino]-3-{5-[(3,5-dichloroisonicotinoyl)amino]pyridin-2-yl}propanoate A solution of NCS (247 mg, 1.85 mmol) in dry THF (10 ml) was added to a stirred (ice-water bath cooled) solution of the compound of Example 71 (800 mg, 1.54 mmol) in THF (10 ml) and DCM (10 ml). After 2 hr the solvent was evaporated in vacuo and the residue partitioned between Et$_2$O (250 ml) and saturated sodium bicarbonate (30 ml). The phases were separated and the organic layer was washed with brine (10 ml), dried (Na$_2$SO$_4$) and evaporated in vacuo and the residue purified by chromatography (silica, 70-100% Et$_2$O/hexane) to give the title compound as white foam (620 mg, 72%). δH (DMSO d$^6$) 8.96 (2H, s), 8.86 (1H, s), 8.20 (1H, d), 7.50 (1H, d), 5.08 (1H, m), 4.32 (2H, q), 3.53-3.31 (2H, br m), 1.72 (9H, m), 1.50 (1H, br), 1.34 (3H, t); m/z (ES$^+$, 70V) 551 (MH$^+$).

EXAMPLE 76

Ethyl (2S)-2-[2-chloro-3-oxaspiro[3.5]non-1-en-1-yl)amino]-3-{5-[(3,5-dichloroisonicotinoyl)amino]pyridin-2-yl}propanoate Hydrochloride The compound of Example 75 (269 mg, 0.48 mmol) was dissolved in EtOAc (20 ml) and HCl gas bubbled through for a short time. The resulting precipitate was collected by filtration, washed with Et$_2$O and dried to give the title compound (230 mg, 80.3%). δH (DMSO d$^6$) 11.21 (1H, s), 8.83 (2H, s), 8.75 (1H, s), 8.08 (1H, d), 7.39 (1H, d), 4.95 (1H, m), 4.20 (2H, q), 3.36 (1H, m), 3.26 (1H, m), 1.71 (1H, m), 1.57 (8H, br), 1.35 (1H, m), 1.21 (3H, t); m/z (ES$^+$, 70V) 587 (MH$^+$).

EXAMPLE 77

(2S)-2-[(2-Chloro-3-oxaspiro[3.5]non-1-en-1-yl)amino]-3-{5-[(3,5-dichloroisonicotinoyl)amino]pyridin-2-yl}propanoic Acid The compound of Example 72 (250 mg, 0.45 mmol) was hydrolysed in a similar manner to the method of Example 2 to give the title compound as a white powder (142 mg, 60%). δH (DMSO d$^6$) 11.19 (1H, s), 8.83 (2H, s), 8.74 (1H, s), 8.07 (1H, d), 7.35 (1H, d), 4.90 (1H, m), 3.37 (1H, m), 3.19 (1H, m), 1.71-1.28 (10H, br m); m/z (ES$^+$, 70V) 523 (MH$^+$).

EXAMPLE 78

Ethyl (2S)-3-{5-[(3,5-dichloroisonicotinoyl)amino]pyridin-2-yl}-2-{[(2-(methylsulfanyl)-3-oxaspiro[3.5]non-1-en-1-yl)amino}propanoate Sulphuryl chloride (49 μL) was added dropwise to a stirred ice-bath cooled solution of dimethyl sulfide (74 μL) in THF (5 ml). The ice bath was removed and the solution stirred for 45 min. This solution was added to a stirred solution of the compound of Example 71 (700 mg, 1.35 mmol) in THF (10 ml) and DCM (10 ml) and stirred at RT. The reaction was worked up in a similar manner to that of Example 79 to give the title compound.

EXAMPLE 79

Ethyl (2S)-3-{5-[(3,5-dichloroisonicotinoyl)amino]pyridin-2-yl}-2-{[(2-(isopropylsulfanyl)-3-oxaspiro[3.5]non-1-en-1-yl)amino}propanoate Sulphuryl chloride (218 μL) was added dropwise to a stirred ice-bath cooled solution of isopropyl disulphide (432 μL) in THF (10 ml). The ice bath removed and the mixture stood for 35 min. 5 ml of this solution was added to a stirred solution of the compound of Example 71 (700 mg, 1.35 mmol) in THF (10 ml) and DCM (10 ml) and stirred at RT for 15 min. The solvent removed and the residue was partitioned between Et$_2$O (130 ml) and saturated sodium bicarbonate (30 ml). The phases were separated and the organic layer was washed with brine (10 ml), dried (Na$_2$SO$_4$) and evaporated in vacuo and the residue purified by chromatography (silica, 2-3% EtOH/DCM) to give the title compound as a white foam. m/z (ES$^+$, 70V) 591 (MH$^+$).

EXAMPLE 80

Ethyl (2S)-3-{5-[(3,5-dichloroisonicotinoyl)amino]pyridin-2-yl}-2-{[(4,4-dimethyl-3-oxo-1-cyclobutenyl)amino}propanoate To a solution of Intermediate 43 (792 mg, 2.06 mmol) in DCM (15 ml) and THF (5 ml) was added 2,2-dimethyl-1,3-cyclobutanedione (0.27 g, 2.41 mmol) with stirring for 24 hr. After evaporation of the solvent the crude product was purified by chromatography (SiO$_2$, 4-8% EtOH/DCM) to give the title compound as a white foam (926 mg, 93%). δH (DMSO d$^6$), 8.78 (2H, s), 8.68 (1H, s), 8.53 (1H, d), 7.30 (1H, d), 4.38 (1H, s), 4.33 (1H, m), 4.11 (2H, q), 3.38-3.10 (2H, m), 1.14 (3H, t), 1.04 (3H, s), 0.94 (3H, s); m/z (ES$^+$, 70V) 477 (MH$^+$).

EXAMPLE 81

Ethyl (2S)-2-[(2-bromo-4,4-dimethyl-3-oxo-1-cyclobutenyl)amino]-3-{5-[(3,5-dichloroisonicotinoyl)amino]pyridin-2-yl}propanoate Prepared from the compound of Example 80 (600 mg, 1.25 mmol) in a similar manner to the method of Example 72 to give the title compound (530 mg, 75%) as a white foam. δH (DMSO d$^6$) 9.20 (1H, s), 8.95 (2H, s), 8.87 (1H, s), 8.20 (1H, d), 7.51 (1H, d), 5.19 (1H, m), 4.32 (2H, q), 3.53-3.30 (2H, m), 1.34 (3H, t), 1.26 (3H, s), 1.13 (3H, s); m/z (ES$^+$, 70V) 556 (MH$^+$).

EXAMPLE 82

Ethyl (2S)-2-[(2-bromo-4,4-dimethyl-3-oxo-1-cyclobutenyl)amino]-3-{5-[(3,5-dichloroisonicotinoyl)amino]-2-pyridinyl}propanoate Hydrochloride The compound of Example 81 was dissolved in EtOAc (10 ml) and HCl gas bubbled through for a short time. The resulting white precipitate was collected by filtration, washed with EtOAc the Et$_2$O and dried to give the title compound as a white powder (252 mg). δH (DMSO d$^6$) 11.30 (1H, s), 9.12 (1H, d), 8.81 (2H, s), 8.80 (1H, s), 8.10 (1H, d), 7.43 (1H, d), 5.04 (1H, m), 4.18 (2H, q), 3.30 (2H, m), 1.20 (3H, t), 1.12 (3H, s), 1.00 (3H, s); m/z (ES$^+$, 70V) 592 (MH$^+$)

EXAMPLE 83

Ethyl (2S)-2-[(2-bromo-4,4-dimethyl-3-oxo-1-cyclobutenyl)amino]-3-{5-[(3,5-dichloroisonicotinoyl)amino]pyridin-2-yl}propanoic Acid The compound of Example 81 (200 mg, 3.59 mmol) was hydrolysed in a similar manner to the method of Example 2 to give the title compound as a white amorphous solid (110 mg, 58%). δH (DMSO d$^6$), 8.96 (1H, d), 8.81 (2H, s), 8.72 (1H, s), 8.04 (1H, d), 7.34 (1H, d), 4.96 (1H, m), 3.35-3.15 (2H, m), 1.11 (3H, s), 0.96 (3H, s); m/z (ES$^+$, 70V) 528 (MH$^+$).

EXAMPLE 84

Ethyl (2S)-2-[(2-chloro-4,4-dimethyl-3-oxo-1-cyclobutenyl)amino]-3-{5-[(3,5-dichloroisonicotinoyl)amino]pyridin-2-yl}propanoate A solution of NCS (294 mg, 2.20 mmol) in dry DCM (10 ml) was added to a solution of the compound of Example 80 (869 mg, 1.82 mmol) in THF (10 ml) at between −10° to 10° with stirring for 1.5 hr. After 30 min the solvent was evaporated in vacuo and the residue purified by chromatography (SiO$_2$, 4-8% EtOH/DCM) to give the title compound as a light yellow foam (786 mg, 84%). δH (DMSO d$^6$) 11.18 (1H, s), 9.02 (1H, d), 8.83 (2H, s), 8.75 (1H, s), 8.08 (1H, d), 7.37 (1H, d), 4.99 (1H, m), 4.20 (2H, q), 3.40-3.21 (2H, m), 1.22 (3H, t), 1.13 (3H, s), 1.01 (3H, s); m/z (ES$^+$, 70V) 511 (MH$^+$).

EXAMPLE 85

(2S)-2-[(2-Chloro-4,4-dimethyl-3-oxo-1-cyclobutenyl)amino]-3-{5-[(3,5-dichloroisonicotinoyl)amino]pyridin-2-yl}propanoic Acid The compound of Example 84 (560 mg, 1.09 mmol) was hydrolysed in a similar manner to the method of Example 2 to give the title compound as an off-white powder (370 mg, 70%). δH (DMSO d$^6$) 11.17 (1H, s), 9.94 (1H, d), 8.83 (2H, s), 8.75 (1H, s), 8.06 (1H, d), 7.35 (1H, d), 4.91 (1H, m), 3.37-3.16 (2H, m), 1.12 (3H, s), 0.97 (3H, s); m/z (ES$^+$, 70V) 483 (MH$^+$).

EXAMPLE 86

Ethyl-(2S)-3-{4-[(3,5-Dichloroisonicotinoyl)amino]phenyl}-2-[2-(1-methyl-pyridin-3-Vi)-3-oxo-spiro[3.5]non-1-en-1-ylamino]-propanoate Iodide Salt To a stirred solution of the compound of Example 64 (126 mg, 0.21 mmol) in DMF (1 ml) was added iodomethane (14 mL, 0.23 mmol). After 18 hrs the solvent was removed in vacuo to give the crude title compound which was used without further purification. m/z (ES$^+$, 70V) 607.0 (MH$^+$).

EXAMPLE 87

Ethyl (2S)-3-{4-[(3,5-dichloroisonicotinoyl)amino]phenyl}-2-[2-(1-methyl-piperidin-3-yl)-3-oxo-spiro[3.5]non-1-en-1-ylamino]propanoate The compound of Example 86 (127 mg, 0.21 mmol) was dissolved in EtOH (10 ml) and hydrogenated over platinum dioxide (50 mg) at room temperature and 1 atmosphere hydrogen for 5 days. The catalyst was removed by evaporation in vacuo to afford the title compound as a yellow oil (129 mg, 100%). δH (DMSO d$^6$) 10.48 (1H, br s), 8.70 (2H, s), 7.59 (2H, d, J 8.1 Hz), 7.30 (2H, d, J 8.1 Hz), 4.25 (1H, m), 4.22 (2H, q, J 4.0 Hz), 3.23 (1H, m), 3.08 (1H, m), 1.70-1.50 (22H, m), 1.26 (3H, m); m/z (ES$^+$, 70V) 613.2 (MH$^+$).

EXAMPLE 88

(2S)-3-{4-[(3,5-Dichloroisonicotinoyl)amino]-phenyl}-2-[2-(1-methyl-piperidin-3-yl)-3-oxo-spiro[3.5]non-1-en-1-ylamino]propanoic Acid The compound of Example 87 was hydrolysed in a similar manner to the method of Example 2. The product was purified by passage through a short column (RP-18-silica; 5% aqueous acetonitrile) to give the title compound as a yellow solid (52%). δH (DMSO d$^6$) 10.47 (1H, br s), 8.70 (2H, s), 7.57 (2H, d, J 7.7 Hz), 7.27 (2H, d, 47.7 Hz), 4.13 (1H, m), 3.19 (1H, m), 3.02 (1H, m), 2.27 (3H, s), 1.70-1.30 (10H, m); m/z (ES$^+$, 70V) 585.1 (MH$^+$).

EXAMPLE 89

(2S)-Ethyl-2-[(2-chloro-3-oxo-7-oxa-spiro[3.5]non-1-en-1-yl)amino]-3-{4-[(3,5-dichloroisonicotinoyl)amino]phenyl}propanoate A stirred solution of the compound of Example 38 (800 mg, 1.54 mmol) in THF (25 ml) at rt was treated in several portions with N-chloro succinimide (226 mg, 1.69 mmol). After 1 h the crude reaction was partitioned between EtOAc (150 ml) and brine (100 ml). The organic layer was removed and washed with a further 100 ml of brine and the organic phase dried (MgSO$_4$), filtered and concentrated in vacuo. Chromatography (SiO$_2$, 50% EtOAc:hexanes) gave the title compound as a white powder (625 mg, 1.13 mmol, 67%). δH (DMSO d$^6$, 390K) 10.39 (1H, brs), 8.69 (2H, s), 8.39 (1H, d, J 8.8 Hz), 7.57 (2H, s), 7.29 (2H, d, J 8.4 Hz), 4.72 (1H, m), 4.24 (2H, q, J 7.1 Hz), 3.83-3.77 (2H, m), 3.73-3.62 (2H, m), 3.28 (1H, dd, J 14.2, 5.5 Hz), 2.04-1.93 (2H, m), 1.54-1.51 (1H, m), 1.44-1.42 (1H, m), 1.27 (3H, t, J 7.1 Hz); m/z (ES$^+$, 70V) 554 (MH$^+$).

EXAMPLE 90

(2S)-2-[(2-Chloro-3-oxo-7-oxa-spiro[3.5]non-1-en-1-yl)amino]-3-{4-[(3,5-dichloroisonicotinoyl)-amino]phenyl}propanoic Acid Hydrolysis of the compound of Example 89 (525 mg, 0.95 mmol) with lithium hydroxide (80 mg, 1.7 mmol) according to the method of Example 2 gave the title compound (412 mg, 0.79 mol, 83%). δH (DMSO d$^6$, 390K) 10.40 (1H, s), 8.68 (2H, s), 8.30 (1H, br s), 7.55 (2H, d, J 5.8 Hz), 7.27 (2H, d, J 5.8 Hz), 4.63 (1H, m), 3.80-3.73 (2H, m), 3.69-3.61 (2H, m), 3.26 (1H, dd, J 14.1, 4.9 Hz), 3.07 (1H, dd, J 14.1, 9.1 Hz), 1.97-1.90 (2H, m), 1.51-1.48 (1H, m), 1.40-1.37 (1H, m); m/z (ES$^+$, 70V) 524.0 (MH$^+$).

EXAMPLE 91

(2S)-Ethyl-2-[(2-chloro-3-oxo-spiro[3.6]dec-1-en-1-yl)amino]-3-{4-[(3,5-dichloroisonicotinoyl)amino]phenyl}propanoate Was prepared according to the method of Example 89 from the compound of Example 45 (800 mg, 1.51 mmol) and N-chloro succinimide (222 mg, 1.66 mmol) to give the title compound as a white powder (625 mg, 1.11 mmol, 74%). δH (DMSO d$^6$, 390K) 10.40 (1H, s), 8.70 (2H, s), 8.11 (1H, br s), 7.57 (2H, br s), 7.29 (2H, d, J 8.3 Hz), 4.68 (1H, m), 4.24 (2H, q, J 7.1 Hz), 3.28 (1H, dd, J 5.5, 14.3 Hz), 3.12 (1H, dd, J 9.1, 14.3 Hz), 1.82-1.52 (12H, m), 1.27 (3H, t, J 7.1 Hz); m/z (ES$^+$, 70V) 566.0 (MH$^+$).

EXAMPLE 92

(2S)-2-[(2-Chloro-3-oxo-spiro[3.6]dec-1-en-1-yl)amino]-3-{4-[(3,5-dichloroisonicotinoyl)amino]phenyl}-propanoic Acid Hydrolysis of the compound of Example 91 (600 mg, 1.07 mmol) with lithium hydroxide (80 mg, 1.7 mmol), according to the method of Example 2, gave the title compound (512 mg, 0.95 mol, 89%). δH (DMSO d$^6$, 390K) 10.37 (1H, s), 8.67 (2H, s), 7.52 (2H, m), 7.25 (2H, d, J 8.3 Hz), 4.44 (1H, m), 3.22 (1H, dd, J 14.0, 5.2 Hz), 3.13 (1H, dd, J 13.9, 8.0 Hz), 1.98-1.41 (12H, m); m/z (ES$^+$, 70V) 536.0 (MH$^+$).

EXAMPLE 93

Ethyl (2S)-2-[4,4-dimethyl-2-(1-methyl-1H-tetrazol-5-ylsulfanyl)-3-oxo-cyclobut-1-enylamino]-3-{4-[(3,5-dichloroisonicotinoyl)amino]-phenyl}propanoate A stirred solution of the compound of Example 5 (1.03 g, 2.16 mmol) in THF (50 ml) at rt, was treated with a slurry of 1-methyl-1H-tetrazol-5-ylsulfanyl chloride (360 mg, 2.4 mmol) in DCM (2 ml). After 30 min the crude reaction was partitioned between EtOAc (150 ml) and saturated aqueous sodium hydrogen carbonate solution (100 ml). The organic phase was removed, washed with brine (100 ml), dried (MgSO$_4$) and concentrated in vacuo. Chromatography (SiO$_2$, EtOAc) gave the title compound as a white powder (1.12 g, 1.89 mmol, 88%). δH (DMSO d$^6$, 390K) 10.40 (1H, s), 9.08 (1H, d, J 2.6 Hz), 8.67 (2H, s), 7.55 (2H, d, J 6.2 Hz), 7.24 (2H, d, J 6.2 Hz), 5.06 (1H, m), 4.17 (2H, q, J 7.1 Hz), 4.05 (3H, s), 3.27 (1H, dd, J 5.5, 14.2 Hz), 3.12 (1H, dd, J 8.9, 14.2 Hz), 1.23 (3H, s), 1.22 (3H, t, J 7.1 Hz), 1.20 (3H, s); m/z (ES$^+$, 70V) 590.0 (MH$^+$).

EXAMPLE 94

(2S)-2-[4,4-Dimethyl-2-(1-methyl-1H-tetrazol-5-ylsulfanyl)-3-oxo-cyclobut-1-enylamino]-3-{4-[(3,5-dichloroisonicotinoyl)amino]-phenyl}propanoic Acid Hydrolysis of the compound of Example 93 (640 mg, 1.08 mmol) with lithium hydroxide (80 mg, 1.7 mmol), according to the method of Example 2, gave the title compound (517 mg, 0.92 mol, 85%). δH (DMSO d$^6$, 390K) 10.41 (1H, s), 9.35 (1H, d, J 2.6 Hz), 8.67 (2H, s), 7.51 (2H, d, J 5.9 Hz), 7.22 (2H, d, J 7.5 Hz), 4.93 (1H, m), 3.97 (3H, s), 3.26 (1H, dd, J 5.5, 14.2 Hz), 3.09 (1H, dd, J 8.9, 14.2 Hz), 1.17 (3H, s), 1.10 (3H, s); m/z (ES$^+$, 70V) 562.0 (MH$^+$).

EXAMPLE 95

Ethyl (2S)-2-[(3,7,7-trioxo-7λ$^6$-thia-spiro[3.5]non-1-en-1-yl)amino]-3-{4-[(3,5-dichloroisonicotinoyl)amino]phenyl}propanoate Prepared from Intermediate 45 (1.1 g, 5.4 mmol) and the free base of Intermediate 27 (2.08 mg, 5.5 mmol), in a similar manner to the compound of Example 11 to give the title compound as a white powder (712 mg, 1.25 mmol, 23%). δH (CDCl$_3$, 300K) 8.51 (1H, s), 8.33 (2H, s), 7.37 (2H, d, J 8.2 Hz), 6.96 (2H, d, J 8.2 Hz), 4.25 (1H, s), 4.10 (2H q, J 7.1 Hz), 4.01 (1H, m), 3.40-3.33 (2H, m), 3.06 (1H, dd, J 4.5, 14.2 Hz), 2.90 (1H, dd, J 14.1, 8.0 Hz), 2.79-2.75 (2H, m), 2.38-2.31 (2H, m), 1.99-1.96 (1H, m), 1.86-1.81 (1H, m), 1.16 (3H, t, J 7.1 Hz); m/z (ES$^+$, 70V) 565.9 (MH$^+$).

EXAMPLE 96

Ethyl (2S)-2-[(2-bromo-3,7,7-trioxo-7λ$^6$-thia-spiro[3.5]non-1-en-1-yl)amino]-3-{4-[(3,5-dichloroisonicotinoyl)amino]phenyl}propanoate A solution of the compound of Example 95 (435 mg, 0.77 mmol) in THF (18 ml) at 0° was treated portionwise with N-bromo succinimide (151 mg, 0.85 mmol). After 10 min the reaction was partitioned between EtOAc (100 ml) and saturated aqueous sodium hydrogencarbonate solution (50 ml), the organic phase removed, dried (MgSO$_4$) and concentrated in vacuo. Chromatography (SiO$_2$, 50% EtOAc:hexanes) gave the title compound as a white powder (411 mg, 0.64 mmol, 83%). δH (DMSO d$^6$, 390K) 10.43 (1H, s), 9.00 (1H, d, J 8.4 Hz), 8.69 (2H, s), 7.58 (2H, d, J 6.8 Hz), 7.28 (2H, d, J 6.8 Hz), 4.85 (1H, m), 4.23 (2H, q, J 7.1 Hz), 3.37-3.25 (3H, m, overlapping), 3.13-3.03 (3H, m, overlapping), 2.56-2.45 (2H, m), 2.09-1.89 (2H, m), 1.27 (3H, t, J 7.1 Hz); m/z (ES$^+$, 70V) 645.9 (MH$^+$).

EXAMPLE 97

(2S)-2-[(2-Bromo-3,7,7-trioxo-7λ$^6$-thia-spiro[3.5]non-1-en-1-yl)amino]-3-{4-[(3,5-dichloroisonicotinoyl)amino]phenyl}propanoic Acid Hydrolysis of the compound of Example 96 (410 mg, 0.63 mmol) with lithium hydroxide (31 mg, 0.7 mmol), according to the method of Example 2, gave the title compound (371 mg, 0.60 mol, 95%). δH (DMSO d$^6$, 390K) 10.41 (1H, s), 9.35 (1H, d, J 2.6 Hz), 8.69 (2H, s), 7.55 (2H, d, J 6.7 Hz), 7.27 (2H, d, J 6.7 Hz), 4.70 (1H, m), 3.37-3.25 (5H, m), 3.05 (1H, dd, J 13.3, 5.4 Hz), 2.3 (2H, m), 2.02 (1H, m), 1.92 (1H, m); m/z (ES+, 70V) 617.8 (MH+).

EXAMPLE 98

Ethyl (2S)-2-[4,4-dimethyl-2-(1-methyl-1H-imidazol-2-ylsulfanyl)-3-oxo-cyclobut-1-enylamino]-3-{4-[(3,5-dichloroisonicotinoyl)amino]phenyl}propanoate Prepared from the compound of Example 5 (1.0 g, 2.1 mmol) and 1-methyl-1H-imidazol-2-ylsulfenyl chloride (340 mg, 2.3 mmol), in a similar manner to the compound of Example 93 to give title compound as a white powder (1.03 g, 1.75 mmol, 83%). δH (DMSO d$^6$, 390K) 10.84 (1H, s), 9.19 (1H, d, J 9.0 Hz), 8.79 (2H, s), 7.53 (2H, d, J 8.5 Hz), 7.23 (2H, d, J 8.5 Hz), 7.21 (1H, d, J 1.1 Hz), 6.88 (1H d, J 1.1 Hz), 5.46 (1H, m), 4.16 (2H, q, J 7.1 Hz), 3.62 (3H, s), 3.26 (1H, dd, J 14.2, 5.2 Hz), 3.06 (1H, dd, J 14.2, 8.9 Hz), 1.20 (3H, t, J 7.1 Hz), 1.09 (3H, s), 0.97 (3H, s); m/z (ES+, 70V) 590.0 (MH+).

EXAMPLE 99

(2S)-2-[4,4-Dimethyl-2-(1-methyl-1H-imidazol-2-yl]sulfanyl)-3-oxo-cyclobut-1-enylamino]-3-{4-[(3,5-dichloroisonicotinoyl)amino]phenyl}propanoic Acid Hydrolysis of the compound of Example 98 (760 mg, 1.25 mmol) with lithium hydroxide (100 mg, 2.2 mmol), according to the method of Example 2, gave the title compound (412 mg, 0.74 mol, 57%). δH (DMSO d$^6$, 390K) 10.83 (1H, s), 9.11 (1H, d, J 9.0 Hz), 8.79 (2H, s), 7.51 (2H, d, J 8.5 Hz), 7.23 (2H, d, J 8.5 Hz), 7.21 (1H, d, J 1.1 Hz), 6.90 (1H, d, J 1.1 Hz), 5.38 (1H, m), 3.63 (3H, s), 3.25 (1H, dd, J 14.2, 5.2 Hz), 3.05 (1H, dd, J 14.2, 8.9 Hz), 1.07 (3H, s), 0.96 (3H, s); m/z (ES+, 70V) 562.0 (MH+).

EXAMPLE 100

(2S)-Ethyl-2-[(3-thioxo-spiro[3.5]non-1-en-1-yl)amino]-3-{4-[(3,5-dichloroisonicotinoyl)amino]phenyl}propanoate A solution of the compound of Example 27 (700 mg, 1.36 mmol) and Lawesson's reagent [2,4-bis(4-methoxyphenyl)-1,2,3,4-dithiadiphosphetane 2,4-disulphide] (561 mg, 1.38 mmol) in toluene (25 ml) was heated to 80° for 24 h. The crude reaction was then partitioned between EtOAc (100 ml) and brine (100 ml). The organic phase was separated, dried (MgSO$_4$) and concentrated in vacuo. Chromatography (SiO$_2$, EtOAc) gave the title compound as a yellow powder (621 mg, 1.17 mmol, 86%). δH (DMSO d$^6$, 390K) 10.84 (1H, s), 8.96 (1H, d, J 8.9 Hz), 8.78 (2H, s), 7.56 (2H, d, J 7.9 Hz), 7.25 (2H, d, J 7.9 Hz), 5.48 (1H, s), 4.37 (1H, m), 4.18 (2H, q, J 7.1 Hz), 3.20 (1H, d, J 13.9, 4.9 Hz), 3.04 (1H, dd, J 13.9, 9.9 Hz), 1.96-1.87 (2H, m), 1.63-1.42 (8H, m), 1.21 (3H, t, J 7.1 Hz); m/z (ES+, 70V) 532.0, 534.0 (MH+).

EXAMPLE 101

(2S)-2-[(3-Thioxo-spiro[3.5]non-1 en-1-yl)amino]-3-{4-[(3,5-dichloroisonicotinoyl)amino]phenyl}propanoic Acid Hydrolysis of the compound of Example 100 (340 mg, 0.66 mmol) with lithium hydroxide (30 mg, 0.67 mmol), according to the method of Example 2, gave the title compound (287 mg, 0.57 mol, 86%). δH (DMSO d$^6$, 390K) 10.84 (1H, s), 8.87 (1H, d, J 8.8 Hz), 8.77 (2H, s), 7.54 (2H, d, J 8.3 Hz), 7.24 (2H, d, J 8.3 Hz), 5.45 (1H, s), 4.23 (1H, m), 3.21 (1H, dd, J 13.9, 4.4 Hz), 3.00 (1H, dd, J 13.9, 9.9 Hz), 1.96-1.87 (2H, m), 1.67-1.41 (8H, m); m/z (ES+, 70V) 562.0 (MH+).

EXAMPLE 102

(2S)-2-[(3-oxo-spiro[3.4]oct-1-en-1-yl)amino]-3-{4-[(3,5-dichloroisonicotinoyl)amino]phenyl}propanoate A solution of 3-hydroxy-spiro[3.4]oct-2-en-1-one (330 mg, 2.39 mmol) [prepared according to the method of Wasserman, H. H. et al J. Org. Chem., 38, 1451-1455, (1973)] and the free base of Intermediate 27 (911 mg, 2.39 mmol), in DCM (5 ml), was stirred at rt for 48 h. The volatiles were removed in vacuo and the residue chromatographed (SiO$_2$, EtOAc) to give the title compound as a white solid (1.03 g, 2.05 mmol, 86%). δH (CDCl$_3$, 300K) 8.97 (1H, s), 8.41 (2H, s), 7.51 (2H, d, J 8.5 Hz), 7.01 (2H, d, J 8.5 Hz), 5.89 (1H, d, J 7.5 Hz), 4.39 (1H, s), 4.21 (3H, obscured m), 3.15 (1H, dd, J 14.0, 5.3 Hz), 3.03 (1H, dd, J 14.0, 5.8 Hz), 1.74-1.49 (10H, m), 1.27 (3K, t, J 7.1 Hz); m/z (ES+, 70V) 502.0 (MH+).

EXAMPLE 103

(2S)-2-[(3-oxo-spiro[3.4]oct-1-en-1-yl)amino]-3-{4-[(3,5-dichloroisonicotinoyl)amino]phenyl}propanoic Acid Hydrolysis of the compound of Example 102 (150 mg, 0.30 mmol) with lithium hydroxide (30 mg, 0.67 mmol), according to the method of Example 2, gave the title compound (112 mg, 0.23 mol 79%). δH (DMSO d$^6$, 390K) 13.08 (1H, s), 10.87 (1H, s), 8.79 (2H, s), 8.39 (1H, d, J 8.5 Hz), 7.57 (2H, d, J 8.2 Hz), 7.26 (2H, d, J 8.2 Hz), 4.39 (1H, s), 4.14 (1H, m), 3.16 (1H, dd, J 13.8, 4.7 Hz), 2.98 (1H, dd, J 13.8, 9.4 Hz), 1.73-1.58 (10H, m); m/z (ES+, 70V) 473.9 (MH+).

EXAMPLE 104

Ethyl (2S)-2-[(2-chloro-3-oxo-spiro[3.4]oct-1-en-1-yl)amino]-3-{4-[(3,5-dichloroisonicotinoyl)amino]phenyl}propanoate Prepared from the compound of Example 102 (1.25 g, 2.49 mmol) and N-chloro succinimide (333 mg, 2.7 mmol), according to the method of Example 61, to give the title compound as a white powder (1.13 g, 2.1 mmol, 84%). δH (DMSO d$^6$, 390K) 10.41 (1H, s), 8.68 (2H, s), 8.33 (1H d, J 5.9 Hz), 7.57 (2H, m), 7.27 (2H, m), 4.66 (1H, m), 4.21 (2H, q, J 7.1 Hz), 3.26 (1H, dd, J 14.1, 5.3 Hz), 3.11 (1H, dd, J 14.1, 9.0 Hz), 1.98-1.58 (10H, m), 1.23 (3H, t, J 7.1 Hz); m/z (ES+, 70V) 535.9 (MH+).

EXAMPLE 105

(2S)-2-[(2-Chloro-3-oxo-spiro[3.4]oct-1-en-1-yl)amino]-3-{4-[(3,5-dichloroisonicotinoyl)amino]phenyl}propanoic Acid Hydrolysis of the compound of Example 104 (1.10 g, 2.05 mmol) with lithium hydroxide (100 mg, 2.2 mmol), according to the method of Example 2, gave the title compound (976 mg, 1.92 mol, 94%). δH (DMSO d$^6$, 390K) 10.41 (1H, s), 8.69 (2H, s), 8.26 (1H, s), 7.57 (2H, d, J 6.2 Hz), 7.28 (2H, d, J 6.2 Hz), 4.61 (1H, m), 3.26 (1H, dd, J 14.1, 5.0 Hz), 3.08 (1H, dd, J 14.1, 9.1 Hz), 1.92-1.60 (10H, m); m/z (ES+, 70V) 509.9 (MH+).

EXAMPLE 106

Ethyl (2S)-2-[(2-bromo-3-oxo-spiro[3.4]oct-1-en-1-yl)amino]-3-{4-[(3,5-dichloroisonicotinoyl)amino]phenyl}propanoate A solution of the compound of Example 102 (1.25 g, 2.49 mmol) in THF (25 ml) at rt was treated with N-bromo succinimide (443 mg, 2.49 mmol) After 30 min the reaction was diluted with EtOAc (100 ml), washed with saturated aqueous sodium hydrogencarbonate solution (50 ml) and the organic phase separated, dried (MgSO$_4$) and concentrated in vacuo. Chromatography (SiO$_2$, EtOAc) gave the title compound as a white powder (1.27 g, 2.18 mmol, 87%). δH (DMSO d$^6$, 390K) 10.43 (1H, s), 8.69 (2H, s), 8.42 (1H, d, J 8.9 Hz), 7.58 (2H, d, J 6.7 Hz), 7.29 (2H, d, J 6.7 Hz), 4.77 (1H, s), 4.22 (2H, q, J 7.1 Hz), 3.26 (1H, dd, J 14.1, 5.4 Hz), 3.12 (1H, dd, J 14.1, 9.0 Hz), 1.98-1.62 (8H, m), 1.25 (3H, t, J 7.1 Hz); m/z (ES$^+$, 70V) 582.0 (MH$^+$).

EXAMPLE 107

(2S)-2-[(2-Bromo-3-oxo-spiro[3.4]oct-1-en-1-yl)amino]-3-{4-[(3,5-dichloroisonicotinoyl)amino]phenyl}propanoic Acid Hydrolysis of the compound of Example 106 (900 mg, 1.54 mmol) with lithium hydroxide (100 mg, 2.2 mmol), according to the method of Example 2, gave the title compound (721 mg, 1.3 mmol, 84%). δH (DMSO d$^6$, 390K) 10.39 (1H, s), 8.68 (2H, s), 8.12 (1H, brs), 7.54 (2H, d, J 8.2 Hz), 7.27 (2H, d, J 8.2 Hz), 4.64 (1H, m), 3.25 (1H, dd, J 14.1, 5.1 Hz), 3.11 (1H, dd, J 14.1, 8.6 Hz), 1.92-1.62 (8H, m); m/z (ES$^+$, 70V) 553.9 (MH$^+$).

EXAMPLE 108

(2S)-Ethyl-2-[(2-methylsulfanyl-3-oxo-spiro[3.5]non-1-en-1-yl)amino]-3-{4-[(3,5-dichloroisonicotinoyl)amino]phenyl}propanoate A solution of the compound of Example 27 (1.0 g, 1.94 mmol) in THF (25 ml) at rt was treated dropwise with a solution of methanesulfenyl chloride in DCM (2.13 ml, 1.0M) [prepared according to the method of Still, I. W. J., et al., J. Org. Chem., 1982, 47, 560]. After 20 min the reaction was diluted with EtOAc (100 ml) and washed with saturated aqueous sodium hydrogencarbonate solution (50 ml). The organic phase was separated, dried (MgSO$_4$), filtered and concentrated in vacuo. Chromatography (SiO$_2$, 60% EtOAc:hexanes) gave the title compound as a white powder (1.03 g, 1.83 mmol, 94%). δH (DMSO d$^6$, 390K) 10.86 (1H, s), 8.78 (2H, s), 8.70 (1H, d, J 9.2 Hz), 7.57 (2H, d, J 8.4 Hz), 7.26 (2H, d, J 8.4 Hz), 5.11 (1H, m), 4.18 (2H, q, J 7.1 Hz), 3.20 (1H, dd, J 13.9, 4.6 Hz), 3.00 (1H, dd, J 13.9, 9.8 Hz), 1.93 (3H, s), 1.66-1.33 (10H, m), 1.21 (3H, t, J 71 Hz): m/z (ES$^+$, 70V) 562.1 (MH$^+$).

EXAMPLE 109

(2S)-2-[(2-Methylsulfanyl-3-oxo-spiro[3.5]non-1-en-1-yl)amino]-3-{4-[(3,5-dichloroisonicotinoyl)amino]phenyl}propanoic Acid Hydrolysis of the compound of Example 108 (600 mg, 1.07 mmol) with lithium hydroxide (100 mg, 2.2 mmol), according to the method of Example 2, gave the title compound as a white powder (421 mg, 0.79 mmol, 73%). δH (DMSO d$^6$, 390K) 10.84 (1H, s), 8.77 (2H, s), 8.44 (1H, d, J 8.8 Hz), 7.54 (2H, d, J 8.4 Hz), 7.23 (2H, d, J 8.4 Hz), 4.90 (1H, m), 3.19 (1H, dd, J 13.7, 4.4 Hz), 2.98 (1H, dd, J 13.7, 9.1 Hz), 1.93 (3H, s), 1.79-1.54 (8H, m), 1.36-1.22 (2H, m); m/z (ES$^+$, 70V) 534.0 (MH$^+$).

EXAMPLE 110

(2S)-Ethyl-2-[(2-fluoro-3-oxo-spiro[3.5]non-1-en-1-yl)amino]-3-{4-[(3,5-dichloroisonicotinoyl)amino]phenyl}propanoate A solution of the compound of Example 27 (2.02 g, 3.91 mmol) in THF (55 ml) was treated with Selectfluor™ reagent (1.38 g, 3.89 mmol) and heated to 70°. After 48 h the reaction was diluted with EtOAc (300 ml) and washed with saturated aqueous sodium hydrogencarbonate solution (50 ml). The organic phase was dried (MgSO$_4$), filtered and concentrated in vacuo. Chromatography (SiO$_2$, 60% EtOAc:hexanes) gave the title compound as a white powder (1.87 g, 3.50 mmol, 89%). δH (DMSO d$^6$, 390K) 10.89 (1H, s), 8.81 (2H, s), 8.47 (1H, d, J 8.7 Hz), 7.59 (12H, d, J 8.5 Hz), 7.27 (2H, d, J 8.5 Hz), 4.26 (1H, m), 4.19 (2H, q, J 7.1 Hz), 3.21 (1H, dd, J 13.8, 4.9 Hz), 2.98 (1H, dd, J 13.8, 9.8 Hz), 1.70-1.38 (10H, m), 1.22 (3H, t, J 7.1 Hz); m/z (ES$^+$, 70V) 534.1 (MH$^+$).

EXAMPLE 111

(2S)-2-(2-Fluoro-3-oxo-spiro[3.5]non-1-en-1-ylamino)3-{4-[(3,5-dichloroisonicotinoyl)amino]phenyl}propanoic Acid Hydrolysis of the compound of Example 110 (273 mg, 0.51 mmol) with lithium hydroxide (60 mg, 1.3 mmol), according to the method of Example 2, gave the title compound as a white powder (197 mg, 0.39 mmol, 76%). δH (DMSO d$^6$, 390K) 10.87 (1H, s), 8.80 (2H, s), 8.30 (1H, d, J 8.7 Hz), 7.58 (2H, d, J 8.2 Hz), 7.25 (2H, d, J 8.2 Hz), 4.15 (1H, m), 3.19 (1H, dd, J 13.8, 4.5 Hz), 2.96 (1H, dd, J 13.8, 9.5 Hz), 1.92-1.49 (8H, m), 1.37-1.16 (2H, m); m/z (ES$^+$, 70V) 506.0 (MH$^+$).

EXAMPLE 112

(2S)-2-[(2-Fluoro-3-oxo-7-oxa-spiro[3.5]non-1-en-1-yl)amino]-3-{4-[(3,5-dichloroisonicotinoyl)amino]phenyl}propanoic Acid A mixture of the compound of Example 38 (1.0 g, 1.93 mmol) and Selectfluor™ reagent (1.0 g, 2.8 mmol) in THF (25 ml) was heated to reflux for 72 h. The crude reaction was then diluted with EtOAc (100 ml) and washed with saturated aqueous sodium hydrogencarbonate solution (50 ml). The organic phase was dried (MgSO$_4$), filtered and concentrated in vacuo to give a gum. This was then redissolved in THF (20 ml) and treated with lithium hydroxide (80 mg, 1.78 mmol) and water (1 ml) and stirred for 24 h at rt. Acidification with a few drops of AcOH followed by concentration in vacuo and chromatography (SiO$_2$, 10:90:3:2 MeOH:DCM:AcOH:H$_2$O) gave the title compound as a white powder (561 mg, 1.1 mmol, 57%). 5H (DMSO d$^6$, 390K) 10.89 (1H, s), 8.80 (2H, s), 8.58 (1H, d, J 8.8 Hz), 7.59 (2H, d, J 8.4 Hz), 7.27 (2H, d, J 8.4 Hz), 4.23 (1H, m), 3.76 (2H, m), 3.60 (2H, m), 3.23 (1H, dd, J 13.9, 4.4 Hz), 2.96 (1H, dd, J 13.9, 9.8 Hz), 1.98-1.93 (2H, m), 1.47 (1H, m), 1.30 (1H, m); m/z (ES$^+$, 70V) 508.0 (MH$^+$).

EXAMPLE 113

(2S)-2-(2-Fluoro-4,4-dimethyl-3-oxo-cyclobut-1-enyl amino)-3-{4-[(3,5-dichloroisonicotinoyl)amino]phenyl}propanoic Acid Prepared from the compound of Example 5 (1.25 g, 2.49 mmol), Selectfluor™ reagent (1.0 g, 2.8 mmol) and lithium hydroxide (80 mg, 1.8 mmol), according to the methods of Examples 61 and 2, to give the title compound as a white powder (1.13 g, 2.1 mmol, 84%). δH (DMSO $d^6$, 390K) 10.88 (1H, s), 8.80 (2H, s), 8.65 (1H, d, J 8.7 Hz), 7.60 (2H, d, J 8.2 Hz), 7.27 (2H, d, J 8.2 Hz), 4.25 (1H, m), 3.22 (1H, dd, J 13.9, 4.5 Hz), 2.98 (1H, dd, J 13.9, 9.3 Hz), 1.11 (3H, s), 1.03 (3H, s); m/z (ES$^+$, 70V) 466.0 (MH$^+$).

EXAMPLE 114

(2S)-2-[(4,4-Dimethyl-2-methylsulfanyl-3-oxo-cyclobut-1-enyl)amino]-3-{4-[(3,5-dichloroisonicotinoyl)amino]phenyl}propanoic Acid A solution of the compound of Example 5 (700 mg, 1.47 mmol) in THF (15 ml) was treated at rt with a 1.0M solution of methanesulfenyl chloride in DCM (1.5 ml, 1.5 mmol). After 30 min the reaction was partitioned between EtOAc (50 ml) and saturated aqueous sodium hydrogencarbonate solution (25 ml). Separation of the organic phase, followed by drying (MgSO$_4$), filtration and concentration in vacuo gave a solid which was approx. 90% pure. The crude solid was redissolved in THF (20 ml) and treated with lithium hydroxide (60 mg, 1.3 mmol) and water (1 ml) and stirred at rt for 24 h. The reaction was acidified with a few drops of AcOH and concentrated in vacuo. Chromatography (SiO$_2$, 10:90:3:2 MeOH:DCM:AcOH:H$_2$O) gave the title compound as a white powder (289 mg, 0.59 mmol, 40%). δH (DMSO $d^6$, 390K) 10.85 (1H, s), 8.87 (1H, d, J 9.2 Hz), 8.80 (2H, s), 7.59 (2H, d, J 8.0 Hz), 7.29 (2H, d, J 8.0 Hz), 5.04 (1H, m), 2.25 (1H, dd, J 13.5, 3.5 Hz), 3.00 (1H, dd, J 13.5, 9.8 Hz), 2.00 (3H, s), 1.11 (3H, s), 1.02 (3H, s); m/z (ES$^+$, 70V) 493.9 (MH$^+$).

EXAMPLE 115

(2S)-2-[(2-Isopropylsulfanyl-4,4-dimethyl-3-oxo-cyclobut-1-enyl)amino]-3-{4-[(3,5-dichloroisonicotinoyl)amino]phenyl}propanoic Acid Was prepared in two steps from the compound of Example 5 (700 mg, 1.47 mmol), a 1.0M solution of isopropyl sulfenyl chloride in DCM (1.5 ml, 1.5 mmol) and lithium hydroxide (80 mg, 1.8 mmol), according to the method of Example 114, to give the title compound as a pale yellow powder (305 mg, 0.58 mmol, 39%). δH (DMSO $d^6$, 390K) 13.24 (1H, s br), 10.87 (1H, s), 8.92 (1H, d, J 9.5 Hz), 8.80 (2H, s), 7.58 (2H, d, J 8.4 Hz), 7.28 (2H, d, J 8.4 Hz), 5.16 (1H, m), 3.22 (1H, dd, J 13.8, 3.9 Hz), 2.97 (1H, dd, J 13.8, 9.7 Hz), 2.67 (1H, m), 1.14 (3H, s), 1.06-1.04 (9H, m); m/z (ES$^+$, 70V) 522.0 (MH$^+$).

EXAMPLE 116

Ethyl (2S)-2-[(2-isopropylsulfanyl-3-oxo-spiro[3.5]non-1-en-1-yl)amino]-3-{4-[(3,5-dichloroisonicotinoyl)amino]phenyl}propanoate A stirred solution of the compound of Example 27 (1.0 g, 1.93 mmol) in THF (50 ml) at rt was treated dropwise with a 1.0M solution of isopropyl sulfenyl chloride in DCM until a yellow colouration of the reaction mixture just persisted. The reaction was then diluted with EtOAc (200 ml) and washed with saturated aqueous sodium hydrogencarbonate solution (50 ml). The organic phase was separated, dried (MgSO$_4$), filtered and concentrated in vacuo. Chromatography (SiO$_2$, 100% EtOAc) gave the title compound as a pale yellow powder (987 mg, 87%). δH (DMSO $d^6$, 390K) 10.85 (1H, s), 8.79 (2H, s), 8.73 (1H, d, J 9.5 Hz), 7.56 (2H, d, J 8.5 Hz), 7.25 (2H, d, J 8.5 Hz), 5.20 (1H, m), 4.17 (2H, q, J 7.1 Hz), 3.18 (1H, dd, J 13.8, 4.3 Hz), 2.97 (1H, dd, J 13.8, 10.2 Hz), 2.65 (1H, m), 1.73-1.57 (8H, m), 1.36-1.33 (1H, m), 1.21 (3H, t, J 7.1 Hz), 1.17-1.14 (1H, m), 1.02 (6H, d, J 6.6 Hz); m/z (ES$^+$, 70V) 590.0 (MH$^+$).

EXAMPLE 117

(2S)-2-[(2-isopropylsulfanyl-3-oxo-spiro[3.5]non-1-en-1-yl)amino]-3-{4-[(3,5-dichloroisonicotinoyl)amino]phenyl}propanoic Acid Hydrolysis of the compound of Example 116 (400 mg, 0.68 mmol) with lithium hydroxide (100 mg, 2.2 mmol), according to the method of Example 2, gave the title compound as a white powder (333 mg, 0.59 mmol, 89%). δH (DMSO $d^6$, 390K) 10.84 (1H, s), 8.78 (2H, s), 8.62 (1H, d, J 9.4 Hz), 7.55 (2H, d, J 8.1 Hz), 7.25 (1H, d, J 8.1 Hz), 5.12 (1H, m), 3.20 (1H, dd, J 13.7, 3.6 Hz), 2.94 (1H, dd, J 13.7, 10.2 Hz), 2.62 (1H, m), 1.91-1.64 (8H, m), 1.59-1.56 (1H, m), 1.36-1.33 (1H, m), 1.02 (6H, d, J 6.6 Hz); m/z (ES$^+$, 70V) 562.0 (MH$^+$).

EXAMPLE 118

Ethyl (2S)-2-[(2-isopropylsulfanyl-4,4-dimethyl-3-oxo-cyclobut-1-enyl)amino]-3-[4-([2,7]naphthyridin-1-ylamino)phenyl]propanoate A solution of 3-hydroxy-4,4-dimethyl-2-cyclobutenone (333 mg, 2.97 mmol) and Intermediate 12 (1.0 g, 2.98 mmol) in THF (25 ml), was stirred at rt for 48 h. The volatiles were removed in vacuo and the residue chromatographed (SiO$_2$, EtOAc) affording 970 mg of the coupled product of approx 90% purity. This intermediate was redissolved in THF (35 ml) and treated with a 1.0M solution of isopropyl sulfenyl chloride in DCM (3.0 ml, 3.0 mmol) at rt. After 60 min the reaction was diluted with EtOAc (100 ml) and washed with saturated aqueous sodium carbonate solution (50 ml), the organic phase was dried (MgSO$_4$), filtered and concentrated in vacuo. Chromatography (SiO$_2$, EtOAc) gave the title compound as a white powder (817 mg, 1.62 mmol, 54%). δH (DMSO $d^6$, 390K) 9.83 (1H, s), 9.52 (1H, s), 9.01 (1H, d, J 9.4 Hz), 8.65 (1H, d, J 5.7 Hz), 8.16 (1H, d, J 5.7 Hz), 7.81 (2H, d, J 8.5 Hz), 7.68 (1H, d, J 5.7 Hz), 7.23 (2H, d, J 8.5 Hz), 7.13 (1H, d, J 5.7 Hz), 5.24 (1H, m), 4.19 (2H, q, 47.1 Hz), 3.20 (1H, dd, J 13.8, 4.5 Hz), 2.97 (1H, dd, J 13.8, 10.0 Hz), 2.76 (1H, m), 1.22 (3H, t, J 7.1 Hz), 1.13 (3H, s), 1.05 (6H, d, J 6.7 Hz), 1.04 (3H, s); m/z (ES$^+$, 70V) 505.2 (MH$^+$).

EXAMPLE 119

(2S)-2-[(2-Isopropylsulfanyl-4,4-dimethyl-3-oxo-cyclobut-1-enyl)amino]-3-[4-([2,7]naphthyridin-1-ylamino)phenyl]propanoate Hydrolysis of the compound of Example 118 (400 mg, 0.79 mmol) with lithium hydroxide (100 mg, 2.2 mmol), according to the method of Example 2, gave the title compound as a white powder (231 mg, 0.49 mmol, 62%). δH (DMSO d⁶, 390K) 9.83 (1H, s), 9.51 (1H, s), 8.89 (1H, d, J 9.5 Hz), 8.65 (1H, d, J 5.6 Hz), 8.15 (1H, d, J 5.7 Hz), 7.78 (2H, d, J 8.5 Hz), 7.22 (2H, d, J 8.5 Hz), 7.11 (1H, d, J 5.7 Hz), 5.16 (1H, m), 3.21 (1H, dd, J 13.8, 4.1 Hz), 2.94 (1H, dd, J 13.8, 6.7 Hz), 2.75 (1H, m), 1.13 (3H, s), 1.06 (6H, d, J 6.6 Hz), 1.03 (3H, s); m/z (ES⁺, 70V) 477.1 (MH⁺).

EXAMPLE 120

Ethyl (2S)-2-[(2-isopropylsulfanyl-3-oxo-spiro[3.5] non-1-en-1-yl)amino]-3-[4-([2,7]naphthyridin-1-amino)phenyl]propanoate Was prepared in two steps from Intermediate 12 (1.0 g, 2.98 mmol), 1-keto-3-hydroxyspiro[3,5]-non-2-ene (452 mg, 2.97 mmol) [prepared according to the method of Wasserman, H. H. et al, J. Org. Chem., 38, 1451-1455 (1973)] and a 1.0M solution of isopropyl sulfenyl chloride in DCM (3.5 ml, 3.5 mmol) according to the method of Example 118 to give the title compound as a yellow powder (931 mg, 1.71 mmol, 58%). (DMSO d⁶, 390K) 9.89 (1H, s), 9.58 (1H, s), 8.82 (1H, d, J 9.4 Hz), 8.71 (1H, d, J 5.6 Hz), 8.21 (1H, d, J 5.6 Hz), 7.85 (2H, d, J 8.3 Hz), 7.74 (1H, d, J 5.6 Hz), 7.28 (2H, d, J 8.3 Hz), 7.18 (1H, d, J 5.6 Hz), 5.31 (1H, m), 4.24 (2H, q, J 7.1 Hz), 3.24 (1H, dd, J 13.7, 4.1 Hz), 3.03 (1H, dd, J 13.7, 10.3 Hz), 2.80 (1H, m), 1.80-1.71 (8H, m), 1.46-1.43 (1H, m), 1.28 (3H, t, J 7.1 Hz), 1.24-1.21 (1H, m), 1.11 (6H, d, J 6.5 Hz); m/z (ES⁺, 70V) 545.2 (MH⁺).

EXAMPLE 121

(2S)-2-[(2-Isopropylsulfanyl-3-oxo-spiro[3.5]non-1-en-1-yl)amino]-3-[4-([2,7]naphthyridin-1-ylamino) phenyl]propanoic Acid Hydrolysis of the compound of Example 120 (900 mg, 1.62 mmol) with lithium hydroxide (150 mg, 3.3 mmol), according to the method of Example 2, gave the title compound as a bright yellow powder (790 mg, 1.53 mmol, 94%). δH (DMSO d⁶, 390K) 9.83 (1H, s), 9.51 (1H, s), 8.67 (1H, d, J 5.6 Hz), 8.65 (1H, d, J 5.6 Hz), 8.15 (1H, d, J 5.7 Hz), 7.77 (2H, d, J 8.4 Hz), 7.68 (1H, d, J 5.7 Hz), 7.23 (2K, d, J 8.4 Hz), 7.12 (1H, J 5.7 Hz), 5.20 (1H, m), 3.22 (1H, dd, J 13.8, 3.9 Hz), 2.94 (1H, dd, J 13.8, 10.4 Hz), 1.79-1.66 (8H, m), 1.40-1.35 (1H, m), 1.20-1.15 (1H, m), 1.05 (3H, d, J 6.3 Hz), 1.03 (3H, d, J 6.3 Hz); m/z (ES⁺, 70V) 517.2 (MH⁺).

EXAMPLE 122

Ethyl (2S)-2-[(2-isopropylsulfanyl-3-oxo-7-oxa-spiro[3.5]non-1-en-1-yl)amino]-3-[4-([2,7]naphthyridin-1 ylamino)phenyl]propanoate Was prepared in two steps from Intermediate 12 (1.96 g, 5.8 mmol), 7-oxaspiro[3.5]nonane-1,3-dione (1.0 g, 6.5 mmol) [prepared according to the method of Wasserman, H. H. et al, J. Org. Chem., 38, 1451-1455 (1973)]and a 1.0M solution of isopropyl sulfenyl chloride in DCM (5.4 ml, 5.4 mmol) according to the method of 118 to give the title compound as a yellow powder (1.15 g, 2.1 mmol, 36%). δH (DMSO d⁶, 390K) 9.83 (1H, s), 9.52 (1H, s), 8.94 (1H, d, J 9.5 Hz), 8.65 (1H, d, J 5.6 Hz), 8.15 (1H, d, J 5.7 Hz), 7.78 (2H, d, J 8.5 Hz), 7.68 (1H, d, J 5.6 Hz), 7.23 (2H, d, J 8.5 Hz), 7.12 (1H, d, J 5.7 Hz), 5.26 (1H, m), 4.19 (2H, q, J 7.1 Hz), 3.81-3.76 (2H, m), 3.64-3.55 (2H, m), 3.20 (1H, dd, J 13.8, 4.3 Hz), 2.96 (1H, dd, J 13.8, 10.3 Hz), 2.81-2.74 (1H, m), 2.06-1.93 (2H, m), 1.50-1.47 (1H, m), 1.32-1.28 (1H, m), 1.23 (3H, t, J 7.1 Hz), 1.07 (3H, d, J 6.6 Hz), 1.05 (3H, d, J 6.6 Hz); m/z (ES⁺, 70V) 547.2 (MH⁺).

EXAMPLE 123

(2S)-2-[(2-Isopropylsulfanyl-3-oxo-7-oxa-spiro[3.5] non-1-en-1-yl)amino]-3-[4-([2,7]naphthyridin-1-ylamino)phenyl]propanoic Acid Hydrolysis of the compound of Example 122 (906 mg, 1.66 mmol) with lithium hydroxide (150 mg, 3.3 mmol), according to the method of Example 2, gave the title compound as a pale yellow powder (801 mg, 1.54 mmol, 93%). δH (DMSO d⁶, 390K) 9.82 (1H, s), 9.51 (1H, s), 8.86 (1H, d, J 9.5 Hz), 8.65 (1H, d, J 5.5 Hz), 8.14 (1H, d, J 5.6 Hz), 7.76 (2H, d, J 8.1 Hz), 7.68 (1H, d, J 5.5 Hz), 7.28 (2H, d, J 8.1 Hz), 7.12 (1H, d, J 5.6 Hz), 5.24-5.19 (1H, m), 3.78 (2H, m), 3.61 (2H, m), 3.21 (1H, dd, J 13.8, 3.5 Hz), 2.91 (1H, dd, J 13.8, 10.7 Hz), 2.77-2.71 (1H, m), 2.05-1.91 (2H, m), 1.49-1.46 (1H, m), 1.30-1.26 (1H, m), 1.07 (3H, s), 1.03 (3H, s); m/z (ES⁺, 70V) 519.1 (MH⁺).

EXAMPLE 124

Ethyl (2S)-2-[(3-oxo-spiro[3.4]octa-1,6-dien-1-yl) amino]-3-{4-[(3,5-dichloroisonicotinoyl)amino] phenyl}propanoate A solution of Intermediate 47 (1.0 g, 7.3 mmol) and the free base of Intermediate 27 (2.48 g, 7.3 mmol), in DCM (25 ml), was stirred at room temperature for 48 h. The volatiles were removed in vacuo and the residue chromatographed (SiO₂, EtOAc) to give the title compound as a white solid (2.14 g, 4.28 mmol, 59%). δH (CDCl₃, 300K) 9.02 (1H, s), 8.38 (2H, s), 7.49 (2H, d, 8.5 Hz), 7.00 (2H, d, J 8.5 Hz), 6.03 (1H, d, J 7.8 Hz), 5.54 (2H, s), 4.41 (1H, s), 4.21 (2H, q, J 7.1 Hz), 4.20 (11H, m), 3.15 (1H, dd, J 14.0, 5.2 Hz), 3.03 (1H, dd, J 14.0, 6.1 Hz), 1.56-1.51 (2H, m), 2.38-2.34 (2H, m), 1.18 (3H, t, J 7.1 Hz); m/z (ES⁺, 70V) 500.0 (MH⁺).

EXAMPLE 125

(2S)-2-[(3-Oxo-spiro[3.4]octa-1,6-dien-1-yl)amino]-3-{4-[(3,5-dichloroisonicotinoyl)amino] phenyl}propanoic Acid Hydrolysis of the compound of Example 124 (970 mg, 1.94 mmol) with lithium hydroxide (100 mg, 2.2 mmol), according to the method of Example 2, gave the title compound (896 mg, 1.90 mol, 98%). δH (DMSO d⁶, 390K) 10.87 (1H, s), 8.80 (2H, s), 8.45 (1H, d, J 8.4 Hz), 7.57 (2H, d, J 8.5 Hz), 7.27 (2H, d, J 8.5 Hz), 5.63 (2H, s), 4.41 (1H, s), 4.11 (1H, m), 3.17 (1H, dd, J 13.9, 4.8 Hz), 2.98 (1H, dd, J 13.9, 9.3 Hz), 2.46-2.42 (2H, m), 2.36-2.25 (2H, m); m/z (ES⁺, 70V) 471.9 (MH⁺).

EXAMPLE 126

Ethyl (2S)-2-[(2-bromo-3-oxo-spiro[3.4]octa-1,6-dien-1-yl)amino]-3-{4-[(3,5-dichloroisonicotinoyl) amino]phenyl}propanoate Bromination of the compound of Example 124 (206 mg, 0.41 mmol) with N-bromo succinimide (75 mg, 0.57 mmol), according to the method of Example 36 afforded the title compound as a white solid (116 mg, 0.20 mmol, 50%). δH (DMSO d⁶, 390K) 10.36 (1H, s), 8-67 (2H, s), 8.45 (1H, d, J 9.0 Hz), 7.58 (2H, d, J 8.5 Hz), 7.28 (2H, d, J 8.5 Hz), 5.67-5.63 (2H, m), 4.50 (1H, s br), 4.23 (2H, q, J 7.1 Hz), 3.28 (1H, dd, J 14.1, 6.3 Hz), 3.15 (1H, dd, J 14.1, 9.0 Hz), 2.52-2.42 (4H, m), 1.28 (3H, t, J 7.1 Hz); m/z (ES⁺, 70V) 579.0 (MH⁺).

EXAMPLE 127

(2S)-2-[(2-Bromo-3-oxo-spiro[3,4]octa-1,6-dien-1-yl)amino]-3-{4-[(3,5-dichloroisonicotinoyl)amino]phenyl}propanoic Acid Hydrolysis of the compound of Example 126 (190 mg, 0.33 mmol) with lithium hydroxide (60 mg, 1.3 mmol), according to the method of Example 2, gave the title compound (162 mg, 0.29 mol, 88%). δH (DMSO d⁶, 390K) 10.89 (1H, s), 9.09-9.04 (1H, m), 8.81 (2H, s), 7.62 (2H, d, J 8.5 Hz), 7.29 (2H, d, 48.5 Hz), 5.69-5.60 (2H, m), 4.72 (1H, m), 3.03 (1H, dd, J 14.1, 9.0 Hz), 2.98 (1H, dd, J 14.1, 6.7 Hz), 2.62-2.20 (4H, m); m/z (ES⁺, 70V) 551.8 (MH⁺).

EXAMPLE 128

Ethyl (2S)-2-[(4,4-dimethyl-3-oxo-2-pentafluorophenylsulfanyl-cyclobut-1-enyl)amino]-3-{4-[(3,5-dichloroisonicotinoyl)amino]phenyl}propanoate Was prepared from the compound of Example 5 (500 mg, 1.06 mmol) and pentafluorophenyl sulphenyl chloride (273 mg, 1.17 mmol), according to the method of Example 93 to give the title compound as a white powder (459 mg, 0.68 mmol, 64%). δH (CDCl₃, 300K); 8.41 (2H, s), 7.41 (2H, d, J 8.4 Hz), 6.99 (2H, d, J 8.4 Hz), 5.98 (1H, d, J 8.8 Hz), 5.18-5.12 (1H, m), 4.12 (2H, q, J 7.1 Hz), 3.17 (1H, dd, J 14.1, 5.6 Hz), 3.10 (1H, dd, J 14.1, 5.7 Hz), 1.18 (3K, t, J 7.1 Hz), 1.03 (3H, s), 1.01 (3H, s); m/z (ES⁺, 70V) 673.9 (MH⁺).

EXAMPLE 129

(2S)-2-[(4,4-Dimethyl-3-oxo-2-pentafluorophenyl-sulfanyl-cyclobut-1-enyl)amino]-3-{4-[(3,5-dichloroisonicotinoyl)amino]phenyl}propanoic Acid Hydrolysis of the compound of Example 128 (440 mg, 0.65 mmol) with lithium hydroxide (60 mg, 1.4 mmol), according to the method of Example 2, gave the title compound (372 mg, 0.57 mmol, 88%) as a white powder. δH (DMSO d⁶, 390K) 13.75 (1H, br s), 10.62 (1H, s), 9.16 (1H, d, J 9.5 Hz), 8.54 (2H, s), 7.30 (2H, d, J 8.5 Hz), 6.97 (2H, d, J 8.5 Hz), 4.83-4.77 (1H, m), 3.0 (1H, dd, J 14.0, 4.1 Hz), 2.71 (1H, dd, J 14.0, 10.0 Hz), 0.83 (3H, s), 0.75 (3H, s); m/z (ES⁺, 70V) 645.9 (MH⁺).

EXAMPLE 130

Ethyl (2S)-2-(4,4-dimethyl-3-oxo-2-pyrazin-2-yl-cyclobut-1-enylamino)-3-{4[(3,5-dichloroisonicotinoyl)amino]phenyl}propanoate A solution containing vinyl iodide (500 mg, 0.81 mmol), palladium dichloride (14 mg), triphenyl arsine (101 mg), 2-tributylstannyl 1,4-pyridazine (307 mg), and copper iodide (15 mg) in DMF was heated to 95° for 3 h. The reaction was then diluted with saturated aqueous sodium hydrogencarbonate solution (50 ml) and EtOAc (100 ml). The organic phase was removed, dried (MgSO4), filtered and concentrated in vacuo. Chromatography (SiO₂, 50% EtOAc:hexanes) gave the title compound (127 mg, 0.23 mmol, 28%). δH (CDCl₃, 330K) 9.51 (1H, s), 8.72 (1H, s), 8.26 (1H, m), 8.11 (1H, d, J 2.7 Hz), 7.97 (1H, d, J 10.9 Hz), 7.54 (2H, d, J 8.5 Hz), 4.24-4.15 (3H, m), 3.18 (1H, dd, J 13.9, 5.2 Hz), 3.11 (1H, dd, J 13.9, 4.6 Hz), 1.23 (3H, t, J 7.1 Hz), 1.22 (3H, s), 0.98 (3H, s); m/z (ES⁺, 70V) 554.1 (MH⁺).

EXAMPLE 131

(2S)-2-[(4,4-Dimethyl-3-oxo-2-pyrazin-2-yl-cyclobut-1-enyl)amino]-3-{4[(3,5-dichloroisonicotinoyl)amino]phenyl}propanoate Hydrolysis of the compound of Example 130 (50 mg, 0.09 mmol) with lithium hydroxide (10 mg, 0.23 mmol), according to the method of Example 2, gave the title compound (33 mg, 0.064 mmol, 71%) as a white powder. LCMS indicates the presence of two separate atropisomers. δH (DMSO d⁶, 390K, 1 atropisomer) 10.49 (1H, s), 8.90 (1H, br m), 8.69 (2H, s), 8.42 (1H, br m), 8.21 (1H, br m), 7.43 (2H, d, J 8.3 Hz), 7.21 (2H, d, J 8.3 Hz), 5.95 (1H, br s), 4.20 (1H, m), 3.27-3.22 (1H, m), 3.06 (1H, m), 1.28 (3H, s), 1.19 (3H, s); m/z (ES⁺, 70V) 526.0 (MH⁺).

EXAMPLE 132

Ethyl (2S)-2-[(4-methyl-3-oxo-4-phenyl-cyclobut-1-enyl)amino]-3-{4-[(3,5-dichloroisonicotinoyl)amino]phenyl}propanoate Prepared from Intermediate 49 (300 mg, 1.72 mmol) and the free base of Intermediate 27 (400 mg, 1.04 mmol), in a similar manner to the compound of Example 11, to give the title compound as a white powder (329 mg, 0.61 mmol, 59%) as an approx. 1:1 mixture of diastereomers. 6H(CDCl₃, 300K) 10.95 (1H, s), 10.88 (1H, s), 8.89 (1H, d, J 8.6 Hz), 8.81 (2H, s), 8.80 (2H, s), 8.74 (1H, d, J 8.8 Hz), 7.63 (2H, d, J 8.5 Hz), 7.59 (2H, d, J 8.5 Hz), 7.34-7.10 (5H, m), 6.89 (2H, d, J 8.5 Hz), 6.85 (2H, d, J 8.5 Hz), 4.71 and 4.66 (1H, s), 4.48-4.42 and 4.38-4.33 (1H, m), 4.21 (2H, t, J 7.1 Hz), 3.31-3.01 (2H, m), 1.52 and 1.42 (3H, s), 1.25 (3H, t, J 7.1 Hz); m/z (ES⁺, 70V) 537.9 (MH⁺).

EXAMPLE 133

Ethyl (2S)-2-[(4-methyl-3-oxo-4-phenyl-cyclobut-1-enyl)amino]-3-{4-[(3,5-dichloroisonicotinoyl)amino]phenyl}propanoate The compound of Example 132 (100 mg, 0.18 mmol) was hydrolysed in a similar manner to the method of Example 2 to give the title compound as a fine white solid (79 mg, 0.15 mmol, 86%) as an approx. 1:1 mixture of diastereomers. δH (DMSO d⁶, 360K) 10.95 and 10.88 (1H, s), 8.82 and 8.81 (2H, s), 8.65 (1H, d, J 8.7 Hz), 7.63 and 7.59 (2H, d, J 8.5 Hz), 7.23-7.10 (5H, m), 6.88 and 6.85 (2H, d, J 8.5 Hz), 4.70 and 4.63 (1H, s), 4.36-4.25 and 4.25-4.22 (1H, m), 3.31-3.00 (2H, m), 1.41 and 1.25 (3H, s); m/z (ES⁺, 70V) 509.9 (MH⁺).

EXAMPLE 134

Ethyl (2S)-2-[(7-acetyl-2-bromo-3-oxo-7-aza-spiro[3.5]non-1-en-1-yl)amino]-3-{4-[(3,5-dichloroisonicotinoyl)amino]phenyl}propanoate A solution of the compound of Example 51 (100 mg, 0.1 mmol) in THF (10 ml) at rt was treated with N-bromo succinimide (32 mg, 0.19 mmol). After 30 min the reaction was diluted with EtOAc (50 ml) and saturated aqueous sodium hydrogencarbonate solution (30 ml), the organic phase separated and dried (MgSO₄), filtered and concentrated in vacuo.

Chromatography (SiO₂, EtOAc) gave the title compound as a white powder (79 mg, 0.12 mmol, 67%). δH (CDCl₃, 300K) 9.54 (1H, s), 8.65 (1H, d, J 9.4 Hz), 8.19 (2H, s), 7.49 (2H, d, J 8.4 Hz), 7.07 (2H, d, J 8.4 Hz), 4.91-4.81 (1H, m), 4.11 (2H, q, J 7.1 Hz), 3.49-3.44 (1H, m), 3.25-2.66 (5H, m), 1.89 (3H, s), 1.86-1.25 (4H, m), 1.18 (3H, t, J 7.1 Hz); m/z (ES⁺, 70V) 639.0 (MH⁺).

EXAMPLE 135

(2S)-2-[(7-Acetyl-2-bromo-3-oxo-7-aza-spiro[3.5]non-1-en-1-yl)amino]-3-{4-[(3,5-dichloroisonicotinoyl)amino]phenyl}propanoic Acid The compound of Example 134 (50 mg, 0.078 mmol) was hydrolysed in a similar manner to the method of Example 2, to give the title compound as a white powder (21 mg, 0.034 mmol, 44%). δH (DMSO d⁶, 390K) 10.38 (1H, s), 8.96 (2H, s), 7.57 (2H, s br), 7.28 (2H, d, J 7.9 Hz), 4.78 (1H, m), 3.99-3.96 (2H, m), 3.30-3.06 (4H, m), 2.00 (3H, s), 1.94-1.84 (2H, m), 1.48-1.21 (2H, m); m/z (ES⁺, 70V) 610.9 (MH⁺).

EXAMPLE 136

Ethyl (2S)-2-(2-benzyl-4,4-dimethyl-3-oxo-cyclobut-1-enylamino)-3-{4-[(3,5-dichloroisonicotinoyl)amino]phenyl}propanoate A solution of the free acid of Intermediate 27 (0.82 g, 2.1 mmol) and Intermediate 72 (0.48 g, 2.3 mmol, 1.1 eq.) in nitromethane (8 ml) was treated with acetic acid (1 drop). The resulting mixture was heated at 100° for 2 h. and then partitioned between EtOAc (50 ml) and water (25 ml), the organics were separated, washed with water (25 ml), Na₂CO₃ (25 ml, sat. aq.), brine (25 ml), dried (Na₂SO₄), filtered and concentrated in vacuo to give a crude foam. This was purified by column chromatography (SiO₂, gradient elution 1:1, hexane: EtOAc to EtOAc) to give the title compound as a white solid (0.71 g, 59%). δH (DMSO d⁶, 400 MHz) 10.87 (1H, s), 8.81 (2H, s), 8.38 (1H, d, J 9.3 Hz), 7.53 (2H, d, J 8.4 Hz), 7.33 (2H, m), 7.15 (2H, m), 7.09 (2H, d, J 8.5 Hz), 7.03 (2H, d, J 7.2 Hz), 4.15 (1H, m), 4.04 (2H, dq, J 7.1, 1.6 Hz), 3.19 (2H, m), 3.04 (1H, dd, J 13.8, 5.0 Hz), 2.89 (1H, dd, J 9.5, 4.8 Hz), 1.02-1.26 (8H, m); m/z (ES⁺, 70V) 566 (MH⁺).

EXAMPLE 137

(2S)-2-(2-Benzyl-4,4-dimethyl-3-oxo-cyclobut-1-enylamino)-3-{4-[(3,5-dichloroisonicotinoyl)amino]phenyl}propanoic Acid To a solution of the compound of Example 136 (210 mg, 0.4 mmol) in THF (2 ml) was added a solution of lithium hydroxide hydrate (25 mg, 0.6 mmol, 1.5 eq) in water (1 ml). The solution was stirred at room temperature for 3 h. The reaction mixture was concentrated in vacuo and the residue re-dissolved in water (15 ml) and washed with diethyl ether (10 ml). The aqueous was concentrated to approx. 5 ml and taken to pH 4 with HCl (2 M, aq.). The resulting solid was filtered, washed on the sinter with water, diethyl ether and dried in vacuo to give the title compound as a white solid (170 mg, 85%). δH (400 MHz, DMSO d⁶, 380K) 10.42 (1H, br), 8.70 (2H, s), 7.64 (1H, d, J 9.4 Hz), 7.52 (2H, d, J 6.6 Hz), 7.25 (2H, m), 7.13-7.18 (5H, m), 4.13 (1H, m), 3.26 (2H, d, J 2.9 Hz), 3.13 (1H, dd, J 14.0, 4.9 Hz), 2.97 (1H, dd, J 14.0, 9.0 Hz), 1.12 (3H, s), 1.09 (3H, d, J 15.7 Hz); m/z (ES⁺, 70V) 538 (MH⁺).

EXAMPLE 138

Isopropyl (2S)-2-(2-bromo-3-oxo-spiro[3.5]non-1-en-1-ylamino)-3-{4-[(3,5-dichloroisonicotinoyl)amino]phenyl}propanoate To a solution of the compound of Example 32 (0.5 g, 0.9 mmol) in DMF (5 ml) was added EDC (185 mg, 1.1 eq), HOBT (135 mg, 1.1 eq) and isopropanol (0.5 ml). The mixture was stirred at room temperature for 48 h. then partitioned between EtOAc (100 ml) and water (50 ml). The aqueous was separated and the organics washed with water (5×30 ml), brine (30 ml), dried (Na₂SO₄), filtered and concentrated in vacuo to give a crude solid. The crude was triturated with diethyl ether to give the title compound as a white powder (0.35 g, 65%) δH (300 MHz, DMSO d⁶) 10.69 (1H, br), 8.68 (1H, d, J 9.1 Hz), 8.60 (2H, s), 7.39 (2H, d, J 8.5 Hz), 7.08 (2H, d, J 8.5 Hz), 4.78 (1H, sep, J 6.3 Hz), 4.53 (1H, m), 3.01 (1H, dd, J 13.8, 4.9 Hz), 2.83 (1H, dd, J 13.9, 9.5 Hz), 1.36-1.60 (9H, m), 1.19 (1H, d, J 12.7 Hz), 0.98-1.05 (6H, dd); m/z (ES⁺, 70V) 608 (MH⁺).

EXAMPLE 139

1-Methyl-piperidin-4-yl (2S)-2-(2-bromo-3-oxospiro[3.5]non-1-en-1-ylamino)-3-{4-[(3,5-dichloroisonicotinoyl)amino]phenyl}propanoate Using a similar procedure to that for the preparation the compound of Example 138 from the compound of Example 32 (0.5 g, 0.89 mmol), EDC (185 mg, 1.1 eq), HOBT (135 mg, 1.1 eq), 4-hydroxy-1-methylpiperidine (0.5 ml) and DMF (2 ml) was prepared the title compound (0.21 g, 36%). δH (300 MHz, DMSO d⁶) 11.01 (1H, br), 9.01 (1H, d, J 9.4 Hz), 8.92 (2H, s), 7.71 (2H, d, J 8.5 Hz), 7.40 (2H, d, J 8.5 Hz), 4.90 (1H, br), 3.33 (1H, dd, J 13.8, 4.8 Hz), 3.16 (1H, dd, J 13.8, 9.6 Hz), 2.55 (2H, br), 2.40 (2H, br), 2.24 (3H, d, J 8.0 Hz), 1.64-1.95 (12H, m), 1.50 (2H, d, J 12.1 Hz), 1.23 (2H, br); m/z (ES⁺, 70V) 664 (MH⁺).

EXAMPLE 140

Cyclopentyl (2S)-2-(2-bromo-3-oxo-spiro[3.5]non-1-en-1-ylamino)-3-{4-[(3,5-dichloroisonicotinoyl)amino]phenyl}propanoate Using a similar procedure to that for the preparation the compound of Example 138 from the compound of Example 32 (0.5 g, 0.89 mmol, EDC (600 mg, 3 eq), HOBT (400 mg, 3 eq), cyclopentanol (0.5 ml) and DMF (5 ml)] was prepared the title compound. δH (400 MHz, DMSO d⁶) 10.88 (1H, s), 8.85 (1H, d, J 9.0 Hz), 8.78 (2H, s), 7.58 (2H, d, J 8.5 Hz), 7.26 (2H, d, J 8.5 Hz), 5.15 (1H, m), 4.71 (1H, m), 3.18 (1H, dd, J 13.9, 5.2 Hz), 3.02 (1H, dd, J 13.9, 9.5 Hz), 1.17-1.84 (18H, m), 1.14 (1H, m); m/z (ES⁺, 70V) 634 (MH⁺).

EXAMPLE 141

Tetrahydro-furan-3-yl (2S)-2-(2-bromo-3-oxo-spiro [3,5]non-1-en-1-ylamino)-3-{4-[(3,5-dichloroisonicotinoyl)amino]phenyl}propanoate Using a similar procedure to that for the preparation the compound of Example 138 from the compound of Example 32 acid (0.5, 0.89 mmol), EDC (600 mg, 3 eq), HOBT (400 mg, 3 eq), (S)-3-hydroxytetrahydrofuran (0.5 ml) and DMF (5 ml)] was prepared the title compound. δH (300 MHz, DMSO d⁶) 8.87 (1H, d, J 8.9 Hz), 8.79 (2H, s), 7.58 (2H, d, J 8.4 Hz), 7.27 (2H, d, J 8.5 Hz), 5.30 (1H, m), 4.77 (1H, m), 3.72-3.83 (3H, m), 3.65 (1H, d, J 10.4 Hz), 3.20 (1H, dd, J 14.0, 5.1 Hz), 3.04 (1H, dd, J 14.0, 9.7 Hz), 2.11-2.27 (1H, m), 1.87-1.99 (1H, m), 1.37-1.78 (9H, m), 1.07-1.17 (1H, m); m/z (ES⁺, 70V) 636 (MH⁺).

EXAMPLE 142

1-Methyl-pyrrolidin-3-yl (2S)-2-(2-bromo-3-oxo-spiro[3.5]non-1-en-1-ylamino)-3-{4-[(3,5-dichloroisonicotinoyl)amino]phenyl}propanoate Using a similar procedure to that for the preparation the compound of Example 138 from the compound of Example 32 (0.5 g, 0.89 mmol), EDC (600 mg, 3 eq), HOBT (400 mg, 3 eq), 1-methyl-3-pyrrolidinol (0.6 ml) and DMF (5 ml) was prepared the title compound. δH (400 MHz, DMSO d⁶) 10.88 (1H, s), 8.87 (1H, d, J 9.0 Hz), 8.78 (2H, s), 7.58 (2H, d, J 8.3 Hz), 7.26 (2H, d, J 8.5 Hz), 5.13 (1H, m), 4.74 (1H, m), 3.16 (1H, m), 3.04 (1H, m), 2.43-2.73 (2H, m), 2.07-2.26 (2H, m), 1.55-1.75 (11H, m), 1.11 (1H, m). m/z (ES⁺, 70V) 649 (MH⁺).

EXAMPLE 143

Phenyl (2S)-2-(2-bromo-3-oxo-spiro[3.5]non-1-en-1-ylamino)-3-{4-[(3,5-dichloroisonicotinoyl)amino]phenyl}propanoate Using a similar procedure to that for the preparation the compound of Example 138 from the compound of Example 32 (0.5 g, 0.89 mmol, EDC (500 mg, 2.6 eq), HOBT (350 mg, 2.6 eq), phenol (0.5 g) and DMF (5 ml)] was prepared the title compound (0.17 g, 29%). δH (300 MHz, DMSO d⁶) 11.10 (1H, br)), 9.24 (1H, d, J 8.8 Hz), 8.98 (2H, s), 7.81 (2H, d, J 8.5 Hz), 7.47-7.67 (5H, c), 7.31 (2H, dd, J 8.4, 0.9 Hz), 6.93 (1H, d, J 8.1 Hz), 5.20 (1H, br), 3.59 (1H, dd, J 9.3, 6.0 Hz), 3.40 (1H, dd, J 14.0, 9.3 Hz), 1.60-1.97 (10H, m); m/z (ES⁺, 70V) 644 (MH⁺).

EXAMPLE 144

Pyridin-4-ylmethyl (2S)-2-(2-bromo-3-oxo-spiro [3.5]non-1-en-1-ylamino)-3-{4-[(3,5-dichloroisonicotinoyl)amino]phenyl}propanoate Using a similar procedure to that for the preparation the compound of Example 138 from the compound of Example 32 (0.60 g, 1.1 mmol), EDC (222 mg, 1.1 eq), HOBT (162 mg, 1.1 eq), 4-pyridinemethanol (0.36 g, 3.2 mmol) and DMF (5 ml)] was prepared the title compound (0.48 g, 66%). δH (400 MHz, DMSO d⁶, 380K) 10.43 (1H, br), 8.69 (2H, s), 8.57 (2H, d, J 6.0 Hz), 8.38 (11H, d, J 8.1 Hz), 7.57 (2H, m), 7.30 (4H, m), 5.26 (2H, s), 4.95 (1H, br), 3.32 (1H, dd, J 14.2, 5.4 Hz), 3.17 (1H, dd, J 14.1, 9.1 Hz), 1.46-1.71 (9H, m), 1.21 (1H, br m); m/z (ES⁺, 70V) 657 (MH⁺).

EXAMPLE 145

Methyl (2S)-2-[(3-oxo-7-oxaspiro[3.5]non-1-en-yl) amino]-3-(2,6-dimethoxy[1,1'-biphenyl]-4-yl)propanoate Using a similar procedure to that for the preparation the compound of Example 38 from methyl (2S)-2-amino-3-(2,6-dimethoxy[1,1'-biphenyl]-4-yl)propanoate (2.0 g, 6.3 mmol) and 7-oxaspiro[3.5]nonane-1,3-dione (1.1 g, 1.1 eq) in DCM (30 ml) was prepared the title compound as a white foam (2.4 g, 86%). δH (300 MHz, DMSO d⁶) 8.53 (1H, d, J 8.7 Hz), 7.20-7.30 (3H, m), 7.08 (2H, d, J 8.1 Hz), 6.70 (2H, d, J 8.5 Hz), 4.44 (1H, s), 4.30 (1H, m), 3.72 (3H, s), 3.61 (6H, s), 3.22 (1H, dd, J 13.7, 5.0 Hz), 2.98 (1H, dd, J 13.8, 10.1 Hz), 1.74-1.99 (2H, m), 1.48 (1H, d, J 13.6 Hz), 1.31 (1H, d, J 13.0 Hz); m/z (ES⁺, 70V) 439 (MH⁺).

EXAMPLE 146

Methyl (2)-2-{[2-(isopropylsulfanyl)-3-oxo-7-oxaspiro[3.5]non-1-en-yl)]amino}-3-(2,6-dimethoxy[1,1'-biphenyl]-4-yl)propanoate The title compound was prepared in a similar manner to the compound of Example 70 from the bromo derivative of the compound of Example 145 (0.5 g, 1.1 mmol) as a white foam (0.42 g, 73%). δH (400 MHz, DMSO d⁶) 8.91 (1H, d, J 9.4 Hz), 7.29-7.21 (3H, m), 7.09 (2H, d, 48.2 Hz), 6.70 (2H, d, J 8.4 Hz), 5.32 (1H, br), 3.74-3.80 (5H, m), 3.54-3.64 (8H, m), 3.28 (1H, dd, J 16.4, 4.2 Hz), 2.97 (1H, dd, J 13.6, 10.8 Hz), 2.76 (1H, sep, J 6.7 Hz), 1.99 (1H, dt, J 11.5, 4.8 Hz), 1.84 (1H, dt, J 13.0, 4.8 Hz), 1.48 (1H, d, J 12.1 Hz), 1.25 (1H, d, J 12.2 Hz), 1.05 (3H, d, J 6.7 Hz), 1.02 (3H, d, J 6.7 Hz); m/z (ES⁺, 70V) 526 (MH⁺).

EXAMPLE 147

Ethyl (2S)-2-[(4,4,-dimethyl-3-oxo-1-cyclobutenyl) amino]-3-(2,6-dimethoxy[1,1'-biphenyl]-4-yl)propanoate The title compound was prepared in a similar manner to that of the compound of Example 41 from ethyl (2S)-2-amino-3-(2,6-dimethoxy[1,1'-biphenyl]-4-yl)propanoate (1.5 g, 4.5 mol), and 3-hydroxy-4,4-dimethyl-2-cyclobuten-one (0.5 g, 4.5 mmol) in DCM (11 ml) as a white foam (1.8 g, 93%). δH (300 MHz, DMSO d⁶) 8.68 (1H, d, J 8.6 Hz), 7.22-7.37 (3H, m), 7.18 (2H, d, J 8.3 Hz), 6.78 (2H, d, J 8.4 Hz), 4.46 (11H, s), 4.32 (1H, m), 4.21 (2H, q, J 7.1 Hz), 3.69 (6H, s), 3.24 (1H, dd, J 13.8, 5.9 Hz), 3.09 (1H, dd, J 13.8, 9.1 Hz), 1.24 (3H, t, J 7.1 Hz), 1.16 (3H, s), 1.08 (3H, s); m/z (ES⁺, 70V) 424 (MH⁺).

EXAMPLE 148

Ethyl (2S)-2-{[2-(isopropylsulfanyl)-4,4,-dimethyl-3-oxo-1-cyclobutenyl]amino}-3-(2,6-dimethoxy[1,1'-biphenyl]-4-yl)propanoate The title compound was prepared in a similar manner to the compound of Example 70 as a white foam (0.52 g, 87%). δH (400 MHz, DMSO d⁶, 380K) 8.99 (1H, d, J 9.5 Hz), 7.21-7.29 (3H, m), 7.10 (2H, d, J 8.1 Hz), 6.70 (2H, d, J 8.4 Hz), 5.29 (1H, m), 4.17 (2H, q, J 7.1 Hz), 3.60 (6H, s), 3.23 (1H, dd, J 13.8, 5.0 Hz), 2.99 (1H, dd, J 13.8, 10.4 Hz), 2.79 (1H, sep, J 6.6 Hz), 0.99-1.25 (15H, m). m/z (ES⁺, 70V) 498 (MH⁺).

EXAMPLE 149

(2S)-2-{[2-(isopropylsulfanyl)-3-oxo-7-oxaspiro [3.5]non-1-en-yl)]amino}-3-(2,6-dimethoxy[1,1'-biphenyl]-4-yl)propanoic Acid Prepared from the compound of Example 146 (0.25 g, 0.46 mmol) in a similar manner to that of Example 2 to give the title compound as a white powder (0.21 g, 89%). δH (400 MHz, DMSO d⁶) 8.80 (1H, d, J 9.5 Hz), 7.21-7.28 (3H, m), 7.08 (2H, d, J 8.1 Hz), 6.70 (2H, d, J 8.4 Hz), 5.25 (1H, m), 3.76 (2H, m), 3.59 (8H, m), 3.30 (1H), 2.93 (1H, dd, J 13.6, 10.9 Hz), 2.76 (1H, sep, J 6.8 Hz), 1.99 (1H, m), 1.86 (1H, m), 1.46 (1H, d, J 13.1 Hz), 1.23 (1H, d, J 12.7 Hz), 1.06 (3H, d, J 7.8 Hz), 1.03 (3H, d, J 7.8 Hz); m/z (ES⁺, 70V) 512 (MH⁺).

EXAMPLE 150

(2S) 2-{[2-(isopropylsulfanyl)-4,4,-dimethyl-3-oxo-1-cyclobutenyl]amino}-3-(2,6-dimethoxy[1,1'-biphenyl]-4-yl)propanoic Acid Prepared from the compound of Example 148 (0.31 g, 0.64 mmol) in a similar manner to that of Example 2 to give the title compound as a white powder (0.13 g, 44%). δH (400 MHz, DMSO d⁶) 8.85 (1H, br d), 7.21-7.29 (3H, m), 7.08 (2H, d, J 8.0 Hz), 6.70 (2H, d, J 8.4 Hz), 5.15 (1H, br), 3.61 (6H, s), 3.91 (1H, dd, J 13.7, 8.6 Hz), 2.77 (1H, sep), 0.98-1.14 (6H, m); m/z (ES⁺, 70V) 470 (MH⁺).

EXAMPLE 151

Ethyl (2S)-2-[(2-cyclohexyl-3-oxospiro[3.5]non-1-en-1-yl)amino]-{4-[(3,5-dichloroisonicotinoyl)amino]phenyl}propanoate A mixture of the free amine of Intermediate 27 (1000 mg, 2.61 mmol), Intermediate 52 (611 mg, 2.61 mmol) and nitromethane (10 ml) were heated at reflux for 5 hours. The solvent was removed by evaporation under reduced pressure and the residue chromatographed (SiO₂, 3:2 hexane:EtOAc), to afford the title compound as a colorless oil (310 mg, 20%). δH (CDCl₃) 8.51 (2H, s), 7.80 (1H, br s), 7.52 (2H, d, J 8.5 Hz), 7.07 (2H, d, J 8.5 Hz), 5.15 (1H, d, J 7.6 Hz), 4.32 (1H, m), 4.20 (2H, q, J 7.1 Hz), 3.07 (2H, d, J 5.6 Hz), 1.75-1.40 (20H, m), 1.19 (3H, t, J 7.1 Hz).

EXAMPLE 152

(2S)-2-[(2-Cyclohexyl-3-oxo-spiro[3.5]non-1-en-1-yl)amino]-3-{4-[(3,5-dichloroisonicotinoyl)amino]phenyl}propanoic Acid The compound of Example 151 was hydrolysed by the method of Example 2, giving the title compound (78%). δH (DMSO d⁶) 10.84 (1H, br s), 8.78 (2H, s), 7.60 (1H, s), 7.56 (2H, d, J 8.2 Hz), 7.25 (2H, d, J 7.9 Hz), 4.06 (1H, m), 3.12 (1H, dd, J 13.6, 3.9 Hz), 2.92 (1H, dd, J 13.4, 9.8 Hz), 1.80-1.00 (21H, m); m/z (ES⁺, 70V) 570.1 (MH⁺)

EXAMPLE 153

Ethyl (2S)-3-{4-[(3,5-dichloroisonicotnoyl)amino]phenyl}-2-(2,4,4-trimethyl-3-oxo-cyclobut-1-enylamino)propanoate Prepared in a similar manner to the compound of Example 151 from Intermediate 59 to give the title compound (70%). δH (CDCl₃) 8.78 (1H, br s), 8.44 (2H, s), 7.52 (2H, d, J 8.4 Hz), 7.04 (2H, d, J 8.3 Hz), 5.55 (1H, d, J 9.0 Hz), 4.39 (1H, m), 4.20 (2H, q, J 7.1 Hz), 3.07 (2H, m), 1.41 (3H, s), 1.26 (3H, t, J 7.1 Hz), 1.05 (6H, s); m/z (ES⁺, 70V) 490.0 (MH⁺).

EXAMPLE 154

(2S)-{4-[(3,5-Dichloroisonicotinoyl)amino]phenyl}-2-(2,4,4-trimethyl-3-oxo-cyclobut-1-enylamino)propanoic Acid The compound of Example 153 was hydrolysed by the method of Example 2 to afford the title compound (69%). δH (DMSO d⁶) 7.86 (2H, s), 6.82 (2H, d, J 8.5 Hz), 6.54 (2H, d, J 8.5 Hz), 3.69 (1H, m), 2.57 (1H, m), 2.25 (1H, m), 0.68 (3H, s), 0.38 (3H, s), 0.29 (s, 3H); m/z (ES⁺, 70V) 462.0 (MH⁺).

EXAMPLE 155

Ethyl (2S)-3-{4-[(3,5-dichloroisonicotinoyl)amino]phenyl}-2-(2-ethyl-4,4-dimethyl-3-oxo-cyclobut-1-enylamino)propanoate Prepared in a similar manner to the compound of Example 151 from Intermediate 60 to give the title compound (73%). δH (DMSO d⁶) 8.78 (2H, s), 8.13 (1H, d, J 9.0 Hz), 7.59 (2H, d, J 8.4 Hz), 7.30 (2H, d, J 8.3 Hz), 4.25 (1H, m), 4.17 (2H, q, J 7.0 Hz), 3.12 (1H, m), 3.00 (1H, m), 1.83 (2H, m), 1.20 (4H, m), 1.06 (3H, m), 0.98 (3H, s), 0.84 (3H, t, J 7.5 Hz); m/z (ES⁺, 70V) 504.0 (MH⁺).

EXAMPLE 156

(2S)-3-{4-[(3,5-Dichloroisonicotinoyl)amino]phenyl}-2-(2-ethyl-4,4-dimethyl-3-oxo-cyclobut-1-enylamino)propanoic Acid The compound of Example 155 was hydrolysed by the method of Example 2 to afford the title compound (78%). δH (DMSO d⁶) 7.83 (2H, s), 6.81 (2H, d, J 8.5 Hz), 6.51 (2H, d, J 8.4 Hz), 3.52 (1H, m), 2.51 (1H, m), 2.21 (1H, m), 1.10 (2H, q, J 7.3 Hz), 0.36 (3H, s), 0.26 (3H, s), 0.10 (3H, t, J 7.5 Hz); m/z (ES⁺, 70V) 476.0 (MH⁺).

EXAMPLE 157

Ethyl (2S)-3-{4-[(3,5-dichloroisonicotinoyl)amino]phenyl}-2-(4,4-dimethyl-3-oxo-2-propyl-cyclobut-1-enylamino)propanoate Prepared in a similar manner to the compound of Example 151 from Intermediate 61 to give the title compound (75%). δH (DMSO d⁶) 8.80 (2H, s), 8.11 (1H, d, J 9.3 Hz), 7.59 (2H, d, J 8.3 Hz), 7.30 (2H, d, J 8.3 Hz), 4.26 (1H, m), 4.15 (2H, q, J 7.1 Hz), 3.12 (1H, m), 3.00 (1H, m), 1.75 (2H, m), 1.23 (2H, m), 1.07 (3H, s), 0.99 (3H, s), 0.73 (3H, t, J 7.3 Hz); m/z (ES⁺, 70V) 518.0 (MH⁺).

EXAMPLE 158

(2S)-3-{4-[(3,5-Dichloroisonicotinoyl)amino]phenyl}-2-(4,4-dimethyl-3-oxo-2-propyl-cyclobut-1-enylamino)propanoic Acid The compound of Example 157 was hydrolysed by the method of Example 2 to afford the title compound (93%). δH (DMSO d⁶) 8.78 (2H, s), 8.05 (1H, d, J 9.2 Hz), 7.58 (2H, d, J 8.3 Hz), 7.30 (2H, d, J 8.3 Hz), 4.15 (1H, m), 313 (1H, m), 2.95 (1H, m), 1.75 (2H, m), 1.23 (2H, q, J 7.3 Hz), 1.06 (3H, s), 0.98 (3H, s), 0.72 (3H, t, J 7.3 Hz); m/z (ES⁺, 70V) 490.0 (MH⁺).

EXAMPLE 159

Ethyl (2S)-3-{4-[(3,5-dichloroisonicotinoyl)amino]phenyl}-2-(2-methyl-3-oxo-spiro[3.5]non-1-en-1-ylamino)propanoate Prepared in a similar manner to the compound of Example 151 from Intermediate 64 to give the title compound (68%). δH (DMSO d⁶) 8.79 (2H, s), 7.93 (2H, d, J 8.9 Hz), 7.58 (2H, d, J 8.4 Hz), 7.29 (2H, d, J 8.4 Hz), 4.33 (1H, m), 4.16 (2H, q, J 7.1 Hz), 3.10 (1H, m), 2.99 (1H, m), 1.60 (10H, m), 1.37 (3H, s), 1.18 (3H, t, J 7.1 Hz); m/z (ES⁺, 70V) 530.1 (MH⁺).

EXAMPLE 160

(2S)-3-{4-[(3,5-Dichloroisonocotinoyl)amino]phenyl}-2-(2-methyl-3-oxo-spiro[3.5]non-1-en-1-ylamino)propanoic Acid The compound of Example 159 was hydrolysed by the method of Example 2 to afford the title compound (86%). δH (DMSO d$^6$) 8.82 (2H, s), 7.81 (1H, d, J 9.1 Hz), 7.57 (2H, d, J 8.4 Hz), 7.30 (2K, d, J 8.4 Hz), 4.28 (1H, m), 3.13 (1H, m), 2.96 (1H, m), 1.70-1.49 (8H, m), 1.38 (3H, s), 1.14 (2H, m); m/z (ES$^+$, 70V) 501.9 (MH$^+$).

EXAMPLE 161

Ethyl (2S)-3-{4-[(3,5-dichloroisonicotinoyl)amino]phenyl}-2-(3-oxo-2-propyl-spiro[3.5]non-1-en-1 ylamino)propanoate Prepared in a similar manner to the compound of Example 151 from Intermediate 65 to give the title compound (76%). δH (CDCl$_3$) 8.58 (2H, s), 8.44 (1H, s), 7.65 (2H, d, J 8.5 Hz), 7.16 (2H, d, J 8.4 Hz), 5.38 (1H, m), 4.46 (1H, m), 4.30 (2H, q, J 7.1 Hz), 3.17 (2H, m), 1.85-1.42 (14H, m), 1.38 (3H, t, J 7.1 Hz), 0.90 (3H, t, J 7.3 Hz); m/z (ES$^+$, 70V) 558.1 (MH$^+$).

EXAMPLE 162

(2S)-3-{4-[(3,5-Dichloroisonicotinoyl)amino]phenyl}-2-(3-oxo-2-propyl-spiro[3.5]non-1-en-1-yl amino)propanoic Acid The compound of Example 161 was hydrolysed by the method of Example 2 to afford the title compound (84%). δH (DMSO d$^6$, 380K) 10.42 (1H, br s), 8.69 (2H, s), 7.57 (2H, d, J 7.3 Hz), 7.28 (d, 2H, J 8.3 Hz), 7.12 (1H, d, J 9.1 Hz), 4.21 (1H, m), 3.20 (1H, dd, J 14.0, 4.9 Hz), 3.06 (1H, dd, J 14.0, 8.8 Hz), 1.87 (2H, m), 1.72-1.45 (10H, m), 1.36 (2H, m), 1.23 (1H, m), 0.82 (3H, t, J 7.4 Hz); m/z (ES$^+$, 70V) 530.1 (MH$^+$).

EXAMPLE 163

Ethyl (2S)-3-{4-[(3,5-dichloroisonicotinoyl)amino]phenyl}-2-(2-methyl-3-oxo-7-oxa-spiro[3.5]non-1-en-1-ylamino)propanoate Prepared in a similar manner to the compound of Example 151 from Intermediate 68 to give the title compound (71%). δH NMR (DMSO d$^6$) 8.80 (2H, s), 8.11 (1H, d, J 9.1 Hz), 7.59 (2H, d, J 8.4 Hz), 7.30 (2H, d, J 8.4 Hz), 4.38 (1H, m), 4.17 (2H, q, J 7.1 Hz), 3.75 (2H, m), 3.60 (2H, m), 3.15 (1H, dd, J 13.7, 5.1 Hz), 2.99 (1H, dd, J 13.6, 92 Hz), 1.90 (2H, m), 1.39 (3H, s), 1.19 (3H, t, J 7.1 Hz); m/z (ES$^+$, 70V) 532.0 (MH$^+$).

EXAMPLE 164

(2S)-3-{4-[(3,5-Dichloroisonicotinoyl)amino]phenyl}-2-(2-methyl-3-oxo-7-oxa-spiro[3.5]non-1-en-1-ylamino)propanoic Acid The compound of Example 163 was hydrolysed by the method of Example 2 to afford the title compound (89%). δH (DMSO d$^6$) 8.81 (2H, s), 8.05 (1H, d, J 9.2 Hz), 7.60 (2H, d, J 8.4 Hz), 7.32 (2H, d, J 8.4 Hz), 4.25 (1H, m), 3.75 (2K, m), 3.58 (2H, m), 3.13 (1H, dd, J 13.8, 4.6 Hz), 2.98 (1 HK dd, J 13.8, 9.5 Hz), 1.94 (2H, m), 1.40 (3H, s), 1.29 (2H, m); m/z (ES$^+$, 70V) 504.0 (MH$^+$).

EXAMPLE 165

Ethyl (2S)-3-{4-[(3.5-dichloroisonicotinoyl)amino]phenyl}-2-(3-oxo-2-propyl-7-oxa-spiro[3.5]non-1-en-1-ylamino)propanoate Prepared in a similar manner to the compound of Example 151 from Intermediate 69 to give the title compound (59%). δH (DMSO d$^6$) 8.78 (2H, s), 8.08 (1 HK d, J 8.8 Hz), 7.55 (2H, d, J 8.4 Hz), 7.29 (2H, d, J 8.5 Hz), 4.23 (1H, m), 4.16 (2H, q, J 7.1 Hz), 3.76 (2H, m), 3.58 (2H, m), 3.15 (1H, dd, J 13.6, 4.8 Hz), 2.98 (1H, dd, J 13.6, 9.7 Hz), 1.80 (2H, m), 1.18 (6H, m), 0.73 (3H, t, J 7.4 Hz); m/z (ES$^+$, 70V) 560.0 (MH$^+$).

EXAMPLE 166

Ethyl (2S)-3-{4-[(3,5-dichloroisonicotinoyl)amino]phenyl}-2-(3-oxo-2-propyl-7-oxa-spiro[3,5]non-1-en-1-ylamino)propanoate The compound of Example 165 was hydrolysed by the method of Example 2 to afford the title compound (82%). δH (DMSO d$^6$, 380K) 10.39 (1H, br s), 8.68 (2H, s), 7.57 (2H, m), 7.33 (3H, m), 4.23 (1H, m), 3.70 (4H, m), 3.21 (1H, dd, J 14.0, 4.8 Hz), 3.04 (1H, dd, J 14.0, 9.0 Hz), 2.10 (1H, s), 1.88 (4H, m), 1.87 (3H, t, J 7.0 Hz), 1.40 (4H, m); m/z (ES$^+$, 70V) 532.1 (MH$^+$).

EXAMPLE 167

2-Imidazol-1-yl (2S)-2-(2-bromo-3-oxo-spiro[3.5]non-1-en-1-ylamino)-3-{4-[(3,5-dichloroisonicotinoyl)amino]phenyl}propanoate Prepared in a similar manner to the compound of Example 138 from N-2-hydroxyethylimidazole [prepared according to the method of Yoshino et al, J. C. S. Perkin Trans. 1, 1977, 1266-72] to give the title compound (48%). δH (DMSO d$^6$) 10.88 (1H, s), 8.88 (1H, d, J 9.1 Hz), 8.79 (2H, s), 7.66 (1H, s), 7.58 (2H, d, J 8.5 Hz), 7.29 (2H, d, J 8.5 Hz), 6.89 (1H, s), 4.84 (1H, m), 4.39 (2H, m), 4.29 (2H, m), 3.16 (1H, dd, J 13.9, 4.6 Hz), 2.96 (1H, dd, J 13.9, 9.7 Hz), 1.75-1.45 (8H, m), 1.35 (1H, m), 1.13 (1H, m); m/z (ES$^+$, 70V) 662.1 (MH$^+$).

EXAMPLE 168

2-(2-Bromo-3-oxo-7-oxa-spiro[3.5]non-1-en-1-ylamino)-3-{4-[(3-methyl-[2,7]naphthyridine-1-yl)amino]phenyl}propanoic Acid Prepared by the methods as described herein (77%). δH (d$^6$ DMSO) 8.77 (1H, s), 7.67 (1H, d, J 6.3 Hz), 6.96 (2H, d, J 8.5 Hz), 6.78 (1H, d, J 5.8 Hz), 6.45 (2H, d, J 8.5 Hz), 6.14 (1H, s), 4.19 (1H, m), 3.05-2.85 (4H, m), 2.59 (1H, dd, J 14.0, 4.4 Hz), 2.25 (1H, dd, J 13.9, 9.7 Hz), 1.66 (3H, s), 1.28 (1H, m), 1.16 (1H, m), 0.83 (1H, d, J 13.5 Hz), 0.66 (1H, d, J 13.5 Hz); m/z (ES$^+$, 70V) 537.9 (MH$^+$).

EXAMPLE 169

Ethyl (2S)-3-{4-[(3,5-dichloroisonicotinoyl)amino]phenyl}-2-(2-[1,3]dithian-2-yl-3-oxo-spiro[3.5]non-1-en-1-ylamino)propanoate To a solution of the compound of Example 27 (1.5 g, 2.9 mmol) in DCM (100 ml) was added 1,3-dithienium tetrafluorborate (3.0 g, 14 mmol) [prepared by the method of Paterson I; Price L. G. Tet. Lett. 1981, 22 (29), 2829]. The mixture was stirred overnight and then partitioned between EtOAc (200 ml) and sodium carbonate (100 ml, sat. aq.), the organics were separated, washed with water (3×50 ml), brine (50 ml), dried ($Na_2SO_4$), filtered and concentrated in vacuo to give a crude product which was purified by column chromatography ($SiO_2$, EtOAc:hexane 4:1) to give the title compound as a pale yellow solid (0.6 g, 86%) δH (400 MHz, DMSO d$^6$, 300K) 8.67 (2H, s), 8.15 (1H, d, J 9.5 Hz), 7.67 (2H, d, J 8.5 Hz), 7.12 (2H, d, J 8.5 Hz), 5.06 (1H, m), 4.65 (1H, s), 1.10 (1H, m), 4.08 (2H, t, J 7.1 Hz), 3.17-2.72 (3H, m), 2.65 (2H, m), 1.95 (1H, m), 1.87 (1H, m), 1.78-1.46 (11H, m), 1.25 (1H, d, J 12.3 Hz); m/z (ES$^+$, 70V) 634 (MH$^+$).

EXAMPLE 170

(2S)-3-{4-[(3,5-Dichloroisonicotinoyl)amino]phenyl}-2-(2-[1,3]dithian-2-yl-3-oxo-spiro[3.5]non-1-en-1-ylamino)propanoic Acid To a solution of the compound of Example 169 (0.25 g, 0.4 mmol) in THF (2 ml) was added a solution of lithium hydroxide (25 mg, 0.6 mmol) in water (1 ml). The mixture was stirred at room temperature overnight, concentrated in vacuo and the residue dissolved in the minimum amount of water. HCl (2M, aq.) was added until the pH of the solution was 4, the resulting solid was filtered, washed with ether and ethyl acetate to give the product as a pale yellow solid (0.15 g, 63%). δH (400 MHz, DMSO d$^6$, 300K) 10.85 (1H, s), 8.78 (2H, s), 8.28 (1H, d, J 9.9 Hz), 7.55 (2H, d, J 8.5 Hz), 7.31 (2H, d, J 8.5 Hz), 5.06 (1H, m), 4.75 (1H, s), 3.21-2.78 (3H, m), 2.67 (2H, m), 1.99 (1H, m), 1.75 (1H, m), 1.57 (8H, m), 1.22 (1H, d, J 11.9 Hz), 1.08 (1H, m); m/z (ES$^+$, 70V) 606 (MH$^+$).

EXAMPLE 171

Ethyl (2S)-3-{4-[(3,5-dichloro-1-oxy-pyridine-4-carbonyl)amino]-phenyl}-2-(2-methanesulfinyl-4,4-dimethyl-3-oxo-cyclobut-1-enylamino)propanoate A solution of the compound of Example 5 (800 mg, 1.68 mmol) in THF (20 ml) was treated at rt with a solution of methanesulfenyl chloride in DCM (1.9 ml, 1.0M). After 30 min the reaction was partitioned between EtOAc (50 ml) and saturated aqueous sodium hydrogencarbonate (25 ml). Separation of the organic phase, drying ($MgSO_4$), filtration and concentration in vacuo gave a solid which was approx. 90% pure. The crude solid was redissolved in DCM (20 ml) and treated with mCPBA (1.5 g, 57-75% purity) and sodium hydrogencarbonate (500 mg) and stirred at rt for 24 h. The reaction was diluted with EtOAc (100 ml), washed with $H_2O$ (50 ml), separated, dried ($MgSO_4$), filtered and concentrated in vacuo. Chromatography ($SiO_2$, EtOAc) gave the title compound as a white powder (730 mg, 1.31 mmol, 78%) as an approx. 1:1 mixture of diastereomers. δH (CDCl$_3$, 330K) 8.44 and 8.41 (2H, s), 8.35 and 8.17 (1H, s), 7.57 and 7.47 (2H, d, J 8.4 Hz), 7.15 and 7.08 (2H, d, J 8.4 Hz), 7.04 and 7.01 (1H, d, J 8.9 Hz), 5.24-5.22 (1H, m), 4.25-4.11 (3H, m), 3.31-3.05 (2H, m), 2.97 and 2.93 (3H, s), 1.30-1.16 (9H, m); m/z (ES$^+$, 70V) 553.9 and 556.0 (MH$^+$).

EXAMPLE 172

(2S)-3-{4-[(3,5-Dichloro-1-oxy-pyridine-4-carbonyl)amino]phenyl}-2-(2-methanesulfinyl-4,4-dimethyl-3-oxo-cyclobut-1-enylamino)propanoic Acid The compound of Example 171 (300 mg, 0.54 mmol) was hydrolysed in a similar manner to the method of Example 2, to give the title compound as a white powder (239 mg, 0.45 mmol, 83%) as an approx. 1:1 diasteromeric mixture. δH (DMSO d$^6$, 390K) 9.75 (1H, br s), 8.77 (2H, s), 7.56 (2H, d, J 8.5 Hz), 7.25 (2H, d, J 8.5 Hz), 4.99 (1H, m), 3.18-2.98 (2H, m), 2.85 (3H, s), 1.18 (3H, s), 1.06 (3H, s); m/z (ES$^+$, 70V) 525.9 and 527.9 (MH$^+$).

EXAMPLE 173

(2S)-2-[2-(Methylsulfanyl)-3-oxospiro[3.5]non-1-en-1-yl]amino-3-[4-([2,7]naphthyridin-1-ylamino)phenyl]propanoic Acid The ethyl ester of the title compound was prepared in two steps from the free amine of Intermediate 12 (1.40 g, 0.41 mmol), spiro[3.5]nonane-1,3-dione (650 mg, 0.42 mmol) [prepared according to the method of Wasserman, H. H. et al., J. Org. Chem., 38, 1451-1455 (1973)] and a 1.0M solution of methyl sulfenyl chloride in DCM (0.5 ml, 0.5 mmol) according to the method of Example 108 (1.53 g, 0.30 mmol, 71%). This ester was then subjected to hydrolysis according to the method of Example 2 to give the title compound as a yellow powder (1.15 g, 0.23 mmol, 57%). δH (DMSO d$^6$, 390K) 9.80 (1H, s), 8.61 (1H, d, J 5.6 Hz), 8.13 (1H, d, J 5.4 Hz), 7.67 (2H, d, J 8.3 Hz), 7.60 (1H, d, J 5.5 Hz), 7.18 (1H, d, J 8.3 Hz), 7.05 (1H, d, J 5.5 Hz), 4.37 (1H, m), 3.22-3.12 (2H, m), 2.14 (3H, s), 1.85-1.10 (10H, m); m/z (ES$^+$, 70V) 489.1 (MH$^+$).

EXAMPLE 174

Ethyl (2S)-2-[2-(methylsulfanyl)-3-oxo-7-oxaspiro[3,5]non-1-en-1-yl]amino-3-[4-([2,7]naphthyridin-1-ylamino)phenyl]propanoate Was prepared in two steps from the free amine of Intermediate 12 (1.40 g, 0.41 mmol), 7-oxaspiro[3.5]nonane-1,3-dione (650 mg, 0.42 mmol) [prepared according to the method of Wasserman, H. H. et al., J. Org. Chem., 38, 1451-1455 (1973)] and a 1.0M solution of methyl sulfenyl chloride in DCM (0.5 ml, 0.5 mmol) according to the method of Example 108 to give the title compound as a yellow powder (1.21 g, 0.23 mmol, 55%). δH (DMSO d$^6$, 390K) 9.82 (1H, s), 9.55 (1H, s), 8.93 (1H, d, J 9.2 Hz), 8.65 (1H, d J 5.6 Hz), 8.15 (1H, d, J 5.7 Hz), 7.78 (2H, d, J 8.5 Hz), 7.68 (1H, d, J 5.6 Hz), 7.23 (2H, d, J 8.5 Hz), 7.13 (1H, d, J 5.7 Hz), 5.16-5.10 (1H, m), 4.20 (2H, q, J 7.1 Hz), 3.77 (2H, m), 3.59-3.52 (2H, m), 3.21 (1H, dd, J 13.8, 4.5 Hz), 2.98 (1H, dd, J 13.8, 10.2 Hz), 1.96 (3H, s), 1.48-1.32 (4H, m), 1.23 (3H, t, J 7.1 Hz); m/z (ES$^+$, 70V) 519.1 (MH$^+$).

EXAMPLE 175

(2S)-2-[2-(Methylsulfanyl)-3-oxo-7-oxaspiro[3.5]non-1-en-1-yl]amino-3-[4-([2,7]naphthyridin-1-ylamino)phenyl]propanoic Acid Hydrolysis of the compound of Example 174 (650 mg, 0.12 mmol) with lithium hydroxide (30 mg, 0.7 mmol), according to the method of Example 2, gave the title compound as a pale yellow powder (501 mg, 0.10 mmol, 85%). δH (DMSO d$^6$, 390K) 9.83 (1H, s), 9.54 (1H, s), 8.70 (1H, d, J 8.9 Hz), 8.65 (1H, d, J 5.6 Hz), 8.14 (1H, d, J 5.7 Hz), 7.75 (2H, d, J 8.5 Hz), 7.68 (1H, d, J 5.6 Hz), 7.21 (2H, d, J 8.5 Hz), 7.11 (1H, d, J 5.7 Hz), 4.92 (1H, m), 3.76-3.73 (2H, m), 3.62-3.54 (2H, m), 3.23 (1H, d, J 13.6, 3.9 Hz), 2.94 (1H, dd, J 13.6, 9.9 Hz), 1.91 (3H, s), 1.47-1.28 (4H, m); m/z (ES$^+$, 70V) 491.1 (MH$^+$).

EXAMPLE 176

Methyl (2S)-2-[(2-bromo-4,4-dimethyl-3-oxo-1-cyclobutenyl)amino]-3-[4-([2,7]naphthyridin-1-yloxy)phenyl]propanoate

A stirred solution containing Intermediate 13 (300 mg, 0.72 mmol) in THF (10 ml) at rt was treated dropwise with a 1.0 M solution of bromine in THF (1.0 ml, 1 mmol). After 2 h the reaction was diluted with EtOAc (50 ml), washed with saturated aqueous sodium hydrogencarbonate solution (2×25 ml), dried ($MgSO_4$) and concentrated in vacuo. Chromatography ($SiO_2$, EtOAc) gave the title compound as a white powder (217 mg, 0.43 mmol, 61%). $\delta$H (DMSO $d^6$, 360K) 9.71 (1H, s), 8.71 (1H, d, J 5.7 Hz), 8.04 (1H, d, J 5.8 Hz), 7.56 (1H, d, J 5.7 Hz), 7.23-7.13 (5H, m), 6.19 (1H, d, J 8.1 Hz), 5.06-5.02 (1H, m), 3.79 (3H, s), 3.26 (2H, m), 1.19 (6H, s); m/z ($ES^+$, 70V) 497.9 ($MH^+$).

EXAMPLE 177

(2S)-2-[(2-Bromo-4,4-dimethyl-3-oxo-1-cyclobutenyl)amino]-3-[4-([2,7]naphthyridin-1-yloxy)phenyl]propanoic Acid

Hydrolysis of the compound of Example 176 (80 mg, 0.016 mmol) with LiOH (10 mg, 0.023 mmol) according to the method of Example 2 gave the title compound as a white powder (51 mg, 0.01 mmol, 63%). $\delta$H (DMSO $d^6$, 360K) 9.71 (1H, s), 8.81 (1H, d, J 5.5 Hz), 8.14 (1H, d, J 5.4 Hz), 7.87 (1H, d, J 5.2 Hz), 7.52 (1H, d, J 5.4 Hz), 7.38 (2H, d, J 8.5 Hz), 7.28 (2H, d, J 8.5 Hz), 4.87-4.84 (1H, m), 3.31-3.15 (2H, m), 1.18 (3H, s), 1.10 (3H, s); m/z ($ES^+$, 70V) 483.9 ($MH^+$).

EXAMPLE 178

$N^4$-(4-[3-(2-Bromo-3-oxospiro[3.5]non-1-en-1-yl)-5-oxo-1,3-oxazolan-4-yl]methylphenyl)-3,5-dichloroisonicotinamide

A solution containing the compound of Example 32 (1.0 g, 1.76 mmol), finely ground potassium carbonate (500 mg) and DMAP (50 mg, 0.4 mmol), in DMF (14 ml) was treated dropwise with chloromethyl pivalate (0.5 ml) at room temperature. After 24 h the reaction was diluted with EtOAc (150 ml), washed with brine (3×50 ml), dried ($MgSO_4$) and concentrated in vacuo. Chromatography ($SiO_2$, 1:1 EtOAc:hexanes) gave the title compound as a white powder (475 mg, 0.82 mmol, 47%). $\delta$H (DMSO $d^6$, 390K) 10.97 (1H, s), 8.80 (2H, s), 7.63 (2H, d, J 8.5 Hz), 7.17 (2H, d, J 8.5 Hz), 5.41 (1H, d, J 3.9 Hz), 4.95 (1H, m), 4.69 (1H, d, J 3.9 Hz), 3.39-3.29 (2H, m), 1.99-1.06 (10H, m); m/z ($ES^+$, 70V) 580.9 ($MH^+$).

EXAMPLE 179

3-[2-(Isopropylsulfanyl)-3-oxospiro[3.5]non-1-en-1-yl]-4-[4-([2,7]naphthyridin-1-ylamino)benzyl]-1,3-oxazolan-5-one

Prepared from the compound of Example 121 (450 mg, 0.88 mmol) in a similar manner to the compound of Example 178 to give the title compound as an off-white powder (390 mg, 0.73 mmol, 84%). $\delta$H (DMSO $d^6$, 390K) 9.57 (1H, s), 8.64 (1H, d, J 5.7 Hz), 8.24 (1H, d, J 5.8 Hz), 8.17 (1H, s), 7.74 (2H, d, J 8.4 Hz), 7.53 (1H, d, J 5.6 Hz), 7.16 (2H, d, J 8.4 Hz), 7.06 (1H, d, J 5.8 Hz), 5.20 (1H, br s), 4.93 (1H, br s), 4.26 (1H, br s), 3.58 (1H, br s), 3.33 (1H, br s), 3.27 (1H, m), 1.99-1.06 16H, m); m/z ($ES^+$, 70V) 529.2 ($MH^+$).

EXAMPLE 180

Neopentyl (2S)-2-[(2-bromo-3-oxospiro[3.5]non-1-en-1-yl)amino]-3-{4-[(3,5-dichloroisonicotinoyl)amino]phenyl}propanoate

Using a similar procedure to that for the preparation the compound of Example 138 from the compound of Example 32 (0.5 g, 0.89 mmol), EDC (191 mg, 1.0 mmol), HOBT (120 mg, 0.89 mmol), neopentyl alcohol (0.4 g, 4.5 mmol) and DMF (15 ml) was prepared, after purification by chromatography ($SiO_2$, EtOAc), the title compound as a white powder (400 mg, 0.63 mmol, 71%). $\delta$H (DMSO $d^6$, 390K) 10.87 (1H, s), 8.92 (1H, d, J 9.1 Hz), 8.79 (2H, s), 7.58 (2H, d, J 8.5 Hz), 7.32 (2H, d, J 8.5 Hz), 4.88-4.82 (1H, m), 3.86 (1H, d, J 10.4 Hz), 3.80 (1H, d, J 10.4 Hz), 3.26 (1H, dd, J 13.9, 4.8 Hz), 3.03 (1H, dd, 13.9, 10.1 Hz), 1.99-1.06 (10H, m), 0.91 (9H, br s); m/z ($ES^+$, 70V) 638.0 ($MH^+$).

EXAMPLE 181

Isopropyl (2S)-3-{4-[(3,5-dichloroisonicotinoyl)amino]phenyl}-2-(2-methyl-3-oxo-7-oxa-spiro[3.5]non-1-en-1-ylamino)propanoate

Prepared in a similar manner to the compound of Example 138 from the compound of Example 164 to give the title compound in 79% yield. $\delta$H (DMSO $d^6$) 10.87 (1H, s), 8.80 (2H, s), 8.10 (1H, d, J 8.9 Hz), 7.59 (d, 2H, J 8.2 Hz), 7.31 (d, 2H, J 8.2 Hz), 4.98 (1H, m), 4.30 (1H, m), 3.76 (2H, m), 3.60 (2H, m), 3.11 (1H, dd, J 13.7, 5.3 Hz), 3.00 (1H, dd, J 13.2, 9.1 Hz), 2.00-1.80 (2H, m), 1.42 (3H, s), 1.17 (6H, m); m/z ($ES^+$, 70V) 546.1 ($MH^+$).

EXAMPLE 182

5-Methyl-2-oxo-[1,3]-dioxol-4-ylmethyl (2S)-2-(2-bromo-3-oxo-spiro[3.5]non-1-en-1-ylamino)-3-{4-[(3,5-dichloroisonicotinoyl)amino]phenyl}propanoate

To a stirred solution of the compound of Example 32 (1.0 g, 1.76 mmol) and potassium carbonate (484 mg, 3.52 mmol) in DMF (20 ml) at 0° C. was added Intermediate 73 (408 mg, 2.12 mmol) in one portion. The ice-bath was removed and the mixture allowed to stir at room temperature for 3 hours. The mixture was poured into ice/water and extracted with EtOAc. The extract was washed three times with brine, dried ($MgSO_4$) and the solvent removed in vacuo to afford a yellow solid. Chromatography ($SiO_2$, 1:1 hexane:EtOAc) gave the title compound as a white solid (686 mg, 57%). $\delta$H (DMSO $d^6$) 10.90 (1H, s), 8.95 (1H, d, J 8.9 Hz), 8.80 (2H, s), 7.60 (2H, d, J 8.3 Hz), 7.26 (2H, d, J 8.3 Hz), 4.86 (1H, m), 3.22 (1H, m, J 4.0, 13.6 Hz), 3.06 (1H, m, J 13.2, 10.7 Hz), 2.17 (3H, s), 1.74-1.38 (10H, m); m/z ($ES^+$, 70V) 680.0 ($MH^+$).

EXAMPLE 183

2,3-Dihydroxy-propyl (2S)-2-(2-bromo-3-oxo-spiro[3.5]non-1-en-1-ylamino)-3-{4-[(3,5-dichloroisonicotinoyl)amino]phenyl}propanoate

Prepared in a similar manner to the compound of Example 138 from the compound of Example 32 and glycerol to give the title compound in 48% yield after chromatography on silica gel. $\delta$H (DMSO $d^6$) 10.91 (1H, s), 8.91 (1H, d, J 9.2 Hz), 8.80 (2H, s), 7.60 (2H, d, J 8.5 Hz), 7.28 (2H, d, J 8.3 Hz), 5.01 (1H, m), 4.85 (1H, m), 4.71 (1H, m), 4.20 (1H, m), 4-09 (1H, m), 3.71 (1H, m), 3.57 (1H, m), 3.26 (1H, dd, J 13.8, 3.9 Hz), 3.04 (1H, dd, J 13.8, 9.3 Hz), 1.80-1.45 (10H, m); m/z ($ES^+$, 70V) 640.0 ($MH^+$).

EXAMPLE 184

Tetrahydro-furan-3-ylmethyl (2S)-2-(2-bromo-3-oxo-spiro[3.5]non-1-en-1-ylamino)-3-{4-[(3,5-dichloroisonicotinoyl)amino]phenyl}propanoate Prepared in a similar manner to the compound of Example 138 from the compound of Example 32 and tetrahydrofurfuryl alcohol to give the title compound (52%) after chromatography on silica gel. δH (DMSO d$^6$) 10.88 (1H, s), 8.93 (1H, d, J 9.1 Hz), 8.80 (2H, s), 7.60 (2H, d, J 8.3 Hz), 7.28 (2H, d, J 6.9 Hz), 4.84 (1H, m), 4.15 (2H, m), 4.05 (1H, m), 3.23 (1H, dd, J 13.8, 4.4 Hz), 3.04 (1H, dd, J 13.6, 9.6, Hz), 2.00-1.50 (14H, m); m/z (ES, 70V) 650.1 (MH$^+$).

EXAMPLE 185

Tetrahydropyran-4-yl (2S)-2-(2-bromo-3-oxo-spiro[3.5]non-1-en-1-ylamino)-3-{4-[(3,5-dichloroisonicotinoyl)amino]phenyl}propanoate Prepared in a similar manner to the compound of Example 138 from the compound of Example 32 (0.5 g, 0.89 mmol), EDC (300 mg), HOBT (200 mg) and 4-hydroxytetrahydropyran (0.8 ml) in DMF (5 ml) to give the title compound (0.42 g, 74%). δH (300 MHz, DMSO d$^6$) 11.02 (1H, br), 9.04 (1H, d, J 9.0 Hz), 8.92 (2H, s), 7.73 (2H, d, J 8.4 Hz), 7.42 (2H, d, J 8.5 Hz), 5.13 (1H, br), 4.93 (1H, br), 3.87 (2H, br), 3.60 (2H, br), 3.36 (1H, dd, J 14.0, 5.1 Hz), 3.18 (1H, dd, J 13.9, 9.3 Hz), 1.61-2.06 (12H, m), 1.52 (2H, d, J 12-6 Hz), 1.26 (2H, br); m/z (ES$^+$, 70V) 652 (MH$^+$).

EXAMPLE 186

Isopropyl (2S)-2-(2-bromo-3-oxo-7-oxa-spiro[3.5]non-1-en-1-ylamino)-3-{4-[(3,5-dichloroisonicotinoyl)amino]phenyl}propanoate To a solution of the isopropyl ester of the compound of Example 40 (0.4 g, 8.1 mmol) [prepared in a similar manner to the compound of Example 138] in THF (5 ml) at room temperature was added NBS (0.3 g). The mixture was stirred for 2 h and then partitioned between water (100 ml) and EtOAc (100 ml), the organics were separated and washed with water (3×50 ml), brine (50 ml), dried (Na$_2$SO$_4$), filtered and concentrated in vacuo to give a crude oil. Purification by column chromatography (hexane:EtOAc, 3:2) gave the title compound as a white solid (0.24 g, 52%). δH (400 MHz, DMSO d$^6$) 9.02 (1H, d, J 9.0 Hz), 8.79 (2H, s), 7.59 (2H, d, J 8.5 Hz), 7.27 (2H, d, J 8.5 Hz), 4.97 (1H, m), 4.75 (1H, m), 3.80 (2H, m), 3.58 (2H, q, J 11.7 Hz), 3.20 (1H, dd, J 13.0, 5.0 Hz), 3.03 (1H, dd, J 13.0, 9.4, Hz), 1.97 (2H, m), 1.49 (1H, dd, J 13.0, 1.6 Hz), 1.33 (1H, dd, J 13.2, 1.6 Hz), 1.23 (3H, d, J 11.3 Hz), 1.19 (3H, d, J 11.4 Hz); m/z (ES$^+$, 70V) 612 (MH$^+$).

EXAMPLE 187

Ethyl (2S)-3-{5-[(3,5-dichloroisonicotinoyl)amino]pyridin-2-yl}-2-(4,4-dimethyl-2-methylsulfanyl-3-oxo-cyclobut-1-enylamino)propanoate A mixture of Intermediate 43 (0.44 g, 1.15 mmol) and 3-hydroxy-4,4-dimethyl-2-cyclobutenone (0.14 g, 1.1 eq) was stirred at room temperature for a period of 17 h. The mixture was concentrated in vacuo and triturated with diethyl ether and the resulting solid re-dissolved in THF (10 ml). The solution was treated with a solution of methanesulfenyl chloride at 0-5° C. in DCM until TLC analysis of the mixture indicated complete consumption of starting material. The mixture was partitioned between EtOAc (50 ml) and water (50 ml), the organics were separated and washed with water (2×50 ml), brine (50 ml), dried (MgSO4), filtered and concentrated to give a crude white foam. Purification by column chromatography (EtOAc:hexane, 1:1) gave the title compound as a white solid (0.55 g, 91%). δH (400 MHz, DMSO d$^6$) 11.16 (1H, br), 8.87 (1H, d, J 9.0 Hz), 8.82 (s, 2H), 8.72 (1H, d, J 2.5 Hz), 8.05 (1H, dd, J 8.4, 2.5 Hz), 7.35 (1H, d, J 8.4 Hz), 5.33 (1H, m), 4.18 (2H, q, J 7.1 Hz), 3.36 (1H, dd, J 14.1, 5.0 Hz), 3.32 (3H, s), 3.20 (1H, dd, J 14.1, 9.4 Hz), 0.94 (3H, s), 1.09 (3H, s), 1.21 (3H, t, J 7.1 Hz); m/z (ES$^+$, 70V) 523 (MH$^+$).

EXAMPLE 188

Isopropyl (2S)-3-{5-[(3,5-dichloroisonicotinoyl)amino]pyridin-2-yl}-2-(4,4-dimethyl-2-methylsulfanyl-3-oxo-cyclo but-1-enylamino)propanoate Hydrolysis of the compound of Example 187 (0.35 g, 0.67 mmol) according to the method of Example 2 and re-esterified with isopropanol (EDC, HOBT, DMF) gave the title compound as a white solid (65 mg, 18%). δH (400 MHz, DMSO d$^6$) 11.16 (1H, br), 8.85 (1H, d, J 8.9 Hz), 8.82 (2H, s), 8.72 (1H, d, J 1.8 Hz), 8.04 (1H, m), 7.35 (1H, d, J 8.3 Hz), 5.28 (1H, m), 5.00 (1H, m), 3.35 (1H, dd, J 14.1, 5.0 Hz), 3.32 (3H, s), 3.18 (1H, dd, J 14.1, 9.3 Hz), 1.22 (6H, m), 1.09 (3H, d, J 1.2 Hz), 0.95 (3H, d, J 1.2 Hz); m/z (ES$^+$, 70V) MH$^+$ 537.

EXAMPLE 190

Ethyl (2S)-3-{4-[(3,5-dichloro-1-oxy-pyridine-4-carbonyl)amino]phenyl}-2-(3-oxo-spiro[3.5]non-1-en-1-ylamino)propanoate Intermediate 75 (170 mg, 0.42 mmol) and 1-keto-3-hydroxy[3,5]-non-2-ene (200 mg, 1.3 mmol) were stirred together at room temperature overnight in THF (5 ml) The reaction mixture was diluted with DCM (50 ml), washed with sodium bicarbonate solution (saturated, 2×50 ml), dried (MgSO$_4$) and reduced in vacuo to give a yellow solid. The residue was chromatographed (SiO$_2$ DCM:methanol, 98:2) to give the title compound as a white powder (120 mg). δH (CDCl$_3$) 9.03 (1H, br s), 8.11 (2H, s), 7.64 (2H, d, J 7.9 Hz) 7.18 (2H, d, J 7.5 Hz), 5.01 (1H, m), 4.22 (1H, m), 4.21 (2H, q, J 7.1 Hz), 3.12 (2H, m), 1.45 (10H, m), 1.30 (3H, t, J 7.1 Hz); m/z (ES$^+$, 70V) 532.0 (MH$^+$).

EXAMPLE 191

(2S)-3-{4-[(3,5-Dichloro-1-oxy-pyridine-4-carbonyl)amino]phenyl}-2-(3-oxo-spiro[3.5]non-1-en-1-ylamino)propanoic Acid The compound of Example 190 (30 mg, 0.056 mmol) was hydrolysed by the method of Example 2 to afford the title compound as white powder (20 mg). δH (CD$_3$OD) 8.46 (2H, s), 7.47 (2H, d, J 8.5 Hz), 7.18 (2H, d, J 8.5 Hz), 4.14 (1H, m), 3.21 (1H, m), (obscured by MeOH/water) 2.83 (1H, dd, J 9.6, 4.2 Hz), 1.80-1.10 (9H, m), 1.07 (3H, t, J 7.1 Hz); m/z (ES$^+$, 70V) 505.0 (MH$^+$).

EXAMPLE 192

Ethyl (2S)-2-(2-bromo-3-oxo-spiro[3.5]non-1-en-1-ylamino)-3-{4-[(3,5-dichloro-1-oxy-pyridine-4-carbonyl)amino]phenyl}propanoate Prepared from the compound of Example 190 (85 mg, 0.16 mmol) in a similar manner to the compound of Example 31 to give the title compound (80 mg). δH (CDCl$_3$) 8.94 (1H, br s), 8.14 (2H, s), 7.62 (2H, d, J 8.4 Hz), 7.13 (2H, d, J 8.3 Hz), 5.88 (1H, m), 5.00 (1H, m), 4.26 (2H, q, J 7.1 Hz), 3.26 (2H, m), 2.03-1.41 (10H, m), 1.35 (3H, t, J 7.1 Hz); m/z (ES$^+$, 70V) 612.0 (MH$^+$).

EXAMPLE 193

(2S)-2-(2-Bromo-3-oxo-spiro[3.5]non-1-en-1-ylamino)-3-{4-[(3,5-dichloro-1-oxy-pyridine-4-carbonyl)amino]phenyl}propanoic Acid The compound of Example 192 was hydrolysed by the method of Example 2 to afford the title compound. δH (DMSO d$^6$) 10.80 (1H, s) 8.73 (2H, s), 7.55 (2H, d, J 8.0 Hz), 7.24 (2H, d, J 8.4 Hz), 4.65 (1H, m), 3.22 (1H, dd, J 13.8, 4.4 Hz), 3.00 (1H, dd, J 13.7, 4.4 Hz), 1.82-1.00 (11H, m).

EXAMPLE 194

Ethyl (2S)-2-(2-chloro-3-oxo-spiro[3.5]non-1-en-1-ylamino)-3-{4-[(3,5-dichloro-1-oxy-pyridine-4-carbonyl)amino]phenyl}propanoate Prepared in a similar manner to the compound of Example 61 from the compound of Example 190 (500 mg, 0.94 mmol) and N-chlorosuccinimide (150 mg, 1.13 mmol) to give the title compound as a white powder (220 mg). δH (DMSO d$^6$) 10.85 (1H, s), 8.84 (1H, d, J 9.0 Hz), 8.75 (2H, s), 7.58 (2H, d, J 8.5 Hz) 7.27 (2H, d, J 8.5 Hz), 4.68 (1H, m) 4.20 (2H, q, J 7.0 Hz) 3.22 (1H, dd, J 13.8, 4.7 Hz) 3.01 (1H, dd, J 13.7, 9.7 Hz) 1.74-1.55 (9H, m) 1.38 (1H, m) 1.23 (3H, m, J 7.1 Hz) 1.13 (1H, m); m/z (ES$^+$, 70V) 568.0 (MH$^+$).

EXAMPLE 195

(2S)-2-(2-Chloro-3-oxo-spiro[3.5]non-1-en-1-ylamino)-3-{4-[(3,5-dichloro-1-oxy-pyridine-4-carbonyl)amino]phenyl}propanoic Acid The compound of Example 194 was hydrolysed by the method of Example 2 to afford the title compound. δH (DMSO d$^6$) 10.83 (1H, s), 8.75 (m, 3H), 7.57 (2H, d, J 8.4 Hz) 7.26 (2H, d, J 8.5 Hz), 4.63 (1H, m) 3.22 (1H, dd, J 13.8, 4.5 Hz) 3.00 (1H, m), 1.64-1.55 (9H, m) 1.35 (1H, m), 1.15 (1H, m); m/z (ES$^+$, 70V) 538.0 (MH$^+$).

EXAMPLE 196

Ethyl (2S)-2-[(2-chloro-4,4-dimethyl-3-oxo-1-cyclobutenyl)amino]-3-{4-[(3,5-dichloroisonicotinoyl)amino]phenyl}propanoate Prepared in a similar manner to the compound of Example 61 from the compound of Example 5 (3.2 mmol) and N-chlorosuccinimide (3.5 mmol) to give the title compound as a white powder (0.9 mmol, 31%). δH (DMSO d$^6$, 300K) 9.05 (1H, d, J 9.0 Hz), 8.79 (2H, s) 7.60 (2H, d, J 8.5 Hz) 7.25 (2H, d, J 8.5 Hz) 4.70 (1H, m) 4.19 (2H, q, J 7.1 Hz) 3.22 (1H, dd, J 13.9, 5.0 Hz) 3.02 (1H, dd, J 13.9, 9.2 Hz) 1.21 (3H, q, J 7.1 Hz) 1.23 (3H, s) 1.04 (3H, s); m/z (ES$^+$, 70V) 512.0 (MH$^+$).

EXAMPLE 197

1-Methyl-3-pyrrolidinyl (2S)-2-[(2-bromo-4,4-dimethyl-3-oxo-1-cyclobutenyl)amino]-3-{4-[(3,5-dichloroisonicotinoyl)amino]phenyl}propanoate Prepared in a similar manner to the compound of Example 138 from the compound of Example 34 (0.65 mmol), EDC (0.72 mmol), HOBT (0.72 mmol) and 1-methyl-3-pyrrolidinol (1.95 mmol) in DMF (5 ml) to give the title compound (0.25 mmol, 40%) δH (CD$_3$OD) 8.55 (2H, s), 7.52 (2H, d, J 8.5 Hz), 7.20 (2H, d, J 8.5 Hz), 4.92, (1H, m), 3.38 (1H, dd, obscured by MeOH) 2.96 (1H, dd, J 13.9, 9.2 Hz) 2.50-2.18 (4H, m) 2.18 (3H, s) 1.89-1.56 (m, 4H), 1.12 (3H, s), 1.00 (3H, s), m/z (ES$^+$, 70V) 625.0 (MH$^+$).

EXAMPLE 198

Isopropyl (2S)-2-(2-bromo-4,4-dimethyl-3-oxo-cyclobut-1-enylamino)-3-{4-[(3,5-dichloroisonicotinoyl)amino]phenyl}propanoate Prepared in a similar manner to the compound of Example 138 from the compound of Example 34 (0.65 mmol), EDC (0.84 mmol), HOBT (0.84 mmol) and isopropanol (2.28 mmol) in DMF (5 ml) to give the title compound (0.25 mmol, 34%). δH (DMSO d$^6$) 10.88 (1H, s) 9.69 (1H, d, J 9.0 Hz) 8.79 (2H, s) 7.59 (2H, J 8.5 Hz) 7.28 (2H, d, J 8.5 Hz), 4.97 (1H, m) 4.75 (1H, m) 3.20 (1H, dd, J 13.9, 5.1 Hz) 3.03 (1H, dd, J 14.0, 9.2 Hz) 1.24 (m, 6H) 1.14 (3H, s) 1.05 (3H, s); m/z (ES$^+$, 70V) 570.0 (MH$^+$).

EXAMPLE 199

Ethyl (2S)-3-[4-(2,6-dichlorobenzoylamino)phenyl]-2-(3-oxo-spiro[3.5]non-1-en-1-ylamino)propanoate The title compound was prepared in a similar manner to that of the compound of Example 27 (coupling of amino acid ethyl ester (1.68 mmol), dione (1.68 mmol) in DCM (5 ml)) to give the title compound as a yellow powder (1.1 mmol, 66%). δH (CD$_3$OD) 7.83 (2H, d, J 8.3 Hz), 7.55-7.35 (4H, m), 7.47 (2H, d, J 8.4 Hz), 4.62 (1H, s), 4.50 (3H, m), 3.50 (1H, m), 3.08 (1H, m) 2.05-1.55 (11H, m) 1.49 (3H, t, J 7.1 Hz); m/z (ES$^+$, 70V) 501.0 (MH$^+$).

EXAMPLE 200

Ethyl (2S)-2-(2-bromo-3-oxo-spiro[3.5]non-1-en-1-ylamino)-3-[4-(2,6-dichlorobenzoylamino)phenyl] propanoate Prepared in a similar manner to the compound of Example 72 from the compound of Example 199 (1.08 mmol) to give the title compound as yellow powder (0.86 mmol, 80%). δH (CD$_3$OD) 7.53 (2H, d, J 8.4 Hz), 7.38-7.15 (4H, m), 7.17 (2H, d, J 8.4 Hz), 5.32 (1H, m) 4.65 (1H, m), 3.22 (1H, dd, J 13.9, 4.4 Hz), 3.18 (q, 2H, J 7.1 Hz) 2.95 (1H, dd J 13.9, 9.5 Hz), 1.85-1.20 (14H, m); m/z (ES$^+$, 70V) 581.0 (MH$^+$).

EXAMPLE 201

(2S)-2-(2-Bromo-3-oxo-spiro[3.5]non-1-en-1-ylamino)-3-[4-(2,6-dichlorobenzoylamino)phenyl] propanoic Acid Prepared in a similar manner to the compound of Example 2 from the compound of Example 200 (0.85 mmol) to give the title compound as white powder (0.60 mmol, 60%). δH (DMSO d$^6$) 13.39 (1H, br s), 10.70 (1H, d, J 6.1 Hz), 8.81 (1H, d, J 9.2 Hz), 7.61 (3H, m), 7.56 (1H, m), 7.23 (2H, d, J 8.2 Hz), 3.18 (1H, dd, J 13.9, 4.4 Hz), 2.98 (1H, dd J 13.8, 9.6 Hz), 2.89-1.20 (11H, m); m/z (ES$^+$, 70V) 567.0 (MH$^+$).

EXAMPLE 202

Isopropyl (2S)-2-(2-bromo-3-oxo-spiro[3.5]non-1-en-1-ylamino)-3-[4-(2,6-dichlorobenzoylamino)phenyl]propanoate Prepared in a similar manner to the compound of Example 138 from the compound of Example 201 (0.78 mmol) to give the title compound (0.49 mmol, 63%). δH (DMSO d$^6$) 10.71 (1H, s), 8.89 (1H, d, J 9.0 Hz), 7.62-7.47 (5H, m), 4.97, (1H, m), 3.17 (1H, dd, J 13.8, 4.8 Hz), 3.00 (1H, dd J 13.8, 9.7 Hz), 1.79-1.50 (8H, m) 1.35 (1H, m) 1.24-1.11 (7H, m). m/z (ES$^+$, 70V) 609.0 (MH$^+$).

EXAMPLE 203

Ethyl (2S)-3-[4-(3-methyl-[2,7]naphthyridin-1-ylamino)phenyl]-2-(3-oxo-spiro[3.5]non-1-en-1-ylamino)propanoate Prepared in a similar manner to that of the compound of Example 3 to give the title compound as a yellow powder (1.5 mmol, 76%). δH (CDCl3) 9.56 (1H, s), 8.53 (1H, d, J 5.8 Hz), 7.78 (2H, d, J 8.4 Hz), 7.45 (1H, d, J 5.8 Hz), 7.08 (2H, d, J 8.5 Hz), 6.89 (1H, s), 5.77 (1H, m), 4.57 (1H, s), 4.27 (2H, q, J 7.1 Hz), 3.10 (2H, m), 2.54 (3H, s), 1.84-1.23 (14H, m); m/z (ES$^+$, 70V) 485.2 (MH$^+$).

EXAMPLE 204

Ethyl (2S)-2-(2-bromo-3-oxo-spiro[3.5]non-1-en-1-ylamino)-3-[4-(3-methyl-[2,7]naphthyridin-1-ylamino)phenyl]propanoate Prepared in a similar manner to the compound of Example 31 from the compound of Example 203 (0.62 mmol), bromine (0.81 mmol) and triethylamine (0.81 mmol) in DCM (5 ml) to give the title compound as yellow powder (0.25 mmol, 40%). δH (CD$_3$OD) 9.44 (1H, s), 8.34 (1H, d, J 5.8 Hz), 7.43 (1H, d, J 5.8 Hz), 7.09 (2H, d, J 8.5 Hz), 6.81 (1H, s), 4.87 (1H, m), 4.89 (1H, m), 4.13 (2H, q, J 7.1 Hz), 3.22 (1H, m), (obscured mostly by MeOH), 2.92 (1H, dd, J 14.0, 9.7 Hz), 2.34 (3H, s), 1.58-1.26 (10H, m), 1.18 (3H, t, J 7.1 Hz); m/z (ES$^+$, 70V) 564.2 (MH$^+$).

EXAMPLE 205

(2S)-2-(2-Bromo-3-oxo-spiro[3.5]non-1-en-1-ylamino)-3-[4-(3-methyl-[2,7]naphthyridin-1-ylamino)phenyl]propanoic Acid Prepared in a similar manner to the compound of Example 2 from the compound of Example 204 (0.22 mmol) to give the title compound as yellow powder (0.20 mmol, 90%). δH (DMSO d$^6$) 9.76 (1H, s), 9.70 (1H, s), 8.87 (1H, s, J 9.5 Hz), 8.56 (1H, d, J 5.6 Hz), 7.87 (2H, d, J 8.4 Hz), 7.56 (1H, d, J 5.6 Hz), 7.20 (2H, d, J 8.4 Hz), 6.96 (1H, s), 4.73 (1H, m), 3.22 (1H, dd, J 13.9, 4.0 Hz), 2.93 (1H, dd J 13.5, 10.1 Hz), 2.42 (3H, s), 1.80-1.00 (11H, m); m/z (ES$^+$, 70V) 535.0 (MH$^+$).

EXAMPLE 206

(2S)-3-[4-(3-Methyl-[2,7]naphthyridin-1-ylamino)phenyl]-2-(3-oxo-spiro[3.5]non-1-en-1-ylamino)propanoic Acid Prepared in a similar manner to the compound of Example 2 from the compound of Example 203 (0.62 mmol) to give the title compound as white powder (0.27 mmol, 43%). δH (DMSO d$^6$) 9.81 (1H, s), 9.52 (1H, s), 8.58 (1H, d, J 5.6 Hz), 8.30 (1H, J 8.6 Hz), 7.86 (2H, d, J 8.4 Hz), 7.57 (1H, d, J 5.6 Hz), 7.22 (2H, d, J 8.5 Hz), 6.97 (1H, s), 4.08 (1H, m), 4.32 (1H, s), 3.15 (1H, dd, J 13.7, 4.7 Hz), 2.97 (1H, dd, J 13.7, 9.5 Hz), 2.44 (3H, s), 1.74-1.45 (9H, m), 1.24-1.15 (2H, m); m/z (ES$^+$, 70V) 457.1 (MH$^+$).

EXAMPLE 207

Ethyl (2S)-3-[4-([2,7]naphthyridin-1-ylamino)phenyl]-2-(3-oxo-spiro[3.5]non-1-en-1-ylamino)propanoate Prepared in a similar manner to the compound of Example 3 to give the title compound as a yellow powder (1.4 mmol, 73%) δH (CDCl$_3$) 9.61 (1H, s), 8.65 (1H, d, J 5.7 Hz), 8.25 (1H, d, J 5.8 Hz), 7.71 (2H, d, J 8.4 Hz), 7.63 (1H, d, J 8.5 Hz), 7.12 (2H, d, J 8.5 Hz), 7.05 (1H, d, J 5.8 Hz), 5.80 (1H, m), 4.55 (1H, s), 4.29 (2H, q, J 7.2 Hz), 3.13 (2H, m), 1.87-1.25 (14H, m); m/z (ES$^+$, 70V) 471.1 (MH$^+$).

EXAMPLE 208

Ethyl (2S)-2-(2-bromo-3-oxo-spiro[3.5]non-1-en-1-ylamino)-3-[4-([2,7]naphthyridin-1-ylamino)phenyl]propanoate Prepared in a similar manner to that of Example 31 from the compound of Example 207 (0.64 mmol) to give the title compound as a yellow powder (0.45 mmol, 76%). δH (CDCl3) 9.81 (1H, s), 8.64 (1H, d, J 5.7 Hz), 8.29 (1H, d, J 5.8 Hz), 7.75 (2H, d, J 8.3 Hz), 7.60 (1H, d, J 5.8 Hz), 7.12 (2H, d, J 8.4 Hz), 7.08 (1H, d, J 5.7 Hz), 5.91 (1H, m), 5.03 (1H, m), 4.28 (2H, q, J 7.1 Hz), 3.29 (2H, m), 1.81-1.39 (10H, m), 1.35 (3H, t, J 7.1 Hz); m/z (ES$^+$, 70V) 550.0 (MH$^+$).

EXAMPLE 209

(2S)-2-(2-Bromo-3-oxo-spiro[3.5]non-1-en-1-ylamino)-3-[4-([2,7]naphthyridin-1-ylamino)phenyl]propionic Acid Prepared in a similar manner to the compound of Example 2 from the compound of Example 208 (0.40 mmol) to give the title compound as white powder (0.25 mmol, 64%) δH (DMSO d$^6$, 300 K) 9.90 (1H, s), 9.56 (1H, s), 8.86 (1H, d, J 9.3 Hz), 8.66 (1H, d, J 5.6 Hz), 8.17 (1H, d, J 5.7 Hz), 7.81 (2H, d, J 8.2 Hz), 7.70 (1H, d, J 5.6 Hz), 7.24 (2H, d, J 8.4 Hz), 7.14 (1H, d, J 5.7 Hz), 4.78 (1H, m) 3.23 (1H, dd, J 13.9, 4.1 Hz), 2.99 (1H, dd, J 13.7, 10.0 Hz), 1.81-1.04 (11H, m); m/z (ES$^+$, 70V) 522.0 (MH$^+$).

EXAMPLE 210

(2S)-3-[4-([2,7]Naphthyridin-1-ylamino)phenyl]-2-(3-oxo-spiro[3.5]non-1-en-1-ylamino)propanoic Acid Prepared in a similar manner to the compound of Example 2 from the compound of Example 207 (0.64 mmol) to give the title compound as white powder (0.21 mmol, 33%). δH (DMSO d$^6$, 300K) 9.85 (1H, s), 9.54 (1H, s), 8.67 (1H, d, J 5.6 Hz), 8.28 (1H, d, J 8.6 Hz), 8.18 (1H, d, J 5.6 Hz), 7.78 (2H, d, J 8.3 Hz), 7.70 (1H, d, J 5.6 Hz), 7.23 (2H, d, J 8.4 Hz), 7.14 (1H, d, J 5.7 Hz), 4.34 (1H, s), 4.08 (1H, m), 3.15 (1H, dd, J 13.8, 4.8 Hz), 2.95 (1H, dd, J 13.8, 9.4 Hz), 1.74-1.39 (9H, m), 1.20 (2H, m); m/z (ES$^+$, 70V) 443.1 (MH$^+$).

EXAMPLE 211

(2S)-3-[4-([2,7]Naphthyridin-1-yloxy)phenyl]-2-(3-oxo-spiro[3.5]non-1-en-1-ylamino)propanoic Acid Prepared in a similar manner to the compound of Example 2 from the compound of Example 35 (0.70 mmol) to give the title compound as a white powder (0.56 mmol, 80%). δH (DMSO d$^6$, 300K) 9.70 (1H, s), 8.81 (1H, d, J 5.7 Hz), 8.30 (1H, d, J 8.8 Hz), 8.10 (1H, d J 5.8 Hz), 7.89 (1H, d, J 5.7 Hz), 7.53 (1H, d, J 5.9 Hz), 7.34 (1H, d, J 8.5 Hz), 7.23 (2H, d, J 8.5 Hz), 4.34 (1H, s), 4.15 (1H, m), 3.21 (1H, dd, J 14.0, 4.8 Hz), 3.00 (1H, dd, J 13.8, 9.7 Hz), 1.71-1.50 (11H, m); m/z (ES$^+$, 70V) 444.6 (MH$^+$).

EXAMPLE 212

Ethyl (2S)-3-{4-[(3,5-dichloroisonicotinoyl)amino]phenyl}-2-(2-hydroxy-3-oxo-spiro[3.5]non-1-en-1-ylamino)propanoate To a solution of the compound of Example 27 (1.0 g, 1.9 mmol) in DCM (40 ml) at −40° C. was added lead tetraacetate (0.94 g, 1.1 eq). The mixture was allowed to warm to 0° C. and stirred at this temperature for 8 h. The reaction mixture was partitioned between EtOAc (200 ml) and water (100 ml), the organics were separated washed with water (2×100 ml), brine (50 ml), dried (MgSO$_4$), filtered and concentrated in vacuo to give a crude oil. The crude was dissolved in ethanol (10 ml) and treated with NaH (100 mg). The mixture was stirred at room temperature until TLC analysis indicated that all starting material had been consumed, The reaction was quenched by the addition of NH$_4$Cl (5 ml, sat. aq.), EtOAc (2×20 ml) extraction of the mixture followed by washing with water (10 ml), brine (10 ml), drying (MgSO$_4$), filtering and concentration in vacuo to give a crude product which was purified by column chromatography (SiO$_2$, EtOAc:Hexane 1:1) to give the title compound as a white foam (0.89 g, 86%). δH (DMSO d$^6$, 400 MHz) 10.83 (1H, br), 8.78 (2H, s), 7.51 (2H, d, J 8.5 Hz), 7.12 (2K, d, J 8.5 Hz), 4.94 (1H, dd, J 11.4, 5.0 Hz), 4.10 (2H, m), 3.33 (1H, dd, J 14.1, 4.9 Hz), 3.14 (1H, dd, J 14.0, 11.4 Hz), 1.40-1.63 (4H, m), 1.19-1.33 (6H, m), 1.16 (3H, t, J 7.1 Hz); m/z (ES$^+$, 70V) 532 (MH$^+$).

EXAMPLE 213

Ethyl (2S)-3-{4-[(3,5-dichloroisonicotinoyl)amino]phenyl}-2-(2-methoxy-3-oxo-spiro[3.5]non-1-en-1-ylamino)propanoate To a solution of the compound of Example 212 (0.8 g, 1.5 mmol) in acetone (15 ml) was added K$_2$CO$_3$ (5 g) and methyl iodide (2.5 ml). The mixture was stirred at room temperature for 5 days. The mixture was filtered and concentrated in vacuo and the residue purified by column chromatography (SiO$_2$, EtOAc:Hexane 1:1) to give the title compound as a white solid (0.45 g, 55%). δH (DMSO d$^6$, 400 MHz) 8.50 (2H, d, J 4.8 Hz), 7.21 (2H, d, J 8.4 Hz), 7.04 (2H, d, J 8.4 Hz), 4.87 (1H, dd, J 11.8, 4.9 Hz), 4.00-4.16 (2H, m), 3.34 (3H, s), 3.26 (1H, dd, J 13.9, 4.9 Hz), 3.07 (1H, dd, J 13.9, 11.6 Hz), 1.15-1.66 (10H, m), 1.12 (3H, t, J 7.0 Hz); m/z (ES$^+$, 70V) 546 (MH$^+$).

EXAMPLE 214

Ethyl (2S)-2-(2-bromo-3-oxo-spiro[3.5]non-1-en-1-ylamino)-3-(2,4,6-trimethoxy[1,1'-biphenyl]-4-yl)propanoate The title compound was prepared by the methods as described herein. 5H (CDCl$_3$) 7.19 (2H, d, J 8.1 Hz), 7.04 (2H, d, J 8.1 Hz), 6.14 (2H, s), 5.84 (1H, d, J 8.6 Hz), 4.98 (1H, m), 4.20 (2H, q, J 7.1 Hz), 3.78 (3H, s), 3.62 (6H, s), 3.21 (2H, d), 1.97-1.40 (10H, m), 1.24 (3H, t, J 7.1 Hz); m/z (ES$^+$, 70V) 572 (MH$^+$).

EXAMPLE 215

(2S)-2-(2-Bromo-3-oxo-spiro[3.5]non-1-en-1-ylamino)-3-(2,4,6-trimethoxy[1,1'-biphenyl]-4-yl) propanoic Acid Prepared from the compound of Example 214 by the method of Example 2 to give the title compound. δH (DMSO d$^6$) 12.30 (1H, br s), 8.79 (2H, d, J 10.0 Hz), 7.19 (2H, d, J 8.1 Hz), 7.08 (2H, d, J 8.1 Hz), 6.29 (2H, s), 4.78 (1H, m), 3.81 (3H, s), 3.61 (6H, s), 3.27 (1H, m), 2.98 (1H, dd, J 13.4, 10.2 Hz), 1.95-1.00 (10H, m); m/z (ES$^+$, 70V) 544 (MH$^+$).

EXAMPLE 216

Tetrahydro-furan-2-yl methyl (2S)-2-(2-bromo-3-oxo-spiro[3.5]non-1-en-1-ylamino)-3-{4-(3,5-dichloroisonicotinoyl)amino]phenyl}propanoate Prepared using a similar procedure to that for the preparation of the compound of Example 138 from the compound of Example 32 (0.25 g, 0.44 mmol), EDC (150 mg), HOBT (100 mg) and tetrahydrofurfurylalcohol (0.5 ml) in DMF (2 ml) to give the title compound (0.15 g, 52%). δH (400 MHz, DMSO d$^6$) 10.88 (1H, s), 8.93 (1H, d, J 9.1 Hz), 8.80 (2H, s), 7.60 (2H, d, J 8.3 Hz), 7.28 (2H, d, J 6.9 Hz), 4.84 (1H, m), 4.15 (2H, m), 4.05 (1H, m), 3.23 (1H, dd, J 13.8, 4.4 Hz), 3.04 (1H, dd, J 13.6, 9.6 Hz), 1.50-2.00 (14H, m); m/z (ES$^+$, 70V) 650 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-Dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

$\alpha_4\beta_7$ Integrin-Dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a sub-line of the β-lympho blastoid cell-line JY was used in place of Jurkat cells. The $IC_{50}$ value for each test compound was determined as described in the $α_4β_1$ integrin assay.

$α_5β_1$ Integrin-Dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing $2.5×10^5$ K562 cells, phorbol-12-myristate-13-acetate at 10 ng/ml, and in the presence or absence of titrated test compounds. Incubation time was 30 minutes. Each plate was fixed and stained as described in the $α_4β_1$ assay above.

$α_mβ_2$-Dependent Human Polymorphonuclear Neutrophils Adhesion to Plastic 96 well tissue culture plates were coated with RPMI 1640/10% FCS for 2 h at 37° C. $2×10^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% $H_2O_2$ (Sigma) and 50 μg/ml TMB (Boehringer Mannheim) in 0.1M sodium acetate/citrate buffer, pH 6.0 and absorbance measured at 630 nm.

αIIb/β3-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of $6×10^8$/ml in autologous plasma. Cuvettes contained equal volumes of PRP and filtered Tyrode's buffer (g/liter: NaCl 8.0; $MgCl_2.H_2O$ 0.427; $CaCl_2$ 0.2; KCl 0.2; D-glucose 1.0; $NaHCO_3$ 1.0; $NaHPO_4.2H_2O$ 0.065). Aggregation was monitored following addition of 2.5 μM ADP (Sigma) in the presence or absence of inhibitors.

In the above assays the preferred compounds of the invention such as the compounds of the Examples generally have $IC_{50}$ values in the $α_4β_1$ and assay of 1 μM and below and in the $α4β_7$ assay of 5 μM and below. In the other assays featuring α integrins of other subgroups the same compounds had $IC_{50}$ values of 50 μM and above thus demonstrating the potency and selectivity of their action against $α_4$ integrins.

The invention is illustrated by the foregoing intermediates and examples, which are not intended to be limiting. Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

The invention claimed is:
1. A compound of formula (2a):

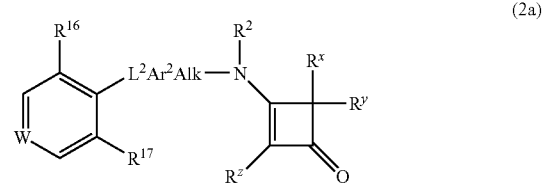

wherein
—W= is —$CR^{18}$;
$R^{16}$, $R^{17}$, and $R^{18}$, are each, independently, a hydrogen atom or -$L^3(Alk^2)_tL^4(R^4)_u$;
$L^3$ and $L^4$ are each, independently, a covalent bond, —O—, —S—, —C(O)—, —C(O)O—, —OC(O)—, —C(S)—, —S(O)—, —S(O)$_2$—, —N($R^8$)—, —CON($R^8$)—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)O—, —ON($R^8$)—, —N($R^8$)N($R^8$)—, —N($R^8$)CON($R^8$)—, —N($R^8$)CSN($R^8$)—, or —N($R^8$)SO$_2$N($R^8$)—;
$R^8$ is a hydrogen atom or a straight or branched $C_{1-6}$alkyl group optionally substituted with one, two, or three substituents selected from halogen, hydroxy and $C_{1-6}$alkoxy;
t is zero or the integer 1;
u is an integer 1, 2 or 3;
$Alk^2$ is an aliphatic or heteroaliphatic chain optionally substituted with one or more substituents selected from halogen, —OH, —$CO_2H$, —$CO_2R^9$, —$CONHR^9$, —CON($R^9$)$_2$, —$COR^9$, $C_{1-6}$alkoxy, thiol, —S(O)$R^9$, —S(O)$_2R^9$, $C_{1-6}$alkylthio, amino, —$NHR^9$ and —N($R^9$)$_2$;
$R^9$ is a straight or branched $C_{1-6}$alkyl group optionally substituted with one, two, or three substituents selected from halogen, hydroxy and $C_{1-6}$alkoxy;
$R^4$ is a hydrogen atom; a halogen atom; $C_{1-6}$alkyl optionally substituted with one, two, or three substituents selected from halogen, hydroxy and $C_{1-6}$alkoxy; $C_{3-8}$cycloalkyl optionally substituted with one, two, or three substituents selected from halogen, hydroxy and $C_{1-6}$alkoxy; —$OR^5$; —$SR^5$; —$NR^5R^6$; —$NO_2$; —CN; —$CO_2R^5$; —$SO_3H$; —$SOR^5$; —$SO_2R^5$; —$SO_3R^5$; —$OCO_2R^5$; —$CONR^5R^6$; —$OCONR^5R^6$; —$CSNR^5R^6$; —$COR^5$; —$OCOR^5$; —N($R^5$)$COR^6$; —N($R^5$)$CSR^6$; —$SO_2N(R^5)(R^6)$; —N($R^5$)$SO_2R^6$; N($R^5$)$CON(R^6)(R^7)$; —N($R^5$)$CSN(R^6)(R^7)$; or —N($R^5$)$SO_2N(R^6)(R^7)$, provided that when t is zero and each of $L^3$ and $L^4$ is a covalent bond, then u is the integer 1 and $R^4$ is other than a hydrogen atom;
$R^5$, $R^6$, $R^7$, and $R^{11}$ are each, independently, a hydrogen atom or a $C_{1-6}$alkyl or $C_{3-8}$cycloalkyl group, wherein each of said alkyl and cycloalkyl groups is optionally substituted with one, two, or three substituents selected from halogen, hydroxy and $C_{1-6}$alkoxy;
$L^2$ is a covalent bond, —O—, —S—, —C(O)—, —C(O)O—, —OC(O)—, —C(S)—, —S(O)—, —S(O)$_2$—, —N($R^8$)—, —CON($R^8$)—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)O—, —ON($R^8$)—, —N($R^8$)N($R^8$)—, —N($R^8$)CON($R^8$)—, —N($R^8$)CSN($R^8$)—, or —N($R^8$)SO$_2$N($R^8$)—;

Ar² is an arylene group optionally substituted with one or more -L³(Alk²)ₜL⁴(R⁴)ᵤ groups;

Alk is a chain
—CH₂—CH(R)—, —CH═C(R)— or

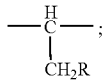

R is a carboxylic acid (—CO₂H), a carboxylic acid ester (—CO₂Alk⁷), a carbocylic acid amide (—CONR⁵R⁶), a tetrazole, phosphonic acid, phosphinic acid, sulphonic acid, sulphinic acid, boronic acid, or an acylsulphonamide group;

Alk⁷ is a straight or branched $C_{1-8}$alkyl group, $C_{2-8}$alkenyl group, $C_{2-8}$alkynyl group, $C_{3-8}$cycloalkyl group, $C_{3-8}$heterocycloalkyl group, $C_{3-8}$cycloalkyl$C_{1-8}$alkyl group, $C_{3-8}$heterocycloalkyl$C_{1-8}$alkyl group, $C_{1-6}$alkyloxy$C_{1-6}$alkyl group, hydroxy$C_{1-6}$alkyl group, $C_{1-6}$alkylthio$C_{1-6}$alkyl group, $C_{1-6}$alkylsulfinyl$C_{1-6}$alkyl group, $C_{1-6}$alkylsulfonyl$C_{1-6}$alkyl group, $C_{3-8}$cycloalkyloxy$C_{1-6}$alkyl group, $C_{3-8}$cycloalkylthio$C_{1-6}$alkyl group, $C_{3-8}$cycloalkylsulfinyl$C_{1-6}$alkyl group, $C_{3-8}$cycloalkylsulfonyl$C_{1-6}$alkyl group, $C_{1-6}$alkyloxycarbonyl$C_{1-6}$alkyl group, $C_{1-6}$alkyloxycarbonyl$C_{1-6}$alkenyl group, $C_{1-6}$alkyloxycarbonyloxy$C_{1-6}$alkyl group, $C_{1-6}$alkyloxycarbonyloxy$C_{1-6}$alkenyl group, $C_{3-8}$cycloalkyloxycarbonyloxy$C_{1-6}$alkyl group, N-di-$C_{1-8}$alkylamino$C_{1-8}$alkyl group, N—$C_{6-12}$aryl-N—$C_{1-6}$alkylamino$C_{1-6}$alkyl group, N-di-$C_{1-8}$alkyl-carbamoyl$C_{1-8}$alkyl group, $C_{6-12}$aryl$C_{1-6}$alkyl group, hetero$C_{6-10}$aryl$C_{1-6}$alkyl group, $C_{6-12}$aryl group, a $C_{6-12}$aryloxy$C_{1-8}$alkyl group, a $C_{6-12}$arylthio$C_{1-8}$alkyl group, a $C_{6-12}$arylsulfinyl$C_{1-8}$alkyl group, a $C_{6-12}$arylsulfonyl$C_{1-8}$alkyl group, $C_{1-8}$alkanoyloxy$C_{1-8}$alkyl group, $C_{4-8}$imido$C_{1-8}$alkyl group, a $C_{6-12}$aroyloxy$C_{1-8}$alkyl group, or a triglyceride, optionally substituted with one or more $R^{13a}$ groups;

$R^{13a}$ is a halogen atom, or an amino (—NH₂), $NHR^{14}$, —N($R^{14}$)₂, nitro, cyano, amidino, hydroxyl (—OH), —OR¹⁴, formyl, carboxyl (—CO₂H), esterified carboxyl, thiol (—SH), —SR¹⁴, —SC(═NH)NH₂, —COR¹⁴, —CSR¹⁴, —SO₃H, —SOR¹⁴, —SO₂R¹⁴, —SO₃R¹⁴, —SO₂NH₂, —SO₂NHR¹⁴, SO₂N(R¹⁴)₂, —CONH₂, —CSNH₂, —CONHR¹⁴, —CSNHR¹⁴, —CON(R¹⁴)₂, —CSN(R¹⁴)₂, —N(R¹⁴)SO₂R¹⁴, —N(SO₂R¹⁴)₂, —NH(R¹¹)SO₂NH₂, —N(R¹¹)SO₂NHR¹⁴, —N(R¹¹)SO₂N(R¹⁴)₂, —N(R¹¹)COR¹⁴, —N(R¹¹)CONH₂, —N(R¹¹)CONHR¹⁴, —N(R¹¹)CON(R¹⁴)₂, —N(R¹¹)CSNH₂, —N(R¹¹)CSNHR¹⁴, N(R¹¹)CSN(R¹⁴)₂, —N(R¹¹)CSR¹⁴, —N(R¹¹)C(O)OR¹⁴, —SO₂NHet¹, —CONHet¹, —CSNHet¹, —N(R¹¹)SO₂NHet¹, —N(R¹¹)CONHet¹, —N(R¹¹)CSNHet¹, —SO₂N(R¹¹)Het², -Het², —CON(R¹¹)Het², —CSN(R¹¹)Het², —N(R¹¹)CON(R¹¹)Het², —N(R¹¹)CSN(R¹¹)Het², aryl or heteroaryl group;

$R^{14}$ is an -Alk⁶($R^{13a}$)ₘ, aryl, or heteroaryl group;

Alk⁶ is a straight or branched $C_{1-6}$alkylene, $C_{2-6}$alkenylene or $C_{2-6}$alkynylene chain, optionally interrupted by one, two or three —O— or —S— atoms or —S(O)p or —N(R¹⁵)— groups;

m is zero or the integer 1, 2 or 3;

p is an integer 1 or 2;

$R^{15}$ is a hydrogen atom or $C_{1-6}$ alkyl group;

Het¹ is a $C_{5-7}$cyclicamino group optionally containing one or more —O— or —S— atoms or —N(R¹¹)—, —C(O)—, —C(S)—, S(O) or —S(O)₂ groups and optionally substituted with one or more substituents selected from halogen, —OH, —CO₂H, —CO₂R⁹, —CONHR⁹, —CON(R⁹)₂, —COR⁹, $C_{1-6}$alkoxy, thiol, —S(O)R⁹, —S(O)₂R⁹, $C_{1-6}$alkylthio amino, —NHR⁹ and —N(R⁹)₂;

Het² is a monocyclic $C_{5-7}$-carbocyclic group optionally containing one or more —O— or —S— atoms or —N(R¹¹)—, —C(O)— or —C(S)— groups and optionally substituted with one or more substituents selected from halogen, —OH, —CO₂H, —CO₂R⁹, —CONHR⁹, —CON(R⁹)₂, —COR⁹, $C_{1-6}$alkoxy, thiol, —S(O)R⁹, —S(O)₂R⁹, $C_{1-6}$alkylthio amino, —NHR⁹ and —N(R⁹)₂;

R² is a hydrogen atom or a $C_{1-6}$alkyl group;

$R^z$ is an atom or group -L¹(Alk¹)ₙ(R³)ᵥ;

$R^x$, $R^y$, and $R^z$, which may be the same or different, are each an atom or group -L¹(Alk¹)ₙ(R³)ᵥ;

L¹ is a covalent bond, an —O—, —S—, or —Se— atom, or a —C(O)—, —C(O)O—, —OC(O)—, —C(S)—, —S(O)—, —S(O)₂—, —N(R⁸)—, —CON(R⁸)—, —OC(O)N(R⁸)—, —CSN(R⁸)—, —N(R⁸)CO—, —N(R⁸)C(O)O—, —N(R⁸)CS—, —S(O)₂N(R⁸)—, —N(R⁸)S(O)₂—, —N(R⁸)O—, —ON(R⁸)—, —N(R⁸)N(R⁸)—, —N(R⁸)CON(R⁸)—, —N(R⁸)CSN(R⁸)—, or —N(R⁸)SO₂N(R⁸)— group;

Alk¹ is an aliphatic or heteroaliphatic chain optionally substituted with one or more substituents selected from halogen, —OH, —CO₂H, —CO₂R⁹, —CONHR⁹, —CON(R⁹)₂, —COR⁹, $C_{1-6}$alkoxy, thiol, —S(O)R⁹, —S(O)₂R⁹, $C_{1-6}$alkylthio amino, —NHR⁹ and —N(R⁹)₂;

R³ is a hydrogen or halogen atom or a group selected from
—OR$^{3a}$;
—SR$^{3a}$;
—CN; and
a $C_{3-10}$cycloalkyl; $C_{3-10}$cycloalkenyl; $C_{3-10}$heterocycloalkyl or $C_{3-10}$heterocycloalkenyl containing 1, 2, 3 or 4 heteroatoms or heteroatom-containing groups L⁵, where L⁵ is defined as for L; aromatic or heteroaromatic group optionally substituted with one or more substituents selected from halogen, $C_{1-6}$alkyl, halo$C_{1-6}$alkyl, —C(O—H)(CF₃)₂, $C_{1-6}$alkoxy, halo$C_{1-6}$alkoxy, thiol, $C_{1-6}$alkylthio, -(Alk⁴)$_g$R¹⁰, —CN, —CO₂R¹¹, —NO₂, —CON(R¹¹)₂, —CSN(R¹¹)₂, —COR¹¹, —CSN(R¹¹)₂, —N(R¹¹)COR¹¹, —N(R¹¹)CSR¹¹, —SO₂N(R¹¹)₂, —N(R¹¹)SO₂R¹¹, —N(R¹¹)CON(R¹¹)₂, —N(R¹¹)CSN(R¹¹), —N(R¹¹)SO₂N(R¹¹)₂, and phenyl optionally substituted with one, two or three R¹³ groups;

R¹³ is —R$^{13a}$ or -Alk⁶(R$^{13a}$)ₘ;

Alk⁴ is a straight or branched $C_{1-3}$alkylene chain;

g is zero or an integer 1;

R¹⁰ is —OH, —SH, or —N(R¹¹)₂;

$R^{3a}$ is a hydrogen atom or a straight or branched $C_{1-6}$alkyl group or $C_{3-8}$cycloalkyl group, wherein each of said alkyl and cycloalkyl groups is optionally substituted with one, two, or three substituents selected from halogen, hydroxy, or $C_{1-6}$alkoxy;

n is zero or the integer 1;

v is the integer 1, 2 or 3;

provided that when n is zero and L¹ is a covalent bond, v is the integer 1;

or R$^x$ and R$^y$, together with the carbon atom to which they are attached, are joined together to form a spiro inked $C_{3-10}$cycloalkyl group; or $C_{3-10}$cycloalkenyl group optionally substituted with one or more substituents selected from halogen, $C_{1-6}$alkyl, halo$C_{1-6}$alkyl, —C(OH)(CF$_3$)$_2$, $C_{1-6}$alkoxy, halo$C_{1-6}$alkoxy, thiol, $C_{1-6}$alkylthio, -(Alk$^4$)$_g$R$^{10}$, —CN, —CO$_2$R$^{11}$, —NO$_2$, —CON(R$^{11}$)$_2$, —CSN(R$^{11}$)$_2$, —COR$^{11}$, —CSN(R$^{11}$)$_2$, —N(R$^{11}$)COR$^{11}$, —N(R$^{11}$)CSR$^{11}$, —SO$_2$N(R$^{11}$)$_2$, —N(R$^{11}$)SO$_2$R$^{11}$, —N(R$^{11}$)CON(R$^{11}$)$_2$, —N(R$^{11}$)CSN(R$^{11}$), N(R$^{11}$)SO$_2$N(R$^{11}$)$_2$, and phenyl optionally substituted with one, two or three R$^{13}$ groups; or a salt, solvate, hydrate or N-oxide thereof.

2. A compound according to claim 1 in which R$^{18}$ is a hydrogen atom, a methoxy group, or an ethoxy group.

3. A compound according to claim 1 in which R$^{16}$ and R$^{17}$ are each, independently, a halogen atom, $C_{1-6}$alkyl, halo$C_{1-6}$alkyl, $C_{1-6}$alkoxy, or halo$C_{1-6}$alkoxy.

4. A compound according to claim 3 in which R$^{16}$ and R$^{17}$ are each, independently fluorine, chlorine, methyl, ethyl, isopropyl, —CF$_3$, —CHF$_2$, —CH$_2$F, methoxy, ethoxy, —OCF$_3$, —OCHF$_2$, or —OCH$_2$F.

5. A compound according to claim 1 in which Alk is a —CH$_2$CH(R)— or —CH(CH$_2$R)— chain.

6. A compound according to claim 1 in which R is a carboxylic acid (—CO$_2$H) group.

7. A compound according to claim 1 in which R is an esterified carboxyl group of formula —CO$_2$Alk$^7$.

8. A compound according to claim 1 in which R$^2$ is a hydrogen atom.

9. A compound according to claim 1 in which Ar$^2$ is an optionally substituted phenylene group.

10. A compound according to claim 1 in which R$^z$ is a halogen atom.

11. A compound according to claim 1 in which R$^z$ is an optionally substituted $C_{1-8}$alkyl group.

12. A compound according to claim 1 in which R$^z$ is a group -L$^1$(Alk$^1$)$_n$R$^3$ in which L$^1$ is an —O—, —S— or —Se— atom or —S(O)— or —N(R$^8$)— group.

13. A compound according to claim 12 in which n is zero.

14. A compound according to claim 12 in which n is the integer 1 and Alk$^1$ is an optionally substituted $C_{1-6}$alkylene chain.

15. A compound according to claim 12 in which R$^3$ is a hydrogen atom or an optionally substituted $C_{3-10}$cycloalkyl; $C_{3-10}$cycloalkenyl; or $C_{3-10}$heterocycloalkyl or $C_{3-10}$heterocycloalkenyl containing 1, 2, 3 or 4 heteroatoms or heteroatom-containing groups L$^5$, where L$^5$ is defined as for L$^3$, $C_{6-12}$aromatic or $C_{1-9}$heteroaromatic group.

16. A compound according to claim 1 in which R$^z$ is a group -L$^1$(Alk$^1$)$_n$R$^3$ in which L$^1$ is a covalent bond.

17. A compound according to claim 16 in which n is zero.

18. A compound according to claim 16 in which n is the integer 1 and Alk$^1$ is an optionally substituted $C_{1-6}$alkylene chain.

19. A compound according to claim 16 in which R$^3$ is a hydrogen atom or an optionally substituted $C_{3-10}$cycloalkyl; $C_{3-10}$cycloalkenyl; $C_{3-10}$heterocycloalkyl or $C_{3-10}$heterocycloalkenyl containing 1, 2, 3 or 4 heteroatoms or heteroatom-containing groups L$^5$, where L$^5$ is defined as for L$^3$; $C_{6-12}$aromatic or $C_{1-9}$heteroaromatic group.

20. A compound according to claim 1 in which R$^x$ and R$^y$, together with the carbon atom to which they are attached, are joined to form an optionally substituted spiro linked $C_{3-10}$cycloalkyl group; or a $C_{3-10}$cycloalkenyl group.

21. A compound which is:

(2S)-2-[(2-Bromo-3-oxospiro[3.5]non-1-en-1-yl)amino}-3-(2,6-dimoethoxy[1,1'-biphenyl]-4-yl)propanoic acid;

(2S)-2-{[(2-(isopropylsulfanyl)-3-oxo-oxaspiro[3.5]non-1-en-1-yl)]amino}-3-(2,6-dimethoxy[1,1'-biphenyl]-4-yl)propanoic acid;

or a salt, solvate, hydrate, N-oxide, or carboxylic acid ester thereof.

22. A pharmaceutical composition comprising a compound according to claim 1 together with one or more pharmaceutically acceptable carriers, excipients or diluents.

23. A method for the treatment of multiple sclerosis, allograft rejection, asthma, or inflammatory bowel disease comprising administering to a mammal suffering from such a disease or disorder a therapeutically effective amount of a compound according to claim 1.

\* \* \* \* \*